US006828125B1

(12) United States Patent
Hoffman et al.

(10) Patent No.: US 6,828,125 B1
(45) Date of Patent: *Dec. 7, 2004

(54) DNA ENCODING FUSED DI-ALPHA GLOBINS AND USE THEREOF

(75) Inventors: Stephen J. Hoffman, Denver, CO (US); Douglas L. Looker, Lafayette, CO (US); Kiyoshi Nagai, Cambridge (GB)

(73) Assignee: Baxter Biotech Technology, S.a.r.l., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 08/453,485

(22) Filed: May 30, 1995

Related U.S. Application Data

(63) Continuation of application No. 07/789,179, filed on Nov. 8, 1999, now Pat. No. 5,545,727, which is a continuation-in-part of application No. 07/671,707, filed on Apr. 1, 1991, now abandoned, which is a continuation-in-part of application No. PCT/US90/02654, filed on May 10, 1990, now abandoned, which is a continuation-in-part of application No. 07/379,116, filed on Jul. 13, 1989, now abandoned, which is a continuation-in-part of application No. 07/374,161, filed on Jun. 30, 1989, now abandoned, which is a continuation-in-part of application No. 07/349,623, filed on May 10, 1989, now abandoned.

(51) Int. Cl.[7] .......................... C12P 21/06; C07H 17/00; C07K 14/805

(52) U.S. Cl. .................. 435/69.6; 435/69.1; 435/320.1; 536/23.1; 530/385

(58) Field of Search ........................ 530/385; 536/23.1; 435/69.1, 320.1, 240.1, 69.6

(56) References Cited

U.S. PATENT DOCUMENTS

| 4,001,200 | A |   | 1/1977 | Bonsen et al. | |
|---|---|---|---|---|---|
| 4,001,401 | A |   | 1/1977 | Bonsen et al. | |
| 4,473,496 | A | * | 9/1984 | Scannon | 260/112 B |
| 4,529,719 | A | * | 7/1985 | Tye | 514/6 |
| 4,584,130 | A | * | 4/1986 | Bucci et al. | 260/112 B |
| 4,600,531 | A | * | 7/1986 | Walder | 530/385 |
| 4,840,896 | A | * | 6/1989 | Reddy et al. | 135/69.1 |
| 5,250,665 | A | * | 10/1993 | Kluger et al. | 530/385 |
| 5,545,727 | A | * | 8/1996 | Hoffman et al. | 536/234 |

FOREIGN PATENT DOCUMENTS

| WO | 09179 | * | 1/1988 | ................ | 135/69.1 |
|---|---|---|---|---|---|
| WO | 09179 | * | 12/1988 | ................ | 435/69.1 |

OTHER PUBLICATIONS

Antonini, et al., *Assembly of Multisubunit Respiratory Protein*, Ann. Rev. Biophys. Bioeng., vol. 6, pp. 239–271, 1977.
De Baere, et al., *Polar zipper sequence in the high–affinity hemoglobin of Ascaris suum: Amino acid sequence and structural interpretation*, Proc. Natl. Acad. Sci. USA, vol. 89, pp. 4638–4642, May 1992.
DiFeo, et al., *Kinetic and spectroscopic studies of haemoglobin and myoglobin from Urechis caupo*, Biochem. J., vol. 269, pp. 739–747, 1990.
Garlick, Robert Lee, *Structure of Annelid High Molecular Weight Hemoglobins (Erythrocruorins)*, Amer. Zool., vol. 20, pp. 69–77, 1980.
Garlick, et al., *The Amino Acid Sequence of a Major Polypeptide Chain of Earthworm Hemoglobin*, The Journal of Biological Chemistry, vol. 257, No. 15, pp. 9005–9015, Aug. 10, 1982.
Garey, et al., *Structure and Function of Hemoglobin from Urechis caupo* Archives of Biochemistry and Biophysics, vol. 228, No. 1, pp. 320–331, 1984.
Garey, et al., *The Hemoglobin of Urechis caupo*, The Journal of Biological Chemistry, vol. 261, No. 35, pp. 16446–16450, Dec. 15, 1986.
Hall, et al., *Hemoglobins and Myoglobin of the Echiuran Urechis Caupo (Fisher and Macginitie)*, Comp. Biochem. Physiol., vol. 70B, pp. 353–357, 1981.
Keilin, et al., *Relationship Between Haemoglobin and Erythrocruorin*, Nature, vol. 168, pp. 266–269, Aug. 18, 1951.
Kolatkar, et al., *Structure Determination and Refinement of Homotetameric Hemoglobin from Urechis caupo at 2.5 Å Resolution*, Acta Crystallographica, vol. B48, pp. 191–199, 1992.
Kolatkar, et al., *Structural Analysis of Urechis caupo Hemoglobin*, J. Mol. Biol., vol. 237, pp. 87–97, 1994.
Magnum, et al., *Oxygen Binding of Intact Coelomic Cells and Extracted Hemoglobin of the Echiuran Urechis Caupo*, Comp. Biochem. Physiol., vol. 76A, No. 2, pp. 253–257, 1983.
Manning, et al., *Evolution of a polymeric globin in the brine shrimp Artemia*, Nature, vol. 348, pp. 653–656, Dec. 13, 1990.
Martin, et al., *Kinetics and Thermodynamics of Oxygen and Carbon Monoxide Binding to the T–State Hemoglobin of Urechis caupo*, Biochemistry, vol. 29, pp. 5718–5726, 1990.
Moens, et al., *Structural Interpretation of the Amino Acid Sequence of a Second Domain from the Artemia Covalent Polymer Globin*, The Journal of Biological Chemistry, vol. 265, No. 24, pp. 14285–14291, Aug. 25, 1990.
Ownby, et al., *The Extracellular Hemoglobin of the Earthworm, Lumbricus terrestris*, The Journal of Biological Chemistry, vol. 268, No. 18, pp. 13539–13547, Jun. 25, 1993.

(List continued on next page.)

*Primary Examiner*—Karen Cochrane Carlson
(74) *Attorney, Agent, or Firm*—Senniger, Powers, Leavitt & Roedel

(57) ABSTRACT

The alpha subunits of hemoglobin, which in nature are formed as separate polypeptide chains which bind noncovalently to the beta subunits, are here provided in the form of the novel molecule di-alpha globin, a single polypeptide chain defined by connecting the two alpha subunits either directly via peptide bond or indirectly by a flexible amino acid or peptide linker. Di-alpha globin may be combined in vivo or in vitro with beta globin and heme to form hemoglobin. Di-alpha globin is expressed by recombinant DNA techniques. Di-beta globin may be similarly obtained.

46 Claims, 70 Drawing Sheets

OTHER PUBLICATIONS

Padlan, et al., *Three–Dimensional Structure of Hemoglobin from the Polychaete Annelid, Glycera dibranchiata, at 2.5 Å Resolution*, The Journal of Biological Chemistry, vol. 249, No. 13, pp. 4067–4078, Jul. 10, 1974.

Suzuki, et al., *Linker Chain L1 of Earthworm Hemoglobin*, The Journal of Biological Chemistry, vol. 268, No. 18, pp. 13548–13555, Jun. 25, 1993.

Terwilliger, Robert C., *Structure of Invertebrate Hemoglobins*, Amer. Zool., vol. 20, pp. 53–67, 1980.

Terwilliger, et al., *The Quaternary Structure of a Molluscan (Helisoma Trivolvis) Extracellular Hemoglobin*, Biochimica et Biophysica Acta, vol. 453, pp. 101–110, 1976.

Trotman, et al., *Interdomain Linkage in the Polymeric Hemoglobin Molecule of Artemia*, J. Mol. Evol., vol. 38, pp. 628–636, 1994.

Trotman, et al., *The Polymeric Hemoglobin Molecule of Artemia*, The Journal of Biological Chemistry, vol. 266, No. 21, pp. 13789–13795, Jul. 25, 1991.

Weber, Roy E., *Functions of Invertebrate Hemoglobins with Special Reference to Adaptations to Environmental Hypoxia*, Amer. Zool., vol. 20, pp. 79–101, 1980.

Zhu, et al., *Stoichiometry of Subunits and Heme Content of Hemoglobin from the Earthworm Lumbricus terrestris*, The Journal of Biological Chemistry, vol. 271, No. 47, pp. 29999–30006.

Hallewell et al, (1989) *J. Biol. Chem,* 264, 5260–5268.*

Naga et al. PNAS 82 (1985): 7252–7255.*

Lebhaher et al. PNAS (1980) 79:7410–11.*

Schones et al. Meth. Fingnol. 153 (1987): 401.*

Schoner et al. PNAS (1986) 83: 8506–8510.*

So Lo et al. J. Biochem 101, 1281 (1987).*

Springs et al. PNAS 84 (1987) 8961–8965.*

Naga et al. PNAS USA 82 (1985): 7252–7255.* de Bactselier et al. Molecl. Fac.*

Guasconte et al. PNAS USA (1987) 9:7410–4, abstract.*

Lichhaber et al. PNAS 77:7054–58 (1980).*

Springer et al. PNAS 84 (1987) 8961–8965.*

* cited by examiner

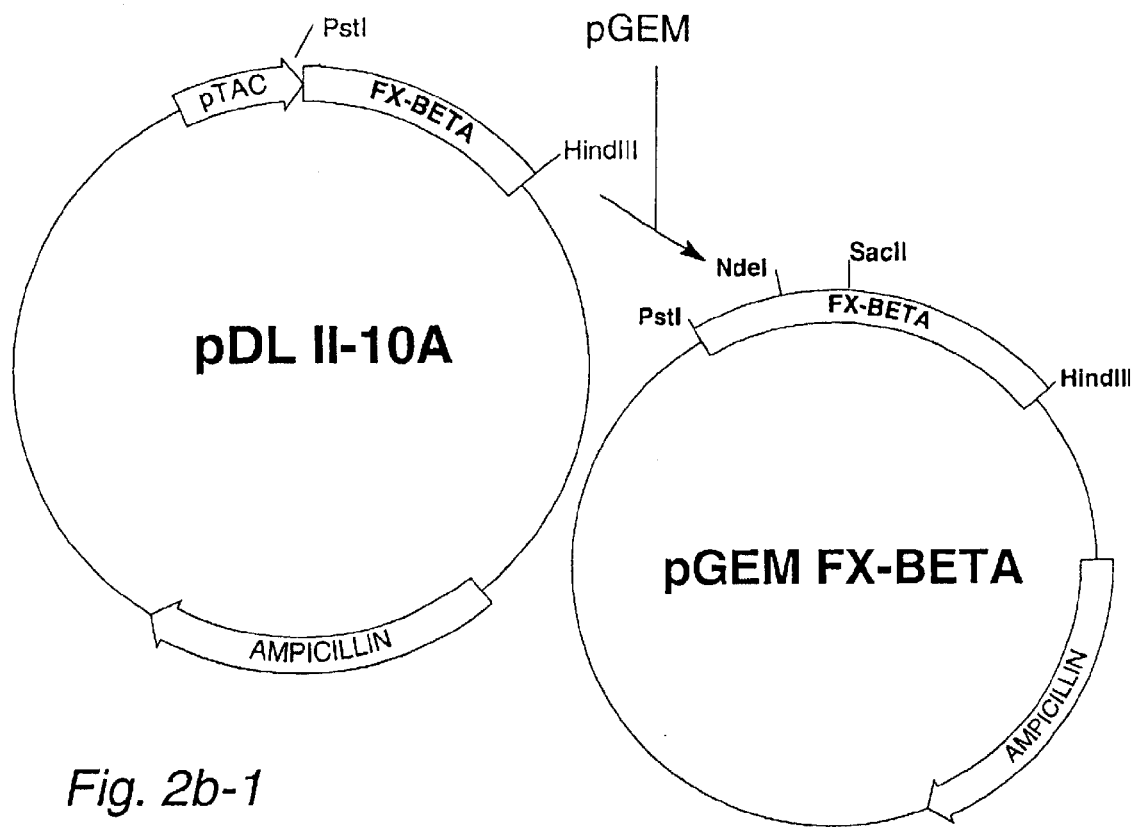
Fig. 2b-1
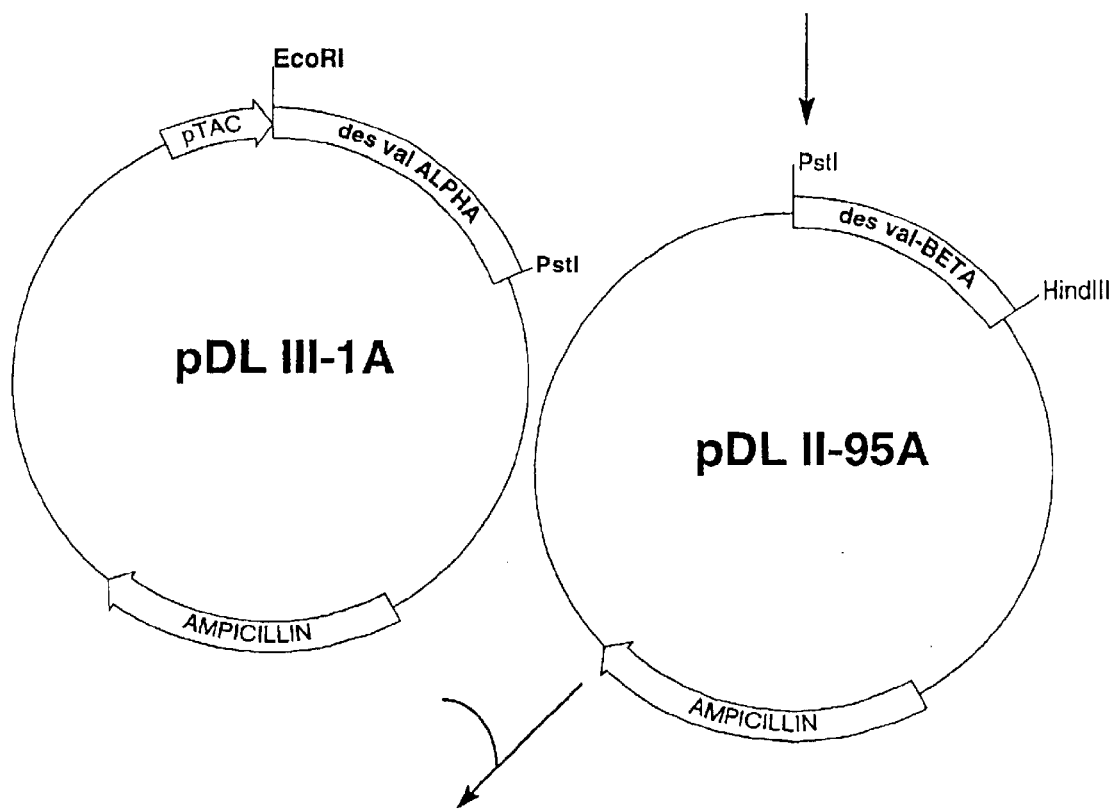

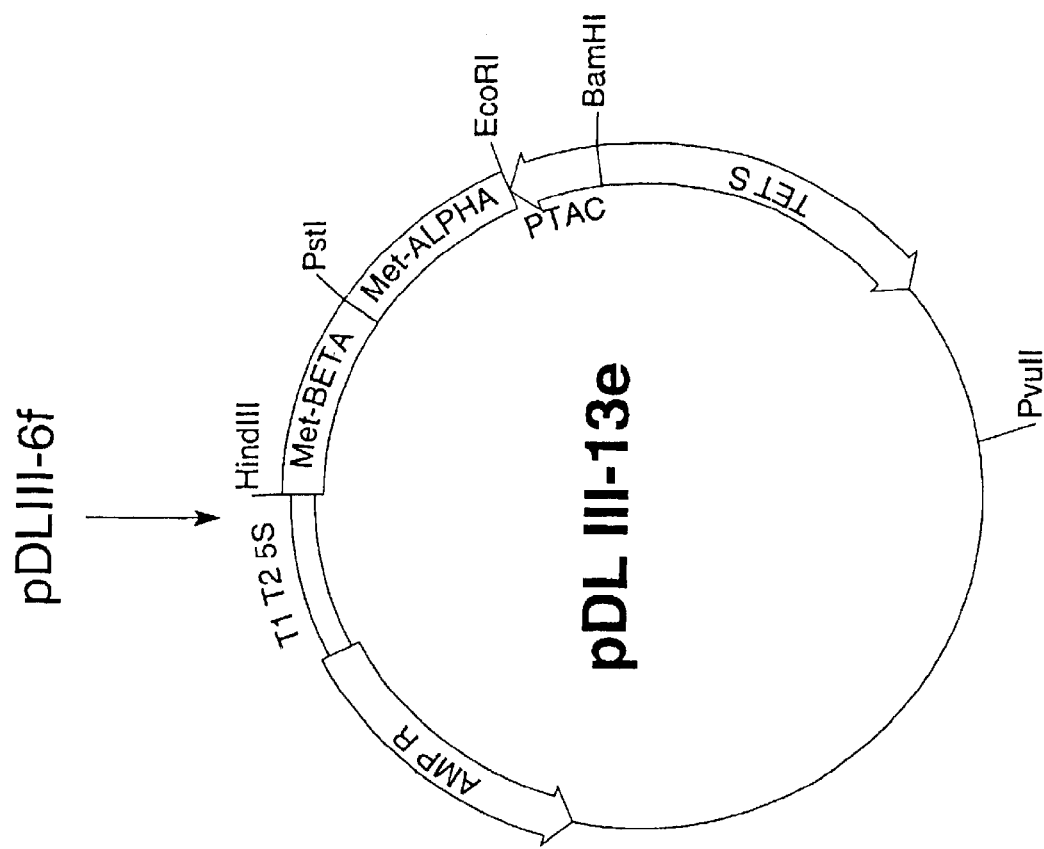
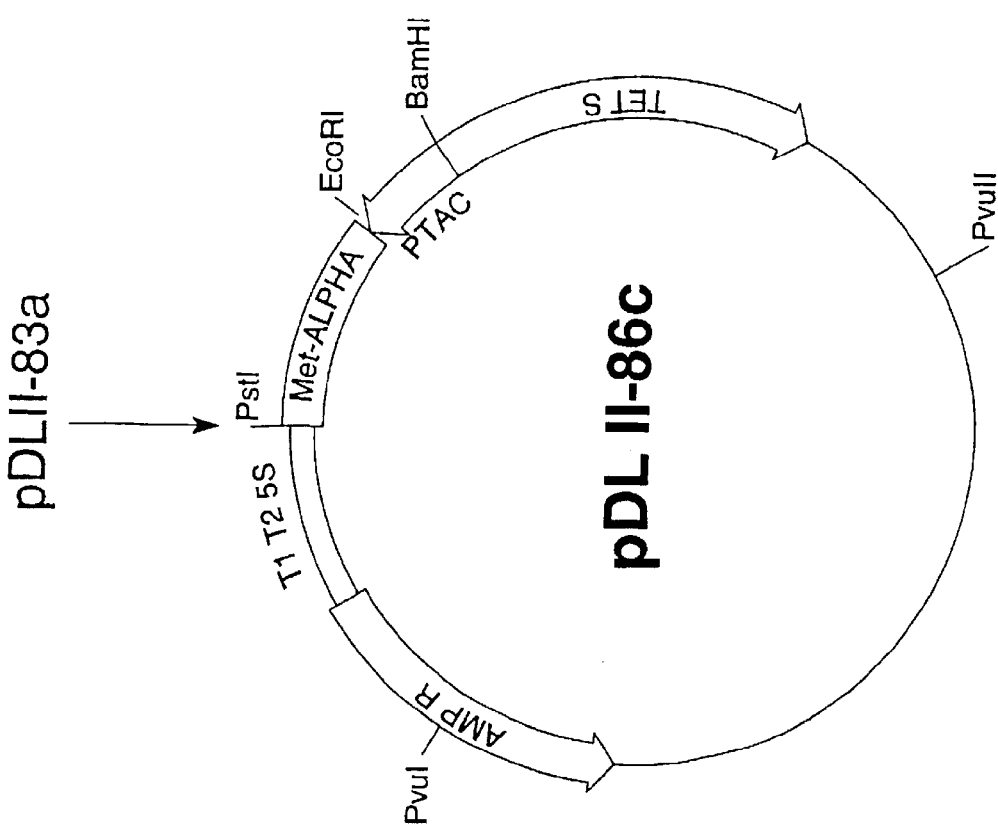
Fig. 3b

FIG. 4a

SJH I-33a
SEQ ID NO:88 CCGGGCTACATGGAGAGATTAACTCAATCTAGAGGGTATTAATAATGTATCGCTTAAATAAGGAGGAATAACATATGATC
SEQ ID NO:89 cgatgtacctctaattgagttagatctcccataattattacatagcgaattTattCCTCCTTATTGTATACTAG SJH I-33b                                                SJH I - 33d SJH I-33c
gaaggtcgtgtttctgtctccggccgataaaaccaacgttaaagctgcttggggtaaagttggcgcacgcTGGTGAA  SJH I-33e
CTTCCAGCACAAGACAGAGAGGCCCGGCTATTTTGCAATTTGCAATTTGCAATTTGCAATTCAACCGCGGTGGCGACCACTT
                      SJH I-33f TACGGGTGCTGAAGCTCTCGAGGCGTATGTTCCGTCTTTCCCGACCACCAAAACCTACTTCCCGCACTTCgacctgtct  SJH I-34a
atgccacgacttcgagagctcgcatacaagaagggctggtggtttGATGAAGGGCTGAAGCTGAAGCTGGACAGA
                                  SJH I-34b                           SJH I-34c cacggtttctcgccaggttaaaggtcacggtaaaaaagttgctgatgctctgaccaacgctgtTGCTCACGTTGATGAT
GTGCCAAGAGCGGGTCCAATTTTTCAAGACTACgagactggtgcgacaacgagtgcaactacta
                                                SJH I-34d                SJH I-34e ATGCCGAACGCGGTTGTTGCTCTTGTCTCTGATCTGCACGCTCACAAACTGCTGTGATCCGTtaacttcaaactgctg
tacggcttgccgcaacagacgagacagactagacgtgcgagtgtttGACGCACAACTAGGCCAATTGAAGTTTGACGAC
                                                         SJH I-34f

FIG. 4b tctcactgcctgctggttactctgctgctcatctgccggctgaatttacccgcggctgtTCATGCGTCTCTGGATAAA
SJH I-35a AGAGTGACGGACGACCAATGAGACCGAGTAGACGGCCgacttaaatggggccgacaagtacgcagagacctattt
SJH I-35b TTCCTGGCTTCTGTTTCTACCGTTCTGACTTCGAAATACCGTTAATGACTGCAgctacatggagattaactcaatcta
SJH I-36a aaggaccgaagacaaagatggcaagactgaagctttatggcaattactgACGTGATACTCTAATTGAGTTAGAT
SJH I-36b gagggtattaatgtatcgcttaaataaggaggaataacatatgatcgaAGGTCGTGTTCACCTGACTCCGAAGA
SJH I-36c CTCCCATAATTATTACATAGCCGAATTTATTCCTccttattgtatactagcttccagcagaagtggactgaggcctct
SJH I-36d

FIG. 4c

SJH I-36e

AAATCCGGGTTACTGCTCTGTGGGTAAAGTGACGAAGTTGGTGtgaagctctgggacgtctgctgt
ttttaggcgccaatgacgagacacccccattttcacttgcaacTGCTTCAACCACTTCGAGACCCTGCAGACGACCA

SJH I-36f

SJH I-37a tgtttacccgtgtgactcagcgtttcttgaatctttcggagatctgtcTACCCCGGACGCTGTTATGGGTAACCCGAA
ACAAATGGGCACCTGAGTCGCAAAGAAACTtagaaagcctctagacagatggggcctgcgacaataccccattgggctt

SJH I-37b

SJH I-37c

AGTTAAAGCCCATGGTAAAAAAAGTTCTGGGTGCTTTCTGACggtctgctcacctgacaacctgaaaggtaccctt
tcaatttcgggtaccattttttcaagaCCCACAGAGACTGCCAGACCGAGTGGACTTGTTGGACTTTCCATGGAA

SJH I-37d

SJH I-37e cgctactctgtctgagctctccactgcgcacgttgacccggaAAACTTCCGTCTGCTGGGTAACGTACTAGT
GCGATGAGACAGAGACTCGAGGTGACGCTGTTTGAcgtgcaactgggcctttgaaggcagacgaccattgcatgatca

SJH I-37f

SJH I-38a

TTGCGTTCTGGCTCACCACTTCGCGGTAAAGAATTCACTCCGCCGGttcaggctgcttaccagaaagttgttgctggtgt
aacgcaagaccgagtggtgaagccattcCTTAAGTGAGGCGGCCAAGTCCGACGAATGGTCTTTCAACAACGACCACA

SJH I-38b tgctaacgcgctagctcacaaataccactaatga
ACGATTGCGCGCGATCGAGTGTTTATGGTGATTACTTCGA

FIG. 5a

SEQ ID NO:90  GA ATT CGA GCT CGG TAC CCG GGC TAC ATG GAG ATT AAC TCA ATC TAG A
              CGT CGA GCC ATG GGC CCG ATG TAC CTC TAA TTG AGT TAG ATC

/Xmal

SD#1
AGG GTA TTA ATA ATG TAT CGC TTA AAT AAG GAG GAA TAA CAT ATG ATC
TCC CAT AAT TAT TAC ATA GCG AAT TTA TTC CTC CTT AAT GTA TAC TAG

SD#2  /Ndel

SEQ ID NO:91  met (ile

/Eagl

GAA GGT CGT GTT CTG TCT CCG GCC GAT AAA ACC AAC GTT AAA GCT CGT
CTT CCA GCA CAA GAC AGA GGC CGG CTA TTT TGG TTG CAA TTT CGA CGA
glu gly arg)val leu ser pro ala asp lys thr asn val lys ala ala
Factor X sequence /Xhol TGG GGT AAA GTT GGC GCG CAC GCT GGT GAA TAC ATG AAA GCT GAA CTC
ACC CCA TTT CAA CCG CGC GTG CGA CCA CTT ATG TTT CGA CTT GAG
trp gly lys val gly ala his ala gly glu tyr met lys ala glu leu GAG CGT ATG TTC CTG TCT TTC CCG ACC GGC TAC ACC TGG TAC ATG CAC
CTC GCA TAC AAG GAC AGA AAG GGC TGG CCG ATG TGG ACC ATG TAC GTG
glu arg met phe leu ser phe pro thr lys tyr phe pro his /Mstl TTC GAC CTG TCT CAC GCT TCT GCG CAG GTT CAA GGT CAC GTG AAA AAA
AAG CTG GAC AGA GTG CGA AGA CGC GTC CAA CCA GTG CAC TTT TTT
phe asp leu ser his ala ser ala gln val lys gly his gly lys lys GTT GCT GAT GCT CTG GAC TGG TTG CGA GAT CTA CAT GAT CTA CGA GAT ATG CCG
CAA CGA CTA CGA GAC CTG ACC AAC GCT GTT CAA CGA GTA CTA TAC GGC
val ala asp ala leu asp trp leu thr asn ala val ala his val asp asp met pro

FIG. 5b

```
     /MluI
AAC GCG TTG TCT GCT CTG TCT GAT CTG CAC GCT CAC AAA CTG CGT GTT
TTG CGC AAC AGA CGA GAC AGA CTA GAC GTG CGA GTG TTT GAC GCA CAA
asp ala leu ser ala leu ser asp leu his ala his lys leu arg val /HpaI
GAT CCG GTT AAC TTC AAA CTG CTG TCT CAC TGC CTG CTG GTT ACT CTG
CTA GGC CAA TTG AAG TTT GAC GAC AGA GTG ACG GAC GAC CAA TGA GAC
asp pro val asn phe lys leu leu ser his cys leu leu val thr leu /NaeI
GCT GCT CAT CTG CCG GCT GAA TTT ACC CCG GCT GTT CAT GCG TCT CTG
CGA CGA GTA GAC GGC CGA CTT AAA TGG GGC CGA CAA GTA CGC AGA GAC
ala ala his leu pro ala glu phe thr pro ala val his ala ser leu GAT AAA TTC CTG GCT TCT GTT TCT ACC GTT CTG ACT TCG AAA TAC CGT
CTA TTT AAG GAC CGA AGA CAA AGA TGG CAA GAC TGA AGC TTT ATG GCA
asp lys phe leu ala ser val ser thr val leu thr ser lys tyr arg /PstI                              SD#1
TTA TGA   C TGC AGC TAC ATG GAG ATT AAC TCA ATC TAG AGG GTA TTA
ATT ACT   G ACG TCG ATG TAC CTC TAA TTG AGT TAG ATC TCC CAT AAT SD#2
ATA ATG TAT CGC TTA AAT AAG GAG GAA TAA CAT ATG ATC GAA GGT CGT
TAT TAC ATA GCG AAT TTA TTC CTC CTT ATT GTA TAC TAG CTT CCA GCA
                         SEQ ID NO:92  met(ile glu gly arg)
                                        Factor X sequence /SacII
GTT CAC CTG ACT CCG GAA GAA AAA TCC GCG GTT ACT GCT CTG TGG GGT
CAA GTG GAC TGA GGC CTT CTT TTT AGG CGC CAA TGA CGA GAC ACC CCA
val his leu thr pro glu glu lys ser ala val thr ala leu trp gly AAA GTG AAC GTT GAC GAA GTT GGT GGT GAA GCT CTG GGA CGT CTG CTG
TTT CAC TTG CAA CTG CTT CAA CCA CCA CTT CGA GAC CCT GCA GAC GAC
lys val asn val asp glu val gly gly glu ala leu gly arg leu leu /BglII
GTT GTT TAC CCG TGG ACT CAG CGT TTC TTT GAA TCT TTC GGA GAT CTG
CAA CAA ATG GGC ACC TGA GTC GCA AAG AAA CTT AGA AAG CCT CTA GAC
val val tyr pro trp thr gln arg phe phe glu ser phe gly asp leu TCT ACC CCG GAC GCT GTT ATG GGT AAC CCG AAA GTT AAA GCC CAT GGT
AGA TGG GGC CTG CGA CAA TAC CCA TTG GGC TTT CAA TTT CGG GTA CCA
ser thr pro asp ala val met gly asn pro lys val lys ala his gly AAA AAA GTT CTG GGT GCT TTC TCT GAC GGT CTG GCT CAC CTG GAC AAC
TTT TTT CAA GAC CCA CGA AAG AGA CTG CCA GAC CGA GTG GAC CTG TTG
lys lys val leu gly ala phe ser asp gly leu ala his leu asp asn
```

FIG. 5c

```
              /KpnI                              /SacI
CTG AAA GGT ACC TTC GCT ACT CTG TCT GAG CTC CAC TGC GAC AAA CTG
GAC TTT CCA TGG AAG CGA TGA GAC AGA CTC GAG GTG ACG CTG TTT GAC
leu lys gly thr phe ala thr leu ser glu leu his cys asp lys leu /SpeI
CAC GTT GAC CCG GAA AAC TTC CGT CTG CTG GGT AAC GTA CTA GTT TGC
GTG CAA CTG GGC CTT TTG AAG GCA GAC GAC CCA TTG CAT GAT CAA ACG
his val asp pro glu asn phe arg leu leu gly asn val leu val cys /EcoRI
GTT CTG GCT CAC CAC TTC GGT AAA GAA TTC ACT CCG CCG GTT CAG GCT
CAA GAC CGA GTG GTG AAG CCA TTT CTT AAG TGA GGC GGC CAA GTC CGA
val leu ala his his phe gly lys glu phe thr pro pro val gln ala GCT TAC CAG AAA GTT GTT GCT GGT GTT GCT AAC GCG CTA GCT CAC AAA
CGA ATG GTC TTT CAA CAA CGA CCA CAA CGA TTG CGC GAT CGA GTG TTT
ala tyr gln lys val val ala gly val ala asn ala leu ala his lys /HindIII
TAC CAC TAA TGA
ATG CTG ATT ACT TCG A
tyr his
```

FIG. 7

Hemoglobin Beth Israel (beta asn -> ser):

```
                                    /SacI
         SEQ ID NO:93     C CAC TGC GAC AAA CTG
                         TC GAG GTG ACG CTG TTT GAC
         SEQ ID NO:94      leu his cys asp lys leu
                                                /SpeI
CAC GTT GAC CCG GAA tct TTC CGT CTG CTG GGT AAC GTA
CTG CAA CTG GGC CTT aga AAG GCA GAC GAC CCA TTG CAT GAT C
his val asp pro glu SER phe arg leu leu gly asn val leu
```

Hemoglobin Cheverly (beta phe -> ser):

```
                                    /SerII
         SEQ ID NO:95     CG GTT ACT GCT CTG TGG GGT
                        G CGC CAA TGA CGA GAC ACC CCA
         SEQ ID NO:96      ala val thr ala leu trp gly AAA GTG AAC GTT GAC GAA GTT GGT GGT GAA GCT CTG GGA CGT CTG CTG
TTT CAC TTG CAA CTG CTT CAA CCA CCA CTT CGA GAC CCT GCA GAC GAC
lys val asn val asp glu val gly gly glu ala leu gly arg leu leu
                                                /BglII
GTT GTT TAC CCG TGG ACT CAG CGT TTC TTT GAA TCT tct GGA
CAA CAA ATG GGC ACC TGA GTC GCA AAG AAA CTT AGA aga CCT CTA G
val val tyr pro trp thr gln arg phe phe glu ser SER gly asp
```

Hemoglobin beta val -> ile:

```
                                            /NcoI  G
                           SEQ ID NO:97  CAT G/T
                                              CA
                           SEQ ID NO:98      gly
AAA AAA atc CTG GGT GCT TTC TCT GAC GGT CTG GCT CAC CTG GAC AAC
TTT TTT tag GAC CCA CGA AAG AGA CTG CCA GAC CGA GTG GAC CTG TTG
lys lys ile leu gly ala phe ser asp gly leu ala his leu asp asn
          /KpnI
CTG AAA GGT AC
GAC TTT C
leu lys gly
```

Hemoglobin Kansas (beta asn -> thr):

```
                                    /SacI
         SEQ ID NO:99     C CAC TGC GAC AAA CTG
                         TC GAG GTG ACG CTG TTT GAC
         SEQ ID NO:0100    glu leu his cys asp lys leu
                                                /SpeI
GAC GTT GAC CCG GAA acc TTC CGT CTG CTG CTG GGT AAC GTA
GTG CAA CTG GGC CTT tgg AAG GCA GAC GAC GAC CCA TTG CAT GAT C
his val asp pro glu asn phe arg leu leu gly asn val leu val
```

FIG. 8 des-FX Alpha

```
/NdeI                    /EagI
 T  ATG GTT CTG TCT CC           SEQ ID NO:101
    AC  CAA GAC AGA GGC CGG
        met val leu ser pro ala  SEQ ID NO:102
``` des-FX Beta

SEQ ID NO:103

```
 /NdeI                                                /SacII
 T  ATG GTT CAC CTG ACT CCG GAA GAA AAA TCC GC
    AC  CAA GTG GAC TGA GGC CTT CTT TTT AGG
        met val his leu thr pro glu glu lys ser ala
```
SEQ ID NO:104 des-val Alpha

```
/NdeI                /EagI
 T  ATG CTG TCT CC           SEQ ID NO:105
    AC  GAC AGA GGC CGG
        met leu ser pro ala  SEQ ID NO:106
``` des-val Beta

```
/NdeI                                            /SacII
 T  ATG CAC CTG ACT CCG GAA GAA AAA TCC GC   SEQ ID NO:107
    AC  GTG GAC TGA GGC CTT CTT TTT AGG
        met his leu thr pro glu glu lys ser ala  SEQ ID NO:108
```

FIG. 12a

```
                            /EcoRI                    /Xmal                          A
          SEQ ID NO:109  A ATT CGA GCT CGG TAC CCG GGC TAC ATG GAG
                           GCT CGA GCC ATG GGC CCG ATG TAC CTC SD # 1                                    SD # 2
  ATT AAC TCA ATC TAG AGG GTA TTA ATA ATG TAT CGC TTA AAT AAG GAG
  TAA TTG AGT TAG ATC TCC CAT AAT TAT TAC ATA GCG AAT TTA TTC CTC
                       SEQ ID NO:110 Met Tyr Arg Leu Asn Lys Glu /NdeI                           /EagI
   GAA TAA CAT ATG CTG TCT CCG GCC GAT AAA ACC AAC GTT AAA GCT GCT
   CTT ATT GTA TAC GAC AGA GGC CGG CTA TTT TGG TTG CAA TTT CGA CGA
   Glu        Met Leu Ser Pro Ala Asp Lys Thr Asn Val Lys Ala Ala
SEQ ID NO:111
                                                                /XhoI
   TGG GGT AAA GTT GGC GCG CAC GCT GGT GAA TAC GGT GCT GAA GCT CTC
   ACC CCA TTT CAA CCG CGC GTG CGA CCA CTT ATG CCA CGA CTT CGA GAG
   Trp Gly Lys Val Gly Ala His Ala Gly Glu Tyr Gly Ala Glu Ala Leu GAG CGT ATG TTC CTG TCT TTC CCG ACC ACC AAA ACC TAC TTC CCG CAC
   CTC GCA TAC AAG GAC AGA AAG GGC TGG TGG TTT TGG ATG AAG GGC GTG
   Glu Arg Met Phe Leu Ser Phe Pro Thr Thr Lys Thr Tyr Phe Pro His
                                 /MstI
   TTC GAC CTG TCT CAC GGT TCT GCG CAG GTT AAA GGT CAC GGT AAA AAA
   AAG CTG GAC AGA GTG CCA AGA CGC GTC CAA TTT CCA GTG CCA TTT TTT
   Phe Asp Leu Ser His Gly Ser Ala Gln Val Lys Gly His Gly Lys Lys GTT GCT GAT GCT CTG ACC AAC GCT GTT GCT CAC GTT GAT GAT ATG CCG
   CAA CGA CTA CGA GAC TGG TTG CGA CAA CGA GTG CAA CTA CTA TAC GGC
   Val Ala Asp Ala Leu Thr Asn Ala Val Ala His Val Asp Asp Met Pro
       /MluI
   AAC GCG TTG TCT GCT CTG TCT GAT CTG CAC GCT CAC AAA CTG CGT GTT
   TTG CGC AAC AGA CGA GAC AGA CTA GAC GTG CGA GTG TTT GAC GCA CAA
   Asn Ala Leu Ser Ala Leu Ser Asp Leu His Ala His Lys Leu Arg Val
         /HpaI
   GAT CCG GTT AAC TTC AAA CTG CTG TCT CAC TGC CTG CTG GTT ACT CTG
   CTA GGC CAA TTG AAG TTT GAC GAC AGA GTG ACG GAC GAC CAA TGA GAC
   Asp Pro Val Asn Phe Lys Leu Leu Ser His Cys Leu Leu Val Thr Leu
                    /NaeI
   GCT GCT CAT CTG CCG GCT GAA TTT ACC CCG GCT GTT CAT GCG TCT CTG
   CGA CGA GTA GAC GGC CGA CTT AAA TGG GGC CGA CAA GTA CGC AGA GAC
   Ala Ala His Leu Pro Ala Glu Phe Thr Pro Ala Val His Ala Ser Leu
                                                         /BstBI
   GAT AAA TTC CTG GCT TCT GTT TCT ACC GTT CTG ACT TCG AAA TAC CGT
   CTA TTT AAG GAC CGA AGA CAA AGA TGG CAA GAC TGA AGC TTT ATG GCA
   Asp Lys Phe Leu Ala Ser Val Ser Thr Val Leu Thr Ser Lys Tyr Arg
```

FIG. 12b

```
                                    /EagI
GGT GGT GTT CTG TCT CCG GCC GAT AAA ACC AAC GTT AAA GCT GCT
CCA CCA CAA GAC AGA GGC CGG CTA TTT TGG TTG CAA TTT CGA CGA
Gly Gly Val Leu Ser Pro Ala Asp Lys Thr Asn Val Lys Ala Ala
linker
                                                            /XhoI
TGG GGT AAA GTT GGC GCG CAC GCT GGT GAA TAC GGT GCT GAA GCT CTC
ACC CCA TTT CAA CCG CGC GTG CGA CCA CTT ATG CCA CGA CTT CGA GAG
Trp Gly Lys Val Gly Ala His Ala Gly Glu Tyr Gly Ala Glu Ala Leu GAG CGT ATG TTC CTG TCT TTC CCG ACC ACC AAA ACC TAC TTC CCG CAC
CTC GCA TAC AAG GAC AGA AAG GGC TGG TGG TTT TGG ATG AAG GGC GTG
Glu Arg Met Phe Leu Ser Phe Pro Thr Thr Lys Thr Tyr Phe Pro His
                            /MstI
TTC GAC CTG TCT CAC GGT TCT GCG CAG GTT AAA GGT CAC GGT AAA AAA
AAG CTG GAC AGA GTG CCA AGA CGC GTC CAA TTT CCA GTG CCA TTT TTT
Phe Asp Leu Ser His Gly Ser Ala Gln Val Lys Gly His Gly Lys Lys GTT GCT GAT GCT CTG ACC AAC GCT GTT GCT CAC GTT GAT GAT ATG CCG
CAA CGA CTA CGA GAC TGG TTG CGA CAA CGA GTG CAA CTA CTA TAC GGC
Val Ala Asp Ala Leu Thr Asn Ala Val Ala His Val Asp Asp Met Pro
/MluI
AAC GCG TTG TCT GCT CTG TCT GAT CTG CAC GCT CAC AAA CTG CGT GTT
TTG CGC AAC AGA CGA GAC AGA CTA GAC GTG CGA GTG TTT GAC GCA CAA
Asn Ala Leu Ser Ala Leu Ser Asp Leu His Ala His Lys Leu Arg Val
        /HpaI
GAT CCG GTT AAC TTC AAA CTG CTG TCT CAC TGC CTG CTG GTT ACT CTG
CTA GGC CAA TTG AAG TTT GAC GAC AGA GTG ACG GAC GAC CAA TGA GAC
Asp Pro Val Asn Phe Lys Leu Leu Ser His Cys Leu Leu Val Thr Leu
            /NaeI
GCT GCT CAT CTG CCG GCT GAA TTT ACC CCG GCT GTT CAT GCG TCT CTG
CGA CGA GTA GAC GGC CGA CTT AAA TGG GGC CGA CAA GTA CGC AGA GAC
Ala Ala His Leu Pro Ala Glu Phe Thr Pro Ala Val His Ala Ser Leu
                                                /BstBI
GAT AAA TTC CTG GCT TCT GTT TCT ACC GTT CTG ACT TCG AAA TAC CGT
CTA TTT AAG GAC CGA AGA CAA AGA TGG CAA GAC TGA AGC TTT ATG GCA
Asp Lys Phe Leu Ala Ser Val Ser Thr Val Leu Thr Ser Lys Tyr Arg
        /PstI                                                   B
TAA TGA    C TGC A                    GC TAC ATG GAG ATT AAC TCA
ATT ACT    G                          ACG TCG ATG TAC CTC TAA TTG AGT
    SD # 1                                    SD # 2      /NdeI
ATC TAG AGG GTA TTA ATA ATG TAT CGC TTA AAT AAG GAG GAA TAA CAT
TAG ATC TCC CAT AAT TAT TAC ATA GCG AAT TTA TTC CTC CTT ATT GTA
        SEQ ID NO:112  Met Tyr Arg Leu Asn Lys Glu Glu
```

FIG. 12c

```
                                                        /SacII
     ATG CAC CTG ACT CCG GAA GAA AAA TCC GCG GTT ACT GCT CTG TGG GGT
     TAC GTG GAC TGA GGC CTT CTT TTT AGG CGC CAA TGA CGA GAC ACC CCA
     Met His Leu Thr Pro Glu Glu Lys Ser Ala Val Thr Ala Leu Trp Gly
     SEQ ID NO:113

AAA GTG AAC GTT GAC GAA GTT GGT GGT GAA GCT CTG GGA CGT CTG CTG
     TTT CAC TTG CAA CTG CTT CAA CCA CCA CTT CGA GAC CCT GCA GAC GAC
     Lys Val Asn Val Asp Glu Val Gly Gly Glu Ala Leu Gly Arg Leu Leu

/BglII
     GTT GTT TAC CCG TGG ACT CAG CGT TTC TTT GAA TCT TTC GGA GAT CTG
     CAA CAA ATG GGC ACC TGA GTC GCA AAG AAA CTT AGA AAG CCT CTA GAC
     Val Val Tyr Pro Trp Thr Gln Arg Phe Phe Glu Ser Phe Gly Asp Leu

/NcoI
     TCT ACC CCG GAC GCT GTT ATG GGT AAC CCG AAA GTT AAA GCC CAT GGT
     AGA TGG GGC CTG CGA CAA TAC CCA TTG GGC TTT CAA TTT CGG GTA CCA
     Ser Thr Pro Asp Ala Val Met Gly Asn Pro Lys Val Lys Ala His Gly

AAA AAA GTT CTG GGT GCT TTC TCT GAC GGT CTG GCT CAC CTG GAC AAC
     TTT TTT CAA GAC CCA CGA AAG AGA CTG CCA GAC CGA GTG GAC CTG TTG
     Lys Lys Val Leu Gly Ala Phe Ser Asp Gly Leu Ala His Leu Asp Asn

/KpnI                        /SacI
     CTG AAA GGT ACC TTC GCT ACT CTG TCT GAG CTC CAC TGC GAC AAA CTG
     GAC TTT CCA TGG AAG CGA TGA GAC AGA CTC GAG GTG ACG CTG TTT GAC
     Leu Lys Gly Thr Phe Ala Thr Leu Ser Glu Leu His Cys Asp Lys Leu

/SpeI
     CAC GTT GAC CCG GAA AAC TTC CGT CTG CTG GGT AAC GTA CTA GTT TGC
     GTG CAA CTG GGC CTT TTG AAG GCA GAC GAC CCA TTG CAT GAT CAA ACG
     His Val Asp Pro Glu Asn Phe Arg Leu Leu Gly Asn Val Leu Val Cys

/EcoRI
     GTT CTG GCT CAC CAC TTC GGT AAA GAA TTC ACT CCG CCG GTT CAG GCT
     CAA GAC CGA GTG GTG AAG CCA TTT CTT AAG TGA GGC GGC CAA GTC CGA
     Val Leu Ala His His Phe Gly Lys Glu Phe Thr Pro Pro Val Gln Ala

GCT TAC CAG AAA GTT GTT GCT GGT GTT GCT AAC GCG CTA GCT CAC AAA
     CGA ATG GTC TTT CAA CAA CGA CCA CAA CGA TTG CGC GAT CGA GTG TTT
     Ala Tyr Gln Lys Val Val Ala Gly Val Ala Asn Ala Leu Ala His Lys

/HindIII
     TAC CAC TAA TGA
     ATG GTG ATT ACT TCG A
     Tyr His
```

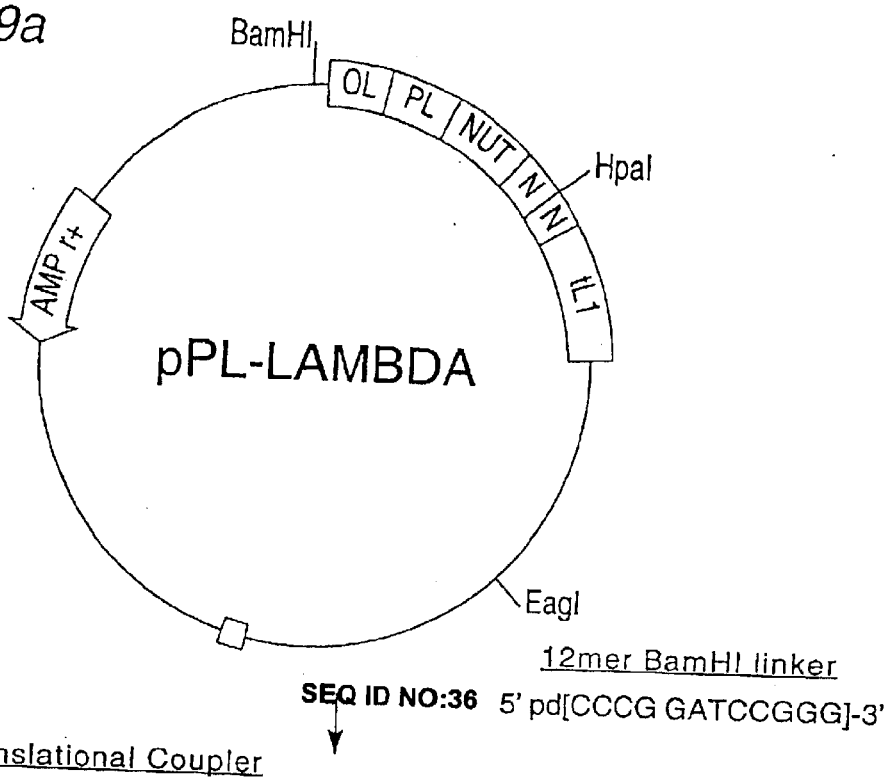
Fig. 19a
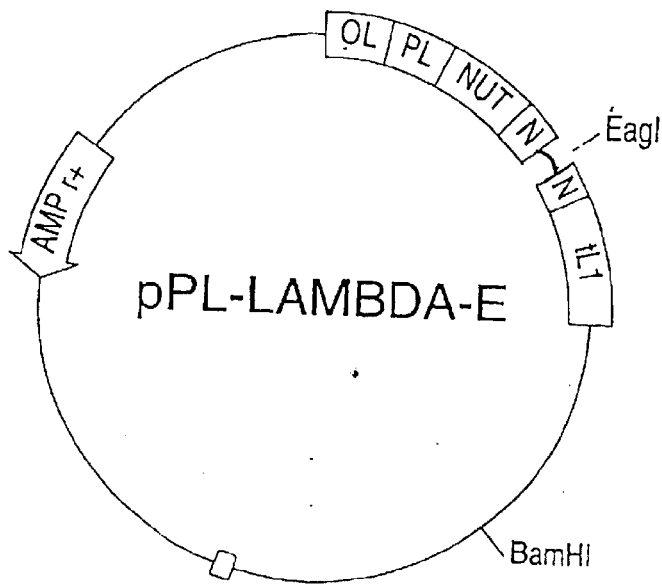
Translational Coupler
SEQ ID NO:34  5' AAT AAG GAG GAA TAA CAT ATG CTG TCT CCG GCC GAT
3' TTA TTC CTC CTT ATT GTA TAC GAC AGA GGC CGG CTA
AAG GCC CCA AGC TTG GGG 3'
TTC CGG GGT TCG AAC CCC 5'

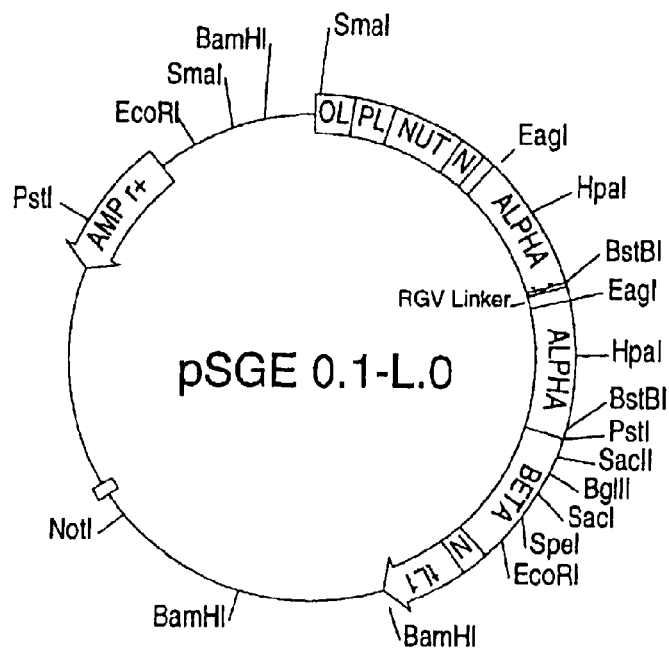
Fig. 19c
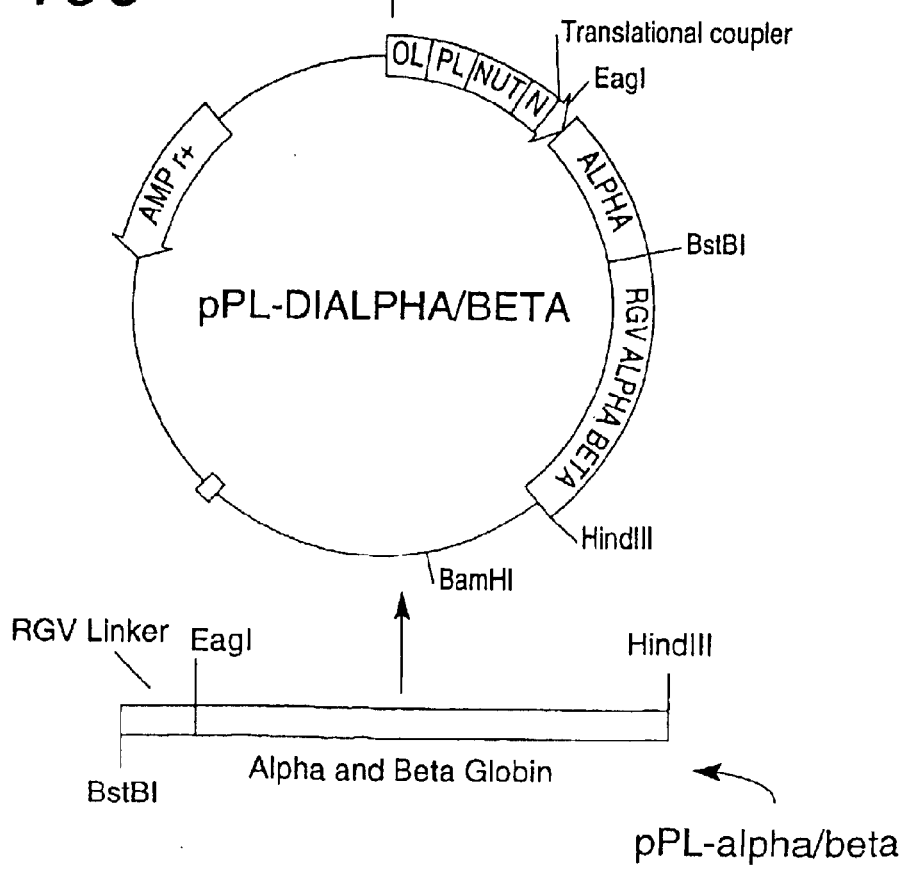

FIG. 20a

From 1 to 451. Numbered from position 1.

```
                                                              →Cfr101
       →Nsp(7524)1                                                ↓
          →Sph1                                                  80
            →NspH1
SEQ ID NO:114  10        20        30        40        50        60        70
   ↓  GCATGCGTAC GGATTAGAAG CCGCCGAGCG GGTGACAGCC CTCCGAAGGA AGACTCTCCT CCGTGCGTCC TCGTCTTCAC
              90        100       110       120       130       140       150       160
      CGGTCGCGTT CCTGAAACGC AGATGTGCCT CGGCGCCGAC TGCTCCGAAC AATAAAGATT CTACAATACT AGCTTTTATG
                                                                                    →EcoR5
                                                                                     ↑↓
             170       180       190       200       210       220       230       240
      GTTATGAAGA GGAAAAATTG CAGTAACCTG GCCCCACAAA CCTCAAATGA ACGAATCAAA TTAACAACCA GATATCTGA
                Dra1      →Xmn1
                 ↑↓        ↑↓
             Aha3
             250       260       270       280       290       300       310       320
      CTGAAAAAAA AGGTTTAAAC CAGTTCCCTG AAATTATTCC CCTACTTGAC TAATAAGTAT ATAAAGACGG TAGGTATTGA
```

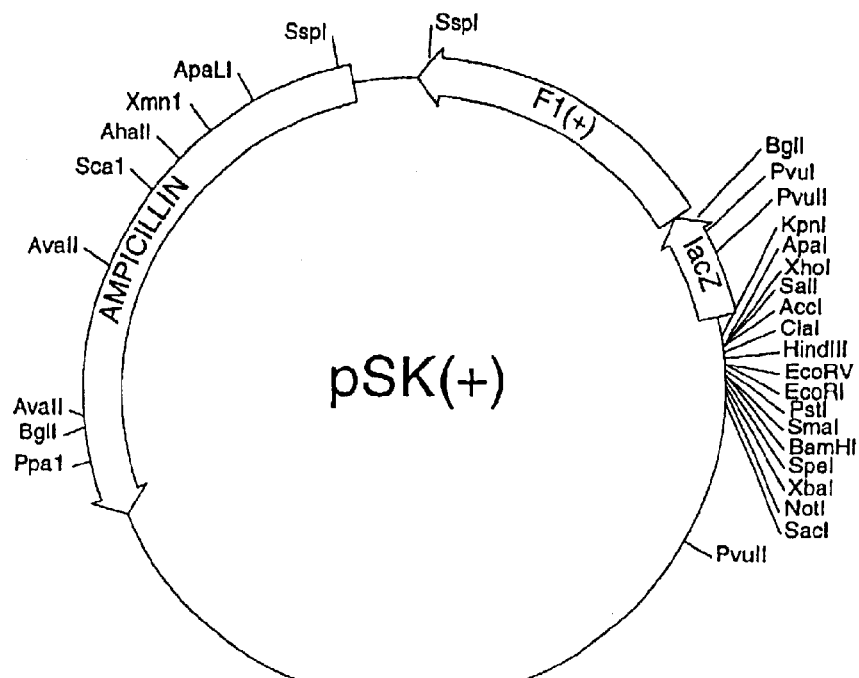
*Fig. 21a-1*
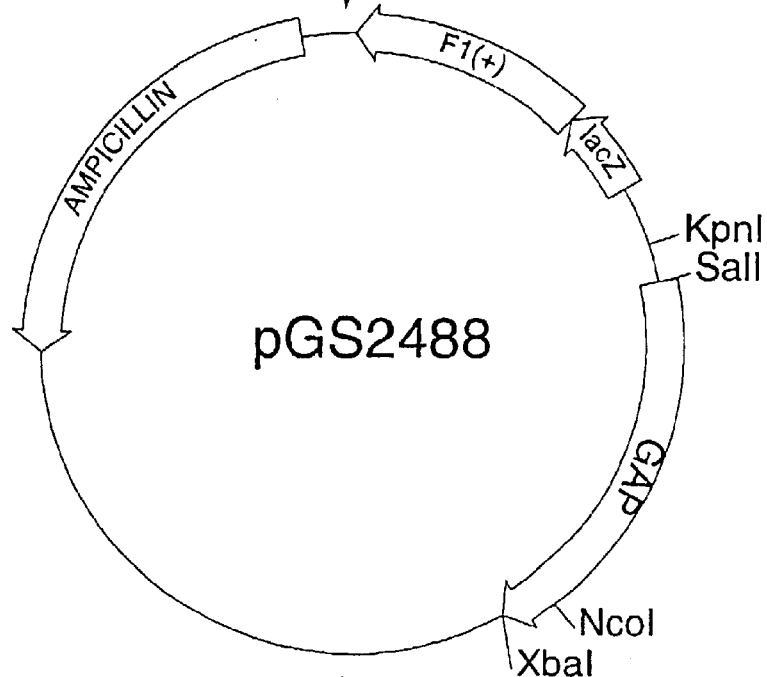

pGS1188 pC1U digested with BamHI and SalI + BglII-SalI fragment from YRp7 containing the TRPI gene.

pGS2989

4-HELIX BUNDLE

SEQUENCE LISTING

<160> NUMBER OF SEQ ID NOS: 114

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence:
      Hypothetical alpha-helical coiled coil

<400> SEQUENCE: 1

Lys Cys Ala Glu Leu Glu Gly Arg Leu Glu Ala Leu Glu Gly Arg Leu
 1               5                  10                  15

Glu Ala Leu Glu Gly Arg Leu Glu Ala Leu Glu Gly Arg Leu Glu Ala
            20                  25                  30

Leu Glu Gly Lys Leu
         35

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: 4-helical
      bundle crosslinker

<400> SEQUENCE: 2

Gly Glu Leu Glu Glu Leu Leu Lys Lys Leu Lys Glu Leu Leu Lys Gly
 1               5                  10                  15

<210> SEQ ID NO 3
<211> LENGTH: 14
<212> TYPE: PRT
<213> ORGANISM: Artificial Sequence
<220> FEATURE:
<221> NAME/KEY: VARIANT
<222> LOCATION: (1)
<223> OTHER INFORMATION: (G)n; n>or=0 wherein n is the number of G
      residues; an indeterminable number of Glycine
      residues exist
<223> OTHER INFORMATION: Description of Artificial Sequence: Artemia
      linker
<221> NAME/KEY: VARIANT
<222> LOCATION: (14)
<223> OTHER INFORMATION: (G)n; n>or=0 wherein n is the number of G
      residues; an indeterminable number of Glycine
      residues exist

<400> SEQUENCE: 3

Gly Leu Pro Arg Gln Ile Asp Leu Glu Val Thr Gly Leu Gly
 1               5                  10

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Helical
      coiled coil
<221> NAME/KEY: VARIANT
<222> LOCATION: (1)
<223> OTHER INFORMATION: (G)n; n>or=0 wherein n is the number of G
      residues; an indeterminable number of Glycine
      residues exist

<400> SEQUENCE: 4

Gly Lys Cys Ala Glu Leu Gly Lys Leu Glu Ala Leu Gly Lys Leu Glu

```
              1               5              10              15
Ala Leu Gly Lys Leu Glu Ala Leu Gly Lys Leu Glu Ala Leu Gly
             20              25              30
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Mutagenic
      Oligonucleotides: alpha S81C

<400> SEQUENCE: 5
ccgaacgcgt tgtgcgctct gtctgat                                       27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Mutagenic
      Oligonucleotides: alpha D75C

<400> SEQUENCE: 6
ggtgctcacg ttgattgcat gccgaacgcg                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Mutagenic
      Oligonucleotides: alpha A71C

<400> SEQUENCE: 7
ctgaccaacg ctgtttgcca cgttgatgat                                    30

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Hybird
      fusion protein: CII FxB-globin

<400> SEQUENCE: 8

```
Ile Glu Gly Arg Val His Leu Thr
  1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Hybird
      fusion protein: Hu prothrombin

<400> SEQUENCE: 9

```
Ile Leu Glu Gly Arg Thr Ala Thr Ser
  1               5
```

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Hybird -continued

```
      fusion protein: Bo prothrombin

<400> SEQUENCE: 10

Ile Glu Gly Arg Thr Ser Glu Asp
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Hybird
      fusion protein: Hu prothrombin

<400> SEQUENCE: 11

Ile Asp Gly Arg Ile Val Glu Gly
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Hybird
      fusion protein: Bo prothrombin

<400> SEQUENCE: 12

Ile Glu Gly Arg Ile Val Glu Gly
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Hybird
      fusion protein: Hu antithrombin III

<400> SEQUENCE: 13

Ala Glu Gly Arg Asp Asp Leu Thr
 1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Peptide:
      Factor Xa recognition sequence

<400> SEQUENCE: 14

Ile Glu Gly Arg
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: peptide:
      first 4 bases of human beta globin

<400> SEQUENCE: 15

Val His Leu Thr
 1

<210> SEQ ID NO 16
```

```
<211> LENGTH: 5
<212> TYPE: PRT
<213> ORGANISM: Artificial Sequence
<220> FEATURE:
<223> OTHER INFORMATION: Description of Artificial Sequence:
      Oligopeptide sequence preceding native globin (alpha or beta)
      to produce FX-beta and FX-alpha globins

<400> SEQUENCE: 16

Met Ile Glu Gly Arg
 1               5

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: spacer
      region

<400> SEQUENCE: 17 aggagg                                                              6

<210> SEQ ID NO 18
<211> LENGTH: 9
<212> TYPE: RNA
<213> ORGANISM: Artificial Sequence
<220> FEATURE:
<223> OTHER INFORMATION: Description of Artificial Sequence: spacer
      region
<221> NAME/KEY: variation
<222> LOCATION: (3)
<223> OTHER INFORMATION: n= a or g

<400> SEQUENCE: 18 ccnccaugg                                                           9

<210> SEQ ID NO 19
<211> LENGTH: 8
<212> TYPE: RNA
<213> ORGANISM: Artificial Sequence
<220> FEATURE:
<223> OTHER INFORMATION: Description of Artificial Sequence: spacer
      region

<400> SEQUENCE: 19 aaaaaugu                                                            8

<210> SEQ ID NO 20
<211> LENGTH: 216
<212> TYPE: PRT
<213> ORGANISM: Artificial Sequence
<220> FEATURE:
<221> NAME/KEY: STRAND
<222> LOCATION: (1)..(14)
<223> OTHER INFORMATION: alpha chain, amino acid residues 1-14
<221> NAME/KEY: STRAND
<222> LOCATION: (18)..(163)
<223> OTHER INFORMATION: Beta chain, chain amino acid residues
<221> NAME/KEY: VARIANT
<222> LOCATION: (164)..(166)
<223> OTHER INFORMATION: gly (1-3)repetitions
<221> NAME/KEY: VARIANT
<222> LOCATION: (180)..(182)
<223> OTHER INFORMATION: gly (1-3)repetitions
<221> NAME/KEY: STRAND
<222> LOCATION: (183)..(216)
<223> OTHER INFORMATION: Beta chain amino acid residues 1-34
<223> OTHER INFORMATION: Description of Artificial Sequence: Linker
      sequencing for fusing alpha 1 and beta 2
```

-continued

```
<400> SEQUENCE: 20

Xaa Xaa Xaa Xaa Xaa Xaa Xaa Xaa Xaa Xaa Xaa Xaa Xaa Gly Gly
 1               5                  10                  15

Gly Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
         100                 105                 110

Xaa Xaa Xaa Xaa Xaa Xaa Xaa Xaa Xaa Xaa Xaa Xaa Xaa Xaa Xaa
     115                 120                 125

Xaa Xaa Xaa Xaa Xaa Xaa Xaa Xaa Xaa Xaa Xaa Xaa Xaa Xaa Xaa
 130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Gly Gly Gly Ala Ala Ala Ala Ala Ala Ala Ala Ala
             165                 170                 175

Ala Ala Ala Gly Gly Gly Xaa Xaa Xaa Xaa Xaa Xaa Xaa Xaa Xaa
         180                 185                 190

Xaa Xaa Xaa Xaa Xaa Xaa Xaa Xaa Xaa Xaa Xaa Xaa Xaa Xaa Xaa
     195                 200                 205

Xaa Xaa Xaa Xaa Xaa Xaa Xaa Xaa
 210                 215

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: peptide
      linker

<400> SEQUENCE: 21

Gly Gly Gly Gly Gly Gly Gly
 1               5

<210> SEQ ID NO 22
<211> LENGTH: 18
<212> TYPE: PRT
<213> ORGANISM: Artificial Sequence
<220> FEATURE:
<221> NAME/KEY: VARIANT
<222> LOCATION: (1)..(3)
<223> OTHER INFORMATION: gly (1-3) repetitions
<221> NAME/KEY: HELIX
<222> LOCATION: (4)..(15)
<223> OTHER INFORMATION: alpha helix
<221> NAME/KEY: VARIANT
<222> LOCATION: (16)..(18)
<223> OTHER INFORMATION: gly(1-3) repetitions
<223> OTHER INFORMATION: Description of Artificial Sequence: polyproline
      helix

<400> SEQUENCE: 22

Gly Gly Gly Ala Ala Ala Ala Ala Ala Ala Ala Ala Ala Ala Ala Gly
```

Gly Gly

<210> SEQ ID NO 23
<211> LENGTH: 22
<212> TYPE: PRT
<213> ORGANISM: Artificial Sequence
<220> FEATURE:
<221> NAME/KEY: VARIANT
<222> LOCATION: (1)..(3)
<223> OTHER INFORMATION: gly(1-3)
<221> NAME/KEY: VARIANT
<222> LOCATION: (4)..(19)
<223> OTHER INFORMATION: pro(12-16)
<221> NAME/KEY: VARIANT
<222> LOCATION: (20)..(22)
<223> OTHER INFORMATION: gly(1-3)
<223> OTHER INFORMATION: Description of Artificial Sequence: polyproline
    helix
<221> NAME/KEY: HELIX
<222> LOCATION: (12)..(16)
<223> OTHER INFORMATION: Pro helix

<400> SEQUENCE: 23

Gly Gly Gly Pro Pro Pro Pro Pro Pro Pro Pro Pro Pro Pro Pro
1               5                   10                  15
Pro Pro Pro Gly Gly Gly
            20

<210> SEQ ID NO 24
<211> LENGTH: 7
<212> TYPE: PRT
<213> ORGANISM: Artificial Sequence
<220> FEATURE:
<221> NAME/KEY: VARIANT
<222> LOCATION: (1)..(3)
<223> OTHER INFORMATION: gly(1-3)
<221> NAME/KEY: VARIANT
<222> LOCATION: (4)
<223> OTHER INFORMATION: x> or =1; x=Asp
<221> NAME/KEY: VARIANT
<222> LOCATION: (5)..(7)
<223> OTHER INFORMATION: gly(1-3)
<223> OTHER INFORMATION: Description of Artificial Sequence: peptide
    linker

<400> SEQUENCE: 24

Gly Gly Gly Xaa Gly Gly Gly
1               5

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 25
cgtatgttcc tgtctttt                                                17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 26
acaaactgcg tgttgat                                                 17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 27
gctggttgtt tacccgt                                                    17

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 28
acccggaaaa cttccgtc                                                   18

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: peptide
      linker

<400> SEQUENCE: 29

Met Ile Glu Gly Arg
 1               5

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: 5' Sac I
      primer

<400> SEQUENCE: 30
ccactgtgac aaactgcacg ttgacccgga aaacttccgt ctgctgggta aagta         55

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence: 3' Sac I
      primer

<400> SEQUENCE: 31
tcgaggtgac gctgtttgac gtgcaactgg gccttttgaa ggcagacgac ccatttcatg    60
atc                                                                  63

<210> SEQ ID NO 32
<211> LENGTH: 76
<212> TYPE: DNA
<213> ORGANISM: Artificial Sequence
<220> FEATURE:
<223> OTHER INFORMATION: Description of Artificial Sequence: enzyme
      linker

<400> SEQUENCE: 32
gatcctgcag agctgttgac aattaatcat cggctcgtat aatgtgtgga attgtgagcg    60

```
gataacaatt tcacac                                              76

<210> SEQ ID NO 33
<211> LENGTH: 74
<212> TYPE: DNA
<213> ORGANISM: Artificial Sequence
<220> FEATURE:
<223> OTHER INFORMATION: Description of Artificial Sequence: enzyme
      linker

<400> SEQUENCE: 33
gacgtctcga caactgttaa ttagtagccg agcatattac acacttaaca tcgcctattg    60
ttaaagtgtg gatc                                                     74

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence:
      transitional coupler

<400> SEQUENCE: 34
aataaggagg aataacatat gctgtctccg gccgataagg ccccaagctt gggg          54

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence:
      transitional coupler

<400> SEQUENCE: 35
ttattcctcc ttattgtata cgacagaggc cggctattcc ggggttcgaa c             51

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 36
cccggatccg gg                                                       12

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 37
caatggaaag cagcaaatcc                                               20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 38
acccggaaaa cttccgtc                                                 18
```

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: 5' RGV
      crosslinker

<400> SEQUENCE: 39
cgaaataacg tggtgttctg tctgc                                        25

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: 3' RGV
      crosslinker

<400> SEQUENCE: 40
tttatggcac cacaagacag acgccgg                                      27

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 41
ttgcggccgc aa                                                      12

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: adaptor

<400> SEQUENCE: 42
ctagaaccat gg                                                      12

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence: adaptor

<400> SEQUENCE: 43
tgcaccatgg tt                                                      12

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 44
gaattccatg gtgctgtctc ctgccgacaa gacc                              34

<210> SEQ ID NO 45
<211> LENGTH: 41

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 45
ctgcagtcga cttaacggta tttggaggtc agcacggtgc t              41

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide employed for site directed
      mutagenesis to generate a Presbyterian mutation

<400> SEQUENCE: 46
aggctcctgg gcaaggtgct ggtctgt                              27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide employed for site directed
      mutagenesis to generate an Ag enogi mutation

<400> SEQUENCE: 47
gccacactga gtaagctgca ctgtgac                              27

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide employed for site directed
      mutagenesis to generate a BV67I mutation

<400> SEQUENCE: 48
catggcaaga aaatccgtgc cttt                                 24

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide employed for site directed
      mutagenesis to generate a Kansas mutation

<400> SEQUENCE: 49
gtggatcctg agactttcag gctcctg                              27

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: adaptor

<400> SEQUENCE: 50
aactagtaag tacagacctg ttttgtctcc tgca                      34
```

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: adaptor

<400> SEQUENCE: 51
ggagacaaaa caggtctgta cttactagtt           30

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: adaptor

<400> SEQUENCE: 52
aactagtaag tacagaggtg ttttgtctcc tgca           34

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: adaptor

<400> SEQUENCE: 53
ggagacaaaa cacctctgta cttactagtt           30

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 54
aagcttcagc accgtattca           20

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:
    x1(Arg)-Gly-Met(Leu)x2 linker

<400> SEQUENCE: 55
cgaaataccg tggtatgctg tctcc           25

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:
    x1(Arg)-Gly-Met(Leu)x2 linker

<400> SEQUENCE: 56
ggccggagac agcataccac ggtattt           27

<210> SEQ ID NO 57
<211> LENGTH: 28
<212> TYPE: DNA
<213> ORGANISM: Artificial Sequence
<220> FEATURE:

```
<223> OTHER INFORMATION: Description of Artificial Sequence:
      x1(Arg)-Gly-Gly-(Val)x2 Linker

<400> SEQUENCE: 57
cgaaataccg tggtggtgtt ctgtctcc                                    28

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence:
      x1(Arg)-Gly-Gly-(Val)x2 Linker

<400> SEQUENCE: 58
ggccggagac agaacaccac cacggtattt                                  30

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence:
      x1(Arg)-Gly-(Val)x2 Linker

<400> SEQUENCE: 59
cgaaataccg tggtgttctg tctcc                                       25

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence:
      x1(Arg)-Gly-(Val)x2 Linker

<400> SEQUENCE: 60
ggccggagac agaacaccac ggtattt                                     27

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence:
      x1(Arg)-Gly-Gly-(Leu)x2

<400> SEQUENCE: 61
cgaaataccg tggtggtctg tctcc                                       25

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence:
      x1(Arg)-Gly-Gly-(Leu)x2

<400> SEQUENCE: 62
ggccggagac agaccaccac ggtattt                                     27

<210> SEQ ID NO 63
<211> LENGTH: 46
<212> TYPE: DNA
<213> ORGANISM: Artificial Sequence
<220> FEATURE:
<223> OTHER INFORMATION: Description of Artificial Sequence:
```

-continued

```
      x1(Arg)-(Val)x2

<400> SEQUENCE: 63
cgaaataccg tgttctgtct cctttatggc acaagacaga ggccgg          46

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:
      x1(Arg)-(Val)x2

<400> SEQUENCE: 64
ggccggagac agaacacggt attt                                  24

<210> SEQ ID NO 65
<211> LENGTH: 65
<212> TYPE: DNA
<213> ORGANISM: Artificial Sequence
<220> FEATURE:
<223> OTHER INFORMATION: Description of Artificial Sequence: 5'
      oligonucleotide employed in site directed
      mutagenesis to generate beta globin mutation
      (Val63---> Ile)

<400> SEQUENCE: 65
catggtaaaa aaatcctggg tgctttctct gacggtctgg ctcacctgga caacctgaaa   60
ggtac                                                              65

<210> SEQ ID NO 66
<211> LENGTH: 57
<212> TYPE: DNA
<213> ORGANISM: Artificial Sequence
<220> FEATURE:
<223> OTHER INFORMATION: Description of Artificial Sequence: 3'
      oligonucleotide employed in site directed
      mutagenesis to generate beta globin mutation
      (Val63---> ILE)

<400> SEQUENCE: 66
ctttcaggtt gtccaggtga gccagaccgt cagagaaagc acccaggatt tttttac     57

<210> SEQ ID NO 67
<211> LENGTH: 68
<212> TYPE: DNA
<213> ORGANISM: Artificial Sequence
<220> FEATURE:
<223> OTHER INFORMATION: Description of Artificial Sequence: 5'
      oligonucleotide employed in site directed
      mutatgenesis to generate beta globin mutation
      (Val67--->Ile; Lys82--->Arg)

<400> SEQUENCE: 67
catggtaaaa aaatcctggg tgctttctct gacggtctgg ctcacctgga caacctgcgt   60
ggtaccat                                                           68

<210> SEQ ID NO 68
<211> LENGTH: 56
<212> TYPE: DNA
<213> ORGANISM: Artificial Sequence
<220> FEATURE:
<223> OTHER INFORMATION: Description of Artificial Sequence: 3'
      oligonucleotide employed in site directed
      mutagenesis to generate beta globin mutation
      (Val67--->Ile; Lys82--->Arg)
```

```
<400> SEQUENCE: 68
cacgcagttg tccaggtgac cagaccgtca gagaaaagca cccaggattt ttttac         56

<210> SEQ ID NO 69
<211> LENGTH: 55
<212> TYPE: DNA
<213> ORGANISM: Artificial Sequence
<220> FEATURE:
<223> OTHER INFORMATION: Description of Artificial Sequence: 5'
      oligonucleotide employed in site directed
      mutagenesis to generate beta globin mutation
      (Asn102--->Thr)

<400> SEQUENCE: 69
ccactgcgac aaactgcacg ttgacccgga aaccttccgt ctgctgggta acgta          55

<210> SEQ ID NO 70
<211> LENGTH: 63
<212> TYPE: DNA
<213> ORGANISM: Artificial Sequence
<220> FEATURE:
<223> OTHER INFORMATION: Description of Artificial Sequence: 3'
      oligonucleotide employed in site directed
      mutagenesis to generate beta globin mutation
      (Asn102--->Thr)

<400> SEQUENCE: 70
ctagtacgtt acccagcaga cggaaggttt ccgggtcaac gtgcagtttg tcgcagtgga    60
gct                                                                  63

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 71
tcgactgaaa aaaaggtttt aaaccagttc cctgaaatta ttcccctact tgactaataa    60
gtatataaag                                                           70

<210> SEQ ID NO 72
<211> LENGTH: 77
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 72
caatacctac cgtttatata cttattagtc aagtagggga ataatttcag ggaactggtt    60 taaaccttt ttttcag                                                    77

<210> SEQ ID NO 73
<211> LENGTH: 85
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 73
acggtaggta ttgattgtaa ttctgtaaat ctatttctta aacttcttga attctacttt    60
```
tatagttagt ctttttttta gtttt                                                  85

<210> SEQ ID NO 74
<211> LENGTH: 84
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 74
aagttcttgg tgttttaaaa ctaaaaaaaa gactaactat aaaagtagaa agaagtttaa            60
gaaatagatt tacagaatta caat                                                  84

<210> SEQ ID NO 75
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 75
aaaacaccaa gaacttagtt tcgaataaac acacataaat aaaccatggt taact              55

<210> SEQ ID NO 76
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide used for synthesis of pGAP

<400> SEQUENCE: 76
ctagagttaa ccatggttta tttatgtgtg tttattcgaa act                            43

<210> SEQ ID NO 77
<211> LENGTH: 82
<212> TYPE: DNA
<213> ORGANISM: Artificial Sequence
<220> FEATURE:
<223> OTHER INFORMATION: Description of Artificial Sequence:
      Oligonucleotide used for synthesis of galactose
      upstream activator

<400> SEQUENCE: 77
cgtacggatt agaagccgcc gagcgggtga cagccctccg aaggaagact ctcctccgtg            60
cgtcctcgtc ttcaccggtc gc                                                    82

<210> SEQ ID NO 78
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide used for synthesis of galactose
      upstream activator

<400> SEQUENCE: 78
aggacgcacg gaggagagtc ttccttcgga gggctgtcac ccgctcgggg cttctaatcc            60
gtacgcatg                                                                    69

<210> SEQ ID NO 79
<211> LENGTH: 90
<212> TYPE: DNA

<213> ORGANISM: Artificial Sequence
<220> FEATURE:
<223> OTHER INFORMATION: Description of Artificial Sequence:
       Oligonucleotide used for synthesis of galactose
       upstream activator

<400> SEQUENCE: 79
gttcctgaaa cgcagatgtg cctcgcgccg cactgctccg aacaataaag attctacaat    60
actagctttt atggttatga agaggaaaat    90

<210> SEQ ID NO 80
<211> LENGTH: 93
<212> TYPE: DNA
<213> ORGANISM: Artificial Sequence
<220> FEATURE:
<223> OTHER INFORMATION: Description of Artificial Sequence:
       Oligonucleotide used for syntheis of galactose
       upstream activator

<400> SEQUENCE: 80
ataaccataa aagctagtat tgtagaatct ttattgttcg gagcagtgcg gcgcgaggca    60
catctgcgtt tcaggaacgc gaccggtgaa gac    93

<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence:
       Oligonucleotide used for synthesis of galactose
       upstream activator

<400> SEQUENCE: 81
tggcagtaac ctggccccac aaacctcaaa tgaacgaaat caaattaaca accagatatc    60

<210> SEQ ID NO 82
<211> LENGTH: 75
<212> TYPE: DNA
<213> ORGANISM: Artificial Sequence
<220> FEATURE:
<223> OTHER INFORMATION: Description of Artificial Sequence:
       Oligonucleotide used for synthesis of galactose
       upstream activator

<400> SEQUENCE: 82
tcgagatatc tggttgttaa tttgattcgt tcatttgagg tttgtggggc caggttactg    60
ccaattttcc tcttc    75

<210> SEQ ID NO 83
<211> LENGTH: 95
<212> TYPE: DNA
<213> ORGANISM: Artificial Sequence
<220> FEATURE:
<223> OTHER INFORMATION: Description of Artificial Sequence:
       Oligonucleotide used for construction of a gene
       encoding a tandem alpha globin dimer

<400> SEQUENCE: 83
tgcacgcttc tttggacaag ttcttggctt ctgtttctac tgtgttaact agtaagtaca    60
gaggtggtgt tttgtctcct gcagacaaga ctaac    95

<210> SEQ ID NO 84
<211> LENGTH: 78
<212> TYPE: DNA
<213> ORGANISM: Artificial Sequence
<220> FEATURE:
<223> OTHER INFORMATION: Description of Artificial Sequence:
    Oligonucleotide used for construction of a gene
    encoding a tandem alpha globin dimer

<400> SEQUENCE: 84
gttaaggctg cttggggtaa ggttggtgct cacgctggtg aatacggtgc tgaagctttg     60
gaaaggatgt tcttgtct                                                   78

<210> SEQ ID NO 85
<211> LENGTH: 79
<212> TYPE: DNA
<213> ORGANISM: Artificial Sequence
<220> FEATURE:
<223> OTHER INFORMATION: Description of Artificial Sequence:
    Oligonucleotide used for construction of a gene
    encoding a tandem alpha globin dimer

<400> SEQUENCE: 85
tgcaggagac aaaacaccac ctctgtactt actagttaac acagtagaaa cagaagccaa     60
gaacttgtcc aaagaagcg                                                  79

<210> SEQ ID NO 86
<211> LENGTH: 95
<212> TYPE: DNA
<213> ORGANISM: Artificial Sequence
<220> FEATURE:
<223> OTHER INFORMATION: Description of Artificial Sequence:
    Oligonucleotide used for construction of a gene
    encoding a tandem alpha globin dimer

<400> SEQUENCE: 86
ggaaagacaa gaacatcctt tccaaagctt cagcaccgta ttcacccagc gtgagcacca     60
accttacccc aagcagcctt aacgttagtc ttgtc                                95

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence:
    Oligonucleotide

<400> SEQUENCE: 87 aattcccgg ggatccgtcg acctgcagcc aagctt                                36

<210> SEQ ID NO 88
<211> LENGTH: 1048
<212> TYPE: DNA
<213> ORGANISM: Artificial Sequence
<220> FEATURE:
<223> OTHER INFORMATION: Description of Artificial Sequence:
    Oligonucleotide

<400> SEQUENCE: 88
ccgggctaca tggagattaa ctcaatctag agggtattaa taatgtatcg cttaaataag     60
gaggaataac atatgatcga aggtcgtgtt ctgtctccgg ccgataaaac caacgttaaa    120
gctgcttggg gtaaagttgg cgcgcacgct ggtgaatacg gtgctgaagc tctcgagcgt    180
atgttcctgt ctttcccgac caccaaaacc tacttcccgc acttcgacct gtctcacggt    240
tctcgccagg ttaaaggtca cggtaaaaaa gttgctgatg ctctgaccaa cgctgttgct    300
cacgttgatg atatgccgaa cgcgttgtct gctctgtctg atctgcacgc tcacaaactg    360

```
cgtgttgatc cggttaactt caaactgctg tctcactgcc tgctggttac tctggctgct    420
catctgccgg ctgaatttac cccggctgtt catgcgtctc tggataaatt cctggcttct    480
gtttctaccg ttctgacttc gaaataccgt taatgactgc agctacatgg agattaactc    540
aatctagagg gtattaataa tgtatcgctt aaataaggag gaataacata tgatcgaagg    600
tcgtgttcac ctgactccgg aagaaaaatc cgcggttact gctctgtggg gtaaagtgaa    660
cgttgacgaa gttggtggtg aagctctggg acgtctgctg gttgtttacc cgtggactca    720
gcgtttcttt gaatctttcg gagatctgtc taccccggac gctgttatgg gtaacccgaa    780
agttaaagcc catggtaaaa aagttctggg tgctttctct gacggtctgg ctcacctgga    840
caacctgaaa ggtaccttcg ctactctgtc tgagctccac tgcgacaaac tgcacgttga    900
cccggaaaac ttccgtctgc tgggtaacgt actagtttgc gttctggctc accacttcgg    960
taaagaattc actccgccgg ttcaggctgc ttaccagaaa gttgttgctg gtgttgctaa    1020
cgcgctagct cacaaatacc actaatga                                      1048
```

<210> SEQ ID NO 89
<211> LENGTH: 1048
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 89

```
agcttcatta gtggtatttg tgagctagcg cgttagcaac accagcaaca actttctggt     60
aagcagcctg aaccggcgga gtgaattctt taccgaagtg gtgagccaga acgcaaacta    120
gtacgttacc cagcagacgg aagttttccg ggtcaacgtg cagtttgtcg cagtggagct    180
cagacagagt agcgaaggta cctttcaggt tgtccaggtg agccagaccg tcagagaaag    240
cacccagaac tttttttacca tgggctttaa ctttcgggtt acccataaca gcgtccgggg    300
tagacagatc tccgaaagat tcaaagaaac gctgagtcca cgggtaaaca accagcagac    360
gtcccagagc ttcaccacca acttcgtcaa cgttcacttt accccacaga gcagtaaccg    420
cggatttttc ttccggagtc aggtgaagac gaccttcgat catatgttat tcctcccttat    480 ttaagcgata cattattaat accctctaga ttgagttaat ctccatgtag ctgcagtcat    540
taacggtatt tcgaagtcag aacggtagaa acagaagcca ggaatttatc cagagacgca    600
tgaacagccg gggtaaattc agccggcaga tgagcagcca gagtaaccag caggcagtga    660
gacagcagtt tgaagttaac cggatcaaca cgcagtttgt gagcgtgcag atcagacaga    720
gcagacaacg cgttcggcat atcatcaacg tgagcaacag cgttggtcag agcatcagca    780 actttttac cgtgaccttt aacctggcga gaaccgtgag acaggtcgaa gtgcgggaag    840
taggttttgg tggtcgggaa agacaggaac atacgctcga gagcttcagc accgtattca    900
ccagcgtgcg cgccaacttt accccaagca gctttaacgt tggttttatc ggccggagac    960
agaacacgac cttcgatcat atgttattcc tccttattta agcgatacat tattaatacc    1020
ctctagattg agttaatctc catgtagc                                     1048
```

<210> SEQ ID NO 90
<211> LENGTH: 1075
<212> TYPE: DNA
<213> ORGANISM: Artificial Sequence
<220> FEATURE:
<223> OTHER INFORMATION: Description of Artificial Sequence:
      Oligonucleotide

```
<221> NAME/KEY: CDS
<222> LOCATION: (93)..(527)
<221> NAME/KEY: CDS
<222> LOCATION: (607)..(1065)

<400> SEQUENCE: 90
```

| | |
|---|---:|
| gaattcgagc tcggtacccg ggctacatgg agattaactc aatcatctag agggtattaa | 60 |
| taatgtatcg cttaaataag gagaggtaac at atg atc gaa ggt cgt gtt ctg<br>                                           Met Ile Glu Gly Arg Val Leu<br>                                            1             5 | 113 |
| tct ccg gcc gat aaa acc aac gtt aaa gct cgt tgg ggt aaa gtt ggc<br>Ser Pro Ala Asp Lys Thr Asn Val Lys Ala Arg Trp Gly Lys Val Gly<br>       10                15                    20 | 161 |
| cac gct ggt gga tac ggt gct gaa gct ctc gag cgt atg ttc ctg tct<br>His Ala Gly Gly Tyr Gly Ala Glu Ala Leu Glu Arg Met Phe Leu Ser<br> 25                     30                    35 | 209 |
| ttc ccg acc acc aaa acc tac ttc ccg cac ttc gac ctg tct cac gct<br>Phe Pro Thr Thr Lys Thr Tyr Phe Pro His Phe Asp Leu Ser His Ala<br> 40                  45                    50                    55 | 257 |
| tct gcg cag gtt aaa ggt cac ggt aaa aaa gtt gct gac gct ctg acc<br>Ser Ala Gln Val Lys Gly His Gly Lys Lys Val Ala Asp Ala Leu Thr<br>              60                    65                    70 | 305 |
| aac gct gtt gct cac gtt gat gat atg ccg aac gcg ttg tct gct ctg<br>Asn Ala Val Ala His Val Asp Asp Met Pro Asn Ala Leu Ser Ala Leu<br>                  75                    80                    85 | 353 |
| tct gat ctg cac gct cac aaa ctg cgt gtt gat ccg gtt aac ttc aaa<br>Ser Asp Leu His Ala His Lys Leu Arg Val Asp Pro Val Asn Phe Lys<br>          90                    95                    100 | 401 |
| ctg ctg tct cac tgc ctg ctg gtt act ctg gct gct cat ctg ccg gct<br>Leu Leu Ser His Cys Leu Leu Val Thr Leu Ala Ala His Leu Pro Ala<br>105                   110                    115 | 449 |
| gaa ttt acc ccg gct gtt cat gcg tct ctg gat aaa ttc ctg gct tct<br>Glu Phe Thr Pro Ala Val His Ala Ser Leu Asp Lys Phe Leu Ala Ser<br>120                   125                    130                    135 | 497 |
| gtt tct acc gtt ctg act tcg aaa tac cgt ttatgactgc agctacatgg<br>Val Ser Thr Val Leu Thr Ser Lys Tyr Arg<br>              140                    145 | 547 |
| agattaactc aatctagagg gtattaataa tgtatcgctt aaataaggag gaataacat | 606 |
| atg atc gaa ggt cgt gtt cac ctg act ccg gaa gaa aaa tcc gcg gtt<br>Met Ile Glu Gly Arg Val His Leu Thr Pro Glu Glu Lys Ser Ala Val<br>                  150                    155                    160 | 654 |
| act gct ctg tgg ggt aaa gtg aac gtt gac gaa gtt ggt ggt gaa gct<br>Thr Ala Leu Trp Gly Lys Val Asn Val Asp Glu Val Gly Gly Glu Ala<br>                  165                    170                    175 | 702 |
| ctg gga cgt gga cgt ctg ctg gtt gtt tac ccg tgg act cag cgt ttc<br>Leu Gly Arg Gly Arg Leu Leu Val Val Tyr Pro Trp Thr Gln Arg Phe<br>180                   185                    190 | 750 |
| ttt gaa tct ttc gga gat ctg tct acc ccg gac gct gtt atg ggt aac<br>Phe Glu Ser Phe Gly Asp Leu Ser Thr Pro Asp Ala Val Met Gly Asn<br>                  195                    200                    205 | 798 |
| ccg aaa gtt aaa gcc cat ggt aaa aaa gtt ctg ggt gct ttc tct gac<br>Pro Lys Val Lys Ala His Gly Lys Lys Val Leu Gly Ala Phe Ser Asp<br>210                   215                    220                    225 | 846 |
| ggt ctg gct cac ctg gac aac ctg aaa ggt acc ttc gct act ctg tct<br>Gly Leu Ala His Leu Asp Asn Leu Lys Gly Thr Phe Ala Thr Leu Ser<br>                  230                    235                    240 | 894 |
| gag ctc cac tgc gac aaa ctg cac gtt gac ccg gaa aac ttc cgt ctg<br>Glu Leu His Cys Asp Lys Leu His Val Asp Pro Glu Asn Phe Arg Leu<br>                  245                    250                    255 | 942 |

-continued

```
ctg ggt aac gta cta gtt tgc gtt ctg gct cac cac ttc ggt aaa gaa      990
Leu Gly Asn Val Leu Val Cys Val Leu Ala His His Phe Gly Lys Glu
        260                 265                 270 ttc act ccg ccg gtt cag gct gct tac cag aaa gtt gtt gct ggt gtt     1038
Phe Thr Pro Pro Val Gln Ala Ala Tyr Gln Lys Val Val Ala Gly Val
275                 280                 285 gct aac gcg cta gct cac aaa tac cac taatgaagct                      1075
Ala Asn Ala Leu Ala His Lys Tyr His
290                 295
```

<210> SEQ ID NO 91
<211> LENGTH: 145
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 91

```
Met Ile Glu Gly Arg Val Leu Ser Pro Ala Asp Lys Thr Asn Val Lys
 1               5                  10                  15

Ala Arg Trp Gly Lys Val Gly His Ala Gly Gly Tyr Gly Ala Glu Ala
            20                  25                  30

Leu Glu Arg Met Phe Leu Ser Phe Pro Thr Thr Lys Thr Tyr Phe Pro
        35                  40                  45

His Phe Asp Leu Ser His Ala Ser Ala Gln Val Lys Gly His Gly Lys
    50                  55                  60

Lys Val Ala Asp Ala Leu Thr Asn Ala Val Ala His Val Asp Asp Met
65                  70                  75                  80

Pro Asn Ala Leu Ser Ala Leu Ser Asp Leu His Ala His Lys Leu Arg
                85                  90                  95

Val Asp Pro Val Asn Phe Lys Leu Leu Ser His Cys Leu Leu Val Thr
            100                 105                 110

Leu Ala Ala His Leu Pro Ala Glu Phe Thr Pro Ala Val His Ala Ser
        115                 120                 125

Leu Asp Lys Phe Leu Ala Ser Val Ser Thr Val Leu Thr Ser Lys Tyr
    130                 135                 140

Arg
145
```

<210> SEQ ID NO 92
<211> LENGTH: 153
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 92

```
Met Ile Glu Gly Arg Val His Leu Thr Pro Glu Glu Lys Ser Ala Val
 1               5                  10                  15

Thr Ala Leu Trp Gly Lys Val Asn Val Asp Glu Val Gly Gly Glu Ala
            20                  25                  30

Leu Gly Arg Gly Arg Leu Leu Val Val Tyr Pro Trp Thr Gln Arg Phe
        35                  40                  45

Phe Glu Ser Phe Gly Asp Leu Ser Thr Pro Asp Ala Val Met Gly Asn
    50                  55                  60

Pro Lys Val Lys Ala His Gly Lys Lys Val Leu Gly Ala Phe Ser Asp
65                  70                  75                  80
```

```
Gly Leu Ala His Leu Asp Asn Leu Lys Gly Thr Phe Ala Thr Leu Ser
                85                  90                  95

Glu Leu His Cys Asp Lys Leu His Val Asp Pro Glu Asn Phe Arg Leu
            100                 105                 110

Leu Gly Asn Val Leu Val Cys Val Leu Ala His Phe Gly Lys Glu
        115                 120                 125

Phe Thr Pro Pro Val Gln Ala Ala Tyr Gln Lys Val Val Ala Gly Val
    130                 135                 140

Ala Asn Ala Leu Ala His Lys Tyr His
145                 150

<210> SEQ ID NO 93
<211> LENGTH: 63
<212> TYPE: DNA
<213> ORGANISM: Artificial Sequence
<220> FEATURE:
<223> OTHER INFORMATION: Description of Artificial Sequence: Hemoglobin
      Beth Israel (beta asn->ser)
<221> NAME/KEY: CDS
<222> LOCATION: (3)..(62)
<221> NAME/KEY: misc_feature
<222> LOCATION: (1)..(63)
<223> OTHER INFORMATION: Double stranded

<400> SEQUENCE: 93 ag ctc cac tgc gac aaa ctg cac gtt gac ccg gaa tct ttc cgt ctc      47
   Leu His Cys Asp Lys Leu His Val Asp Pro Glu Ser Phe Arg Leu
   1               5                  10                  15 tgg ggt aac gta cta g                                               63
Trp Gly Asn Val Leu
                20

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Hemoglobin
      Beth Israel (beta asn->ser)

<400> SEQUENCE: 94

Leu His Cys Asp Lys Leu His Val Asp Pro Glu Ser Phe Arg Leu Trp
1               5                  10                  15

Gly Asn Val Leu
            20

<210> SEQ ID NO 95
<211> LENGTH: 116
<212> TYPE: DNA
<213> ORGANISM: Artificial Sequence
<220> FEATURE:
<221> NAME/KEY: CDS
<222> LOCATION: (2)..(115)
<221> NAME/KEY: misc_feature
<222> LOCATION: (1)..(116)
<223> OTHER INFORMATION: Double stranded
<223> OTHER INFORMATION: Description of Artificial Sequence:  Hemoglobin
      Cheverly (beta phe-> ser)

<400> SEQUENCE: 95 c gcg gtt act gct ctg tgg ggt aaa gtg aac gtt gac gaa gtt ggt ggt   49
  Ala Val Thr Ala Leu Trp Gly Lys Val Asn Val Asp Glu Val Gly Gly
  1               5                  10                  15 gaa gct ctg gga cgt ctg ctg gtt gtt tac ccg tgg act cag cgt ttc     97
Glu Ala Leu Gly Arg Leu Leu Val Val Tyr Pro Trp Thr Gln Arg Phe
                20                  25                  30
```

```
ttt gaa tct tct gga gac g                                    116
Phe Glu Ser Ser Gly Asp
        35

<210> SEQ ID NO 96
<211> LENGTH: 38
<212> TYPE: PRT
<213> ORGANISM: Artificial Sequence
<220> FEATURE:
<223> OTHER INFORMATION: Description of Artificial Sequence:
      Hemoglobin Cheverly (beta phe-> ser)

<400> SEQUENCE: 96

Ala Val Thr Ala Leu Trp Gly Lys Val Asn Val Asp Glu Val Gly Gly
  1               5                  10                  15

Glu Ala Leu Gly Arg Leu Leu Val Val Tyr Pro Trp Thr Gln Arg Phe
             20                  25                  30

Phe Glu Ser Ser Gly Asp
        35

<210> SEQ ID NO 97
<211> LENGTH: 65
<212> TYPE: DNA
<213> ORGANISM: Artificial Sequence
<220> FEATURE:
<223> OTHER INFORMATION: Description of Artificial Sequence:
      Hemoglobin beta val -> ile
<221> NAME/KEY: CDS
<222> LOCATION: (4)..(63)
<221> NAME/KEY: misc_difference
<222> LOCATION: (5)..(61)
<223> OTHER INFORMATION: Double stranded

<400> SEQUENCE: 97 cat gct aaa aaa atc gtc ggt gct ttc tct gac ggt ctg gct cac ctg     48
    Ala Lys Lys Ile Val Gly Ala Phe Ser Asp Gly Leu Ala His Leu
      1               5                  10                  15 gac aac ctg aaa ggt ac                                              65
Asp Asn Leu Lys Gly
            20

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence:
      Hemoglobin beta val -> ile

<400> SEQUENCE: 98

Ala Lys Lys Ile Val Gly Ala Phe Ser Asp Gly Leu Ala His Leu Asp
  1               5                  10                  15

Asn Leu Lys Gly
            20

<210> SEQ ID NO 99
<211> LENGTH: 63
<212> TYPE: DNA
<213> ORGANISM: Artificial Sequence
<220> FEATURE:
<223> OTHER INFORMATION: Description of Artificial Sequence:
      Hemoglobin Kansas (beta asn -> thr)
<221> NAME/KEY: CDS
<222> LOCATION: (3)..(62)
<221> NAME/KEY: misc_feature
<222> LOCATION: (1)..(63)
<223> OTHER INFORMATION: double stranded
```

```
<400> SEQUENCE: 99 ag ctc cac tgc gac aaa ctg gac gtt gac ccg gaa acc ttc cgt ctg        47
   Leu His Cys Asp Lys Leu Asp Val Asp Pro Glu Thr Phe Arg Leu
     1               5                  10                  15 ctg ctg ggt aac gta g                                                 63
Leu Leu Gly Asn Val
            20

<210> SEQ ID NO 100
<211> LENGTH: 20
<212> TYPE: PRT
<213> ORGANISM: Artificial Sequence
<220> FEATURE:
<223> OTHER INFORMATION: Description of Artificial Sequence: Hemoglobin
      Kansas (beta asn -> thr)

<400> SEQUENCE: 100

Leu His Cys Asp Lys Leu Asp Val Asp Pro Glu Thr Phe Arg Leu Leu
  1               5                  10                  15

Leu Gly Asn Val
            20

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: des-FX
      Alpha
<221> NAME/KEY: CDS
<222> LOCATION: (2)..(19)
<221> NAME/KEY: misc_feature
<222> LOCATION: (3)..(19)

<400> SEQUENCE: 101 t atg gtt ctg tct ccg gcc                                             19
  Met Val Leu Ser Pro Ala
   1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: des-FX
      Alpha

<400> SEQUENCE: 102

Met Val Leu Ser Pro Ala
  1               5

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: des-FX Beta
<221> NAME/KEY: CDS
<222> LOCATION: (2)..(31)
<221> NAME/KEY: misc_feature
<222> LOCATION: (3)..(31)
<223> OTHER INFORMATION: Double stranded

<400> SEQUENCE: 103 t atg gtt cac ctg act ccg gaa gaa aaa tcc gc                          33
  Met Val His Leu Thr Pro Glu Glu Lys Ser
   1               5                  10
```

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: des-FX Beta

<400> SEQUENCE: 104

Met Val His Leu Thr Pro Glu Glu Lys Ser
 1               5                  10

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: des-val
      Beta
<221> NAME/KEY: CDS
<222> LOCATION: (2)..(16)
<221> NAME/KEY: misc_feature
<222> LOCATION: (3)..(16)
<223> OTHER INFORMATION: Double stranded

<400> SEQUENCE: 105 t atg ctg tct ccg gcc                                             16
  Met Leu Ser Pro Ala
   1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: des-val
      Beta

<400> SEQUENCE: 106

Met Leu Ser Pro Ala
 1               5

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: des-val
      Beta
<221> NAME/KEY: CDS
<222> LOCATION: (2)..(28)
<221> NAME/KEY: misc_feature
<222> LOCATION: (3)..(28)
<223> OTHER INFORMATION: Double stranded

<400> SEQUENCE: 107 t atg cac ctg act ccg gaa gaa aaa tcc gc                          30
  Met His Leu Thr Pro Glu Glu Lys Ser
   1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: des-val
      Beta

<400> SEQUENCE: 108

```
Met His Leu Thr Pro Glu Glu Lys Ser
  1               5
```

<210> SEQ ID NO 109
<211> LENGTH: 1467
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: misc_feature
<222> LOCATION: (4)..(1466)
<221> NAME/KEY: CDS
<222> LOCATION: (59)..(82)
<221> NAME/KEY: CDS
<222> LOCATION: (89)..(940)
<221> NAME/KEY: CDS
<222> LOCATION: (990)..(1013)
<221> NAME/KEY: CDS
<222> LOCATION: (1020)..(1457)

<400> SEQUENCE: 109

```
aattcgagct cggtacccgg gctacatgga gattaactca atctagaggg tattaata              58 atg tat cgc tta aat aag gag gaa taacat atg ctg tct ccg gcc gat             106
Met Tyr Arg Leu Asn Lys Glu Glu        Met Leu Ser Pro Ala Asp
  1               5                             10 aaa acc aac gtt aaa gct gct tgg ggt aaa gtt ggc gcg cac gct ggt            154
Lys Thr Asn Val Lys Ala Ala Trp Gly Lys Val Gly Ala His Ala Gly
 15                  20                  25                  30 gaa tac ggt gct gaa gct ctc gag cgt atg ttc ctg tct ttc ccg acc            202
Glu Tyr Gly Ala Glu Ala Leu Glu Arg Met Phe Leu Ser Phe Pro Thr
                 35                  40                  45 acc aaa acc tac ttc ccg cac ttc gac ctg tct cac ggt tct gcg cag            250
Thr Lys Thr Tyr Phe Pro His Phe Asp Leu Ser His Gly Ser Ala Gln
             50                  55                  60 gtt aaa ggt cac ggt aaa aaa gtt gct gat gct ctg acc aac gct gtt            298
Val Lys Gly His Gly Lys Lys Val Ala Asp Ala Leu Thr Asn Ala Val
         65                  70                  75 gct cac gtt gat gat atg ccg aac gcg ttg tct gct ctg tct gat ctg            346
Ala His Val Asp Asp Met Pro Asn Ala Leu Ser Ala Leu Ser Asp Leu
     80                  85                  90 cac gct cac aaa ctg cgt gtt gat ccg gtt aac ttc aaa ctg ctg tct            394
His Ala His Lys Leu Arg Val Asp Pro Val Asn Phe Lys Leu Leu Ser
 95                 100                 105                 110 cac tgc ctg ctg gtt act ctg gct gct cat ctg ccg gct gaa ttt acc            442
His Cys Leu Leu Val Thr Leu Ala Ala His Leu Pro Ala Glu Phe Thr
                115                 120                 125 ccg gct gtt cat gcg tct ctg gat aaa ttc ctg gct tct gtt tct acc            490
Pro Ala Val His Ala Ser Leu Asp Lys Phe Leu Ala Ser Val Ser Thr
            130                 135                 140 gtt ctg act tcg aaa tac cgt ggt ggt gtt ctg tct ccg gcc gat aaa            538
Val Leu Thr Ser Lys Tyr Arg Gly Gly Val Leu Ser Pro Ala Asp Lys
        145                 150                 155 acc aac gtt aaa gct gct tgg ggt aaa gtt ggc gcg cac gct ggt gaa            586
Thr Asn Val Lys Ala Ala Trp Gly Lys Val Gly Ala His Ala Gly Glu
    160                 165                 170 tac ggt gct gaa gct ctc gag cgt atg ttc ctg tct ttc ccg acc acc            634
Tyr Gly Ala Glu Ala Leu Glu Arg Met Phe Leu Ser Phe Pro Thr Thr
175                 180                 185                 190 aaa acc tac ttc ccg cac ttc gac ctg tct cac ggt tct gcg cag gtt            682
Lys Thr Tyr Phe Pro His Phe Asp Leu Ser His Gly Ser Ala Gln Val
                195                 200                 205 aaa ggt cac ggt aaa aaa gtt gct gat gct ctg acc aac gct gtt gct            730
```

```
            Lys Gly His Gly Lys Lys Val Ala Asp Ala Leu Thr Asn Ala Val Ala
                        210                 215                 220 cac gtt gat gat atg ccg aac gcg ttg tct gct ctg tct gat ctg cac       778
His Val Asp Asp Met Pro Asn Ala Leu Ser Ala Leu Ser Asp Leu His
            225                 230                 235 gct cac aaa ctg cgt gtt gat ccg gtt aac ttc aaa ctg ctg tct cac       826
Ala His Lys Leu Arg Val Asp Pro Val Asn Phe Lys Leu Leu Ser His
    240                 245                 250 tgc ctg ctg gtt act ctg gct gct cat ctg ccg gct gaa ttt acc ccg       874
Cys Leu Leu Val Thr Leu Ala Ala His Leu Pro Ala Glu Phe Thr Pro
255                 260                 265                 270 gct gtt cat gcg tct ctg gat aaa ttc ctg gct tct gtt tct acc gtt       922
Ala Val His Ala Ser Leu Asp Lys Phe Leu Ala Ser Val Ser Thr Val
                275                 280                 285 ctg act tcg aaa tac cgt taatgactgc agctacatgg agattaactc              970
Leu Thr Ser Lys Tyr Arg
            290 aatctagagg gtattaata atg tat cgc tta aat aag gag gaa taacat atg      1022
                    Met Tyr Arg Leu Asn Lys Glu Glu          Met
                        295                 300 cac ctg act ccg gaa gaa aaa tcc gcg gtt act gct ctg tgg ggt aaa      1070
His Leu Thr Pro Glu Glu Lys Ser Ala Val Thr Ala Leu Trp Gly Lys
            305                 310                 315 gtg aac gtt gac gaa gtt ggt ggt gaa gct ctg gga cgt ctg ctg gtt      1118
Val Asn Val Asp Glu Val Gly Gly Glu Ala Leu Gly Arg Leu Leu Val
        320                 325                 330 gtt tac ccg tgg act cag cgt ttc ttt gaa tct ttc gga gat ctg tct      1166
Val Tyr Pro Trp Thr Gln Arg Phe Phe Glu Ser Phe Gly Asp Leu Ser
335                 340                 345 acc ccg gac gct gtt atg ggt aac ccg aaa gtt aaa gcc cat ggt aaa      1214
Thr Pro Asp Ala Val Met Gly Asn Pro Lys Val Lys Ala His Gly Lys
350                 355                 360                 365 aaa gtt ctg ggt gct ttc tct gac ggt ctg gct cac ctg gac aac ctg      1262
Lys Val Leu Gly Ala Phe Ser Asp Gly Leu Ala His Leu Asp Asn Leu
                370                 375                 380 aaa ggt acc ttc gct act ctg tct gag ctc cac tgc gac aaa ctg cac      1310
Lys Gly Thr Phe Ala Thr Leu Ser Glu Leu His Cys Asp Lys Leu His
            385                 390                 395 gtt gac ccg gaa aac ttc cgt ctg ctg ggt aac gta cta gtt tgc gtt      1358
Val Asp Pro Glu Asn Phe Arg Leu Leu Gly Asn Val Leu Val Cys Val
        400                 405                 410 ctg gct cac cac ttc ggt aaa gaa ttc act ccg ccg gtt cag gct gct      1406
Leu Ala His His Phe Gly Lys Glu Phe Thr Pro Pro Val Gln Ala Ala
    415                 420                 425 tac cag aaa gtt gtt gct ggt gtt gct aac gcg cta gct cac aaa tac      1454
Tyr Gln Lys Val Val Ala Gly Val Ala Asn Ala Leu Ala His Lys Tyr
430                 435                 440                 445 cac taatgaagct                                                        1467
His

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 110

Met Tyr Arg Leu Asn Lys Glu Glu
  1               5
```

<210> SEQ ID NO 111
<211> LENGTH: 284
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 111

Met Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg Gly Gly Val
    130                 135                 140

Leu Ser Pro Ala Asp Lys Thr Asn Val Lys Ala Ala Trp Gly Lys Val
145                 150                 155                 160

Gly Ala His Ala Gly Glu Tyr Gly Ala Glu Ala Leu Glu Arg Met Phe
                165                 170                 175

Leu Ser Phe Pro Thr Thr Lys Thr Tyr Phe Pro His Phe Asp Leu Ser
            180                 185                 190

His Gly Ser Ala Gln Val Lys Gly His Gly Lys Lys Val Ala Asp Ala
        195                 200                 205

Leu Thr Asn Ala Val Ala His Val Asp Asp Met Pro Asn Ala Leu Ser
    210                 215                 220

Ala Leu Ser Asp Leu His Ala His Lys Leu Arg Val Asp Pro Val Asn
225                 230                 235                 240

Phe Lys Leu Leu Ser His Cys Leu Leu Val Thr Leu Ala Ala His Leu
                245                 250                 255

Pro Ala Glu Phe Thr Pro Ala Val His Ala Ser Leu Asp Lys Phe Leu
            260                 265                 270

Ala Ser Val Ser Thr Val Leu Thr Ser Lys Tyr Arg
        275                 280

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 112

Met Tyr Arg Leu Asn Lys Glu Glu
 1               5

```
<210> SEQ ID NO 113
<211> LENGTH: 146
<212> TYPE: PRT
<213> ORGANISM: Artificial Sequence
<220> FEATURE:
<223> OTHER INFORMATION: Description of Artificial Sequence:
      Oligonucleotide

<400> SEQUENCE: 113

Met His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 114
<211> LENGTH: 451
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 114
gcatgcgtac ggattagaag ccgccgagcg ggtgacagcc ctccgaagga agactctcct      60
ccgtgcgtcc tcgtcttcac cggtcgcgtt cctgaaacgc agatctgcct cgcgccgcac     120
tgctccgaac aataaagatt ctacaatact agcttttatg gttatgaaga ggaaaattgg     180
cagtaacctg gccccacaaa cctcaaatga acgaatcaaa ttaacaacca gatatctcga     240
ctgaaaaaaa aggtttaaac cagttccctg aaattattcc cctacttgac taataagtat     300
ataaagacgg taggtattga ttgtaattct gtaaatctat ttcttaaact tcttgaattc     360
tacttttata gttagtcttt tttttagttt taaaacacca agaacttagt ttcgaataaa     420
cacacataaa taaaccatgg ttaactctag a                                    451
```

DNA ENCODING FUSED DI-ALPHA GLOBINS AND USE THEREOF

This is a continuation of application Ser. No. 07/789,179 filed Nov. 8, 1991, now U.S. Pat. No. 5,545,727, which is a CIP of Ser. No. 07/671,707 filed Apr. 1, 1991, now abandoned, which is a CIP of PCT/US90/02654 filed May 10, 1990, now abandoned, which is a CIP of (a) Ser. No. 07/374,161 filed Jun. 30, 1989, now abandoned, (b) Ser. No. 07/379,116 filed July 13, 1989, now abandoned, and (c) Ser. No. 07/349,623 filed May 10, 1989, now abandoned, all hereby incorporated by reference herein.

CROSS-REFERENCE TO RELATED APPLICATIONS

Hoffman and Nagai, U.S. Ser. No. 07/194,338, filed May 10, 1988, now U.S. Pat. No. 5,028,588, presently owned by Somatogen, Inc., relates to the use of low oxygen affinity and other mutant hemoglobins as blood substitutes, and to the expression of alpha and beta globin in nonerythroid cells. Hoffman and Nagai, U.S. Ser. No. 07/443,950, filed Dec. 1, 1989, and file-wrappered continued as Ser. No. 08/158,488 filed Nov. 29, 1993, now U.S. Pat. No. 5,449,759, discloses certain additional dicysteine hemoglobin mutants; it is a continuation-in-part of 07/194,338, filed May 16, 1998, now U.S. Pat. No. 5,028,588. Anderson, et al., HEMOGLOBINS AS DRUG DELIVERY AGENTS U.S. Ser. No. 07/789,177, filed Nov. 8, 1991, discloses use of conjugation of hemoglobins with drugs as a means for delivery of the drug to a patient.

FIELD OF THE INVENTION

The present invention relates to the intracellular assembly of a hemoglobin-like protein in biologically functional, substantially soluble form through co-expression of alpha and beta globin-like polypeptides in bacterial or yeast cells.

It further relates to the genetic cross-linking of the two alpha subunits of hemoglobin to form a novel polypeptide, di-alpha globin, which may be considered a partially assembled intermediate leading to a hemoglobin-like protein, and the use of this compound in the production of synthetic hemoglobins having an increased intravascular half-life as compared to stroma-free hemoglobins. It also relates to the analogous polypeptide di-beta globin.

INFORMATION DISCLOSURE STATEMENT

It is not always practical to transfuse a patient with donated blood. In these situations, use of a red blood cell substitute is desirable. The product must effectively transport $O_2$, just as do red blood cells. ("Plasma expanders", such as dextran and albumin, do not transport oxygen.) The two types of substitutes that have been studied most extensively are hemoglobin solutions and fluorocarbon emulsions.

A. Structure and Function of Hemoglobin

Hemoglobin (Hgb) is the oxygen-carrying component of blood. Hemoglobin circulates through the blood stream inside small enucleate cells called erythrocytes (red blood cells). Hemoglobin is a protein constructed from four associated polypeptide chains, bearing prosthetic groups known as hemes. The erythrocyte helps maintain hemoglobin in its reduced, functional form. The heme iron atom is susceptible to oxidation, but may be reduced again by one of two enzyme systems within the erythrocyte, the cytochrome $b_5$ and glutathione reduction systems.

About 92% of the normal adult human hemolysate is hemoglobin A (designated alpha2 beta2, because it comprises two alpha and two beta chains). The alpha chain consists of 141 amino acids. The iron atom of the heme (ferroprotoporphyrin IX) group is bound covalently to the imidazole of His 87 (the "proximal histidine"). The beta chain is 146 residues long and heme is bound to it at His 92. Apohemoglobin is the heme-free analogue of hemoglobin; it exists predominantly as the αβ-globin dimer.

Separated, heme-free, alpha and beta globins have been prepared from the heme-containing alpha and beta subunits of hemoglobin. The separated heme-free globin chains are folded very differently, even though, the heme-containing subunits are highly similar in secondary structure and basic folding features. This shows that the binding of the prosthetic heme group to globin subunits has quite different effects on alpha and beta globin. Yip, et al., J. Biol. Chem., 247: 7237–44 (1972).

Native human hemoglobin has been fully reconstituted from separated heme-free alpha globin and beta globin and hemin. Preferably, heme is first added to the alpha globin subunit. The heme-bound alpha globin is then complexed to the heme-free beta subunit. Finally, heme is added to the half-filled globin dimer, and tetrameric hemoglobin is obtained. Yip, et al., PNAS (USA), 74: 64–68 (1977).

In cell-free systems prepared from unfractionated rabbit reticulocyte hemolysates, globin is actively synthesized for approximately five minutes, and then protein synthesis abruptly ceases. Prior addition of hemin prevents or delays the cessation of synthetic activity, as a result of the effect of hemin on an inhibitory protein known as "hemin-regulated inhibitor" (HRI). Hemin deficiency has a more severe effect on alpha chain synthesis than on a beta chain synthesis as alpha globin mRNA is less efficient than beta globin mRNA in initiating polypeptide chain synthesis. It has been speculated that alpha chains are released from their site of synthesis only in the presence of free beta chains, which immediately complex the released alpha chains to form αβ globin dimers. These then combine with heme to form tetrameric hemoglobin. Winterhalter and Huehns, J. Biol. Chem., 239: 3699 (1964). It is certainly known that the addition of heme to αβ globin dimers (apohemoglobin) leads to the rapid formation of hemoglobin.

The human alpha and beta globin genes reside on chromosomes 16 and 11, respectively. Bunn and Forget, *Hemoglobin: Molecular, Genetic and Clinical Aspects* (W. B. Saunders Co., Philadelphia Pa. 1986). Both genes have been cloned and sequenced. Liebhaber, et al., PNAS 77: 7054–58 (1980) (alpha globin genomic DNA); Marotta, et al., J. Biol. Chem.; 252: 5040–53 (1977) (beta globin cDNA); Lawn, et al., Cell, 21:647 (1980) (beta globin genomic DNA).

Hemoglobin exhibits cooperative binding of oxygen by the four subunits of the hemoglobin molecule (two alpha globins and two beta globins in the case of hemoglobin A), and this cooperativity greatly facilitates efficient oxygen transport. Cooperativity, achieved by the so-called heme-heme interaction, allows hemoglobin to vary its affinity for oxygen. Hemoglobin reversibly binds up to four moles of oxygen per mole of hemoglobin.

Oxygen-carrying compounds are frequently compared by means of a device known as an oxygen dissociation curve. This curve is obtained when, for a given oxygen carrier, oxygen saturation or content is graphed against the partial pressure of oxygen. For hemoglobin, the percentage of saturation increases with partial pressure according to a sigmoid relationship. The $P_{50}$ is the partial pressure at which the oxygen-carrying solution is half saturated with oxygen. It is thus a measure of oxygen-binding affinity; the higher the $P_{50}$, the more loosely the oxygen is held.

When the oxygen dissociation curve of an oxygen-carrying solution is such that the $P_{50}$ is less than that for whole blood, it is said to be "left-shifted."

The oxygen affinity of hemoglobin is lowered by the presence of 2,3-diphosphoglycerate (2,3-DPG), chloride ions and hydrogen ions. Respiring tissue releases carbon dioxide into the blood and lowers its pH (i.e. increases the hydrogen ion concentration), thereby causing oxygen to dissociate from hemoglobin and allowing it to diffuse into individual cells.

The ability of hemoglobin to alter its oxygen affinity, increasing the efficiency of oxygen transport around the body, is dependent on the presence of the metabolite 2,3-DPG. Inside the erythrocyte 2,3-DPG is present at a concentration nearly as great as that of hemoglobin itself. In the absence of 2,3-DPG "conventional" hemoglobin binds oxygen very tightly and would release little oxygen to respiring tissue.

Aging erythrocytes release small amounts of free hemoglobin into the blood plasma where it is rapidly bound by the scavenging protein haptoglobin. The hemoglobin-haptoglobin complex is removed from the blood and degraded by the spleen and liver.

B. Blood Substitutes, Generally

It is clear from the above considerations that free native hemoglobin A, injected directly into the bloodstream, would not support efficient oxygen transport about the body. The essential allosteric regulator 2,3-DPG is not present in sufficient concentration in the plasma to allow hemoglobin to release much oxygen at venous oxygen tension.

Nonetheless, solutions of conventional hemoglobin have been used as red blood cell substitutes. The classic method of preparing hemoglobin solutions employs outdated blood. The red cells are lysed and cellular debris is removed, leaving what is hopefully "stroma-free hemoglobin" (SFH).

Several basic problems have been observed with this approach. The solution must be freed of any toxic components of the red cell membrane without resorting to cumbersome and tedious procedures which would discourage large-scale production. DeVenuto, "Appraisal of Hemoglobin Solution as a Blood Substitute", *Surgery, Gynecology and Obstetrics*, 149: 417–436 (1979).

Second, as expected such solutions are "left-shifted" (lower $P_{50}$) as compared to whole blood. Gould, et al., "The Development of Polymerized Pyridoxylated Hemoglobin Solution as a Red Cell Substitute", *Ann. Emerg. Med.* 15: 1416–1419 (Dec. 3, 1986). As a result, the oxygen affinity is too high to unload enough oxygen into the tissues. Benesch and Benesch, Biochem. Biophys. Res. Comm., 26:162–167 (1976).

Third, SFH has only a limited half-life in the circulatory system. This is because oxy hemoglobin partially dissociates into a dimer ($\alpha\beta$) that is rapidly cleared from the blood by glomerular filtration and binding to circulating haptoglobulin. If large amounts of soluble hemoglobin are introduced into the circulation, glomeruler filtration of the dimers may lead to a protein and iron load on the kidney capable of causing renal damage. Bunn, H. F., et al. (1969). The renal handling of hemoglobin I. Glomerular filtration. J. Exp. Med. 129:909–923; Bunn, H. F., and J. H. Jandl;(1969) The renal handling of hemoglobin II. Catabolism. J. Exp. Med. 129:925–9334; Lee, R. L., et al. (1989) Ultrapure, stroma-free, polymerized bovine hemoglobin solution: Evaluation of renal toxicity (blood substitutes) J. Surgical Res. 47:407–411; Feola, M., et al. (1990) Nephrotoxicity of hemoglobin solutions. Biomat. Art. Cell Art. Org., 18(2): 233–249; Tam, S. C. and J. T. F. Wong (1988) Impairment of renal function by stroma-free hemoglobin in rats. J. Lab. Clin. Med. 111:189–193.

Finally, SFH has a high colloid osmotic pressure (COD) Thus, administration of SFH in a dose that would have the same oxygen-carrying capacity as a unit of packed red blood cells is inadvisable, since the high osmotic pressure (60 mm Hg) would cause a massive influx of water from the cells into the bloodstream, thus dehydrating the patient's tissues. This consideration limits the dose of SFH to that which provides a final concentration of about 6–8 gm /dl.

In an effort to restore the desired $P_{50}$, researchers added 2,3-DPG to the hemoglobin solution. Unfortunately, 2,3-DPG was rapidly eliminated from the circulation. Scientists then turned to other organic phosphates, particularly pyridoxal phosphate. Like 2,3-DPG, these compounds stabilized the "T state" of the hemoglobin by forming a salt bridge between the N-termini of the two beta chains. The pyridoxylated hemoglobin had a $P_{50}$ of 20–22 torr, as compared to 10 torr for SFH and 28 torr for whole blood. While this is an improvement over SFH, the pyridoxylated hemoglobin remains "high affinity" relative to whole blood.

C. Chemical Crosslinking of Hemoglobin Subunits

The properties of hemoglobin have been altered by specifically chemically crosslinking the alpha, chains between the Lys99 of alpha1 and the Lys99 of alpha2. Walder, U.S. Pat. Nos. 4,600,531 and 4,598,064; Snyder, et al., PNAS (USA) 84:7280–84 (1987); Chaterjee, et al., J. Biol. Chem., 261: 9927–37 (1986). The $P_{50}$ was 29 mm Hg, and renal excretion was abrogated by the crosslinking, but the plasma half-life was increased just 2–3 fold.

This chemical crosslinking was accomplished by reacting bis(3,5-dibromosalicyl) fumarate with deoxyhemoglobin A in the presence of inositol hexaphosphate. This reaction has a low yield (10–20%). Moreover, purification is required to eliminate derivatives modified at other sites (there are 42 other lysine residues and the amino terminal amino groups of the four chains at which competing reactions could occur).

A further problem with the use of a "diaspirin" crosslinking agent is that it can participate in a side reaction yielding a carcinogenic halophenol.

In the hemoglobin analogue of the present invention, the N-terminal valine and C-terminal arginine of the alpha globins are connected by means of an amino acid or peptide linker, without resort of special coupling agents.

The beta chains have also been chemically crosslinked. Kavanaugh, et al., Biochemistry, 27: 1804–8(1988). Kavanaugh notes that the beta N-termini are 16 Å apart in the T state and 20 Å apart in the R state. Not surprisingly, the introduction of a DIDS bridge between the N-termini of T state hemoglobin hindered the shift to the R state, thereby decreasing the $O_2$ affinity of the molecule. While the Kavanaugh analogue has desirable oxygen binding and renal clearance characteristics, it too is obtained in low yield.

D. Gene Expression, Generally

Gene expression embraces the transcription of DNA into messenger RNA, and the translation of messenger RNA into protein. The process of transcription begins when an enzyme, DNA-directed RNA polymerase, binds to DNA. The binding site for this enzyme is often called the "promoter," and the binding of the enzyme to the promoter may be controlled by various repressors or inducers of transcription. The RNA polymerase slides along the DNA molecule, manufacturing a messenger RNA transcript. When it encounters a second regulatory element, the "terminator," the enzyme falls off, and the mRNA transcript is formed.

Messenger RNA is used by the ribosomes, the protein factories of the cell, as a template for the construction of the corresponding protein. The ribosomal binding site comprises the so-called Shine Delgarno (SD) sequence and a properly spaced initiation (start) codon. Beginning at a special RNA triplet known as the initiation codon, transfer RNAs bind to corresponding codons of the messenger. Each transfer RNA is two-handed; it binds to the messenger codon by means of a complementary anti-codon, while holding the corresponding amino acid in position to be linked into the growing polypeptide chain. The chain falls off when the ribosome encounters one of three special triplets known as "stop" codons. That part of the original gene which corresponds to the messenger sequence from the initiator codon to the last codon before the stop codon is known as the coding sequence. There is also a 5'-flanking sequence, which begins with the promoter, and a 3'-flanking sequence which ends with the terminator.

E. Polycistronic Expression

It is possible for a single messenger RNA transcript to have one promoter, but two or more pairs of start and stop codons that define distinctly translatable sequences. Each such sequence is known as a "cistron," and the polypeptides corresponding to the cistrons are thus co-expressed under the control of the single promoter.

The majority of bacterial operons are polycistronic, that is, several different genes are transcribed as a single message from their operons. Examples include the lactose operon with three linked genes (lacZ, lacY and lacA) and the tryptophan operon with five associated genes (trpE, trpD, trpC, trpB, and trpA). In these operons, the synthesis of messenger RNA is initiated at the promoter and, within the transcript, coding regions are separated by intercistronic regions of various lengths. (An operon is a cluster of genes that is controlled as a single transcriptional genetic unit). Translational efficiency varies from cistron to cistron. Kastelein, et al., Gene, 23: 245–54 (1983).

When intercistronic regions are longer than the span of the ribosome (about 35 bases), dissociation at the stop codon of one cistron is followed by independent initiation at the next cistron. With shorter intercistronic regions, or with overlapping cistrons, the 30S subunit of a terminating ribosome may fail to dissociate from the polycistronic mRNA, being instantly attracted to the next translational initiation site. Lewin, *Gene Expression*, 143–148 (John Wiley & Sons: 1977).

Unlike bacterial mRNAs, eukaroytic mRNAs are generally monocistronic in nature. Lewin, *Gene Expression*, 157.

Synthetic polycistronic operons have been constructed and expressed in both prokaryotes and eukaryotes.

Lee, et al., Nucleic Acids Res., 12:6797 (1984) describe a special case of a synthetic polycistronic operon in which all of the cistrons express the same polypeptide. This homopolycistronic structure was constructed to maximize the gene dosage effect.

Schoner, et al., PNAS, 83: 8506–10 (1986) translated a synthetic two-cistron mRNA in *E. coli*. The first cistron was a short, arbitrary AU-rich sequence, while the second cistron was a mammalian gene (bGH). It was found that "read through" translation occurred if the stop codon of the first cistron followed the SD element of the second cistron and lay close to the start codon of the second cistron. Schoner's purpose was to overcome his failure to express Met-bGH with its native codons at high levels, possibly as a result of inhibition of translation by local secondary structures. The first cistron was engineered to favor ribosome binding (by placing the SD sequence and the AUG initiation codon in an AU-rich region free of local secondary structure). See also Schoner, et al., Meth. Enzymol., 153: 401–416 (1987) which reveals that bGH overproduction by this technique was associated with the formation of protein granules.

Saito, et al., J. Biochem., 101: 1281–88 (1987) expressed a synthetic somatomedin C gene in *E. coli* using a two cistron system. They theorized that the instability of somatomedin C, a basic polypeptide, might be overcome by complexing it with an acidic polypeptide. Thus, they constructed a two-cistron system which could express both polypeptides. The termination codon of the first cistron overlapped the initiation codon of the second cistron. The transformants accumulated Somatomedin C at high levels. However, the somatomedin C was recovered in the form of insoluble pellets (see page 1282).

The ribosomes of mammalian cells are likewise capable of reinitiating translation at an initiation codon downstream from a termination codon. Thus, Boel, et al., FEBS Lett., 219:181 (1987) expressed a dicistronic transcription unit in mammalian (CHO) cells. This unit directed synthesis of both the precursor of human pancreatic polypeptide and of a selectable genetic marker (mouse DHFR).

CODON, WO88/05486 describes the production of dicistronic mRNA which encodes both a protein of interest (e.g., tissue plasminogen activator) and a selectable phenotype (e.g., neomycin resistance). The common promoter was, in each of the examples a derivative of the Harvey murine sarcoma virus, and the dicistronic mRNA was translated in suitable eukaryotic cells.

GENENTECH, EP Appl 117,058 discloses the expression in vertebrate host cells of a dicistronic expression vector wherein one cistron codes for the desired protein (e.g., HbsAg) and a second codes for a second protein (e.g., DHFR) whose synthesis is subject to environmental control (e.g., with methotrexate).

F. Fused Genes and Proteins, Generally

Genes may be fused together by removing the stop codon of the first gene, and joining it in phase to the second gene. Parts of genes may also be fused, and spacer DNAs which maintain phase may be interposed between the fused sequences. The product of a fused gene is a single polypeptide, not a plurality of polypeptides as is expressed by a polycistronic operon. Different genes have been fused together for a variety of purposes. Thus, Gilbert, U.S. Pat. No. 4,338,397 inserted a rat preproinsulin gene behind a fragment of the *E. coli* penicillinase gene. His purpose was to direct *E. coli* transformants to secrete the expression product of the fused gene. Fused genes have also been prepared so that a non-antigenic polypeptide may be expressed already conjugated to an immunogenic carrier protein. The present invention, however, contemplates the joining of two copies of the same gene.

The use of linker DNA sequences to join two different DNA sequences is known. These linkers are used to provide restriction sites for DNA cleavage, or to encode peptides having a unique character that facilitates purification of the encoded fusion protein or a fragment thereof. See, e.g., Rutter, U.S. Pat. No. 4,769,326.

The lectin of Pisum sativum seeds is synthesized as a single 275-amino acid preprotein consisting of a signal sequence followed first by the beta chain and then by the alpha chain. The signal sequence is removed in the endoplasmic reticulum, and in the protein bodies the resulting "prolectin" is cleaved into a 187-AA beta chain and a 58-AA alpha chain. (Further processing results in truncation at the carboxyl termini) While the pea seed isolate is thus a heterodimer, it was discovered that the uncleaved naturally-occurring "prolectin" also binds carbohydrates, and that this "prolectin" could be expressed in *E. coli* and recovered in functional form. Stubbs, et al., J. Biol. Chem., 261: 6141–44 (1986).

Toth, U.S. Pat. No. 4,774,180 teaches the expression of polyprotein. This polyprotein was made from a fused DNA sequence encoding both a first polypeptide which catalyzes the reaction of glycine with ATP to form glycyl-adenylate and a second polypeptide which reacts glycyl adenylate with tRNA$^{GLY}$ to obtain the glycine-charged tRNA. These two polypeptides are the alpha and beta subunits of glycine tRNA synthetase which has an $\alpha_2\beta_2$ quaternary structure. The two subunits, in the *E. coli* genome, are encoded by a single dicistronic gene. Toth linked the coding region of the alpha chain to the coding region of the beta chain by means of a linker encoding six amino acids. See also Toth and Schimmel, J. Biol. Chem., 261: 6643–46 (May 1986).

Ladner, U.S. Pat. No. 4,704,692 describes an expert system for finding linkers which may be used to convert two naturally aggregated but chemically separated polypeptide chains into a single polypeptide chain with a similar conformation after folding. This system relies on a database containing amino acid sequences for which 3-D structures are known. The database is examined for candidate amino acid sequences with a span similar in length to the interchain gap to be bridged. The direction and orientation of the candidate peptides is then checked. The algorithm assumes that these peptides will maintain the same length and orientation regardless of the flanking sequences.

Ladner, WO88/06601 presents a hypothetical approach to the preparation of "pseudodimeric" analogues of dimeric repressor proteins. In essence, an amino acid linker is introduced to convert the dimeric molecule into a single chain. According to Ladner, this linker may be designed directly by the method of the '692 patent; alternatively, the linker-encoding DNA is a random oligonucleotide and in vivo selection is used to find a pseudodimer whose linker permits the molecule to fold correctly and bind sequence-specifically to DNA.

Hallewell, et al., J. Biol. Chem., 264: 5260–68 (1989) prepared an analogue of CuZn superoxide dismutase. Each dismutase molecule is a dimer of two identical subunits; a copper ion and a zinc ion are liganded to the subunit. The dimer interaction in CuZn superoxide dismutase is so strong that the subunits have not been separated without inactivating the enzyme. The enzyme has considerable conformational similarity to immunoglobulins; Hallewell, et al., joined two human superoxide dismutase genes, either directly or with DNA encoding a 19-residue human immunologlobulin IgA1 hinge region and expressed the fused genes in a transformed host. In attempting to express the directly joined genes, recombination occurred to eliminate one of the tandem genes in some plasmid molecules. Hallewell, et al., postulated that the direct connection distorted the dimer, causing the exposure of hydrophobic areas which then had a toxic effect. This would have provided selection pressure favoring gene deletion. No recombination was detected with the IgA1 linker construction.

Unfortunately, it cannot be assumed that a pseudodimeric fusion protein containing a peptide linker will fold properly so to be a functional equivalent of its parental heterodimer.

G. Expression of Soluble Proteins

Efforts to produce heterologous proteins in transformed cells sometimes result in the precipitation of some or all of the protein as insoluble inclusion bodies, also known as refractile bodies. See, e.g., Paul, et al., Eur. J. Cell Biol., 31:171–174 (1983) (human proinsulin/*E. coli* trpE fusion protein); Denefle, et al., Gene, 56:61–70 (1987) (angogenin); Langley, et al., Eur. J. Biochem., 163:313–321 (1987) (bovine growth hormone); Petrov, et al., Biology of the Cell, 61:1–4 (1987) (calcitonin); Richardson, et al., Biochim. Biophys. Acta, 950:385–94 (1988) (ricin B chain); Davis, et al., Biochemistry, 26:1322–26 (1987) (tumor necrosis factor); Lee, et al., Biochim. Biophys. Res. Commun., 151:598–607 (1988) (gamma interferon); Meng, et al., J. Chromatogr., 443:183–92 (1988) (Somatomedin C); Tsuji, et al., Biochemistry, 26:3129–34 (1987) (interleukin-2). The term "refractile" refers to the ability to observe these bodies by phase contrast microscopy. Frequently, this insoluble protein retains only a fraction of the expected biological activity, possibly due to incorrect folding. It has been suggested that inclusion bodies are formed when molecules of partially folded proteins interact with each other faster than they can fold into their native, active conformation. Kruger, et al., Biopharm, 40 (March 1989); Haase-Pettingell and King, J. Biol. Chem., 263:4977–83 (1988). "Factors contributing to the formation of inclusion bodies in recombinant bacteria remain obscure and it is not easy to predict the physical state of the product of a newly expressed eukaryotic gene in *E. coli*." Petrov, supra.

While the formation of these inclusion bodies results in enrichment of the recombinant protein, and is therefore sometimes desirable, it also necessitates solubilization of the aggregates and regeneration of the protein's biological activity. Petrov, supra at 4, comments, "sometimes these obstacles seem to be the most critical point of the recombinant technology."

Attempts have been made to solubilize and renature these proteins. Wetzel, U.S. Pat. No. 4,599,197; Builder, U.S. Pat. No. 4,620,948; Olson, U.S. Pat. No. 4,511,503; Jones, U.S. Pat. No. 4,512,922. However, such efforts can be laborious and uncertain of success. See Giantini and Shatkin, Gene, 56:153–160 (1987). As stated by Weir and Sparks, Biochem. J., 245: 85–91 (1987), "proteins vary considerably in their optimal conditions for renaturation; various factors such as pH, salt concentration and type, rate of removal of denaturant, concentration of the target protein and of contaminants may strongly affect the recovery of authentic protein." These complications are avoided if the protein of interest is expressed in soluble form.

Gatenby, et al., Eur. J. Biochem., 168: 227–31 (1987) has discussed difficulties in the preparation of the higher plant enzyme ribulose-bisphosphate carboxylase. This enzyme has the subunit structure $L_8S_8$, where L is a large subunit and S is a small subunit. In nature, a binding protein apparently maintains L in soluble form prior to assembly with S. Attempts to assemble an active higher plant RuBPCase in *E. coli* have been frustrated by the formation of an insoluble, inactive aggregate of L.

H. Bacterial Expression of Human Alpha and beta Globins

Nagai and Thorgerson (Nature, 309: 810–812, 1984) expressed in *E. coli* a hybrid protein consisting of the 31 amino-terminal residues of the lambda cII protein, an Ile-Glu-Gly-Arg linker, and the complete human beta globin chain. They cleaved the hybrid immediately after the linker with blood coagulation factor Xa, thus liberating the beta globin chain. Later, Nagai, et al., P.N.A.S. (U.S.A.), 82:7252–55 (1985) took the recombinant DNA-derived human beta globin, naturally derived human alpha globin, and a source of heme and succeeded in producing active human hemoglobin. Because the alpha globin was derived from erythrocytes, the final product may contain undesirable erythrocyte membrane constituents.

More recently, an efficient bacterial expression system for human alpha globin was reported. U.S. Pat. No. 5,028,588. This led to the production of wholly synthetic human hemoglobin by separate expression of the insoluble globin subunits in separate bacterial cell lines, and in situ refolding of the chains in the presence of oxidized heme cofactor to obtain tetrameric hemoglobin. This procedure is laborious and low in yield. It requires the use of denaturing solvents (urea and guanidine), and chemical reduction of ferric ion to the ferrous state (see example). One object of the present invention is to overcome these disadvantages.

While human alpha and beta globins may be expressed separately in *E. coli*, Walder, Proceedings, Biotech USA 1988 (San Francisco, Nov. 14–16, 1988) warns at page 360, "isolated alpha and beta [globin] chains are unstable and tend to precipitate." If human alpha and beta globin are not produced in soluble form, they must be solubilized with denaturing agents and then refolded to restore activity. Moreover, when a wild-type alpha globin gene is expressed in *E. coli*, alpha globin accumulates only slowly. It is not certain whether this is due to inefficient translation or to the action of host proteases, but WO 88/09179 teaches that this problem may be overcome by fusing a short section of the beta globin gene to the alpha globin gene, so that a hybrid protein is produced. This hybrid protein must then be cleaved, e.g., with a protease, to release the globin. If the protease is not completely selective (perhaps because of contamination by other proteases), the desired cleavage product may not be the only one obtained. In any event, that product must be separated from other *E. coli* polypeptides, and any contaminants associated with the protease.

Sperm whale myoglobin has been expressed in *E. coli*, demonstrating that bacteria can incorporate prosthetic heme groups into a protein expressed from a cloned eukaryotic gene. Springer and Sligar, PNAS (USA) 84: 8961–65 (1987). Walder says, "it remains to be seen if hemoglobin can be similarly made if both the alpha and beta chains are expressed within the same cell." While there is a high degree of tertiary structure similarity between myoglobin (a single chain protein) and the individual alpha and beta globin subunits of hemoglobin, hemoglobin is a heterotetrameric protein, in which the primary globin sequences have no more than a 27% homology to myoglobin and moreover myoglobin is now known to enjoy significantly higher stability than either alpha or beta globin. Thus, it could not be predicted that co-expression of alpha and beta globin in the same cell would result in intracellular assembly of a functional hemoglobin, which requires proper folding of the alpha and beta chains and incorporation of heme.

I. Human Gene Expression in Yeast, Generally

A number of human proteins have been expressed in transformed yeast cells, especially *Saccharomyces cerevisiae*, either cytoplamically or by secretion into the culture medium. King, et al., Biochm. Soc. Transac., 16:1083–1086 (1988). But success is not guaranteed. Thim, et al., FEBS Lett., 212:307–312 (1987) experienced difficulty in obtaining properly crosslinked insulin from yeast cells in which the intact proinsulin-encoding gene had been inserted. They overcame this problem by constructing a modified proinsulin gene which encoded the B and A chains linked by a hexapeptide spacer. The product of this gene was cleaved and the two chains were properly folded and crosslinked by the cells.

Richardson, et al., Biochim. Biophys. Acta, 950:385–94 (1988) expressed the B chain of the heterodimeric protein ricin in *E. coli*. They reported that it was hard to obtain high levels of secretion of a yeast alpha factor leader/ricin B chain fusion protein. No attempt was made to co-express and assemble the ricin A and B chains.

Murakami, et al., DNA, 6:189–97 (1987) reported production of a heme-containing fused enzyme in transformed yeast cells.

Horwitz, et al., PNAS (USA), 85:8678–82 (Nov. 1988) described the construction of yeast strains which secrete functional mouse variable region/human IgG1 constant region chimeric antibodies into the culture medium. They characterize their paper as the first report of the secretion of a foreign multimeric or heterodimeric protein in yeast. But see also Carlson, Mol. Cell. Biol., 8:2638–46 (June 1988), showing transcription and translation of heavy and light-chain cDNAs into polypeptides which associate and bind antigen.

Beggs, et al., Nature, 283:835 (1980) attempted to express a chromosomal rabbit beta globin gene in *S. cerevisiae*. However, these yeast cells were unable to properly splice the intron-containing globin mRNA transcript.

No admission is made that any references cited herein is prior art. The description of the work and the citation of publication date are based solely on the published information, and the applicants reserve the right to question the accuracy of that information.

SUMMARY OF THE INVENTION

It is the object of this invention to overcome the aforementioned deficiencies of the prior art. For example, Applicants have achieved the first complete expression and assembly of tetrameric (including pseudotetrameric) hemoglobin in cells which do not produce hemoglobin in nature. Prior work has related to the separate expression of alpha and beta globin and their extracellular combination with heme to form hemoglobin.

A central feature of the present invention is the intracellular assembly of alpha and beta globin-like polypeptides and intracellular incorporation of heme to form a biologically functional hemoglobin-like protein. This intracellular assembly is achieved by expressing the alpha and beta globin-like polypeptides in the same cell so that they fold together and incorporate heme. An important characteristic of this invention is a substantial reduction in the formation of insoluble globin aggregates, in particular of beta globin, as compared to what is observed when globins are separately expressed in *E. coli* or *S. cerevisiae*. Co-expression may be achieved from genes on two separate but compatible plasmids in the same cell or from two different operons on the same plasmid, or from a single polycistronic operon.

In one embodiment, the alpha and beta globin-like polypeptides are co-expressed in bacterial cells. The corresponding genes may be included in the same synthetic operon (i.e., driven by one promoter), or placed in separate operons with separate promoters (which may be the same or different). Preferably, expression of the alpha and beta globin is enhanced by placing a "ribosomal loader" sequence as hereafter described before each globin gene. This is particularly advantageous in the case of alpha globin which is more difficult to produce in quantity.

In another embodiment, the alpha and beta globin-like polypeptides are co-expressed in yeast cells. Improvements in both the yield of the alpha globin and the solubility of beta globin are obtained.

A further aspect of the invention is the production of novel intermediates, di-alpha globin and di-beta globin (and mutants thereof), which can be expressed in a cell (including, but not limited to, bacterial and yeast cells) and assembled with each other or with beta or alpha globin-like polypeptides, respectively, into a pseudotetrameric hemoglobin-like protein. While intracellular assembly is not strictly required, di-alpha and di-beta globin may be considered specially adapted to intracellular assembly of a functional hemoglobin since expression of, e.g., a di-alpha globin is analogous in some respects to intracellular assembly of two alpha globin subunits, differing from assembly as previously discussed in that the association is accomplished by expression of a covalent peptide linker rather than by noncovalent interaction of the subunits. Di-alpha and Di-beta globin-like polypeptides may be expressed in, preferably, bacterial cells or in yeast cells.

Moreover, the expression of di-alpha or di-beta (genetically stabilized) hemoglobin-like proteins and the utilization of such as a blood substitute, prolongs the half-life of recombinant hemoglobin by reducing extravasation and glomerular filtration of dissociated subunits in vivo compared to native human hemoglobin. Our studies of hemoglobin excretion in rat urine have demonstrated that genetically stabilized recombinant human hemoglobin is excreted at levels similar to control levels, while a similar recombinant hemoglobin that was not so genetically stabilized, undergoes significant dissociation into dimers and is excreted at substantially higher levels. Furthermore, genetic stabilization of hemoglobin results in a two fold or greater increase in half-life of hemoglobin in the plasma of rats.

The invention further relates to production of octameric hemoglobins, and of certain higher multimers, by linkage of pseudotetramers in various configurations.

These facets of the invention are now discussed in greater detail.

Yeast Expression of Hemoglobin-Like Proteins

Applicants have discovered that it is possible to produce human hemoglobin (or mutants thereof) in yeast, especially *Saccharomyces cerevisiae*. The use of yeast expression system obviates the need to separate the hemoglobin from bacterial endotoxins. We have also found that alpha and beta globins with the correct N-terminal amino acid may be obtained without first expressing the globin as a part of selectively cleavable fusion protein. We believe that this is because the yeast enzyme methionyl aminopeptidase is capable of removing the N-terminal methionine from Met-alpha-globin and Met-beta-globin to expose the desired N-terminal amino acid (Valine). Production of altered oxygen affinity mutants as discussed in WO88/09179 is of special interest. Such mutants may be produced by site-specific mutagenesis of globin genes followed by cloning and expression in yeast.

In a preferred embodiment, expression is controlled by a "gal-gap49" hybrid promoter as hereafter defined.

Co-Expression of Alpha and Beta Globin Genes in Yeast Cells

In a preferred embodiment, the alpha and beta globin genes are both expressed within the same yeast cell. Expression of the beta globin gene alone results in the production of beta globin as a largely insoluble, difficult-to-extract protein comprising less than 2% of the total cell protein. Expression of the alpha alobin aene alone results in production of alpha globin at very low levels (under 0.5% of the total cell protein). In neither case is heme incorporated. When, however, the alpha and beta globin genes are co-expressed, the transformed yeast cells fold the alpha and beta globin chains together and incorporate heme groups to obtain functional recombinant human hemoglobin in soluble form, accumulating to about 10% of the total cell protein, without any change in the promoters operably linked to the genes.

The alpha and beta globin genes may, in turn, be carried on different plasmids or on the same plasmid within the host cell.

Polycistronic Co-Expression of the Alpha and Beta Globin Genes in Bacterial Cells.

Applicants have translationally coupled alpha and beta globin genes to a small "ribosomal loader" gene encoding a small consumable peptide that will lead the ribosome directly into the ATG of the desired alpha and beta globin message and thus enhance translational efficiency. The have also placed the alpha and beta globin genes in the same operon so they are transcribed into a single polycistronic mRNA transcript. The globins are then translated as separate polypeptide chains which subsequently are folded together and joined with intracellular heme by transformed cells to form the hemoglobin tetramer. Applicant's method overcomes the problem associated with separate purification of precipitated alpha and beta globins.

The polycistronic expression and assembly of a heterooligomeric human protein in soluble, active form in a heterologous host has not been previously reported. It is especially noteworthy that this was a mammalian protein expressed in a prokaryotic (bacterial) host. It should further be considered that this protein incorporates prosthetic groups, which add a further complication to the goal of proper post-translational processing.

In one embodiment, Met-FX-alpha globin and Met-FX-beta globin are co-expressed, where FX denotes a leader peptide which a recognition site for Factor Xa cleavage activity. FX-alpha globin and FX-beta globin assemble to form a mutant hemoglobin with reversible oxygen binding activity, albeit higher in affinity for oxygen than native hemoglobin. Alternatively, the FX leader, or other fused leader, may be cleaved to obtain a duplicate of native hemoglobin.

In another embodiment, Met-alpha globin and Met-beta globin are co-expressed. This eliminates the need for a cleavage step.

In a third embodiment, des-val-alpha globin and des-val beta globin are co-expressed. Native alpha and beta globin both begin with valine. The valine may, however, be replaced with methionine, which is of similar hydrophobicity.

In further embodiments, one or more codons of the native genes are altered so that an alpha and/or beta globin-related protein characterized by one or more amino acid differences (insertions, deletions or substitutions) from the native species is produced. Globin Pseudodimers (Expecially Di-Alpha and Di-Beta Globins) and Genetically Fused Hemoglobin Pseudotetramers, etc.

A new protein, di-alpha globin, has been prepared, which consists of two alpha globin amino acid sequences covalently connected by peptide bonds, preferably through an intermediate linker of one or more amino acids. Surprisingly, these "genetically fused" alpha globin chains were capable of appropriately folding and combining with beta globin and heme to produce a functional hemoglobin analogue. The term "genetically fused" refers to the method of production. Two copies of the globin gene are fused together, preferably with a spacer DNA encoding the amino acid linker, so the construct directly encodes the desired di-alpha globin. The term "analogue" is used because in native hemoglobin, the alpha1 and alpha2 subunits are noncovalently bound. The analogous preparation of di-beta globin has also been accomplished. Methods for preparation of an analogous $\alpha_1\beta_2$ (or $\beta_2\alpha_1$) globin pseudodimer have been proposed.

The preparation of "genetically fused" hemoglobins avoids the disadvantages of chemical crosslinking. The latter is inefficient and often requires deoxygenation of the hemoglobin solution and the presence of another molecule (e.g., inositol hexaphosphate or 2,3-DPG) to prevent competing reactions.

In a preferred embodiment, the di-alpha globin and/or the beta globin contain mutations which reduce the oxygen-binding affinity of the hemoglobin analogue in solution so as to approach the oxygen-binding characteristics of whole blood.

The di-alpha hemoglobin advantageously exhibits a substantially longer half-life in the circulatory system than does conventional (des-val) recombinant hemoglobin. Preferably, in humans, the half-life exceeds 9 hours at a dose of at least 1 gm/kgm body weight. This would be expected to correspond to a half-life of about 3 hours in rats given a comparable does.

Since the fusion prevents dissociation of the hemoglobin into αβ dimers, kidney function is protected.

The di-alpha, di-beta and alphabeta globins can be expressed in cells conventionally used for expression of recombinant proteins especially bacteria and yeast.

BRIEF DESCRIPTION OF THE DRAWINGS

FIGS. 2a-1 to 2b-3 : Flowcharts for construction of plasmid pDL III-1a (2a-1 and 2a-2) bearing dicistronic Des-Val-Alpha globin gene under control of TAC promoter, and polycistronic di-alpha/beta co-expression plasmid pDL III-47a (2b-1 to 2b-3).

FIGS. 3a and 3b: Flowchart for construction of plasmid for co-expression of Met-alpha and Met-beta globins, pDL III-13e (3a and 3b).

FIGS. 4a to 4c: Oligonucleotides for construction of synthetic FX-alpha and FX-beta globin genes (4a to 4c). The top strand is shown 5' to 3' and the bottom strand as 3' to 5'. Areas of overlap between complementary synthetic oligonucleotides are shown as areas where both strands are shown in the same case letters. The PstI site that joins FX-alpha and FX-beta occurs at the overlap of SJH I-35a and SJH I-36b.

FIGS. 5a to 5c: Synthetic gene for expression of Met-FX-alpha and Met-FX-beta globin (5a to 5c). Region A contains the alpha globin gene and region B the beta globin gene. The location of the Factor X sequence and the two Shine-Delgarno sequences (SD#1 and SD#2) in both regions is indicated. Selected restriction sites are also found. The translated amino acid sequences for the ribosomal loader and Met-FX-alpha/and beta-globin are given.

FIG. 7: Oligonucleotides for construction of mutant hemoglobins (differing in amino acid sequence from conventional hemoglobin).

FIG. 8: Oligonucleotides for construction of plasmids which do not encode the Factor Xa substrate recognition site.

FIGS. 12a to 12c: Shows the sequence of a preferred synthetic gene for expression of (des-Val)-alpha-(GlyGly)-alpha and des-Val beta globin (12a to 12c). A shows the region (EcoRI to PstI) containing Shine-Delgarno ribosomal binding sites (SD#1 and SD#2), the sequence expressing the octapeptide Met . . . Glu) which serves as a cotranslational coupler, and the sequence encoding the two nearly identical alpha globin-like polypeptides and the interposed Gly-Gly linker. The first alpha globin sequence begins "Met-Leu", that is, it contains an artifactual methionine, omits the valine which is the normal first residue of mature alpha globin, and continues with the second residue, leucine. The second alpha globin sequence begins "Val-Leu", immediately after the underlined "Gly-Gly" linker. Start and stop codons are underlined. B shows the analogous region (PstI to HindIII) containing the coding sequence for des-Val beta globin. A and B are connected at the PstI site to form a single polycistronic operon.

FIG. 13a shows an XbaI-BamHI fragment of PDL III-47a.

FIG. 16: Plasmid pDL IV-67a

FIG. 17: Plasmid pJR VI-54a

FIGS. 19a to 19c: Flowchart showing the construction of various expression vectors featuring lambda $P_L$ regulation of various polycistronic globin operons (19a to 19c).

FIGS. 20a and 20b: Nucleotide Sequence of GAL-GAP promoter, with restriction sites indicated (20a and 20b). The region from SphI to EcoRV contains a synthetic $GAL_{1-10}$ regulatory region (M. Johnston and R. Davis. 1984. Molecular and Cellular Biology, 4:1440–1448). The UAS is in the region numbered 29–63 on this Figure. The region from EcoRV to the XbaI site contains the consensus GAP491 transcriptional start region, with the approximate start of transcription being at 395. (L. McAlister and M. J. Holland. 1983. J. Biol. Chem., 260:15019–15027; J. Holland, et al. 1983. J. Biol. Chem., 258:5291–5299.)

FIGS. 21a-1 21b-3: Flowcharts showing construction of beta globin expression cassette (21a to 21a-4 and 21b-1 to 21b-3).

FIGS. 22a-1 to 22b: Flowcharts showing construction of beta globin expression vector pGS4988 (22a-1 and 22a-2) and alpha globin expression vectors pGS4688 and pGS4488 (22b).

FIGS. 23b-1 23b-3: Flowcharts (23a-1 and 23a-2 and 23b-1 to 23b-3) showing construction of an alpha globin expression cassette and of vectors pGS289 and pGS389 for co-expression of alpha and beta globin from the same plasmid. Note that alpha and beta globin are expressed from separate promoters.

FIGS. 25a-1 25b: Flowchart (25a-1 to 25a-3) showing construction of di-alpha/beta hemoglobin yeast expression vector and map of plasmid pGS3089 (25b).

FIG. 28(c) is a top view of a 4-helical bundle, with attachment sites marked.

DETAILED DESCRIPTION OF THE PREFERRED EMBODIMENTS

Hemoglobin Structure

Figure 1:
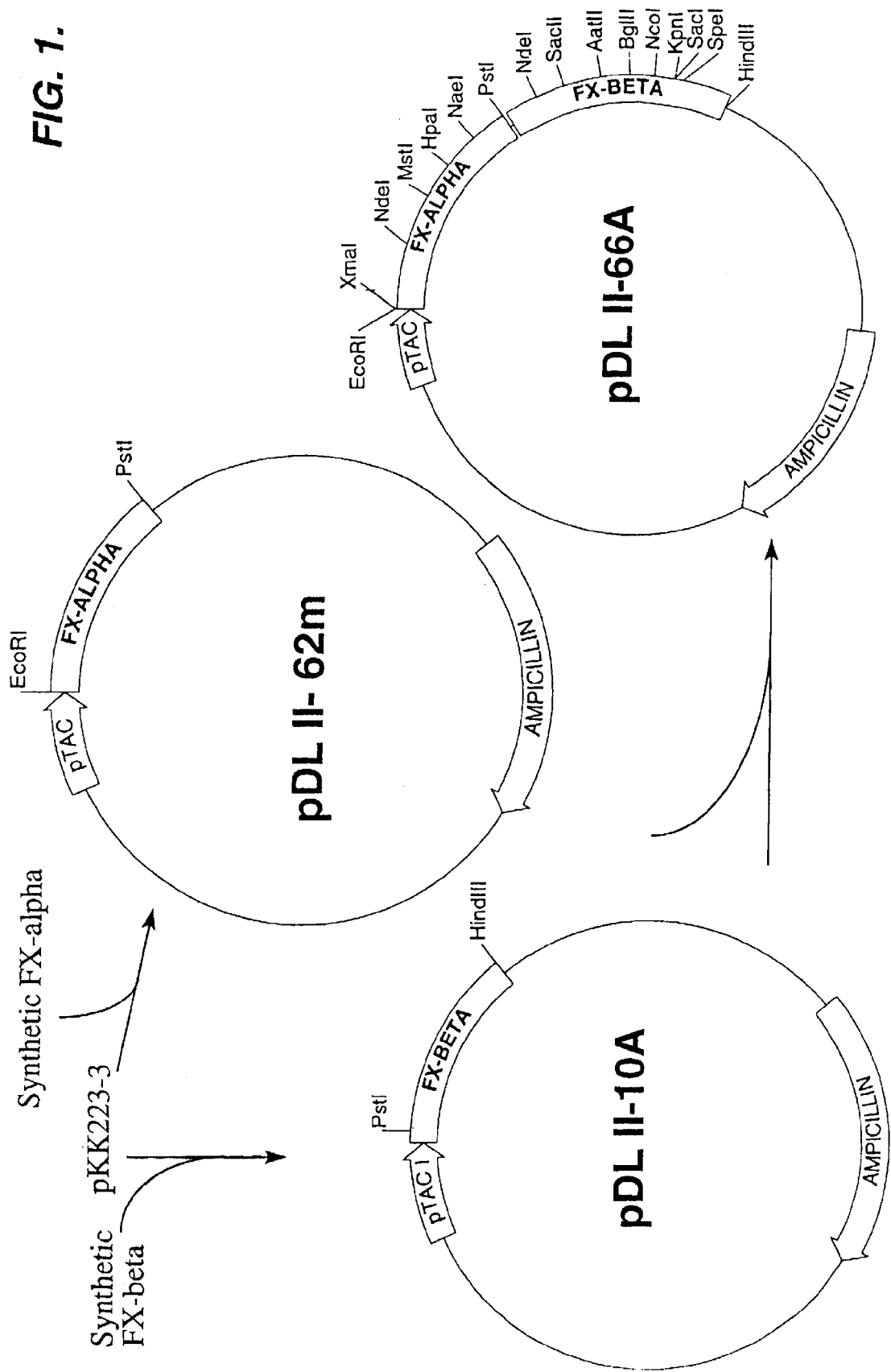
FIG. 1: Flowchart for construction of plasmids for expression of FX-alpha globin (pDL II-62m), FX-beta globin (pDL II-10a), and FX-hemoglobin (pDL II-66a).
Figures 1, 2A:
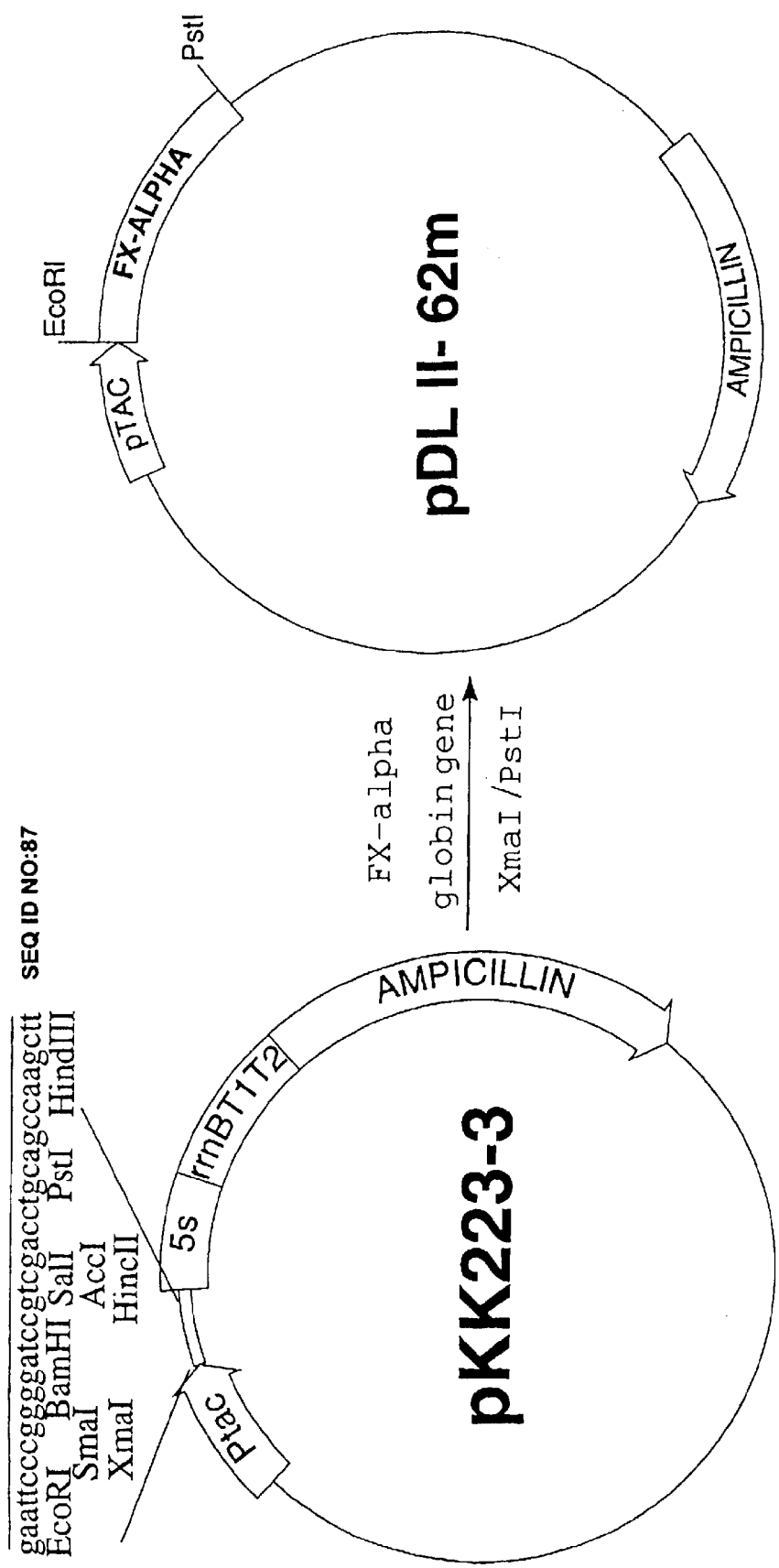
Figures 2, 2A:
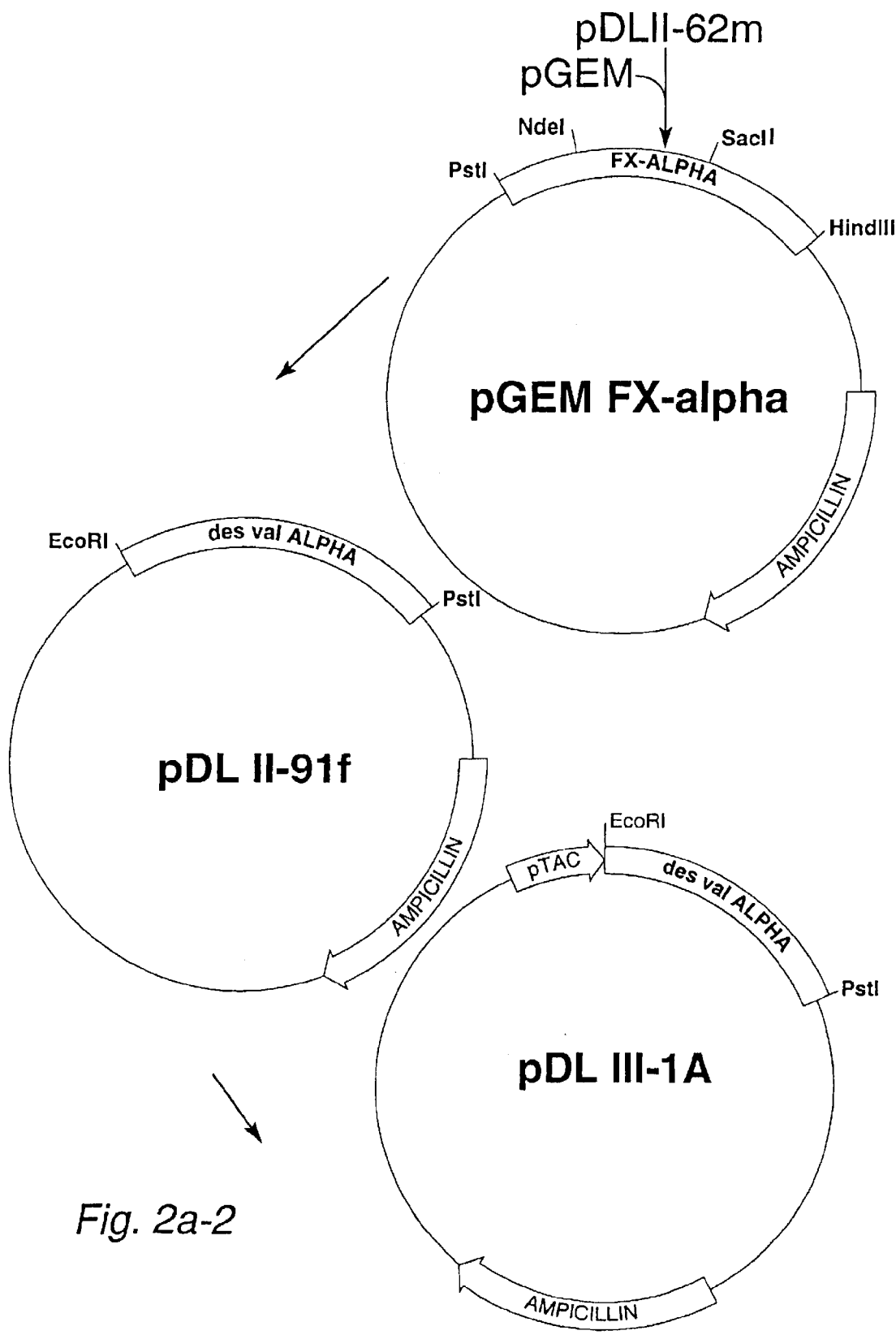
Figures 2, 2B:
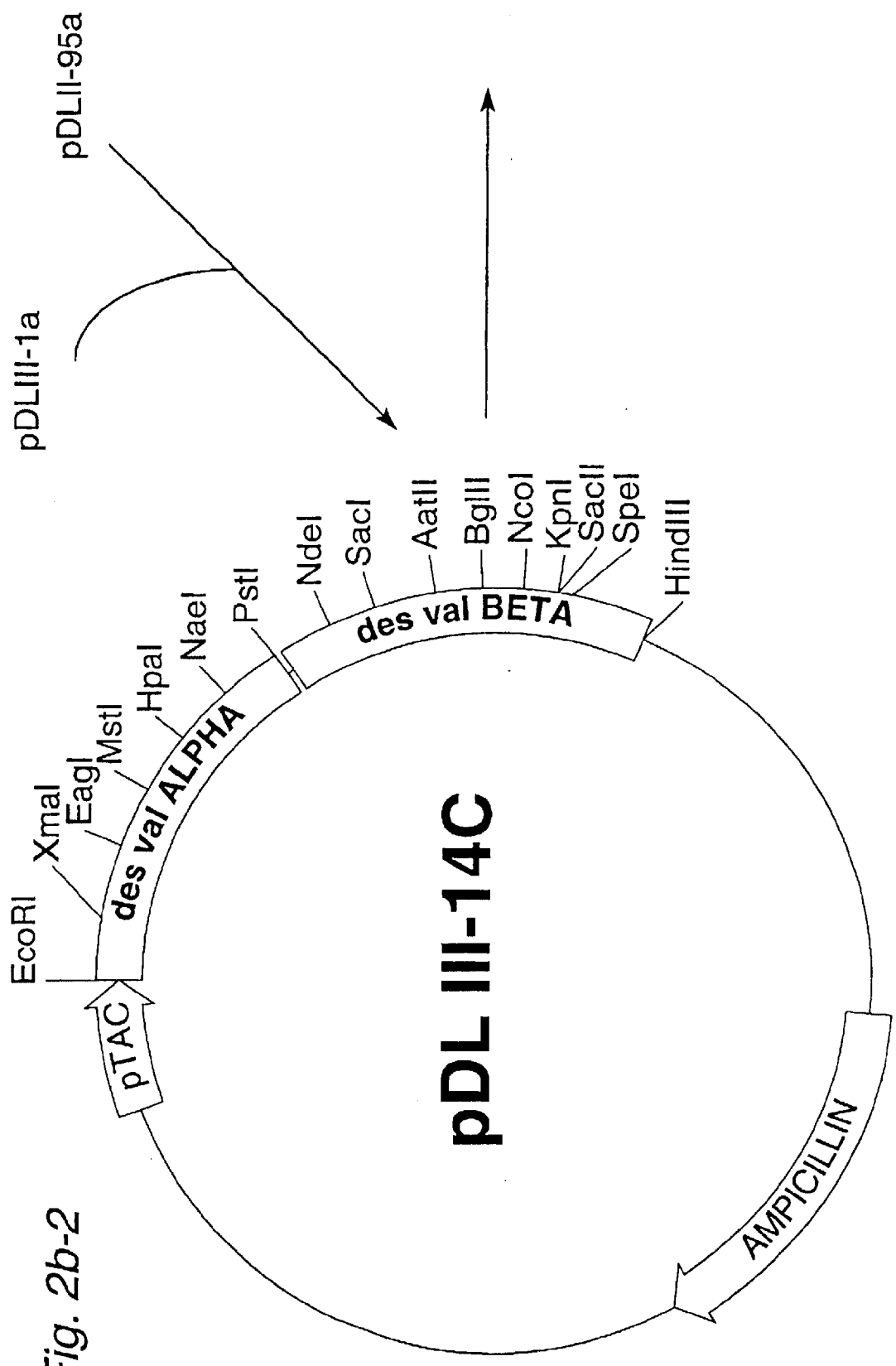
Figures 2, 2B, 3:
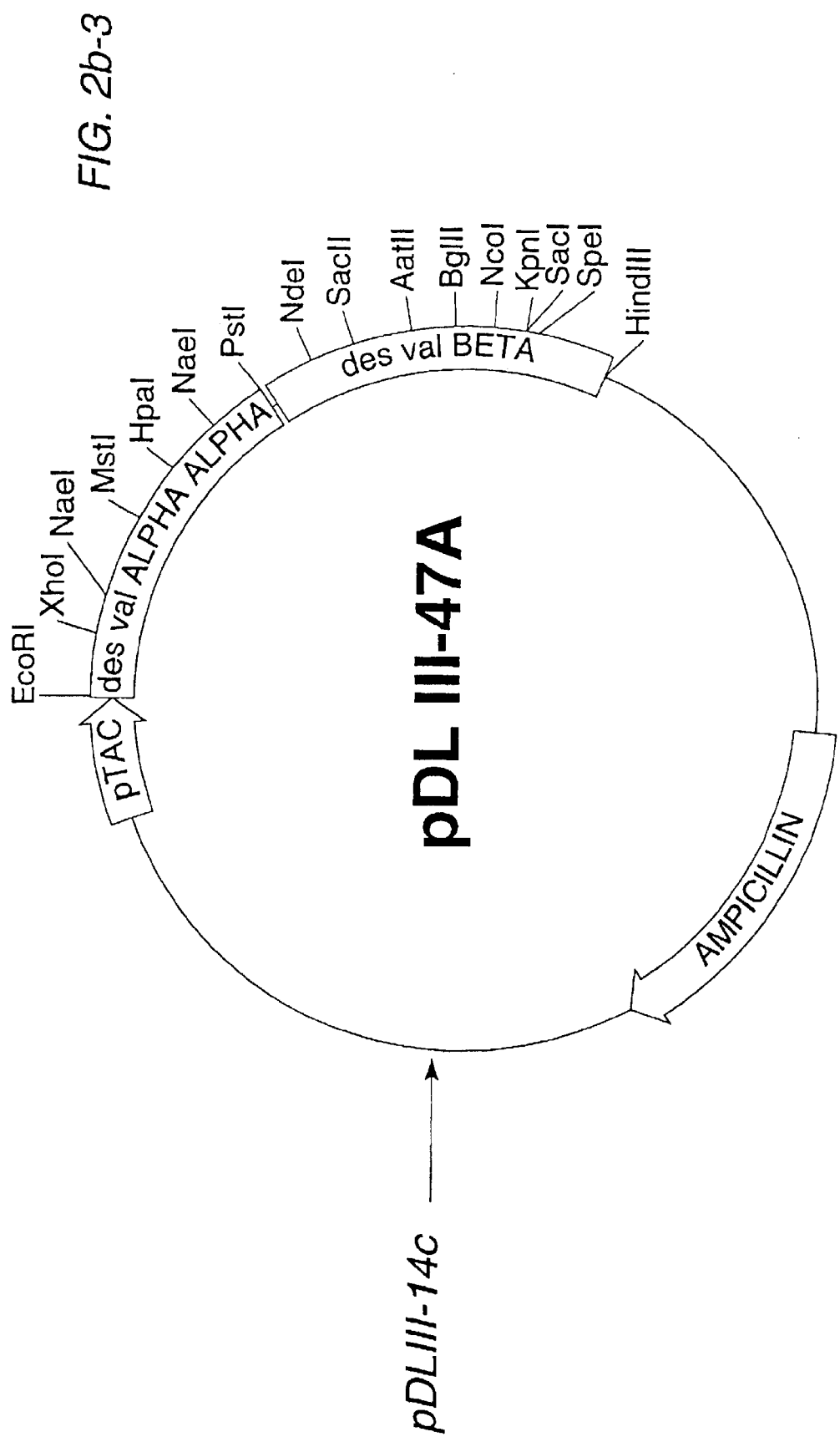
Figure 3A:
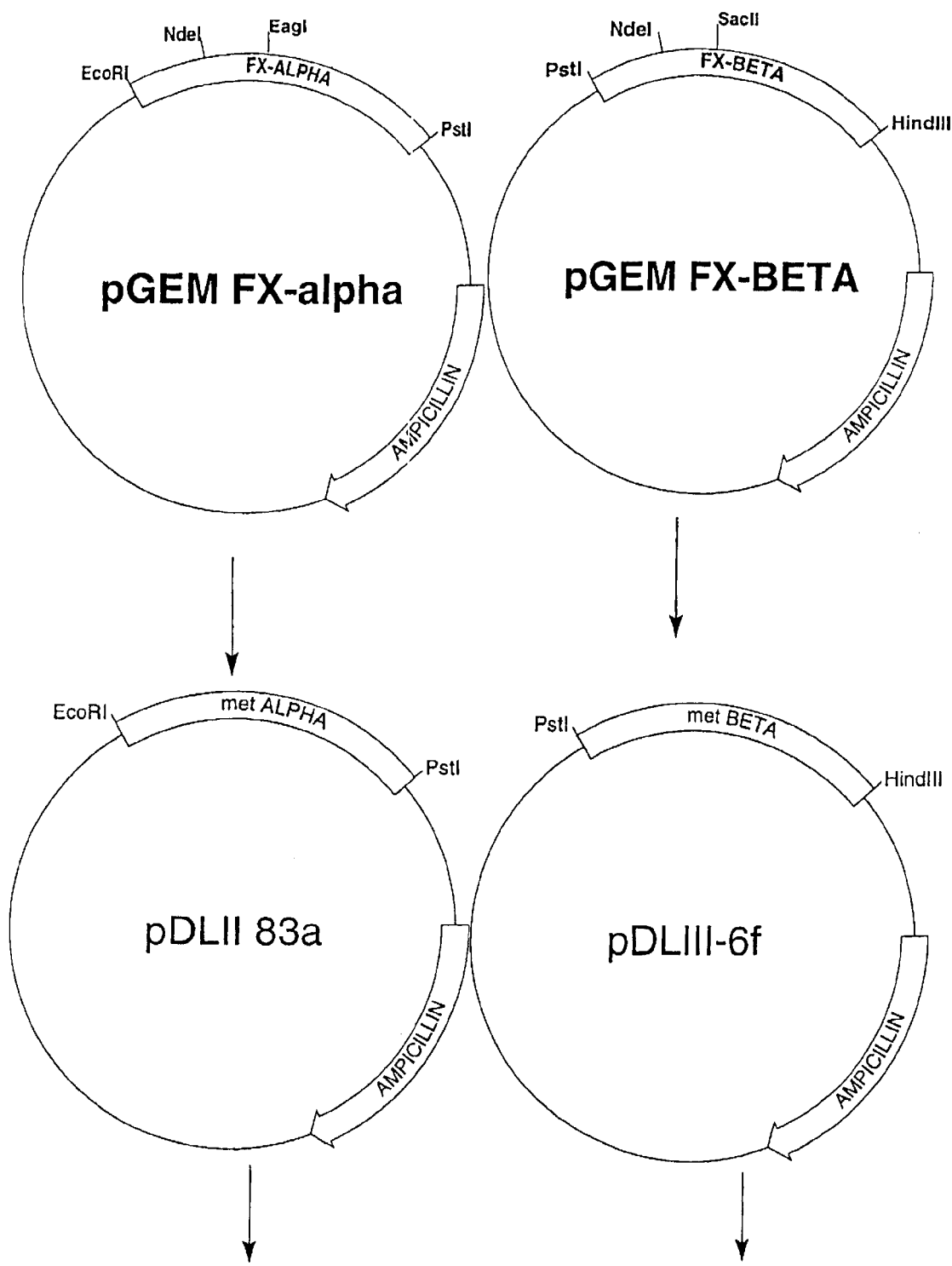

The structure of conventional hemoglobin is well known. We herewith incorporate by reference the entire text of Bunn and Forget, eds., *Hemoglobin: Molecular, Genetic and Clinical Aspects* (W. B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981).

The primary structure of a polypeptide is defined by its amino acid sequence and by identification of any modifications of the side chains of the individual amino acids.

About 92% of the normal adult human hemolysate is Hgb A (designated alpha2 beta2, because it comprises two alpha and two beta chains). The alpha chain consists of 141 amino acids (See FIG. 12). The iron atom of the heme (ferroprotoporphyrin IX) group is bound covalently to the imidazole of his 87 (the "proximal histidine"). The beta chain is 146 residues long (see FIG. 12) and heme is bound to it at his 92.

Other recognized hemoglobin species are Hgb A$_2$ ($\alpha_2$ $\alpha_2$ $\delta_2$) Hgb A$_{1a}$, Hgb A$_{1b}$, and Hgb A$_{1c}$, as well as the rare species Hgb F ($\alpha_2$ gamma$_2$), Hgb Gower-1 (Zeta$_2$ epsilon$_2$), Hgb Gower-2 (alpha$_2$ epsilon$_2$), Hgb Portland (Zeta$_2$ gamma$_2$), and Hgb H (beta$_4$) and Hgb Bart (gamma$_4$). They are distinguished from Hgb A by a different selection of polypeptide chains.

Segments of polypeptide chains may be stabilized by folding into one of two common conformations the alpha helix and the beta pleated sheet. In its native state, about 75% of the hemoglobin molecule is alpha-helical. Alpha-helical segments are separated by segments wherein the chain is less constrained it is conventional to identify the alpha-helical segments of each chain by letters, e.g., the proximal histidine of the alpha chain is F8 (residue 8 of helix F). The non-helical segments are identified by letter pairs, indicating which helical segments they connect. Thus, non-helical segment BC lies between helix B and helix C. In comparing two variants of a particular hemoglobin chain, it may be enlightening to attempt to align the helical segments when seeking to find structural homologies. For the amino acid sequence and helical residue notation for conventional human hemoglobin A$_o$ alpha and beta chains, see Bunn and Forget, supra, and Table 1 herein.

The tertiary structure of the hemoglobin molecule refers to the steric relationships of amino acid residues that are far apart in the linear sequence, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the very atoms of the molecule.

In its unoxygenated ("deoxy", or "T" for "tense") form, the subunits of hemoglobin (alpha1, alpha2, beta1, and beta2) form a tetrahedron having a twofold axis of symmetry. The axis runs down a water-filled "central cavity". The subunits interact with one another by means of Van der Waals forces, hydrogen bonds and by ionic interactions (or "salt bridges"). The alpha1beta1 and alpha2beta2 interfaces remain relatively fixed during oxygenation. In contrast, there is considerable flux at the alpha1beta2 (and alpha2beta1) interface. In its oxygenated ("oxy", or "R" for "relaxed" form), the intersubunit distances are increased.

The tertiary and quaternary structures of native oxyhemoglobin and deoxyhemoglobin are sufficiently well known that almost all of the nonhydrogen atoms can be positioned with an accuracy of 0.5 Å or better. For human deoxyhemoglobin, see Fermi, et al., J. Mol. Biol., 175: 159 (1984), and for human oxyhemoglobin, see Shaanan, J. Mol. Biol., 171: 31 (1983), both Incorporated by reference.

While analyses of hemoglobin structure tend to focus on the alpha-beta interfaces, it is known that the distance between the amino terminus of one alpha subunit and the carboxyl terminus of the other is about 5.6 Å in the deoxy configuration and 3.3 Å in the oxy configuration.

Definitions

For the purpose of the appended claims, a hemoglobin-like protein is an oxygen binding protein with a plurality of heme prosthetic groups and comprising one or more heterotetramers composed of (a) two alpha globin-like and two beta globin-like polypeptides, (b) one di-alpha globin-like and two beta globin-like polypeptides, (c) two alpha globin-like and one di-beta globin-like polypeptides, (d) one di-alpha globin-like and one di-beta globin-like polypeptides, (e) one fused alpha/beta globin-like polypeptide and separate alpha and beta globin-like polypeptides, or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octamer hemoglobin (2 tetramers), as well as higher multimers.

A human alpha globin-like domain or polypeptide is native human alpha- globin or a mutant thereof differing from the native sequence by one or more substitutions, deletions or insertions, while remaining substantially homologous (as hereafter defined) with human alpha globin, and still capable of incorporating heme and associating with beta globin. A beta globin-like domain or polypeptide is analogously defined. Subunits of animal hemoglobins or mutants thereof which are sufficiently homologous with human alpha or beta globin are embraced by the term "human alpha or beta globin-like domain or polypeptide." For example, the subunits of bovine hemoglobin are within the scope of these terms. The alpha and beta globin-like polypeptides may be referred to collectively as "globins". For the sake of convenience the term "polypeptide" may refer to a unitary chain or to a domain of a longer polypeptide chain.

A "genetically fused hemoglobin" is a hemoglobin-like protein comprising at least one "genetically fused globin-like polypeptide" (globin pseudooligomer), the latter comprising two or more globin-like domains which may be the same or different. A di-alpha globin-like polypeptide is one which consists essentially of two alpha globin-like polypeptide sequences (domains) connected by peptide bonds between the normal C-terminus of the first alpha globin-like polypeptide (domain) and the normal N-terminus of the second alpha globin-like polypeptide (domain). These two sequences may be directly connected, or connected through a peptide linker of one or more amino acids; the term "peptide bonds" is intended to embrace both possibilities. Alpha globin chains crosslinked at the N- and C-terminals other than by peptide bonds (e.g., by DIDS) are not di-alpha globins. The di-alpha globin-like polypeptide must be capable of folding together with beta globin and incorporating heme to form functional hemoglobin-like protein. The di-beta globin-like polypeptide is analogously defined. A di-alpha or di-beta globin-like polypeptide with a mutation in only one of the component domains is called "asymmetric".

It is also possible to provide an "alpha/beta globin-like pseudodimer" in which an alpha globin-like domain is connected by peptide bonds to a beta globin-like domain. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha globin-like polypeptides or domains) of the present invention have at least about 75% sequence identity with wild-type human alpha globin. However; a polypeptide of lesser sequence identity may still be considered "substantially homologous" with alpha globin if it has a greater sequence identity than would be expected from chance and also has the characteristic higher structure of alpha globin and similar biological activity. (Note that, as elsewhere explained, an alteration in oxygen affinity (P50), intravascular retention, or cooperativity may be desired, and does not render the mutant nonhomologous if it can still contribute to reversible oxygen-binding activity.) By way of comparison, Artemia's heme-binding domains are considered homologous with myoglobin even though the primary sequence similarity is no more than 27%, as alignment of the heme-binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

Over a hundred mutants of human hemoglobin are known, affecting both the alpha and beta chains, and the effect of many of these mutations on oxygen-binding and other characteristics of hemoglobin are known. The human alpha and beta globins themselves differ at 84 positions. In addition, interspecies variations in globin sequence have been extensively studied. Dickerson, *Hemoglobin: Structure, Function, Evolution and Pathology*, ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin-like protein which, in keeping with the definition thereof, will reversibly bind oxygen. The following resources may be used to identify conservative substitutions (and deletions or insertions):

(a) data on functional hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other oxygen-binding proteins, and molecular modelling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer-Verlag: 1979) and FIGS. 3–9 of Creighton, *Proteins: Structure and Molecular Properties* (W. H. Freeman: 1983).

While the data from (a)–(α) is moss useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative:

| | |
|---|---|
| I | small aliphatic, nonpolar or slightly polar residues - Ala, Ser, Thr (Pro, Gly) |
| II | negatively charged residues and their amides - Asn Asp Glu Gln |
| III | positively charged residues - His Arg Lys |
| IV | large aliphatic nonpolar residues - Met Leu Ile Val (Cys) |
| V | large aromatic residues - Phe Tyr Trp |

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schimer would merge I and II above. Note also that Tyr, because of its hydrogen bonding potential, has some kinship with Ser, Thr, etc.

In general, functionality is less likely to be affected by mutations at surface residues, at least those not involved in either the heme crevice or the subunit contacts. In addition, "loops" connecting alpha helices, as well as free amino or carboxy termini, are more tolerant of deletions and insertions.

A "Met FX alpha globin" is an alpha globin-like polypeptide comprising an N-terminal methionine, a oligopeptide which acts as a recognition site for Factor Xa (e.g., Ile-Glu-Gly-Arg), and an alpha globin-like sequence (e.g., Val-His-Leu-Thr-Pro . . . ) which may correspond to wild-type alpha globin or to a mutant thereof as taught herein. The term "Met FX alpha globin" is sometimes abbreviated as "FX alpha globin". "FX beta globin" is an analogously defined beta globin-like polypeptide.

"Met-alpha globin" is an alpha globin-like polypeptide with an extra N-terminal methionine. The second amino acid is valine, which is the first amino acid of mature wild-type alpha globin. Met-beta globin is analogously defined. A "Des-FX alpha globin" gene (or "dFX alpha globin") is a Met-alpha globin gene obtained by excising the FX codons from a Met-FX alpha globin gene. Note that "Met-Hgb" is used to refer to methionyl Hgb formed from methionyl-alpha globin and methionyl-beta globin.

"Des-Val-alpha globin" (or "dVal alpha globin") is an alpha globin-like polypeptide wherein methionine is substituted for the valine which begins the sequence of mature wild-type alpha globin. Des-Val-beta globin is analogously defined. Des-Val-alpha/alpha globin (di-Des-Val-alpha globin) is a "di-alpha globin" in which a "Des-Val-alpha" sequence is linked via an appropriate peptidyl linker to an alpha globin-like sequence which begins with Val.

The alpha and beta globin-like chains need not correspond exactly in sequence to the alpha and beta globins of "conventional" hemoglobin. Rather, mutations may be introduced to alter the oxygen affinity or stability of the hemoglobin, or the ease of expression and assembly of the individual chains. By way of example and not limitation, several mutant hemoglobins have been prepared by the method of this invention. Guidance as to further mutations is provided, e.g., by Hoffman and Nagai, U.S. Pat. No. 5,028,588, and Ser. No. 07/443,950, incorporated by reference herein.

The term "low affinity hemoglobin-like protein" refers to a hemoglobin-like protein having a $P_{50}$ which is at least 10% greater than the $P_{50}$ of cell free hemoglobin $A_0$ under the same conditions. Preferably, the protein, if used as a blood substitute, qualifies as a low affinity protein, and more preferably, its $P_{50}$ is closer to the $P_{50}$ of whole blood cells than to that of cell free hemoglobin.

The term "high affinity hemoglobin-like protein" refers to a hemoglobin-like protein having a $P_{50}$ which is at least 10% less than the $P_{50}$ cell free hemoglobin $A_0$ under the same conditions.

Low and High Affinity Mutants

Low affinity mutant hemoglobins, i.e., those with "right shifted" oxygen equilibrium binding curves relative to cell-free conventional hemoglobin, have many potential uses. Most notably, mutant hemoglobins that have an oxygen affinity similar to whole red blood cells may be used as an oxygen-carrying transfusion substitute in place of donated red blood cells, eliminating the risk of infection and alleviating problems with supply. Cell-free native human hemoglobin cannot function as a transfusion substitute, among other reasons because oxygen is bound too tightly. In addition, because cell-free hemoglobin solutions do not need to be cross-matched and are expected to have a longer shelf life than whole blood, low affinity hemoglobin solutions may be widely used in situations where whole blood transfusion is not feasible, for example in an ambulance or on a battlefield. Mutant hemoglobins that have an even lower oxygen affinity than red blood cells may in fact deliver oxygen more effectively in many situations. Mutant hemoglobins that have a somewhat higher oxygen affinity than whole blood (but a lower affinity than cell-free native human hemoglobin) will still function as an adequate transfusion substitute and may in fact deliver oxygen more effectively than red blood cells in some situations. This is because oxygen is released directly to plasma from hemoglobin-based solutions, without the need to diffuse through the red cell membrane, and because cell-free hemoglobin may penetrate into regions not accessible to red blood cells. As an example, low affinity mutant hemoglobin is expected to deliver oxygen effectively during coronary artery balloon angioplasty procedures, whereas circulation of red blood cells is obstructed during such procedures. Low affinity mutant hemoglobin may also be useful as a perfusion component in organ preservation prior to transplantation or as a mammalian cell culture additive.

High affinity mutant hemoglobin may have utility in other situations. For example, perfluorocarbon-based blood substitute preparations are under clinical study tor enhancement of radiation therapy and certain chemotherapy treatments of solid tumors (Dowling, S., Fischer, J. J., and Rockwell, S. (1991) Biomat. Art. Cells Imnobil. Biotech, 19, 277; Herman, T. S. and Teicher, B. A. (1991) Biomat. Art. Cells and Immobil. Biotech, 19, 395; Holden, S. A., Teicher, B. A. and Herman, T. S. (1991) Biomat. Art. Cells and Immobil. Biotech, 19, 399. ) The basis of these investigations is the fact that oxygen is a required component of the cell toxicity action of radiation and certain chemotherapy reagents. Solid tumors frequently exhibit extremely low partial oxygen pressure in the interior of the tumor, rendering therapy inefficient. Perfluorocarbon-based oxygen-carrying solutions appear to dramatically enhance certain tumor therapies, and hemoglobin-based blood substitutes are expected to have a similar utility. It is likely that cell-free hemoglobin, unlike whole red blood cells, will be able to penetrate the interior region of tumors for delivery of oxygen. Actual percent of oxygen released by a cell-free hemoglobin preparation is not a direct function of $P_{50}$, but rather depends on the shape of the oxygen equilibrium binding curve between the two pressures representing the partial oxygen pressure of the lungs (where oxygen is loaded onto hemoglobin) and the partial pressure of the tissue where oxygen is unloaded. Therefore, it is possible that a high affinity mutant hemoglobin would be preferred as a tumor therapy adjuvant. A high affinity hemoglobin would retain its bound oxygen throughout the normal circulatory system, where partial oxygen pressure remains relatively high, but release its oxygen in the extremely oxygen-depleted tumor interior. Normal or low affinity oxygen might have less oxygen available for release by the time it reaches the interior of the tumor.

Possible low affinity mutants are discussed in detail, by way of example and not of limitation, in Table 1 (natural low affinity hemoglobin mutants) and Table 2-(candidate non-naturally occurring low affinity hemoglobin mutants) of Hoffman, et al., U.S. Pat. No. 5,028,588. Low affinity mutants of particular interest are the Presbyterian (beta $Lys^{108}$) beta $Phe^{63}$, beta $Ile^{67}$, and Kansas (beta $Thr^{102}$) mutants.

Naturally occurring high affinity hemoglobin mutants are also known, see Bunn and Forget, Table 14-1, and candidate non-naturally occurring high affinity hemoglobin mutants may be proposed in view of the known mutants and hemoglobin structure. Particularly preferred high affinity mutants are set forth in Table 400.

It should be noted that genetic fusion and crosslinking can affect oxygen binding affinity.

Cysteine Mutations and Disulfide Bridge Formation

Cysteine mutations are of value for increasing the stability of the tetramer (See U.S. Pat. No. 5,028,588 and Ser. No. 07/443,950. They also facilitate constructing poly (tetrameric) (n>=2) hemoglobins with increased intravascular half-life. This is because the cysteines on adjacent tetramers (including pseudotetramers) can be oxidized to form a disulfide bridge, covalently coupling the tetramers.

A variety of sites are available for introduction of cysteines into a hemoglobin-like protein.

The criteria governing site selection are: (1) the mutation does not affect functionality; (2) the side chain is accessible to water in oxy or deoxy structure; (3) the site should lie on the surface of the folded protein; (4) the sulfhydryl of the side chain should extend away from the surface rather than toward the interior of the molecule; (5) the site should be in a portion of the molecule that is not directly involved in the R->T transition; (6) the change should be in a portion of the molecule that does not have a tightly fixed position (such regions generally give indistinct X-ray diffraction patterns); (7) the mutations will not destroy the local secondary structure, i.e., avoid pro->cys mutations, Which might result in a refolding problem; and (8) if possible, a conservative change should be made such as ser->cys or ala>cys. A mutation does not necessarily have to meet all of the above requirements to be useful. For example, one might envision a site that is involved in the R->T transition (cf. 5 above) but confers a beneficial change in $P_{50}$ (cf. 1 above) because of that involvement. The most important considerations are that the mutation does not abolish $O_2$ binding and that the cysteine is accessible for participation in disulfide bonding.

Candidate sites on the alpha surface include: his72, asn 78, asn68, ala71, thr67, lys7, lys11, thr8, ala12, thr118, lys16, ala45, glu116, gly15, his112, thr24, glu23, lys60, lys56, his50, gly51, glu53, ser49, asp47, gln54, his45, lys90, ala82, lys61, ala19, his20, asp85, ser81, asp75, asp74, lys139, asp64, and gly18 (total 40 amino acids).

Candidate sites on the beta surfaces includes: asp79, his2, leu3, thr4, glu6, ser9, thr12, ala13, gly16, lys17, val18, asn19, val20, asp21, glu22, lys65, ser72, ala76, his77, asp79, asn80, gly83, ala86, thr87, glu90, lys95, lys59, glu43, ser44, asp47, ser49, thr50, ala53, asp52, lys61, glu121, lys120, thr123, lys66, asp73, ala62, his116, his117 (total 45 amino acids).

There are a number of naturally occurring mutants which already show mutations at these sites. These are listed below:

| Residues | Region | Mutation |
| --- | --- | --- |
| 19 | AB1 | ALA->GLU |
|  |  | ALA->ASP |
| 54 | E3 | GLN->ARG |
|  |  | GLN->GLU |
| 71 | E20 | ALA->GLU |
| 75 | EF4 | ASP->GLY |
|  |  | ASP->HIS |
|  |  | ASP->TYR |
|  |  | ASP->ASN |
| 81 | F2 | SER->CYS |
| 47 | CE5 | ASP->GLY |
|  |  | ASP->HIS |
|  |  | ASP->ASN |

If the pseudo-octamer (n=2) is formed by directly linking two pseudo-tetramers via a disulfide bond, the halflife in serum may be influenced by the rate at which endogenous serum small molecule thiols (such as glutathione) reduce the disulfide bond. The mechanism of these reactions involves the thiolate anion as the actual reducing species (Creighton, T. E. (1978) *Prog. Biophys. Molec. Biol.*, 33:259–260; Creighton, T. E. (1975) *J. Mol. Biol.*, 96:767; Creighton, T. E. (1977) *J. Mol. Biol.*, 113:313). Thus the rate of reduction will be a function of the molecular electrostatic environment in the vicinity of the disulfide bond. A slower rate of reduction would be predicted if the disulfide was located in an electrostatically negative environment, due to the repulsion of the thiolate anion. In the case of glutathione, even the unreactive transient protonated species has a net negative charge and would be repulsed, thus further reducing the rate of disulfide reduction.

A surface or near-surface amino acid residue of di-alpha or di-beta hemoglobin that is located in close proximity to a negatively charged surface residue might therefore be a good choice for location of a single cysteine mutation in the di-alpha or di-beta polypeptide. Although formation of the initial disulfide bond between two such cysteines might also be slower because of repulsion between the negative charges on the two hemoglobin molecules in the vicinity of the cysteines, the reaction could be facilitated by use of high salt or high pH during the in vitro bond formation reaction. If carried out under deoxy conditions in a redox buffer, the reaction might also be facilitated by temperature elevation.

Preferred Sites for cys Mutations Proximal to Negative Charged Residues

| alpha ser49 | near asp47 | naturally occurring ser49 to arg has normal $O_2$ affinity |
|---|---|---|
| alpha his20 | near glu23 | naturally occurring his20 to tyr, gln, arg have no known undesirable properties |
| alpha lys16 | near glu116 | naturally occurring lys to glu has normal $O_2$ affinity |
| alpha his50 | near glu30 | naturally occurring his50 to asp has no known undesirable properties |
| beta thr50 | near asp52 | naturally occurring thr50 to lys has no known undesirable properties |
| beta lys65 | near asp21 | |
| beta asn19 | near asp21 | |

Surface or near-surface cysteine mutations in general are not expected to have major effects on the functionality of the hemoglobin pseudotetramer. Cysteine mutations would not be expected to significantly destabilize alpha helices, and surface residues are not directly involved in the oxygen binding properties of hemoglobin. Most surface residues undergo considerable motion and are not tightly constrained. It should also be noted that because of protein breathing motions, the cysteine side chain would not necessarily have to point directly into solution to be accessible for disulfide bond formation.

In addition to the use in construction of a pseudo-octamer, there may be additional uses of surface cysteine mutations. These include: (1) construction of multimeric hemoglobins (n>2) by use of synthetic sulfhydryl reactive peptides with more than two reactive sites; (2) surface cysteine residues could be used to attach chelates that bind radioisotopes for imaging; and (3) surface cysteines could be used to attach bio-active peptides or other therapeutic agents to increase their circulating half-life, or target their delivery. If the attachment of the drug were via a disulfide, the rate of release of the peptide from its carrier could be controlled by neighboring residues. For uses (2) and (3), restriction to one cysteine per di-alpha or di-beta is unnecessary.

Gene Construction and Expression

The DNA sequences encoding the individual alpha (or di-alpha) and beta (or di-beta) globin chains may be of genomic, cDNA and synthetic origin, or a combination thereof. Since the genomic globin genes contain introns, genomic DNA must either be expressed in a host which can properly splice the premessenger RNA or modified by excising the introns. Use of an at least partially synthetic gene is preferable for several reasons. First, the codons encoding the desired amino acids may be selected with a view to providing unique or nearly unique restriction sites at convenient points in the sequence, thus facilitating rapid alteration of the sequence by cassette mutagenesis. Second, the codon selection may be made to optimize expression in a selected host. For codon preferences in *E. coli*, see Konigsberg, et al., PNAS, 80:687–91 (1983). For codon preferences in yeast, see the next section. Finally, secondary structures formed by the messenger RNA transcript may interfere with transcription or translation. If so, these secondary structures may be eliminated by altering the codon selections.

Of course, if a linker is used to genetically crosslink subunits, the linker will normally be encoded by a synthetic DNA. While the di-alpha globin and the beta globin may be expressed separately and then combined with each other and heme in vitro, they are preferably placed on one plasmid.

The present invention is not limited to the use of any particular host cell, vector, or promoter. The host cell may be a microbial, plant or animal cell and, if a plant or animal, it may be in cell, tissue or organ culture, or a cell of a transgenic or chimeric plant or animal. The promoter selected must be functional in the desired host cells. However, the preferred host cells are bacterial (especially, *E. coli*) and yeast (especially *S. cerevisiae*) cells. It preferably is an inducible promoter which, upon induction, provides a high rate of transcription. A preferred bacterial promoter is the Tac promoter, a trp/lac hybrid described fully in DeBoer, U.S. Pat. No. 4,551,433 and commercially available from Pharmacia-LKB. Other promoters which might be used include the temperature sensitive lambda $P_L$ and $P_R$ promoters, as well as the lac, trp, trc, pIN (lipoprotein promoter and lac operator hybrid), gal and heat shock promoters. The promoter used need not be identical to any naturally-occurring promoter. Guidance for the design of promoters is provided by studies of promoter structure such as that of Harley and Reynolds, Nucleic Acids Res., 15:2343–61 (1987) and papers cited therein. The location of the promoter relative to the first structural gene may be optimized. See Roberts, et al., PNAS (USA), 76:760–4 (1979). The use of a single promoter is favored. Suitable yeast expression systems are described in detail elsewhere in this specification.

The vector used must be one having an origin of replication which is functional in the host cell. It desirably also has unique restriction sites for insertion of the globin genes and the desired regulatory elements and a conventional selectable marker. A vector may be modified to introduce or eliminate restriction sites to make it more suitable for further manipulations.

The alpha and beta globin chains may be expressed either directly or as part of fusion proteins. When expressed as fusion proteins, the latter may include a site at which they may be cleaved to release the alpha and beta globin free of any extraneous polypeptide. If so, a site sensitive to the enzyme Factor Xa may be provided, as taught in Nagai and Thorgenson, EP Appl 161,937, incorporated by references herein. Alternatively, the alpha and beta fusion proteins may be synthesized without a cleavable leading amino acid sequence, folded and heme incorporated to yield a hemoglobin analogue.

The direct expression of the alpha and beta globin subunits is desirable. Factor Xa is a blood derivative. Preparations of Factor Xa may therefore contain undesirable blood-associated substances or etiologic agents. In any event, the hemoglobin must be separated from the Factor Xa.

Nagai and Thorgerson, EP Appl 161,937, incorporated by reference herein, teach the construction of fused genes in which DNA coding for a polypeptide of interest is immediately preceded by DNA encoding a cleavage site for Factor Xa, a serine protease. Certain of the peptide sequences to be cleaved by Factor Xa are quoted below (wherein the cleavage site is denoted by an "=")

Ile-Glu-Gly-Arg=Val-His-Leu-Thr CII Fxβ-globin (SEQ ID NO:8)

Ile-Glu-Gly-Arg=Thr-Ala-Thr-Ser Hu prothrombin (SEQ ID NO:9)

Ile-Glu-Gly-Arg=Thr-Ser-Glu-Asp Bo prothrombin (SEQ ID NO:10)

Ile-Asp-Gly-Arg=Ile-Val-Glu-Gly Hu prothrombin (SEQ ID NO:11)

Ile-Glu-Gly-Arg=Ile-Val-Glu-Gly Bo prothrombin (SEQ ID NO:12)

Ala-Glu-Gly-Arg=Asp-Asp-Leu-Tyr Hu antithrombin III (SEQ ID NO:13)

In the above list, "CIIFXβ-globin" refers to a hybrid fusion protein comprising the 31 amino-terminal residues of the lambdaCII protein, the Factor Xa recognition sequence "Ile-Glu-Gly-Arg," (SEQ ID NO:14) and the complete amino acid sequence of human beta globin (which begins "Val-His-Leu-Thr-..." (SEQ ID NO:15)). It will be evident from study of FIG. 4 of the present invention that FX-alpha and FX-beta globins of Example 1 correspond to the native globin preceded by "Met-Ile-Glu-Gly-Arg." (SEQ ID NO:16)

In bacterial mRNA, the site at which the ribosome binds to the messenger is a polypurine stretch which lies 4–7 bases upstream of the start (AUG) codon. The consensus sequence of this stretch is 5'... AGGAGG... 3' (SEQ ID NO:17), and is frequently referred to as the Shine-Dalgarno sequence. Shine and Dalgarno, Nature, 254: 34 (1975). The exact distance between the SD sequence and the translational start codon, and the base sequence of this "spacer" region, affect the efficiency of translation and may be optimized empirically. Shepard, et al., DNA 1: 125 (1985); DeBoer, et al., DNA 2: 231 (1983); Hui, et al., EMBO J., 3: 623 (1984).

In addition, the SD sequence may itself be modified to alter expression. Hui and DeBoer, PNAS (USA), 84:4762–66 (1987). Comparative studies of ribosomal binding sites, such as the study of Scherer, et al., Nucleic Acids Res., 8:3895–3907 (1987), may provide guidance as to suitable base changes. If the hemoglobin is to be expressed in a host other than E. coli, a ribosomal-binding site preferred by that host should be provided. Zaghbil and Doi, J. Bacteriol., 168:1033–35 (1986).

Any host may be used which recognizes the selected promoter and ribosomal binding site and which has the capability of synthesizing and incorporating heme. Bacterial and yeast hosts are preferred.

The intracellularly assembled hemoglobin may be recovered from the producing cells and purified by any art-recognized technique.

Polycistronic Co-Expression of Alpha and Beta Globins and Their Assembly Into Hemoglobin In one embodiment, expression of the alpha and beta globin genes is driven by a single promoter, and the genes are arranged so that a polycistronic messenger RNA transcript is transcribed, from which the separate alpha and beta globin polypeptides are subsequently translated. However, the present invention includes the co-expression of the alpha and beta globin genes from separate promoters, i.e., the host transcribes separate alpha and beta globin mRNAs.

The use of a single promoter is favored on theoretical grounds. Ideally, alpha and beta globin are expressed in stoichiometrically equal amounts. While use of a single promoter does not guarantee equality, it eliminates one unbalancing influence—differences in transcription owing to differences in promoter strength and accessibility. If differences in promoter strength were minimized by use of two identical promoters on the same plasmid, plasmid stability would be reduced as there would be a propensity toward recombination of the homologous regions. We note, however, that in preliminary experiments we have co-expressed alpha and beta globins from separate promoters.

Another justification for using a single promoter is to minimize the number of repressor binding sites.

Preferably, the alpha and beta globin genes are arranged so that the ribosome will translate the alpha globin cistron first. The rationale is that there is some basis for believing that alpha globin affects the folding of beta globin. Nonetheless, the position of the genes may be switched so that beta globin is synthesized first, as is shown in Example G.

The stability of the polycistronic mRNA transcript, the efficiency of its translation into alpha and beta globin, and the folding of the globin chains into tetrameric hemoglobin may be modified by varying the length and base sequence of the intercistronic regions (the region lying between the stop codon of one cistron and the start codon of the next cistron), the phasing of a second cistron relative to a first cistron, and the position and sequence of the ribosomal binding site for the one cistron relative to the preceding cistron.

Figures 2, 21A:
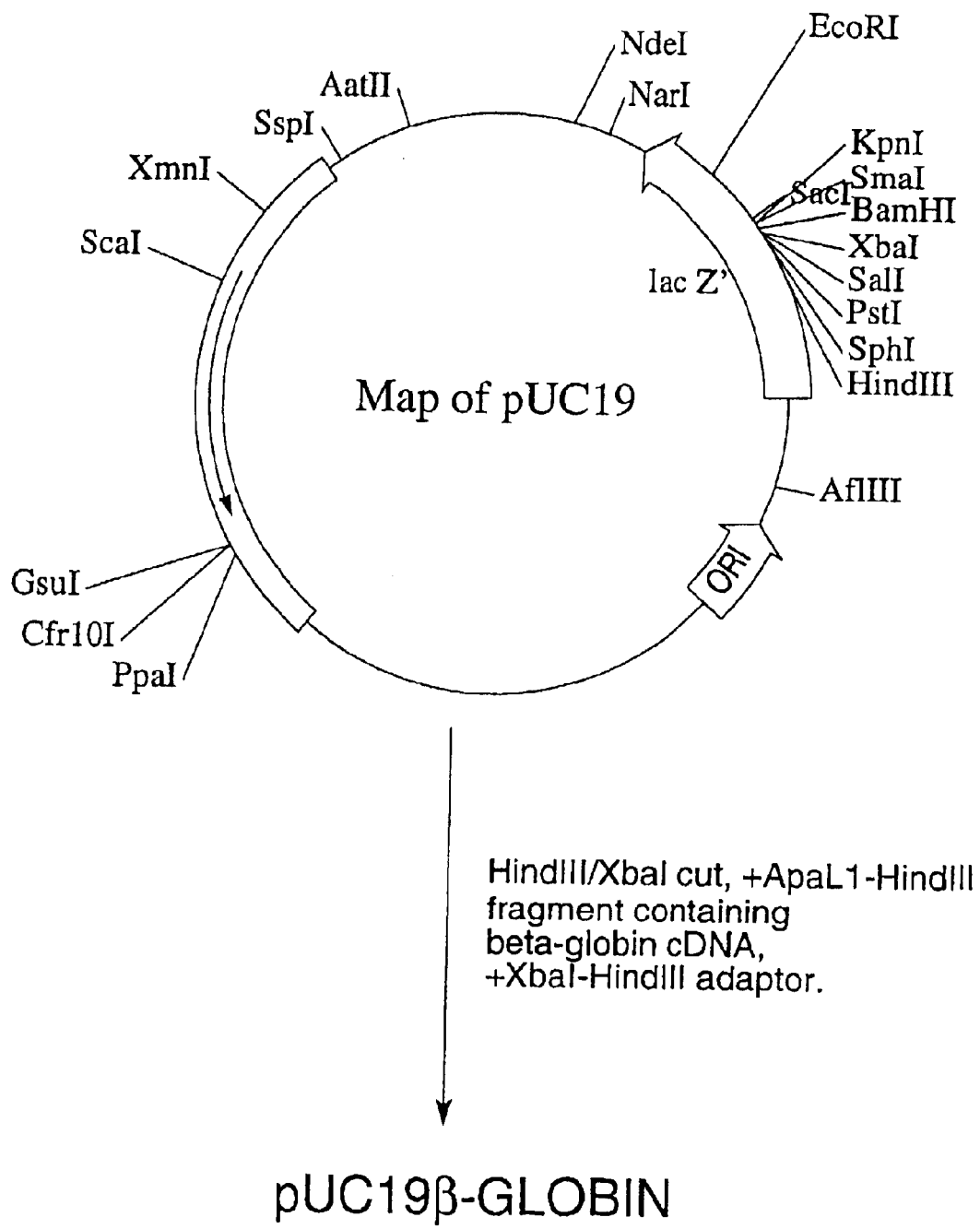
Figures 3, 21A:
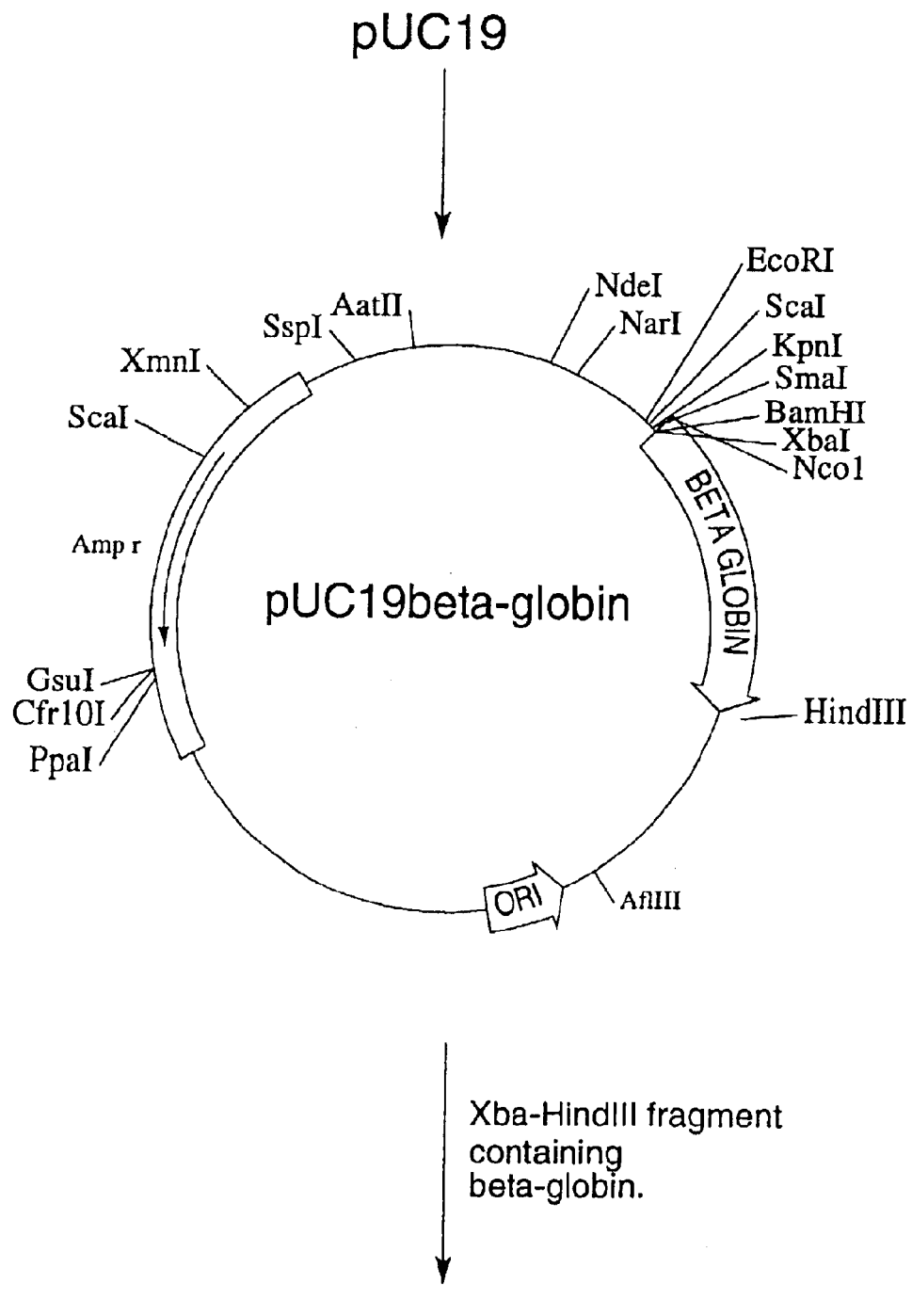
Figures 4, 21A:
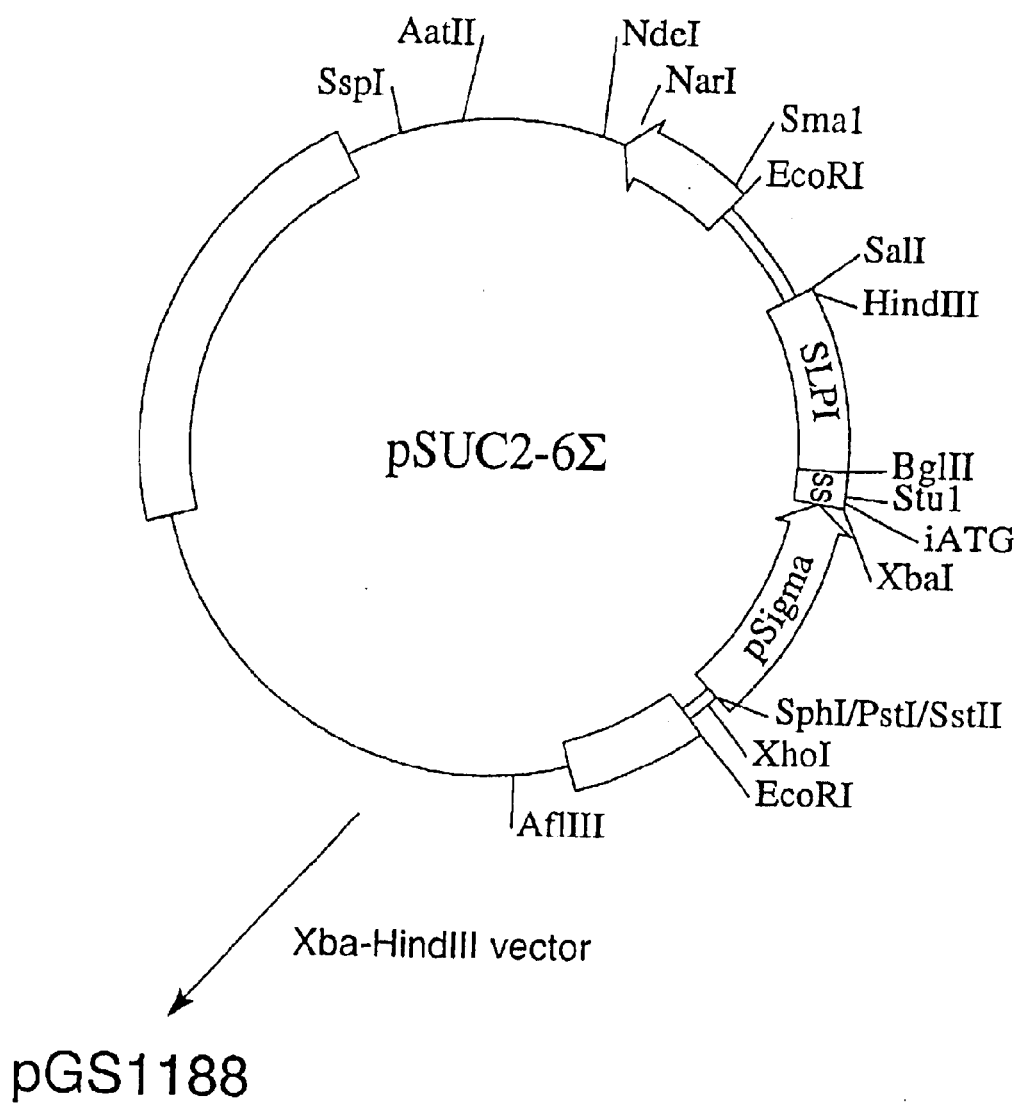

In a preferred embodiment, the alpha and beta globin genes are each preceded by a short "introductory" cistron or "ribosomal loader" which facilities the subsequent translation of the globin cistron. In FIG. 4, region A contains two cistrons and a Shine-Delgarno sequence preceding each cistron. The first Shine-Delgarno sequence (SD#1) is bound by the ribosome, which then translates the first cistron, a short cistron encoding an octapeptide. (This cistron is referred to as an "introductory cistron or ribosomal loader.) The second cistron is a globin gene, in this case, an FX alpha-globin gene. The Shine-Delgarno sequence (SD#2) for facilitating translation of the second cistron actually lies within the first cistron. For this reason, the two are said to be "translationally coupled". Region B is identical in structure, except that the second cistron encodes FX-beta globin. Between regions A and B is a 43-base intercistronic region. The introductory cistrons of regions A and B correspond to the first cistron of the two-cistron expression system denoted pCZ144 in Schoner, et al., Meth. Enzymol., 153: 401–16 (1987). The present invention is not, however, limited to the particular "starter" cistron taught by Schoner, et al.; other introductory cistrons that allow for restart of high level translation of a following cistron may be used.

Guidance as to the design of intercistronic sequences and as to the location of SD Sequences may be obtained by comparing the translational efficiency of spontaneous or controlled mutants of the same polycistronic operon, as exemplified by Schoner, et al., PNAS, 83: 8506–10 (1980). It is also possible to look for consensus features in the intercistronic regions of different operons. McCarthy, et al., EMBO J., 4: 519–26 (1985) have identified a translation-enhancing intercistronic sequence in the E. coli at operon.

The present invention is intended to reduce or avoid the localization of the hemoglobin or its component polypeptides into inclusion bodies. Consequently, a further feature of the invention is that the functional hemoglobin is substantially found (preferably over 80%) in the soluble fraction of the cell. It appears that with this invention, over 90% of the functional hemoglobin can be so directed when alpha$_2$beta$_2$ hemoglobin is assembled from alpha and beta globin chains co-expressed from a tetracistronic operon as described herein. With di-alpha, beta$_2$hemoglobin, nearly 100% is soluble when expression is induced at 25° C. and less at higher induction temperatures. These percentages reflect the percent of all di-alpha and beta chains found in the soluble fraction of the cell and not actual recovery of protein from the cell.

Expression in Yeast

In another embodiment the present invention relates to the production of hemoglobin-like molecules in yeast. Our preferred host for expression of recombinant human hemoglobin in yeast is *Saccharomyces cerevisiae*. However, other fungi or yeast may be used for the purpose, such as strains of Aspergillus or Pichia. For yeast to be a suitable host it must be capable of being transformed with recombinant vectors, either replicating or integrating types. This allows the insertion of the desired DNA sequence for the gene of interest. It must also be capable of high density cell growth, in appropriate volume to provide sufficient cell mass to isolate the desired gene product from the desired reaction vessels, where ideally the growth would be easily controlled by several parameters including nutrient formulation, agitation and oxygen transfer and temperature. It is also desirable to be able to induce the expression of protein synthesis with the manipulation of the media, temperature, or by the addition or consumption of certain chemicals. Finally, to be a suitable host, the yeast must be capable of producing recombinant proteins, preferably in excess of 1% of the total cell protein. This allows more facile isolation of the desired recombinant protein.

With reference to *S. cerevisiae*, haploid strains of potential use include:

| | |
|---|---|
| BJY3501 | Matα pep4::HIS3 prb1-D 1.6R his3 200 ura3-52 can1 GAL$_2$ |
| GSY112 | As above but Leu2::HISG |
| GSY112 cir⁻ | As above but cured of 2μ plasmid |
| BJY3505 | Mata pep4::HIS3 prb1-D 1.6R HIS3 lys2-208 trp1-101 ura3-52 gal2 can1 |
| GSY113 | As above but leu2::HISG |
| RSY330 | Matα pep4-3 prb1-1122 hist7 ura3-52 trp1-289 can1 gal1 |
| BJY2168 | Mata prc1-407 prb1-1122 pep4-3 leu2 trp1 ura3-52 |
| BJY1991 | Matα prb1-1122 pep4-3 leu2 trp1 ura3-52 |
| RSY334 | Matα reg1-501 pep4-3 prb1-1122 ura3-52 leu2-3, 112 gal1 |
| RSY214 | Matα pep4-3 prb1 ura3-52 |

To date, strains such as GSY112, GSY113 and RSY334 have been the best hemoglobin producers. Strains such as RSY334 that carry the reg1-501 mutation may be particularly important as they uncouple glucose repression from galactose induction, allowing one to induce with lower levels of galactose in the presence of glucose. Because this strain carries the gal1 mutation it cannot metabolize galactose, so the galactose concentration remains constant and continues to function as an inducer.

Diploid strains formed from crosses of any off the above compatible strains or similar compatible strains may also be useful as they tend to have faster growth rates than haploid strains.

For example, the following diploid strains, which co-express alpha (or di-alpha) and beta globins, are described in the Examples:

BJY3505 [pGS4988]×RSY330 [pGS4688]

BJY3505 [pGS4988]×BJY 1991 [pGS4688]

Other matings may likewise be used in practicing the present invention.

The use of protease-deficient strains may also be advantageous.

Yeast expression systems can be divided into two main categories: (1) Systems designed to secrete protein and (2) system designed for the cytoplasmic expression of proteins. The advantages of secretion systems are:

(1) The protein is often easier to purify from culture medium than from total cell extracts.

(2) If the protein has essential disulfide bonds, they are more likely to form if the protein passes through the secretory pathway. This is thought to be partly due to the presence of protein disulfide isomerase in the endoplasmic reticulum and to a less reducing environment than in the cytoplasm.

(3) Secretion can also be advantageous if the first amino acid (after the initiating methionine) creates a dipeptide sequence that is poorly processed by methionyl aminopeptidase. The addition of a secretory signal sequence may allow processing by signal peptidase during secretion resulting in a protein with the authentic amino acid at the amino terminus of the protein.

The disadvantages of a secretion system are:

(1) Generally, the expression levels are much lower than those that can be obtained by cytoplasmic expression. This seems to be, in part, due to a rate limiting step in secretion.

(2) Not all proteins are secretable.

(3) Often, particularly with *S. cerevisiae*, misprocessed forms of the protein accumulate and these can be difficult to purify away from correctly processed forms.

The secretory expression system most commonly used in recombinant yeast is the yeast α-factor secretory signal sequence and the α-factor promoter. See A. J. Brake. *Yeast Genetic Engineering* Eds. P. Barr, A. Brake, and P. Valenzuela. Butterworth Publishing, Boston 1989, for a review. The invertase signal sequence coupled to a variety of promoters has also been used to express heterologous proteins in yeast. See G. Stetler et al., Biotechnology, 7:55–60 (1989), R. Smith et al., Science, 229:1219–1229 (1985).

The advantages of cytoplasmic expression are.:

(1) Expression levels can be quite high with reports of proteins expressed at >20% of the total cell protein, usually as a soluble protein.

(2) Some proteins cannot be efficiently secreted.

(3) Proteins that contain glycosylation sites, if secreted from yeast, will be glycosylated with the pattern of sugars unique to yeast. Because these highly hydrophilic, post-translational modifications lie on the surface of proteins they are likely to confer antigenicity on the protein. If the protein is functional without the carbohydrate side chains it may be advantageous to produce the protein without them rather than with the yeast-specific modification (see for ex. Travis et al. 1985. J Biol Chem 260:4384–4389)

(4) Some proteins have other specific modifications that may occur only in the cytoplasm, for example amino-terminal acetylation, modification with lipids, perhaps heme incorporation and so forth.

At present, cytoplasmic expression is preferred since the yeast cells fold together the globin chains and incorporate heme to produce hemoglobin in vivo. However, it is possible to separately express and secrete the alpha and beta globin chains and assemble hemoglobin in vitro.

The globin genes must be placed under the control of a suitable promoter. The commonly used yeast promoters generally fall into two broad categories: regulated and constitutive. Constitutive promoters that are in wide use include GAP, PGK (phosphoglycerate kinase) and the α factor promoter. Regulated promoters have also been used and these include the yeast metallothionein promoter (regulated by copper), the Gal1-10 promoter, GAL7 promoter (regulated by galactose and glucose) the ADHII promoter (regulated by ethanol and glucose) the PH05 promoter (phosphate regulation) and several hybrid promoters such as PH05-GAP, GAL-PGK, ADHII-GAP, and GAL-CYC1.

The use of regulated promoters may be important for plasmid stability. Often expression of recombinant proteins at high levels, inhibits the growth of the host organism. This disadvantage can result in the accumulation of cells in the population with few copies of the plasmid present, a decrease in growth rate and a drop in overall expression levels. By maintaining the gene in a repressed state and inducing late in the fermentation, high growth rates can be maintained and selection against high plasmid copy numbers can be avoided.

It is somewhat difficult to obtain accurate data on the relative strength of yeast promoters because the only true measure of this would be based on kinetics of mRNA synthesis. Most of the data that exists measures only the final protein concentration that has been obtained. Because there can be great differences in protein stability, it is necessary to compare the same protein and mRNA with multiple promoters on identical vectors. A study that approaches this was done by Verbakel et al. (Gene, 61:207–215 (1987)). They compared the GAPDH, CYC1 GAL7, PHO5, and PGK promoters and measured the expression of a β-galactosidase/poliovirus VP2 protein fusion. CYC1 resulted in an expression level of 0.14% of the total cell protein (TCP); GAPDH, 0.22% TCP; PHO5, 0.26% TCP; PGK, 0.9% TCP; and GAL7, 0.96% TCP.

Using our GALGAP hybrid promoter, we have obtained expression levels of hemoglobin that represents ≧15% of the total cell protein. This most probably represents an increased promoter strength along with a highly stable protein product and perhaps mRNA with an extended half life.

The use of a GAL-GAP hybrid promoter is preferred. Both elements (the $GAL_{UAS}$ and the GAP transcriptional initiation site) are well understood. Studies on the mechanisms of transcriptional regulation of the GAL regulon have been fairly extensive. The galactose regulon includes five genes that encode enzymes required for the utilization of galactose. Four of these genes (GAL1, GAL7, GAL10, and GAL2) are expressed only in the presence of galactose. Galactose induction does not occur in the presence of glucose unless the yeast strain bears a mutation in the REG1 gene. The GAL1, 7, 10 and 2 genes are regulated by at least two other genes, GAL80 and GAL4. The GAL4 gene is a transcriptional activator protein that activates mRNA synthesis from the GAL1, 7, 10 and 2 upstream activator sequences ($UAS_{GAL}$). Although GAL4 is constitutively expressed, it is functionally silent in the absence of galactose. Repression of GAL4 activity, in the absence of galactose is maintained by the product of the GAL80 gene. The GAL80 protein apparently interacts physically with GAL4 to prevent transcriptional activation. Presumably galactose or a galactose derivative prevents this interaction to allow GAL4 mediated induction.

Haploid strains of S.cerevisiae have three different genes encoding the enzyme glyceraldehyde-3-phosphate dehydrogenase (GAP). These genes have been designated TDH1, TDH2 and TDH3 and each is present as a single copy per haploid genome. The TDH3 gene produces approximately 60% of the cell's GAP enzyme and TDH1 and 2 produce about 12% and 28%, respectively (McAllister, L and M. J. Holland, 1985. J. Biol Chem, 260: 15019–15027). Holland's group (Holland et al. 1981. J. Biol Chem, 256:1385–1395 and Holland et al. 1983. J Biol Chem 258:5291–5299) has cloned and characterized the three GAP genes of S.cerevisiae. The clones have been designated pGAP11, pGAP63, and pGAP491. pGAP491 corresponds to the TDH3 gene and is therefore, the most highly expressed. This promoter has been used to express a wide variety of proteins in yeast including:

| Protein | REF |
|---|---|
| α Interferon | (1) |
| Hepatitis B antigen | (1) |
| Thaumatin | (2) |
| Hepatitis B antigen | (3) |
| HIV III reverse transcriptase | (4) |
| human SOC | (5) |
| α1 antiprotease | (6) |

(1) Bitter, G. and K. M. Eagan. 1984. Gene, 32. 263–274.
(2) Edens, L. et al. 1984. Cell, 37: 629–633.
(3) Kitano, K. et al. 1987. Biotechnology 5: 281–283.
(4) Hallewell, R. A. et al. 1987. Biotechnology 5: 363–366.
(5) Barr, P. J. et al. 1987. Biotechnology 5: 486–489.
(6) Travis, J. et al. 1985. J Biol Chem 260: 4384–4389.

This promoter is commonly used as a 600–850 bp fragment and is essentially un-regulated. In its long form this is a very powerful promoter. The form we are using consists of only ⁻200 bp 5' of the translational initiation site. This form, with no added enhancer sequences is substantially less active than the longer form of the promoter (Edens, L. et al. Cell, 37:629 (1984)). Our addition of the GAL enhancer region confers both regulation and high levels of expression. With only the GAP491 promoter, alpha and beta globin were produced at a level of less than 0.2% total cell protein; with the GAL-GAP491 hybrid promoter, expression jumped to 7–10% total cell protein.

Several other hybrid promoters are of particular interest:

GAL-SIGMA
    A strong galactose-regulated promoter with the sigma transcriptional start site.

SIGMA-GAP
    A strong peptide hormone-regulated promoter with the GAP491 transcriptional start site.

GAL-EF III
    A strong galactose-regulated promoter with the elongation factor III transcriptional start site.

SIGMA-EF III
    A strong peptide hormone-regulated promoter with the elongation factor III transcriptional start site.

One could easily conceive of other promoter systems that would also work. This would include, but not be limited to, a variety of constitutive promoters. For example, the yeast mating factors (MFα) promoter or the mating factor a promoter MF(a), the phosphoglycerate kinase promoter (PGK), hexokinase1, hexokinase2, glucokinase, pyruvate kinase, triose phosphate isomerase, phosphoglycerate isomerase, phosphoglycerate mutase, phosphofructose kinase or aldolase promoters may all be used. In short, any well expressed yeast promoter may work for expression of hemoglobin in yeast. A wide variety of naturally occurring, regulated promoters could also be used, for example: GAL1-10, GAL7, PHO5, ADHII have all been used to produce heterologous proteins in yeast. A variety of synthetic or semi-synthetic yeast promoters could also be employed such as GAL-PGK, GAL-MFα-1, GAL-MFα1, GAL-SIGMA. ADHII regulatory sequences could also be coupled to strong transcriptional initiation sites derived from a variety of promoters. The PHO5 regulatory sequence or the sigma element regulatory sequences could also be used to construct powerful hybrid promoters. In addition to yeast promoters, it is conceivable that one could use a powerful prokaryotic promoter like the T7 promoter. In this case, one could place the T7 polymerase under the control of a tightly regulated yeast promoter. Induction of the phage polymerase in yeast calls bearing hemoglobin genes under T7 promoter regulation would allow transcription of the genes by this very efficient phage polymerase.

Because most of the yeast regulatory sequences described above serve as targets for proteins that are positive regulators of transcription, it is conceivable that these proteins may limit transcription in situations where the target sequence is present in many copies. Such a situation may obtain with vectors such as pC1B, pCIT, pC1U or pC1N which may be present in excess of 200 copies per cell. Over-expression of the positive regulator (for example GAL4) may result in enhanced expression. It is possible to construct a strain in which the GAL4 gene is altered to remove its promoter and the promoter replaced with the GAL7 or GAL1-10 promoters, both of which are transcribed more efficiently than the GAL4 promoter. In this situation, the positive transcriptional activator protein GAL4 would be expressed at elevated level at the time hemoglobin expression was induced. The consensus sequence for higher eukaryotic ribosome binding sites has been defined by Kozack (Cell, 44:283–292 (1986)) to be: CC CCAUGG (SEQ ID NO:18). Deviations from this sequences, particularly at the −3 position (wherein N equals either A or G), have a large effect on translation of a particular mRNA. Virtually all highly expressed mammalian genes use this sequence. Highly expressed yeast mRNAs, on the other hand, differ from this sequence and instead use the sequence AAAAAUGU (Cigan and Donahue, Gene, 59:1–18 (1987)). The ribosome binding site that we use for expression of the α and β-globins corresponds to the higher eukaryotic ribosome binding site. It is within the contemplation of this invention to systematically alter this ribosome binding site to test the effects of changes that make it more closely resemble the ribosome binding site of yeast. It should e pointed out, however, that alterations at the −2, −1 and +3 positions, in general have been in yeast and in mammals.

Intracellular expression of genes in *S. cerevisiae* is primarily affected by the strength of the promoter associated with the gene, the plasmid copy number (for plasmid-borne genes), the transcription terminator, the host strain, and the codon preference pattern of the gene. When secretion of the gene product is desired, the secretion leader sequence becomes significant. It should be noted that with multicopy plasmids, secretion efficiency may be reduced by strong promoter constructions. Ernst, DNA 5:483–491 (1986).

A variety of extrachromosomally replicating vectors (plasmids) are available for transforming yeast cells. The most useful mutlicopy extrachromosomal yeast vectors are shuttle vectors that use a full length 2µ-circle combined with an *E. coli* plasmid. These vectors carry genes that allow one to maintain the plasmid in appropriate yeast mutants and antibiotic resitance markers that allow selection in *E. coli*. Use of the full-length 2µ-circle, in contrast to vectors containing only a partial 2µ sequence, generally results in much higher plasmid stability, particularly in yeast strains that have been cured of endogenous 2µ plasmid. The pC series of vectors described herein are vectors of this type.

Strains could also be constructed in such a way that GALGAP hemoglobin expression cassettes were integrated into chromosomes by using yeast integrating vectors. Although the copy number of the hemoglobin genes would be lower than for plasmid vectors, they would be quite stable and perhaps not require selection to be maintained in the host cell. Yeast integrating vectors include Yip5 (Struhl, et al, PNAS, 75:1035–39, 1989), Yip1 (Id.), an dpGT6 (Tchumper and Carbon, Gene, 10:157–166, 1980). For information on these and other yeast vectors, see Pouwels, et al., cloning Vector, VI-I, et seq. (Elsevier, 1985).

The alpha and beta globin genes may be introduced by separate plasmids, or both upon the same plasmid. the advantage of a single plasmid system over a double plasmid system is theoretical. It is generally though that there is an upper limit to the total number of plasmid copies per cell. If it is 1000, for example, the two plasmid system could have only 500 copies of α chain plasmid and 500 of the β chain plasmid. A single plasmid of 1000 copies per cell would bear 1000 copies of each α and β chain gene. The number of copies may be irrelevant, however, if other factors are limiting. In fact, several groups favor using strains that contain genes integrated into various chromosomal loci. Such strain very stably maintain the foreign gene and do not require special media to maintain selection for the plasmid.

Highly expressed yeast genes show a very high codon bias. The genes encoding glyceraldehyde-3-phosphate dehydrogenase and ADH-I, for example, show a 90% bias for a set of 25 codons. Highly expressed yeast genes (>1% of the total mRNA) have yeast codon bias indices of >.90. Moderately expressed genes (0.1–0.05% of the total mRNA) have bias indices of 0.6–0.8, and genes expressed at low levels (>0.05% of the total cell protein) have a codon bias of 0.10–0.50 (Bennetzen and Hall, J. Biol. Chem., 257:3026–3031 (1982)). The calculated value for the codons of the human a globin cDNA is 0.23. A similar value can be calculated for the β globin cDNA. Because there is a very high correlation between the most commonly used codons, it is possible that hemoglobin expression from the human cDNA in yeast may be limited by the availability of the appropriate tRNA molecules. If this is so, a complete synthesis of the gene using the most highly favored yeast codons could improve the expression levels. It is quite possible that the greatest negative effect of adverse codon use would be if there was an abundance of codons used in the cDNA that are represented by low abundance tRNAs. In such a case, high level expression of hemoglobin could completely drain that pool of tRNA molecules, reducing translation not only of hemoglobin but of yeast proteins that happen to use that codon as well. In the case of the α globin human cDNA, the most commonly used leucine codon is CTG (14 of 21), this codon is never used in highly expressed yeast genes (Guthrie and Abelson, *The Molecular Biology of the Yeast Saccharomyces*, Eds. Stratern, Jones and Broach, 1982. Cold Spring Harbor, N.Y.). The low codon bias index and the presence of rare yeast codons in the globin cDNAs have been sufficient incentive for us to synthesize a modified form of the alpha and beta globin genes using the preferred yeast codons.

Pseudodimer-containing Hemoglobins

Although the assembly of secreted $F_v$-antibody fragments in which the $V_H$ and $V_L$ domains are fused by a 16 amino acid peptide has been demonstrated in *E. coli*, Better, J., Chang, P. Robinson, R., Horwitz, R., Science 240, 1041–43 (1988), Skerra, A. and Pluckthorn, A., Science 240, 1038–41 (1988), there are no previous examples of the cytoplasmic folding and assembly of a mammalian heterotetramer in which two of the subunits are fused to one another.

The present invention further contemplates in some embodiments the combination of (a) one molecule of a di-alpha globin-like polypeptide with two molecules of a beta globin-like polypeptide to form a "di-alpha" hemoglobin-like protein; (b) two molecules of an alpha globin-like polypeptide with one molecule of a di-beta globin-like polypeptide to form a "di-beta" hemoglobin-like protein; or (c) one molecule of a di-alpha globin-like polypeptide with one molecule of a di-beta globin-like polypeptide to form a "di-alpha/di-beta" hemoglobin-like protein.

It should further be noted that the delta, gamma and epsilon chains have considerable homology with the beta chain and that the zeta chain has considerable homology with the alpha chain. Di-delta, di-gamma, di-epsilon and di-zeta polypeptides are therefore within the compass of the invention and may be used in the preparation of novel hemoglobins of types other than hemoglobin A1.

In the liganded form, hemoglobin readily dissociates into $\alpha\beta$ dimers which are small enough to pass through the renal glomeruli, and hemoglobin is thereby rapidly removed from the circulatory system. Intravenous administration of hemoglobin in amounts far less than that needed to support oxygen transport can result in long term kidney damage or failure. Ackers, G. K. and Halvorson, H. R., Proc. Nat. Acad. Sci. (USA) 71, 4312–16 (1974); Bunn, H. F., Jandl, J., J. Exp. Med. 129,925–34 (1969). If dissociation into dimers is prevented, there is an increase in intravascular half life and a substantial reduction of renal toxicity. Lee, R., Atsumi, N., Jackbs, E., Austen, W., Vlahakes, G., J. Surg. Res. 47, 407–11 (1989). The pseudotetrameric hemoglobin of this invention cannot dissociate into $\alpha\beta$-dimers without the breakage of a peptide bond and should have the advantages of a longer intravascular half life and reduced renal toxicity.

In the crystal structures of both deoxyhemoglobin and oxyhemoglobin the N-terminal Val residue for one $\alpha$ subunit and the C-terminal Arg residue of the other $\alpha$ subunit are only between 2 and $\text{Å}6$ apart, and are bound to one another through a salt bridge in deoxyhemoglobin. Fermi, G., Perutz, M., Shaanan, B., Fourme, R., J. Mol. Biol., 175, 159–74 (1984); Shaanan, B., J. Mol. Biol. 171, 3159 (1983). This distance could be spanned by one or two amino acids. One extra amino acid can be added to the C-terminal Arg residue of the a subunits by trypsin catalyzed reverse hydrolysis without significantly altering the oxygen binding properties. Nagai, K., Enoki, Y., Tomita, S. and Teshima, T., J. Biol. Chem., 257, 1622–25 (1982) Preferably the di-alpha linker (if one is used) consists of 1 to 5 amino acids which may be the same or different. A Mono-Gly linker is especially preferred. In designing such a linker, it is important to recognize that it is desirable to use one or more amino acids that will flexibly connect the two subunits, transforming them into domains of a single di-alpha globin polypeptide.

The preparation of "di-beta" mutants is also contemplated. The distance between the N-terminus of one beta subunit and the C-terminus of the other is 18.4 Å in the deoxy configuration and 5.2 Å in the oxy form. Preferably, the di-beta linker consists of 2 to 9 amino acids which may be the same or different. Glycine amino acids are particularly preferred.

The length of the $(\text{-gly-})_n$ genetically fused link between the N-terminus of one beta chain (at $\text{beta}_1$, 1 Val) and the C terminus of the second beta chain ($\text{beta}_2$, 146 His) in di-beta hemoglobin may range between 1 and approximately 9 glycines. In the oxy and deoxy crystal structures of human hemoglobin $A_0$, the distance between these termini is 5.22 Å and 17.93 Å respectively (from the N-terminal nitrogen to the C terminal carbon of the carboxylate). A single glycine linker, which is a little less than 4 Å in length, may come close to linking the two termini in the oxy structure, however, it is expected that this linker will fall ~14 Å short in the deoxy structure. Significantly more perturbation of the deoxy structure vs the oxy structure might be anticipated with this linker. Some alterations in the oxygen binding properties may be caused by deletion of the positive and negative charges at the two termini and their inclusion in the amide bond. In addition, the linker molecule itself may destabilize the oxy structure less than the deoxy structure, and thus lead to a relative increase in oxygen affinity. Likewise, two glycines inserted as linkers may also differentially stabilize the oxy structure and hence relatively increase the oxygen affinity by the same mechanism described above.

When the number of linking glycines is increased to 5, the linker should just span the cleft between the beta chain termini in the deoxy structure, and, moreover, insert added steric bulk between the termini in the oxy structure, thus leading to a relative stabilization of deoxy (or destabilization of oxy) and perhaps resulting in a concomitant decrease in oxygen affinity. Due to the large space between the beta termini in the deoxy (but not the oxy structure), addition of glycine linkers in the range of 6–9 may further destabilize the oxy structure and, in the same manner, further decrease oxygen affinity.

Figure 36:
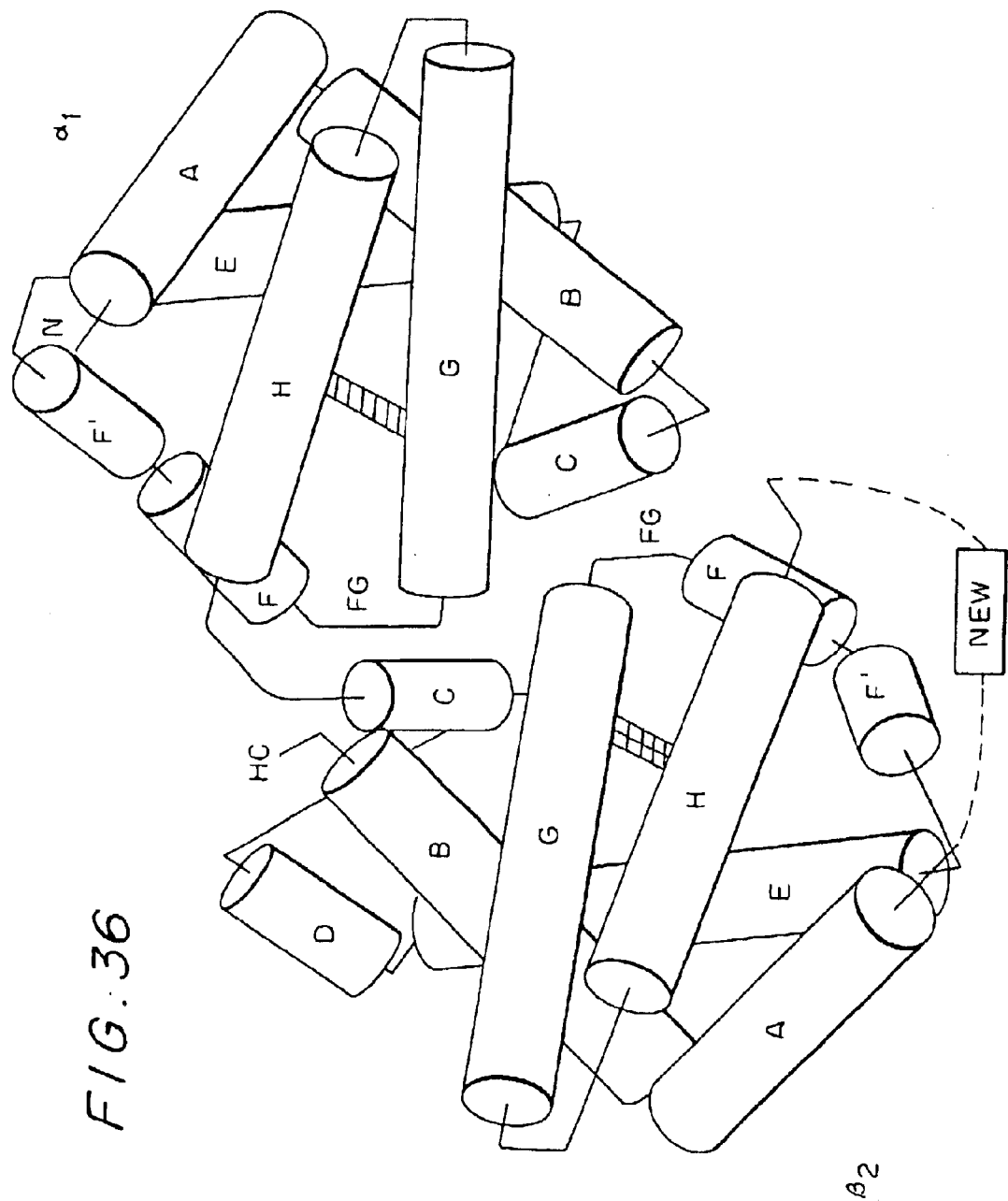
FIG. 36 Proposed alpha$_1$-beta$_2$ globin pseudodimer.

A third form of globin pseudodimer is one comprising both alpha and beta globin domains. A possible route to fusing alpha1 and beta2 and so stabilizing hemoglobin against $\alpha_1\beta_2/\alpha_2\beta_2$ dimer formation, is to fuse the alpha1 C-terminal residue to the N-terminal residue of beta2 C helix, creating a new C-terminus at the end of the beta2 B helix. The original beta N terminus, Val1, would be fused to the original beta subunit C-terminal residue, His146, by means of an intervening new section of protein, thus creating a continuous polypeptide chain comprising the alpha and beta subunits of different dimers. This chain may be described as follows: $\alpha(1-14)\text{-Gly}_3\text{-}\beta(35-146)\text{-Gly}_{1-3}\text{-Ala}_{13}\text{-Gly}_{1-3}\text{-}\beta(1-34)$ (SEQ ID NO:20); See FIG. 36.

Inspection of the structure of human deoxyhemoglobin using a molecular graphics computer indicates the following relevant distances. The distance between the Alpha1 Arg141 carboxyl carbon and Beta2 Tyr35 H atoms is approximately 8.6 Angstroms. A fully extended linear triglycine peptide measured approximately 10.1 Angstroms from the N to C terminal residues. This suggests that three glycine residues could be employed to span the distance between the Arg141 and Tyr35 residues with a minimum of unfavorable steric interactions and maximum conformational freedom. The distance requirements could be different in oxyhemoglobin, and if so, the sequence of the fusion peptide could be altered to best accommodate the requirements of both structures.

In human deoxyhemoglobin, the distance between the Beta2 His146 carboxyl carbon and the Beta2 Val1 nitrogen atoms is approximately 25 Angstroms. A right handed 3.6 Alpha helix constructed from a linear sequence of 13 Alanine residues was found to measure 22 Angstroms front N to C terminus. With the addition of one to three glycine residues at each end of this helix (to give $Gly_n (Ala)_{13} Gly_n$ where n=1 to 3), it could span the required distance and have sufficient conformational flexibility to avoid serious tertiary packing conflicts. Additionally, the amino acid sequence of the helix could be altered to introduce favorable hydrogen bonds and salt bridges between the new helix and the Beta2 helix against which it would pack in the folded protein. Such interactions could aid stabilization of the engineered protein.

Glycine is the preferred amino acid in the linkers, since it is known to be quite flexible, Cantor and Schimmel, *Biophysical Chemistry*, part 1, pp. 266–9 (1980), and also allows chains into which it is incorporated to assume a more compact structure. However, the residues comprising the linker are not limited to glycines; other residues may be included instead of or in addition to glycine, such as alanine, serine, or threonine. Since these amino acids have a more restricted conformational space in a protein, they will likely result in more rigid linking chains, and hence have a more pronounced effect on the relative stabilization/destabilization of the oxy/deoxy structures.

It should be understood that the minimum and maximum number of amino acids in the linker is a function of the distance to be spanned in both the oxy or deoxy forms, the amino acids chosen, and the propensity of the particular amino acid sequence to form a secondary structure. While a random coil is usually preferred, it is not required, and a linker with a larger number of amino acids in a secondary structure may have the same span as a random coil linker with fewer amino acids. A linker may comprise, e.g., 1–3 glycines, followed by a sequence having a secondary structure, followed by 1–3 more glycines. The translation per residue, in angstroms is 1.9 for polyproline I, 3.12 for polyproline II, 3.1 for polyglycine II, 3.4 for an antiparallel β sheet, 3.2 for a parallel β-sheet, 1.5 for a right handed a-helix, 2.0 for a 310 helix, and 1.15 for a n helix. In a fully extended chain, the maximum translation per residue is 3.63 Å if the repeating units are staggered and 3.8 Å if the peptide bond is trans.

The number of amino acids in the linker may be such that a formation of a secondary structure, such as an alpha helix or a beta-sheet, is undesirable, as the span is reduced. Certain amino acids have a greater tendency to participate in such structures. See Chou and Fasman, Biochemistry, 13:222–245 (1974), incorporated by reference. The amino acids are ranked in order of decreasing participation below. The preferred linker amino acids are boldfaced. Glycine is the most suitable amino acid for this purpose. The most preferred di-alpha linkers are Gly or Gly-Gly.

| Alpha Helix Formers | Beta Sheet Formers |
|---|---|
| Glu (1.53) | Met (1.67) |
| Ala (1.45) | Val (1.65) |
| Leu (1.34) Hα | Ile (1.60) Hβ |
| His (1.24) | Cys (1.30) |
| Met (1.20) | Tyr (1.29) |
| Gln (1.17) | Phe (1.28) |
| Val (1.14) | Gln (1.23) |
| Trp (1.14) | Leu (1.22) |
| Phe (1.12) hα | Thr (1.20) |
| Lys (1.07) | Trp (1.19) hβ |
| Ile (1.00) | Ala (0.97) Iβ |
| Asp (0.98) | Arg (0.90) |
| Thr (0.82) | Gly (0.81) |
| Arg (0.79) | Asp (0.80) iβ |
| Ser (0.79) | Lys (0.74) |
| Cys (0.77) iα | Ser (0.72) |
| Asn (0.73) | His (0.71) |
| Tyr (0.61) bα | Asn (0.65) |
| Pro (0.59) | Pro (0.62) bβ |
| Gly (0.53) Bα | Glu (0.26) Bβ |

(The letter symbols are Hα, strong α former; hα, α former; Iα; weak α former; iα, α indifferent; bα, α breaker; and Bα strong α breaker. The β symbols are analogous. Trp is bβ if near the C-terminal of a β-sheet region.)

The alpha helix of a polypeptide chain comprises an average of 3.6 residues per turn. In globular proteins, the average length is about 17 Å, corresponding to 11 residues or 3 helix turns. In alpha and beta globin, the helices range in length from 7 to 21 amino acids (A.A.). The beta pleated sheet comprises 2.3 residues per turn; the average length is about 20 Å or 6 residues.

Chou and Fasman define an alpha helix nucleus as a hexapeptide containing four helix forming residues and not more than one helix breaker, and a beta sheet nucleus as a pentapeptide containing three beta sheet forming residues and not more than one sheet breaker.

The amino acid sequence in the vicinity of the di-alpha linker is as follows:

| residue # | 138 | 139 | 140 | 141 |  | 1 | 2 | 3 | 4 |
|---|---|---|---|---|---|---|---|---|---|
| AA | Ser | Lys | Tyr | Arg | $-(XXX)_n-$ | Val | Leu | Ser | Pro |
| Helix Not | H21 | HC1 | HC2 | HC3 |  | NA1 | NA2 | A1 | A2 |
| Helix Pot | 079 | 107 | 061 | 079 |  | 114 | 134 | 079 | 059 |
| Sheet Pot | 072 | 074 | 129 | 090 |  | 165 | 122 | 072 | 062 |

(Note: Helix- and sheet forming potentials have been multiplied by 100 for typographical reasons.)

The di-alpha linker is preferably only 1–3 amino acids. Thus, it can form an alpha helix only in conjunction with the linker "termini". A one or two residue linker, even if composed of amino acids with strong secondary structure propensities, would be unlikely to assume an alpha helix or beta sheet configuration in view of the disruptive effect of, e.g., Arg 141 or Ser 3. If the linker is 3 residues long, it would be preferable that no more than one residue be a strong alpha helix former, unless the linker also included a strong alpha helix breaker.

The amino acid sequence in the vicinity of the di-beta linker may impose more stringent constraints.

| 143 | 144 | 145 | 146 |           | 1   | 2   | 3   | 4   |
|-----|-----|-----|-----|-----------|-----|-----|-----|-----|
| His | Lys | Tyr | His | -(XXX)$_n$- | Val | His | Leu | Thr |
| H21 | HC1 | HC2 | HC3 |           | NA1 | NA2 | NA3 | A1  |
| 124 | 107 | 061 | 124 |           | 114 | 124 | 134 | 082 |
| 071 | 074 | 129 | 071 |           | 165 | 071 | 122 | 120 |

The di-beta linker is likely to be longer (preferably 1–9 A.A.) and therefore more susceptible to secondary structure formation. If secondary structure formation is not desired, it is desirable that the amino acid adjacent to Val-1 be an alpha helix breaker (e.g., Glycine) in view of alpha-helix propensities of Val-His-Leu. More generally, it is desirable that the linker not contain (or cooperate with the proximately linked amino acids to form) an alpha helix nucleus or beta sheet nucleus.

When secondary structure is not desired, amino acids with a high propensity toward alpha helix formation may be used in the linker if accompanied by "helix breaking" amino acids. Similarly, Beta sheet formation may be prevented by "sheet disrupting" amino acids.

Of course, prediction of secondary structure using Chou and Fasman's approach has its limitations and the ultimate test of the acceptability of a linker is whether or not the di-alpha or di-beta hemoglobin has the desired affinity for oxygen. In particular, a poly-alanine linker, despite its supposed propensity to alpha-helix formation, may well be of value since the alanine group is compact and therefore the linker should be quite flexible if secondary structure does not form.

In an especially preferred embodiment, di-alpha and beta globin genes are combined into a single polycistronic operon. The use of a polycistronic operon is not, however, necessary to practice the present invention, and the alpha (or di-alpha) and beta (or di-beta) globin genes may be expressed from separate promoters which may be the same or different.

While the preferred "genetically fused hemoglobin" of the present invention is one comprising a di-alpha and/or di-beta globin, other globin chains may be genetically fused and used in the production of hemoglobins of species other than Hgb A1 ($\alpha_2\beta_2$).

Pseudo-Octameric (Ditetrameric) Hemoglobin-like Proteins with Disulfide Bridges

Figure 27:
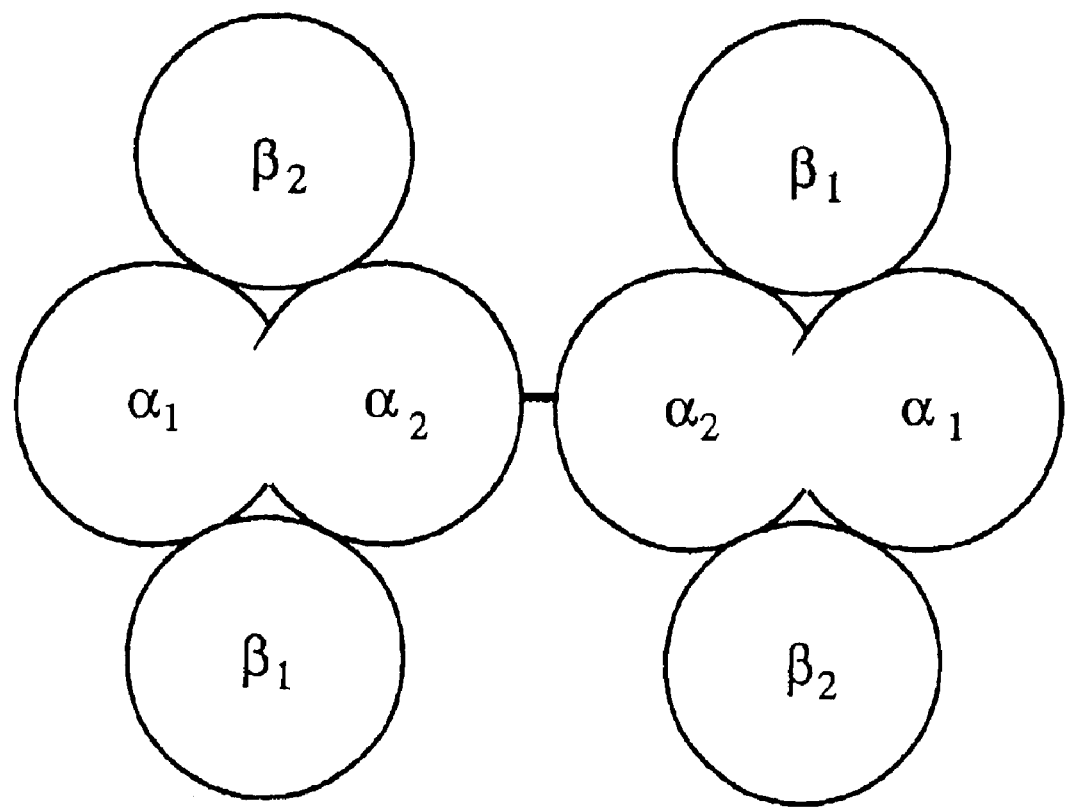
FIG. 27: A stylized representation of one form of pseudooctameric hemoglobin, in which the octameric hemoglobin is formed by linking or crosslinking two molecules of an asymmetric di-alpha hemoglobin.

The ability to produce pseudotetrameric recombinant hemoglobins consisting of a single dialpha polypeptide and two beta chains (or a dibeta polypeptide and two alpha chains) provides a unique opportunity to create an asymmetric pseudotetramer from the normally symmetric pseudotetramer. Because the two alpha globin domains are expressed as a single. polypeptide, it is possible to alter one of the alpha globin domains without altering the other. The result is a protein that, in its final folded state, contains two different alpha globin domains in a strict 1:1 ratio. This type of asymmetric hemoglobin molecule, with its unique chemical properties, cannot be easily constructed by any other method. A preferred embodiment of this invention would involve use of site-directed mutagenesis to substitute a cysteine residue in one of the two alpha globin domains of a di-alpha hemoglobin such as SGE1.1 (a di-alpha hemoglobin with a beta chain Presbyterian mutation) such that the cysteine would be on the surface of the folded recombinant hemoglobin molecule. A homogeneous preparation of pseudo-octameric hemoglobin could then be formed through interhemoglobin linkage of two pseudotetramers either directly by simple oxidation of purified pseudotetramers or by reaction with a bridging molecule (FIG. 27).

Advantages of a pseudo-octamer stem from several possible therapeutic features of this construct: (I) half-life in the bloodstream of the pseudo-octamer (MW~128. 000) is expected to be longer than the halflife of pseudotetrameric Hb (MW~64,000). Studies of halflife as a function of macromolecular size indicate a correlation between increased size and increased circulatory halflife for chemically crosslinked Hb as well as other macromolecules. (II) because the number of oxygen binding heme groups per octamer is twice the number per tetramers, independent of size, the oncotic pressure for a given concentration of heme groups in a solution of octameric Hb is expected to be half that of an equimolar solution of heme contained in tetrameric Hb. Because of oncotic pressure effects, the maximum concentration of free tetrameric Hb that may be introduced into the blood stream is less on a per volume basis than the concentration of Hb normally carried in intact red blood cells. Reduction of oncotic pressure is therefore useful in increasing the per volume oxygen carrying capacity of a blood substitute. (III) although free hemoglobin purified from natural sources may be polymerized by chemical crosslinking to increase halflife via increased molecular weight, and to reduce oncotic pressure, all such preparations are heterogeneous. Not only does the genetic engineering approach provide a means of synthesizing a higher molecular weight complex without the need to involve chemical crosslinking and consequent additional purification steps, this approach also provides the first means of exerting strict control over the degree of polymerization. The ability to strictly control formation of pseudo-octamers will greatly facilitate characterization of the final product and will reduce the chance of adverse reaction to minor components.

Although direct formation of a disulfide bond between two SGE1.1 mon cys hemoglobins is desirable in order to avoid the need for chemical crosslinking, the halflife of such a bond in the bloodstream is unknown. Naturally occurring reducing agents may reduce the disulfide bond in vivo at a rate comparable to or greater than the halflife of the pseudo-octamer. The rate of reduction of the bond may be influenced by the location of the cysteine mutation on the surface of the hemoglobin. It may also be possible to insert two cysteine mutations in each hemoglobin in close enough proximity that steric hindrance would allow formation of a two-disulfide pseudo-octamer but prevent formation of higher molecular weight complexes.

Poly (tetrameric) Hemoglobin with Other Intercysteine Linkages

It is also possible, of course, to couple two SGE1.1 mono cys molecules with a homobifunctional crosslinking reagent resulting in linkage via nonreduceable bonds. The degree of polymerization is still controlled by the use of the mono cys di-alpha or di-beta Hgb starting material. (Note that reference to SGE1.1 mono-cys in this section is for illustration only; other mono-cys di-alpha or di-beta Hbgs could be used in its place.)

By using bi-, tri-, tetra-, hexa-, or octa-functional crosslinkers several properties of multimeric hemoglobin which may contribute to longer serum half life can be controlled. The crosslinkers can be designed to give a nonreducible disulfide bond between two tetramers, to yield high molecular weight multimers of n>2 psuedo-tetramers (e.g. dodecamers, etc.) and/or to drop the overall isoelectric point of a hemoglobin octamer to further increase its half life.

Correlations of molecular weight with serum half life for proteins such as IL-2, demonstrate that a significantly longer half life may be expected as the molecular weight of a protein increases, particularly above the renal filtration limit of 50–70 kDa. SGE 1.1 mono-cys octameric hemoglobin will have a molecular weight of ca. 130 kDa, and this may double or triple its half life. However, a factor potentially limiting the half life of octameric hemoglobin formed by a disulfide link between two mono-cys SGE1.1's is reduction of the cys-cys disulfide bond by endogenous thiol-reducing agents found in the serum. Estimates of small molecule thiol levels in plasma vary from 17 $\mu$M to 5 $\mu$M. The major species is reduced glutathione. Other thiol compounds in plasma include cysteine, homocysteine, and gamma-glutamyl cysteine. Thus, small molecule plasma thiols are available for reduction of disulfide bonds. This may be reflected in the diminished half life seen with antibody-ricin A chains conjugates linked by regular disulfides (6.7 hrs) relative to conjugates linked with sterically hindered, and thus less reducible, alpha-methyl disulfides (42.5 hours)

Thus, in one embodiment, the octameric hemoglobin features a nonreducible disulfide crosslink such as a thioether bond or thiol-maleiimide adduct which may substantially extend the octamer half life. Simple homobifunctional crosslinkers or-polyethylene glycol (peg) derivatives would likely be useful for this purpose (see below). The reaction of a bifunctional cysteine-specific crosslinker with a mono-cys di-alpha or di-beta hemoglobin should limit the products of the reaction to substantially a dumbbell-like octameric hemoglobin (FIG. 22) and unreacted hemoglobin. The reaction should be stoichiometric when the hemoglobin and crosslinker are present at high concentrations and the hemoglobin is present in a slight excess over the crosslinker maleiimides at pH 6.5–7.0. Further, there should not be substantial interference by reaction with SGE1.1 lysines. The preferential reactivity of the thiols to lysines can be roughly calculated as the product of their molar ratios and the ratio of the intrinsic reactivity of a maleiimide to thiols versus amines. This product is ca. [1 cys/40 lys]×[1000]=25 at pH 7. The side products would still be octamers, with one attachment site being a secondary amine and thus might well be functionally equivalent to the 5-crosslinked octamers. Hydrolysis of the maleiimide adduct at pH 7 would be slow, and the ring opening would leave the crosslink intact.

The following are examples of homobifunctional crosslinkers that may form metabolically stable crosslinks between monocysteine pseudo tetramers:
1) 1, 2-bis-(2-iodoethoxy) ethane
2) 4,4'-dimaleiimidylbenzene or N,N'-p-phenylenedimaleiimide
3) N,N'-bis-(3-maleiimidopropionyl)-2-hydroxy-1,3-propane diamine.

Longer half lives may also be obtained by increasing the apparent solution molecular weight by simply lengthening the distance between the two linked tetramers using a long crosslinking agent. The use of some potentially novel polyethylene glycol derivatives as homobifunctional crosslinkers, reacting with SGE1.1 mono-cys, may provide one mechanism for significantly increasing the molecular weight of octameric hemoglobin by virtue of the length of the crosslinker alone.

A suitable crosslinker for this purpose is
maleiimido-$CH_2CH_2C$ (=O) $(OCH_2\ CH_2)_n$ OC(=O) $CH_2CH_2$-maleiimido.

The length may be adjusted by variation of n. A few examples are given below.

| Structure | Max Length | Source |
|---|---|---|
| n = 22 | -49Å | peg -1000 |
| n = 76 | -166Å | peg -3350 |
| n = 227 | -499Å | peg -10000 |

Homobifunctional N-hydroxysuccinimide-activated peg has been used previously to derivatize hemoglobin. Yabuki, et al., Transfusion, 30:516 (1990). This reaction resulted in a mixture of monomeric, dimeric, and trimeric species with an average stiochiometry of peg/hemoglobin of 6.2. However, 83% of the hemoglobin derivatized by peg was not crosslinked to another hemoglobin molecule. Control of the peg-derivitization of wild-type hemoglobin is not possible because there is no site-directed labeling of the hemoglobin starting material.

In contrast, the combination of SGE 1.1 mono-cys starting material and a peg crosslinker should yield a monodisperse dumbbell (pseudo-octameric) product only. The site-direction of the crosslinker attachment site should result in precise control of the apparent molecular weight, which will depend on the size of the crosslinker. Moreover, careful control of the site of the cys mutation on the surface of the recombinant hemoglobin should ensure that the functionality of the derivatized hemoglobin is maintained.

Higher Poly(tetrameric) Hemoglobins

Figure 28A:
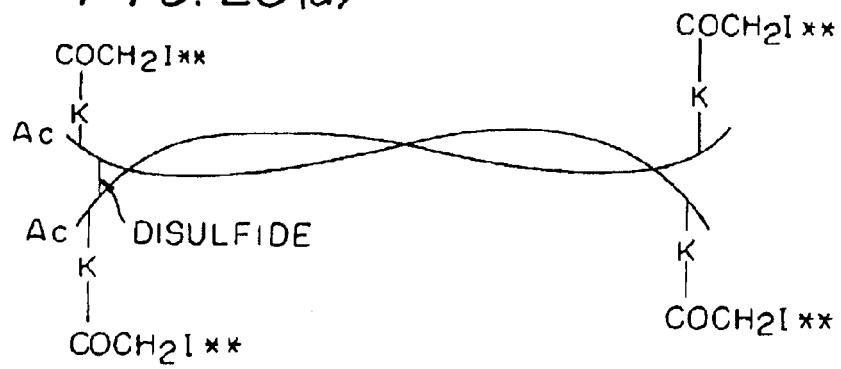
FIGS. 28a to 28c: A depiction of coiled coil crosslinkers suitable for joining (28a) four or (28b) six hemoglobin tetramers.

The above crosslinkers all involve the attachment of two hemoglobins at each end of a crosslinker. It may be advantageous to attach more than two hemoglobins to a single crosslinker to yield more oxygen-carrying capacity and to further increase the molecular weight. A hypothetical 4-hemoglobin coiled-coil linker complex is shown in FIG. 28(a). Design and synthesis of these coiled coil peptides has already been explored (for an example see Cohen and Perry, Proteins, 7:1–15 (1990)). The rationale for a coiled coil is that two intertwined alpha helices will be less sensitive to proteolytic cleavage than a single naked secondary structure like an extended peptide (rapidly cleaved by proteases), an alpha helix or a beta sheet.

Using molecular modeling, an internal disulfide may be designed in the center of a bi-functional coiled coil linker such that the strands are covalently attached. This should stabilize formation of the correct coiled coil crosslinker before mono-cys di-alpha or di-beta Hgb (e.g., sge1.1 cys) is attached. Additionally, a tri-functional crosslinker can be stabilized by use of a orthogonally-protected lysine (lys-FMOC) rather than a disulfide in the center of a proteolytically inert secondary structure. A polyproline helix can be used as the linker, and can be stabilized by branching the synthesis dt the lys-FMOC after removal of the side chain. The three remaining lysines in the branched peptide would then be iodoacetylated to site-specifically attach a thiol-reactive group using either iodoacetic anhydride or N-succinimidyliodo-acetate and subsequently reacted with sge1.1-cys. An analogous tetra-functional crosslinker could be synthesized by inserting 1–2 prolines between two internal branching lysines to rotate them such that the two internal branching chains growing off the orthogonally protected lysines head in (nearly) opposite directions. Analogous structures could be made using D-glutamate(E) or D-aspartate(D) to provide protease resistance, and these would form an extended polyanionic chain at pH 7.

The sequence of a hypothetical alpha-helical coiled coil is modified from that given in Semchuck, et al., in Peptides: Chemistry, Structure and Biology; 566 (Rivier and Marshall, eds:1990), to leave only two lysines (K) at each end:

AcKCAELEGRLEALEGRLEALEGRLEALEGRLEA-LEGKL-(SEQ ID NO:1)

This coiled coil should have about 10 turns of a helix and thus will be ca. 54 Å long, allowing two hemoglobins to attach on each side without steric interference. The exact sequence and length to allow appropriate placement of 4 sge1.1's would depend on the results of molecular modeling. Suggested trifunctional and tetrafunctional crosslinkers are diagrammed below.

TRIFUNCTIONAL

```
      I**                              I**
       |                                |
      CH₂      K—COCH₂I**              CH₂      K—COCH₂I**
       |        |                       |        |
      CO       (P)n                    CO       (D)m
       |        |                       |        |
Ac—K—(P)n—K—(P)n-k              Ac—K—(D)m—K—COCH₂I** n > 6–8                           m > 5–6
```

TRIFUNCTIONAL

```
            COCH₂I**              COCH₂I**
              |                      |
   Ac—K—(P)n—K—(P)m—K—(P)n—K
              |                      |
            COCH₂I              COCH₂I n > 6–8, M = 1 or 2
                   K—COCH₂I**
                      |
   COCH₂I**         (D—)m              COCH₂I**
      |               |                   |
Ac—K—(D—)m—K(D—)n—K(D—)m—K
                      |
                   (D—)mCOCH₂I**
```

(D could be a D-amino acid for greater protease resistance)
(** indicates a reactive site; K is a lysine; P is Proline, Ac is acetyl; I is iodine; D is D- or L-aspartate; K's are on opposite faces so the pseudotetramers attach on opposite faces of the coiled coil.)

See also FIG. 28(a).

Figure 28B:
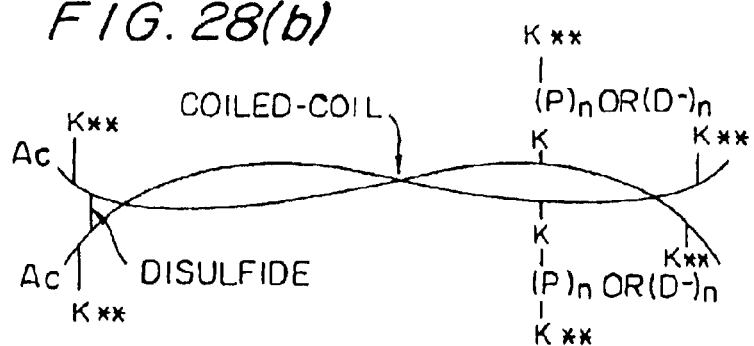
Figure 28C:
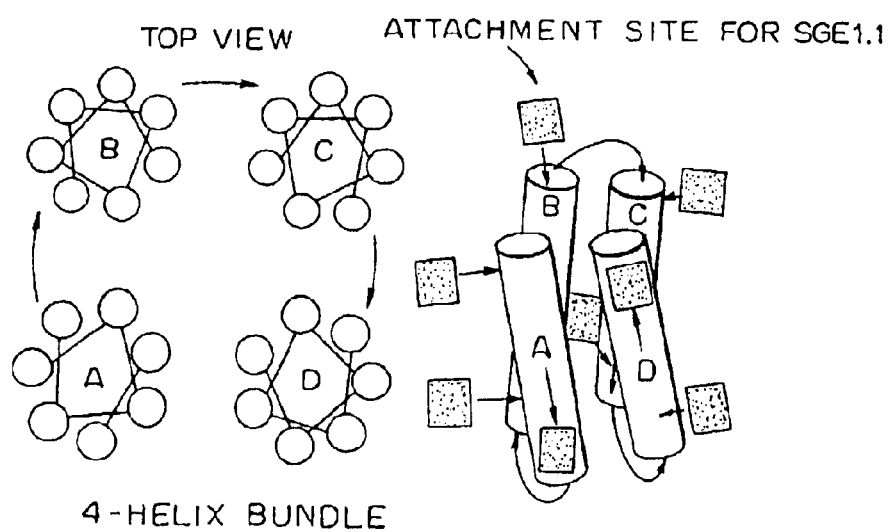

Another possibility is an 8-hemoglobin complex (FIG. 28(b)). The rationale for considering this sort of complex is that it may be the way to obtain a very long half-life SGE1.1, due to the extreme stability of the "crosslinker" and the substantially higher molecular weight of the complex. The crosslinker might take the form of a doubly branched coiled coil, with a Lys(FMOC) replacing an Arg in the middle of the chain to allow the branching, and with a polyproline helix or other protease resistant secondary structure comprising the branching moiety. This structure could allow attachment of 6 SGE1.1's per crosslinker. Alternatively, a 4-helical bundle protein (See FIG. 28(c)) or 4-stranded coiled-coil such as those synthesized by DeGrado, Science, 243:622 (1989), with each helix in the 4-helical bundle containing the consensus sequence GELEELLKKL-KELLKG (SEQ ID NO:2), the helices being linked by three PRR or RPR loops, could be utilized as a suitable core for the linker. This is one of the most stable proteins known, with a G=–22 kcal/mole separating the folded from the unfolded state. Each helix would be 4+ turns or ca. 22 Å long. Since this may not be enough room to fit two hemoglobins with one anchored at each end of the helix, they might have to be attached to different faces of the same helix, to lysines placed at each end of the polar face of each helix. Each helix is amphipathic; this should allow relative freedom to have a total of 8 lysines (and no more) and to change the remaining lysines to arginines. At least two of the i, i+4 salt bridges per helix would be retained for stability of the protein. Attachment of SGE1.1-SH could be via iodoacetylation of the lysine epsilon amino groups and then reaction with SGE1.1-SH.

An example of a modification that might allow more room between hemoglobins would be addition of one turn of the helix to the N-terminus of the A and C helices and the C-terminus of the B and D helices. This and similar modifications would be subject to modeling and experimental constraints.

Analogous core proteins could be made as mutants of known 4-helical bundle proteins such as myohemerythrin or apoferritin, with the surface residues changed so that 8 (or more if topologically possible) lysines (2 per helix) exist on the surface for subsequent modification and attachment of SGE1.1.

Poly(tetrameric) Hemoglobins with Reduced Isoelectric Points

If the isoelectric point of the whole crosslinked conjugate also affects the serum half life, via electrostatic exclusion from the renal filter's "pore", additional negative charges could be included in the crosslink itself (rather than in the hemoglobin, which could change the function of the molecule) to drop the isoelectric point of the overall crosslinked particle. An additional benefit of this might be reduced uptake by the reticuloendothelial system, this uptake being a function of pI for cationized albumin.

We have preliminary evidence from succinylation of SGE1.1 which correlates the number of modified lysines with isoelectric point. This gives a rough estimate of the number of lys to glu and/or lys to asp mutations which may be necessary to reach a pI of 5 or less, the pI range which we expect we need to significantly extend half life. We believe that as many as 8 lysines may have to be modified (a total shift in charge of 16 units) to drop the pI roughly 2 units. It should be less disruptive of the functional properties of hemoglobin to do this via a peptide crosslinker rather than by mutation of the alpha and beta globin subunits proper. However, some mutations could be made in the crosslinker and the remainder in the subunits. As before, the SGE1.1-cys would be attached to iodoacetylated lysine epsilon amino groups by reaction at pH 6.5–7.0.

For human serum albumin in the rat, the half life varied roughly linearly with the pI of the protein, from ca. 4.6 hours for native albumin (pI=4) to 0.8 hrs at a pI above 9.5. Clearance was probably by multiple mechanisms, including potentially increased uptake into the reticuloendothelial system with increased pI. For rat trypsinogens, the difference in serum half life between versions with a pI of 5.0 ($t_{1/2}$ of 4 min) was even larger. Thus a lower pI clearly appears to be an important variable in the serum half life of these proteins.

The following table gives examples of crosslinkers between SGE1.1-cys tetramers which should diminish the isoelectric point of the overall complex.

| Source | Sequence | |
|---|---|---|
| polyasp or polyglu | $\begin{array}{c}\text{COCH}_2\text{I} \quad \text{COCH}_2\text{I}\\ \mid \qquad\qquad \mid\\ \text{Ac—K—(X)n—K}\end{array}$ | n probably ≥ 10–12<br>x = D or E- |
| polyasp or polyglu | $\begin{array}{c}\text{COCH}_2\text{I} \qquad\qquad \text{IH}_2\text{CC}{=}\text{O}\\ \mid \qquad\qquad\qquad \mid\\ \text{Ac—K—(G)n—(X)m—(G)n—K}\end{array}$ | n > 2 to provide flexibility at each terminus, m ≥ 10–12<br>X = D or E |

-continued

| | | |
|---|---|---|
| polyasp or polyglu | 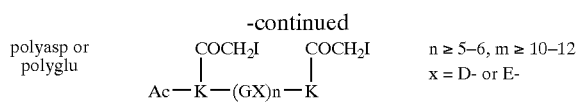 | n ≥ 5–6, m ≥ 10–12<br>x = D- or E- |

A number of the proposed crosslinkers could combine at least two, or possibly three of these attributes for potential additive effects.

It is possible that the unique amine groups in the peptide crosslinkers could be directly iodoacetylated during the peptide synthesis by treating iodoacetic acid as the last amino acid to be added, after deprotecting the lysine amine groups on the resin. In this case, the lysines would be orthogonally protected with N-FMOC or N-nitropyridinesulfenyl groups, or with BNPEOC. This could greatly simplify their synthesis.

Alternate methodologies to iodoacetylation as part of the synthesis could include the reaction of either sge1.1-SH or the peptide crosslinker with a heterobifunctional crosslinker specific for sulfhydryls and amines, such as sulfo-SMCC or similar reagents available from Pierce Chemical Co. (Rockford, Ill.).

Genetically Fused Poly(tetrameric) Hemoglobins

Another approach to the preparation of multimeric (e.g., polytetrameric) hemoglobin involves the genetic fusing of individual tetramers Utilizing other linkers. Two or more tetramers may be crosslinked, depending on the desired molecular weight and the efficiency of folding of the final molecule. The brine shrimp Artemia produces three polymeric hemoglobins with nine genetically fused globin subunits. Manning, et al., Nature, 348:653 (1990). These are formed by variable association of two different subunit types, α and β. Of the eight intersubunit linkers six are 12 residues long, one is 11 residues and one is of 14 residues. Similarly, the dialpha (or dibeta) subunits from different tetramers of a di-alpha or di-beta hemoglobin might be genetically fused together into an extended polypeptide which would link the individual pseudotetrameric domains.

Proteolytically stable extended polypeptide linkages can be envisioned. Desirable linker features might include 1) a number of glycines at each end to allow flexibility in entering the dialpha (or beta) terminal domains, and to decouple the linker secondary structure from that of the dialpha (or beta) terminal domains; 2) stiffness to separate tetramers, obtainable by an extended structure such as a polyproline helix or by polyglutamate or polyaspartate; and 3) inertness to proteases (vide supra or as in a collagen sequence). Several examples of such sequences are listed below. Obviously any other of the peptide linkers mentioned in this specification could be tried after first sterically modeling the fused-dialpha (or dibeta) termini environment. The links would go from the C-terminus of one dialpha to the N-terminus of the next and would be synthesized as a single gene. Besides modeling segments of protease-resistant or negatively charged secondary structure, one or more of the Artemia linkers should be modeled between tetramers. The beta chains could also be joined in this fashion, although the results of this on protein function would be unknown. It might be feasible to make an intermolecular di-beta (sge1.1) with or without additional intrachain crosslinkages.

| Source | Sequence |
|---|---|
| polyproline helix | di α or β C term-(G)n-(P)n-(G)n-di α or β N terminus n probably ≥3, m probably ≥10–12 |
| polyaspartate or -glutamate | -(G)n-(D)n-(G)n-(should drop pI of complex) |
| Artemia linker (example) | -(G)n-LPRQIDLEVTGL-(G)n- (SEQ ID NO: 3); n ≥ 0 |
| a helical coiled coil | -(G) n-KCAELG(KLEALG)4 (SEQ ID NO: 4)<-not fused to terminus (should form octamer with coiled-coil crosslink) |

Two structures of human hemoglobin $A_0$ (either both in the oxy form or both in the deoxy form) taken or assembled from the Brookhaven Protein Data Bank were docked as close together as possible without van der Waals overlap between any residues, using the program Insight (Biosym. Inc., San Diego, Calif.). The distance from the alpha chain C terminal residue arg 141 to the amino terminal nitrogen of the alpha chain N terminal residue val 1 (in one structure) was then measured. This distance was ca. 22 Å when both molecules had the oxy structure and ca. 18 Å when both were in the deoxy structure. In the oxy and deoxy structures, the valine at the alpha chain N terminus is exposed at the side of a cleft in the structure, while the arg carboxylate is at the bottom of the cleft. Thus it is possible to genetically fuse these two termini without suffering a large structural displacement of residues around either terminal amino acid. Linkers which have sufficient length to stretch between these termini when the two hemoglobins are docked together (but without any van der Waals overlap) are listed below.

An alternative fusion may be envisioned between a truncated alpha chain in one hemoglobin and the N terminal alpha val 1 in the second hemoglobin. The first molecule could be truncated at ser 138, which intermolecular N terminal to C terminal distance is about 17 Å (deoxy) and 22 Å (oxy), and examples of genetically inserted linkers spanning this distance are listed below.

Thus two hemoglobin molecules could be linked (by fusing two intermolecular alpha domains) to generate a fusion protein approximately twice the size of normal human hemoglobin. An additional intramolecular crosslink, as introduced into rHb1.1 to prevent dissociation of hemoglobin into dimers, could be included as well, giving a fusion of four alpha-domains.

We expect that the genetically inserted links will be stable in the presence of proteases, due to the steric occlusion by the two hemoglobins surrounding the linkage. This resistance may be further enhanced by the use of glycines, bonds between which may be less susceptible to proteases, since most proteases have side chain specificity for residues other than glycine (which has only a hydrogen as a sidechain, and thus may result in a poor Km of this substrate for a protease). A polyproline helix may also be used as a linker to enhance stability to proteases. Fusion of a polyglutamate or polyaspartate as a linker might allow a much lower isoelectric point for the complex, and thus a longer serum half life.

| linker | end-to-end Distance | conformation | comments |
|---|---|---|---|
| -(gly)$_7$- (SEQ ID NO:21) | 25Å | extended | minimal length for gly linker to span termini in both oxy and deoxy structures. Longer linkers (up to 20–50 residues) may also work favorably. |
| 0(gly)$_{1-3}$-(ala)$_{12}$-(gly)$_{1-3}$- (SEQ ID NO:22) | 20Å–40Å | Ala in right handed alpha helix | the Gly are added for flexibility and minimal disturbance of Hb structure around their fusion with the N and C termini. Length is dependent on the number of glycines and the degree of extension. |
| -(gly)$_{1-3}$- (pro)$_{12-16}$-(gly)$_{1-3}$- (SEQ ID NO:23) | 21–48Å | pro in a left poly- proline helix | 12, 14, 16, handed prolines. Length dependent on number of prolines and glycines. |
| -(gly)$_{1-3}$-(asp)$_n$-(gly$_{1-3}$)- (SEQ ID NO:24) | 26–49Å | | Asp residues add negative charges in pseudooctamer. |

Other residues could be substituted into these linkers while leaving their length essentially the same, including complete linkers taken from the sequence of other known human proteins such as hemoglobin, to prevent any recognition of the pseudooctamer as a foreign protein.

Use of linkers with a maximal length more than 18 Å and less than 22 Å may be differentially stabilize the deoxy structure, and may result in a lowered oxygen affinity for the pseudooctamer.

Octameric Hemoglobins Formed Without use of an Pseudooligomeric Globin

Figure 35A:
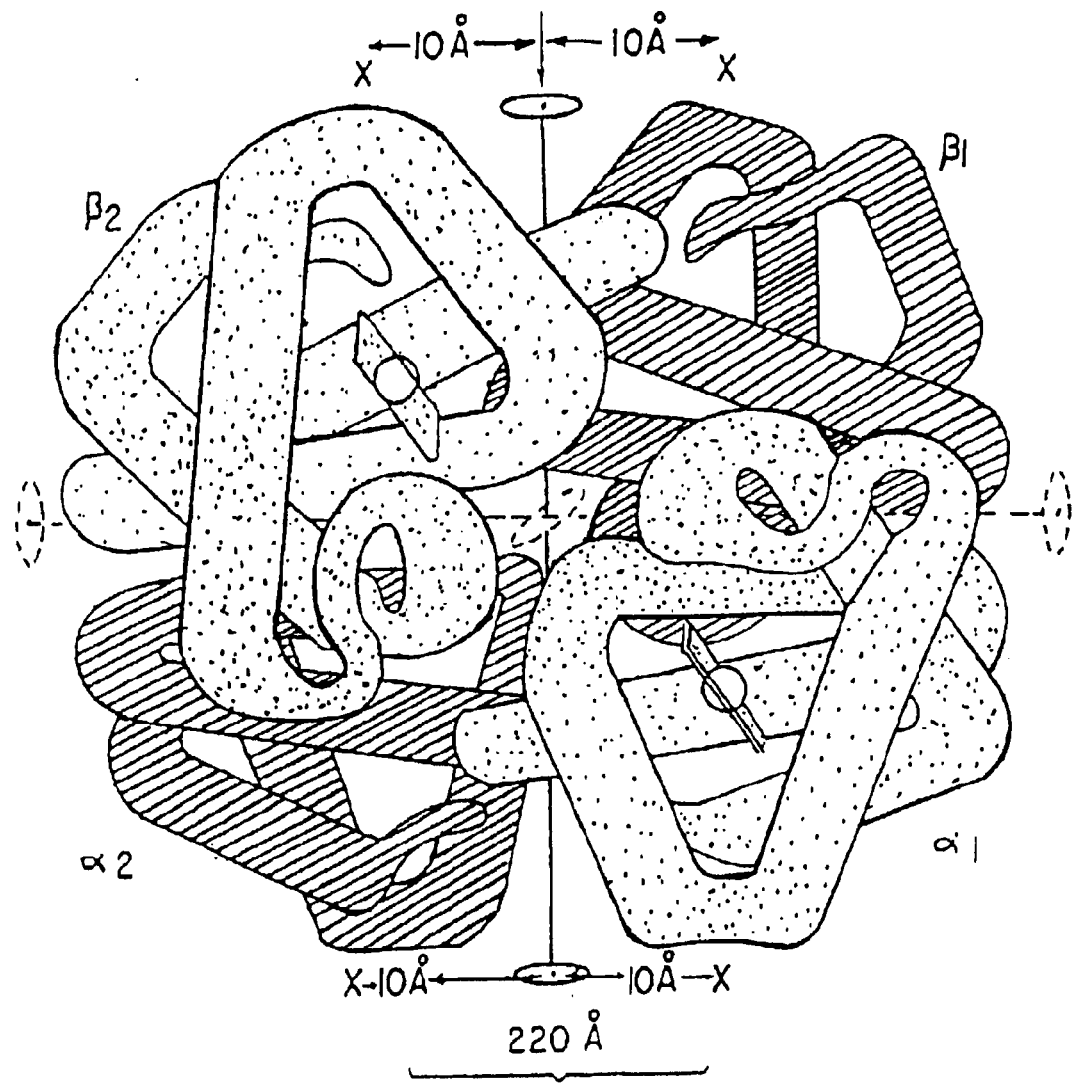
FIGS. 35a and 35b Schematic showing how cysteine mutations can favor formation of octamer without genetic fusion of subunits.
Figure 35B:
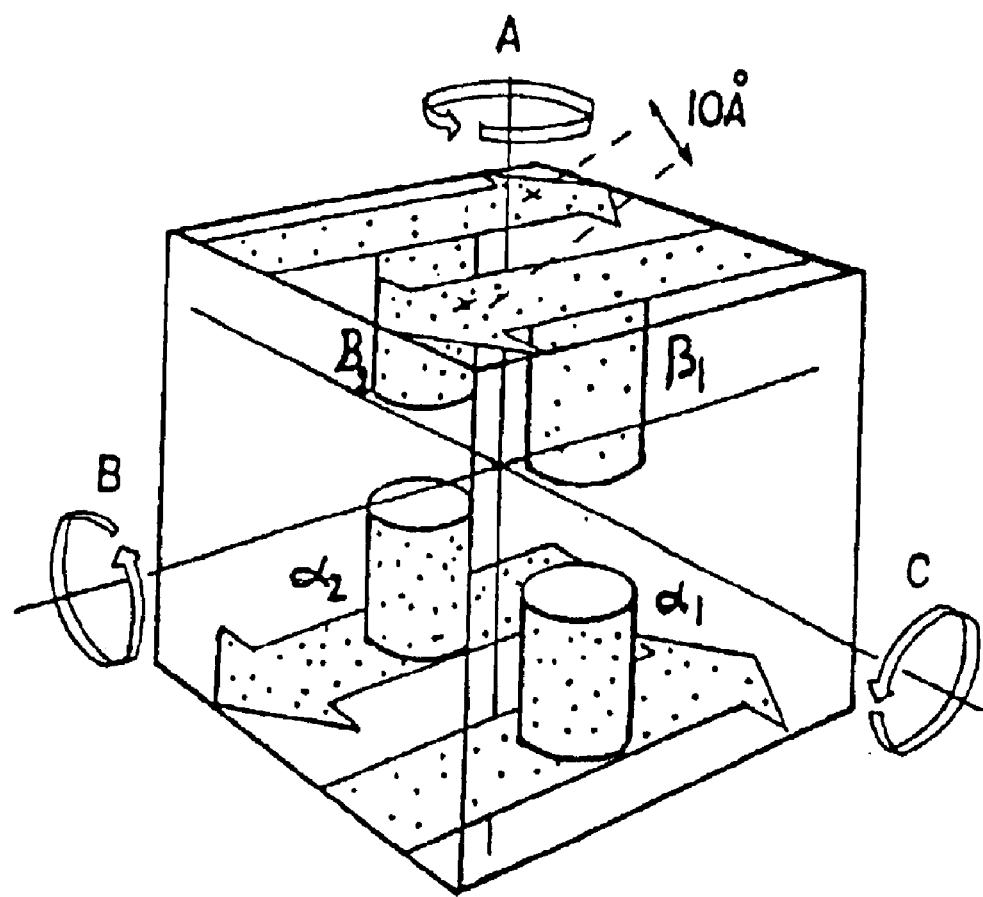

It is possible to produce an octameric hemoglobin, without substantial production of higher multimers, by suitable cysteine mutation of either the alpha or beta chain (see FIG. 35).

Hemoglobin mutants containing one X to cys mutation in the beta chain gene (giving two per tetramer) or in the alpha chain gene (also giving two per tetramer), in which the residues mutated to cysteine are both on or very close to the surface of the subunit and are as close (preferably 10–15 Å) to the dyad axis separating the subunits, may form octamers (two hemoglobins) linked by two disulfides. Polymerization of such mutants should be retarded by the proximity of the two disulfides to each other, such that after one disulfide is formed, a third incoming hemoglobin will be sterically hindered from reacting with either free cysteine on the two original hemoglobins.

Because it is possible that this mutant may form higher order polymers (rather than simply the octamer), a diluted solution may be used in vitro for formation of disulfide bonds. The kinetics of polymerization of hemoglobin should be at least second order (or a higher order) in hemoglobin concentration, while after one disulfide is formed, the formation of the second disulfide between two tetramers should be zero order in hemoglobin. Thus the ratio of polymerized product to octamer should diminish as the hemoglobin concentration is decreased. If formation of octamers is done under oxygenated conditions, the yield of octamers-vs. polymers may increase further, since the distance between the two cys mutations is less in every case in the oxy hemoglobin structure than in the deoxy structure.

A list of preferred mutation sites in both the beta chain and the alpha chain is provided below:

Beta and Alpha Chain Mutations Sites for x to cys Mutation to Form Disulfide-bond Linked Octameric Hemoglobin.

| Chain | mutation | distance | distance, | Comment |
|---|---|---|---|---|
| beta ans | 80 to cys | 22Å | 18Å | no listed deleterious mutations, asn 80 is on surface[a] |
| beta asn | 79 to cys | 24Å | 22Å | Hb Tampa[a] (asp to tyr) has no major abnormal property listed; Hb G-Hsi-Tsou (asp to gly) has increased 0$_2$ affinity; is on surface |
| alpha asn | 78 to cys | 24Å | 20Å | on surface; no major[a] abnormal properties of known mutations of asn 78 |
| alpha asp | 75 to cys | 22Å | 18Å | on surface; no major[a] abnormal properties of known mutations of asp 75 |
| alpha asp | 74 to cys | 26Å | 20Å | on surface; no major[a] abnormal properties of known mutations of asp 74 |

[a]R. N. Wrightstone. Policies of the International Hemoglobin Information Center (IHIC), Comprehensive Sickle Cell Center, Medical College of Georgia. 1988.

Miscellaneous

The appended claims hereby incorporated by reference as a further enumeration of the preferred embodiments. All cited references are incorporated by reference to the extent necessary to enable the practice of the invention as now or hereafter claimed.

By the means suggested in this specification, we have had the following achievements:

(1) Expression of Met-FX-alpha globin in *E. coli* from a dicistronic operon comprising a introductory cistron and a Met-FX-alpha globin gene, both transcribed from a Tac promoter. (Example 2)

(2) Expression of Met-FX beta globin in *E. coli* by similar means. (Example 2)

(3) Co-expression of Met-FX-alpha globin and Met-FX-beta globin in *E. coli* from a tetracistronic operon comprising an introductory cistron, an FX-alpha globin gene, an intercistronic sequence, a second introductory cistron, and an FX-beta globin gene, all controlled by a single Tac promoter. The alpha and beta globins were intracellularly assembled into functional FX hemoglobin. The FX hemoglobin was enzymatically converted to hemoglobin. (Example 3)

(4) Co-expression as in (3) above of mutants of FX-hemoglobin in which the beta globin subunits possessed the Beth Israel, Cheverly, Providence/MSR, Kansas or beta$^{67}$ Val→Ile mutations. (Example 4)

(5) Co-expression as in (3) above of Met-alpha globin and Met-beta globin and intracellular assembly into Met-hemoglobin (a.k.a. Des-FX-hemoglobin). (Example 5)

(6) Co-expression as in (3) above of Des-Val-alpha globin and Des-Val-beta globin. (Example 6)

(7) Co-expression as in (6) above, but with the DesVal-beta globin gene preceding the Des-Val-alpha globin gene within the operon. (Example 6)

(8) Co-expression as in (3) above of (Des-Val)-alpha-(Gly-Gly)-alpha globin and beta globin and intracellular assembly into a di-alpha hemoglobin. (Example 8)

(9) Co-expression as in (8) above of (Des-Val-alpha-(GlyGly)-alpha globin and a mutant (Nagai, Arg-Nagai, or Kansas) of beta globin and intracellular assembly into a mutant di-alpha hemoglobin. (Example 9)

(10) Co-expression as in (3) above of Des-Val-alpha globin and a Des-Val beta globin with the Presbyterian mutation and intracellular assembly into a mutant Des-Val hemoglobin. (Example 11)

(11) Co-expression as in (8) above of a (Des-Val)alpha-(GlyGly)-alpha globin and of a beta globin with the Presbyterian mutation. (Example 11).

(12) Expression of di-alpha globin and beta globin from separate promoters on the same plasmid (Example 12)

(13) Co-expression of di-alpha globin and two copies of beta globin from same operon (Example 13).

(14) Expression of Di-beta hemoglobin (Example 14).

(15) Devised Hypothetical Protocol for co-expression of alpha globin and beta globin under control of separate promoters on the same plasmid (Example 16).

(16) Devised Hypothetical Protocol for co-expression of alpha and beta globin under control of different promoters on different plasmids (Example 17).

(17) Co-expression of α and β globin in S. cerevisiae (Example 19).

(18) Co-expression of di-α globin and β globin in S. cerevisiae. (Example 23).

(19) Construction of Des-Val-alpha globin and Des-Val-beta globin in E. coli under lambda $P_L$ control.

(20) Co-Expression of di-alpha globin and Des-Val-beta globin in E. coli under lambda $P_L$ control.

(21) Co-Expression of alpha and beta globin from separate plasmids in diploid strains of S. cerevisiae.

(22) Co-Expression of di-alpha globin and beta globin Presbyterian mutant in S. cerevisiae.

(23) Preparation of vectors for expression of di-alpha globins with -Gly- or -Pro- linkers.

(24) Evaluation of different strains and induction temperatures for expression of di-alpha hemoglobin in E. coli.

(25) Co-Expression of alpha and mutant beta globin in S. cerevisiae, assembling to form low-affinity hemoglobin mutants.

(26) Construction of vectors for expression of monocysteine (asymmetric) mutants of di-alpha and di-beta hemoglobin.

(27) Hypothetical protocol for expression of a disulfide-bonded pseudooctamer.

(28) Construction of di-α globin mono-cysteine (A71C, D75C, or S81C) mutant expression vector.

(29) Hypothetical protocol for the oxidation of two SGE1.1 mono-cys's to form a pseudo-octomer.

(30) Characterization of di-α hemoglobin.

(31) Hypothetical protocol for the construction of hemoglobin molecules stabilized against dimer formation by fusion across the alpha1-beta2 or alpha2-beta1 dimer interface region.

An unexpected and surprising change in oxygen binding characteristics of hemoglobin was replacement of the N-terminal valine with methionine. As illustrated in Example 11, hemoglobin $A_0$ purified from blood has a $P_{50}$ value of 4.3 with N=2.8 when measured at 25° C. DesFX-hgb produced in E. coli, a hemoglobin identical to $A_0$ except for the addition of a methionine at the N-termini of the alpha and beta chains, has essentially the same $P_{50}$ and N values. (Within experimental error, Example 7). Thus, the addition of a methionine, without altering the adjacent valine residue, has little or no effect on oxygen binding. On the other hand, a higher $P_{50}$ value, 6.6, was observed for desVal-hgb produced in E. coli, a hemoglobin in which the normal N-terminal valine of each chain was replaced with methionine. Cooperativity, as measured by N, was virtually the same, however, for all three molecules.

A similar comparison was made for two hemoglobins each containing the Presbyterian mutation, one produced in E. coli (Example 11) and one in yeast. The E. coli hemoglobin was constructed with a Des-Val alpha chain, i.e., the N-terminus had the normal valine replaced with methionine. Oxygen binding was characterized by $P_{50}$=19.8, N=2.5 at 25° C. and by $P_{50}$=34.5 and N=2.5 at 37° C. (Example 11). The corresponding yeast coding region begins with an additional methionine codon in front of the normal valine codon. Because this initial methionine is removed post translationally in vivo, the purified hemoglobin has a normal N-terminal valine. For this molecule, $P_{50}$=23 to 25 and N=2.5 when measured at 37° C. Thus, in the above instances, the replacement of an N-terminal valine with an N-terminal methionine increased the $P_{50}$ value. Under physiological conditions, it is expected that the genetically fused Presbyterian hemoglobin produced in E. coli will deliver 20–30% more oxygen than the similar hemoglobin, with its altered N-terminus, produced in yeast.

A very large number of different plasmids are referred to in the Examples which follow. In order to highlight the relationships among these plasmids, a Table of vectors has been compiled (See Table 200).

EXAMPLE 1

Construction of FX-alpha Globin (PDLII-62 m')
and BetaGlobin (pDLII-10a) Expression Vectors
1.1 Materials and Methods Unless otherwise stated all electroelutions, phenol/chloroform extractions, ethanol (EtOH) precipitations, alkaline-SDS plasmid purifications, agarose electrophoresis and DNA manipulations were carried out essentially as described by Maniatis et al. ("Molecular Cloning" Cold Spring Harbor, N.Y., 1982).

The following abbreviations and definitions are used: ethylenediaminetetraacetic acid (EDTA); sodium dodecylsulfate (SDS); polyacrylamide gel electrophoresis (PAGE); dimethylsulfoxide (OMSO); dithiothreitol (DTT); isopropyl-beta-D-thiogalactopyranoside (IPTG); 2×YT medium (16 g bacto tryptone, 10 g Bacto yeast extract, 5 g NaCl per liter water); SDS-PAGE loading buffer (0.125M Tris-HCl, pH6.8, 20% v/v glycerol, 2% SDS, 2% 2-mercaptoethanol, 0.01% bromphenol blue); phosphate buffered TB medium (24 g yeast extract, 12 g tryptone, 4 mL glycerol, 17 mL 1M $KH_2PO_4$, 72 mL 1M $K_2HPO_4$ per liter water); Tris-EDTA buffer (TE: 10 mM Tris, pH8.0, 1 mM EDTA); Tris-borate, EDTA buffer (TBE: 0.089 M Tris, 0.089 M boric acid, 0.002 M EDTA); Tris-acetate EDTA buffer (TAE: 0.04 M Tris, 0.04 M acetic acid, 0.001 M EDTA).

Protein electrophoresis was performed by the method of Laemmli, U.K. (*Nature* 1970, 227, 680–685) on 15% SDS-polyacrylamide gels.

*E.coli* JM109 cells were made competent as follows: Two hundred milliliters of 2×YT medium was inoculated with 2 mL of an *E.coli* JM109 overnight culture. The 200 mL culture was then incubated with shaking at 37° C. for 1 hour. Cells were harvested by centrifugation at 6000 rpm at 4° C. for 4 min in a Beckman JS13.1 swinging bucket rotor (Beckman Instruments, Inc., Palo Alto, Calif.). The cells were resuspended in 50 mL total of a buffer containing 45 mM MnC12, 60 mM $CaCl_2$, 40 mM KOAc, pH 6.2, 15% sucrose (w/v) 1.3% RbCl (w/v), and 7.5% (v/v) glycerol. Following centrifugation as above, the cells were resuspended in 20 mL of the same buffer and incubated at 0° C. for 30 minutes. Cells were dispensed in one milliliter aliquots and stored at −80° C. until used.

Unless otherwise stated, all restriction enzyme digests were performed under conditions suggested by the manufacturer. DNA concentrations were determined by Beer's law using measured absorbance at 260 nm ($A_{260}$) against a water reference standard. For synthetic oligonucleotides the following extinctions were used: $E^{260}$=0.05 mL/ug/cm and for double stranded DNA $E^{260}$=0.02 mL/ug/cm.

1.2 Globin Gene Synthesis

Each globin gene was constructed from 14 separate oligonucleotides ranging in length from 50–85 base pairs. The FX-alpha globin gene was synthesized from oligonucleotides SJH I-33a-f, SJH I-34a-f and SJH I-35a,b; FX-beta globin gene was synthesized from SJH I-36a-f, SJH I-37a-f and SJH I-38a,b. Each globin gene is preceeded by a short loader gene as previously described. Oligonucleotides were synthesized on a Biosearch 8600 instrument using beta-cyanoethylphosphoramidite chemistry on 1,000 angstrom CPG columns (0.2 mmole) (Beaucage, S. L. and Caruthers, M. H. *Tet. Lett*. 1981, 22, 1859–1862). The sequence of these oligonucleotides is given in FIG. 4.

Unless otherwise stated, the oligonucleotides were cleaved from the columns using the following protocol: Approximately 0.5 mL of fresh, concentrated $NH_4$ OH was drawn into the column with a 1 mL syringe. The $NH_4$ OH was allowed to react for 20 min then expressed into a glass vial (approximately 4 mL capacity). This process was repeated 2 times, the vial was filled to greater than 75% capacity with $NH_4OH$, and heated at 55° C., overnight. The samples were lyophilized, resuspended in 0.1 mL $H_2O$ and the concentration estimated by measuring $A_{260}$.

Two hundred micrograms of the individual oligonucleotides were purified by urea polyacrylamide gel electrophoresis. To do this, an equal volume of 2× loading buffer (90% formamide (v/v), 0.5×TBE, 0.05% (w/v) bromophenol blue, 0.05% (w/v) xylene cyanol) was added to the oligonucleotide. The sample was heated at 95° C. for 10 min. and applied to a 10% acrylamide gel containing 7M urea and 1×TBE. Electrophoresis was at 800 volts for approximately 2 hrs. The full length oligonucleotide was visualized under ultraviolet light. That region of the gel was then-excised and incubated in 3mL of 100 mM Tris, pH 7.8, 500 mM NaCl, 5 mM EDTA buffer at 60° C., overnight.

The oligonucleotide solution was further purified by reverse phase chromatography as follows: A C18 Sep-Pak cartridge (Waters Associates) was washed with 10 mL 100% methanol followed by 10 mL of $H_2O$. The oligonucleotide solution was applied to the column, washed with 20 mL $H_2O$ and eluted with 3×1 mL aliquots of 50 mM triethylammonium acetate, pH 7.3/methanol (1:1). The purified oligonucleotide was lyophilized, washed with 100% ethanol, dried, and resuspended in 0.1 mL $H_2O$. The concentration was determined by $A_{260}$.

The synthetic FX-beta gene sequence (included in FIG. 5) was constructed as follows: 100 pmole of the following oligo nucleotides were kinased in 3 separate reactions. Reaction 1 contained oligonucleotides SJH I-36b, c, d, e, and f. Reaction 2 contained SJH I-37a, b, c, and e. Reaction 3 contained SJH I-37d, f, and SJH I-38a. After combining the appropriate oligonucleotides, the solutions were lyophilized to dryness and resuspended in 16 uL of $H_2O$. Two uL of 10× kinase buffer (0.5M Tris-HCl, pH7.4, 0.1 $MgCl_2$), 0.5 uL of 100 mM DTT, and 1 uL of 1.0 mM ATP were then added. The reaction was initiated by addition of 1 uL (2U) of T4 polynucleotide kinase (IBI, Inc., New Haven, Conn.). After incubation at 37° C. for 1 hour, the reactions were heated to 95° C. for 10 minutes to inactivate the kinase. The three reactions were combined and 100 pmoles of oligonucleotides SJH I-36a and SJH I-38b were added. After addition of 10 uL of 100 mM Tris, pH 7.8, 100 mM $MgCl_2$, the oligonucleotides were allowed to anneal by incubating at 65° C. for 30 min, 37° C. for 30 min, and 15° C. for 1 hour. Annealed oligonucleotides were ligated by addition of ATP (1 mM, final) and DTT (10 mM final) and 4 uL (20U) T4 DNA ligase (IBI, Inc., New Haven, Conn.) and incubation at 15° C. for 1 hour. Aliquots of this ligation mixture were then cloned directly into M13mp19 (see below).

Oligonucleotides for the construction of FX-alpha globin were similarly purified, kinased, annealed, and ligated. Before ligation into M13mp19, the full length FX-alpha globin gene was purified by electrophoresis through 0.8% agarose in 1×TAE buffer and electroeluted into dialysis tubing using 0.5×TBE as the electroelution buffer by the method of Maniatis et al. Eluted DNA was phenol extracted, EtOH precipitated, and resuspended in 20 uL TE buffer. Aliquots were used for cloning into M13mp19.

1.3 Phage Vectors

For cloning, a 2, 5 or 10 fold molar excess of the individual FX-alpha and FX-beta globin gene sequences were combined with 200 ng of double cut, gel purified M13mp19-RF (New England BioLabs, Inc., Beverly, Md.) and ligated overnight at 15° C. in 50 uL ligation buffer (IBI, Inc., New Haven, Conn.) containing 2U of T4 ligase. FX-Alpha globin was cloned into the XmaI/PstI sites of M13mp19. FX-Beta globin was cloned into the PstI/HindIII sites of M13mp19.

*E. coli* JM109 was transformed with the M13mp19 ligation mixture containing the FX-alpha or FX-beta globin gene sequences using the following transformation protocol: Nine microliters of DMSO was added to 0.25 mL of competent *E. coli* JM109 and the cells were incubated on ice for 10 min. Aliquots of the FX-alpha or FX-beta globin ligation reactions were added and incubated on ice for 40 minutes and at 42° C. for 3 min. One hundred microliters of a JM109 overnight culture was added to each transformation mix followed by 60 $\mu$L of a solution containing 50 $\mu$L of 2% (w/v) 5-bromo-4-chloro-3-indolyl galactopyranoside in dimethylformamide and 10 $\mu$L of 100 mM isopropylthiogalactoside. Molten B-top agar (log Bacto tryptone, 8 g NaCl, 6 g agar per liter), 2.5 mL was added and the mixture poured onto a B-bottom agar plate (10 g Bacto tryptone, 8 g NaCl, 12 g of agar per liter). Following incubation overnight at 37° C. colorless plaques (i.e., clones containing inserted DNA) were removed from the plates using sterile transfer pipettes and inoculated into 1 mL of a JM109 overnight culture diluted 1:100 in 2×YT media.

Bacteriophage clones were grown at 37° C. for 6 to 8 hrs. and centrifuged in a microcentrifuge for 5 minutes. The cell pellets were processed for M13mp19 RF using the alkaline-SDS method and resuspended in 20 µL of TE buffer containing 20 µg/mL DNAase free RNAase (Sigma, St. Louis, Mo.). Aliquots (1–3µL) of the RF preparations were digested with 10–20 units each of the appropriate restriction enzymes (see above) and analyzed on 0.8% agarose electrophoresis gels (see above).

M13mp19 clones containing the correct size inserts were grown in larger quantities to obtain single stranded phage DNA for sequencing. Thirty-five milliliters of 2×YT medium was inoculated with 0.3 mL of a JM109 overnight culture. After growth for 1 hour at 37° C., the 35 mL culture was inoculated with 200 µL of the appropriate phage-containing supernatant. The culture was incubated for 6 hours at 37° C. and the culture supernatant collected by centrifugation at 9000 rpm for 10 min in a JS13.1 roter. The phage were precipitated from 31 mL of supernatant by addition of 5 mL 4M NaCl and 4 mL 40% (w/w) polyethylene glycol 6000 and recentrifuged as above. The phage pellet was resuspended in 0.4 mL of TE, extracted with phenol/chloroform/isoamyl alcohol (50:49:1 (v/v)) three times, chloroform/isoamyl alcohol (49:1 (v/v)) on time, and ethanol precipitated. The DNA pellet was resuspended in 20 µL TE and quantitated spectrophotometrically by $A_{260}$. One microgram of phage DNA was used per set of sequencing reactions.

Sequencing was by the dideoxy method of Sanger (Sanger, F. S. et al. *Proc. Nat. Acad. Sci., USA* 1977, 74, 5463–5467) with M13-20 and M13-40 universal primers (New England BioLabs, Beverly, Mass.) and gene specific primers (for FX-alpha globin the following primers were used: alpha-1 5'-CGTATGTTCCTGTCTTT-3' (SEQ ID NO:25); alpha-2 5'-ACAAACTGCGTGTTGAT-3' (SEQ ID NO:26); for FX-beta globin the following primers were used: beta-1 5'-GCTGGTTGTTTACCCGT-3' (SEQ ID NO:27); beta-2 5'-ACCCGGAAAACTTCCGTC-3' (SEQ ID NO:28)).

1.4 Expression Vectors pDL II-62m and PDL II-10a

The appropriate sequences were excised from the M13mp19 vector and cloned into the pKK-223-3 (Pharmacia/LKB, Piscataway, N.J.)) expression vector under control of the Tac promoter (Brosius, J. and Holy, A. *Proc. Nat. Acad. Sci., USA* 1984, 81, 6929–6933). A DNA sequence encoding alpha globin was removed by cutting with EcoRI and PstI. the globin containing fragment was gel purified and ligated into EcoRI and PstI double cut, gel purified pKK-223-3 using methods described above. *E. coli* JM109 cells were transformed with the ligation reaction containing the desired FX-alpha globin sequence (pDL II-62m) (FIG. 1) and selected for by growth on 2×YT media containing ampicillin (100 µg/mL). Individual clones were screened for the presence of the desired insert (yielding pDL II-62m) by alkalin-SDS purification of plasmids and restriction analysis with the enzymes EcoRI and PstI using the methods described above. Cloning of the FX-beta globin sequence into the pKK-233-3 expression vector, yielding pDL II-10a (FIG. 1) was done analogously except that restriction analysis and cloning was done with PstI and HindIII.

EXAMPLE 2

Separate Expression of Synthetic FX-Alpha and FX-Beta Globin

To assess the expression of the individual FX-globin gene products, *E. coli* JM109 clones transformed with either pDL II-62m or pDL II-10a were inoculated into 2 mL of t5 media containing ampicillin (100 µg/mL). The inoculum was grown at 37° C. for 3–4 hours, then divided into two 1 mL aliquots. One of the aliquots was induced by the addition of IPTG (1 mM, final) and grown for an additional 3–4 hours. The cells were collected by centrifugation, resuspended in 0.5 mL SDS-PAGE loading buffer and heated at 85° C. for 10 minutes. The total cell protein mixture was electrophoresed on 15% SDS-polyacrylamide gels using authentic hemoglobin as a molecular weight standard.

EXAMPLE 3

Polycistronic Coexpression of FX-alpha and FX-beta Globin Gene Products from the same Operon (PDLII-66a) and Conversion of FX-Hemoglobin to Hemoglobin To achieve coexpression of FX-alpha and FX-beta globins from a single polycistronic operon, FX-beta globin sequence from pDL II-10a was excised with HindIII and PstI, gel pDL II-62m. Ligation and transformation conditions were identical to those described above. Note that each globin cistron was preceeded by an "introduction" cistron as previously described, so that the entire Tac promoter driven operon had four cistrons. Clones were individually examined for the presence of both FX-alpha and FX-beta globin genes by digestion of plasmids with EcoRI and separation of fragments by electrophoresis through 0.8% agarose. Plasmids containing both genes (pDL II-66a, FIG. 1) produced a fragment of approximately 1.0 kb following EcoRI digestion.

Clones containing pDL II-66a were grown in 2 mL of TB media containing ampicillin (100 µg/mL) for 4 hours at 370. The culture was divided into two 1 mL aliquots, one of which was induced with 1 mM IPTG. Incubation was continued for 4 hours. Total cell protein extracts for both the uninduced and induced clones were examined by SDS-PAGE electrophoresis to confirm the coexpression of both FX-alpha and FX-beta globin.

To determine if the coexpression of both gene products resulted in the formation of tetrameric FX-alpha globin$_2$ FX-beta globin$_2$ protein, the following experiments were performed. Two liters of TB medium containing ampicillin (100 µg/ml) was inoculated with 20 mL of an overnight culture of an FX-alpha/FX-beta expressing *E. coli* clone and grown to an optical density at 600 nm ($OD_{600}$) of 2.1 at 37° C. The culture was induced with IPTG (2.5 mM final concentration) and grown to an $OD_{600}$ of 3.5.

The cells (40 gm) were collected by centrifugation at 10,000×g and suspended in 80m of lysis buffer (50 mM Tris-HCl, pH 8.0, 25% sucrose, 1 mM EDTA). Ten milliliters of lysozyme solution (18 mg/ml in lysis buffer) was added and the mixture incubated on ice for 30 min. $MgCl_2$, $MnCl_2$, and DNAse I (Sigma, St. Louis, Mo.) were added to final concentrations of 10 mM, 1 mM and 10 g/mL, respectively. The cells were incubated at room temperature for 1 hour and an equal volume of a solution containing 1% one percent deoxycholic acid, 1% Nonidet P-40, 20 mM Tris-HCl pH 7.5, 2 mM EDTA was added to the lysate.

Figure 6:
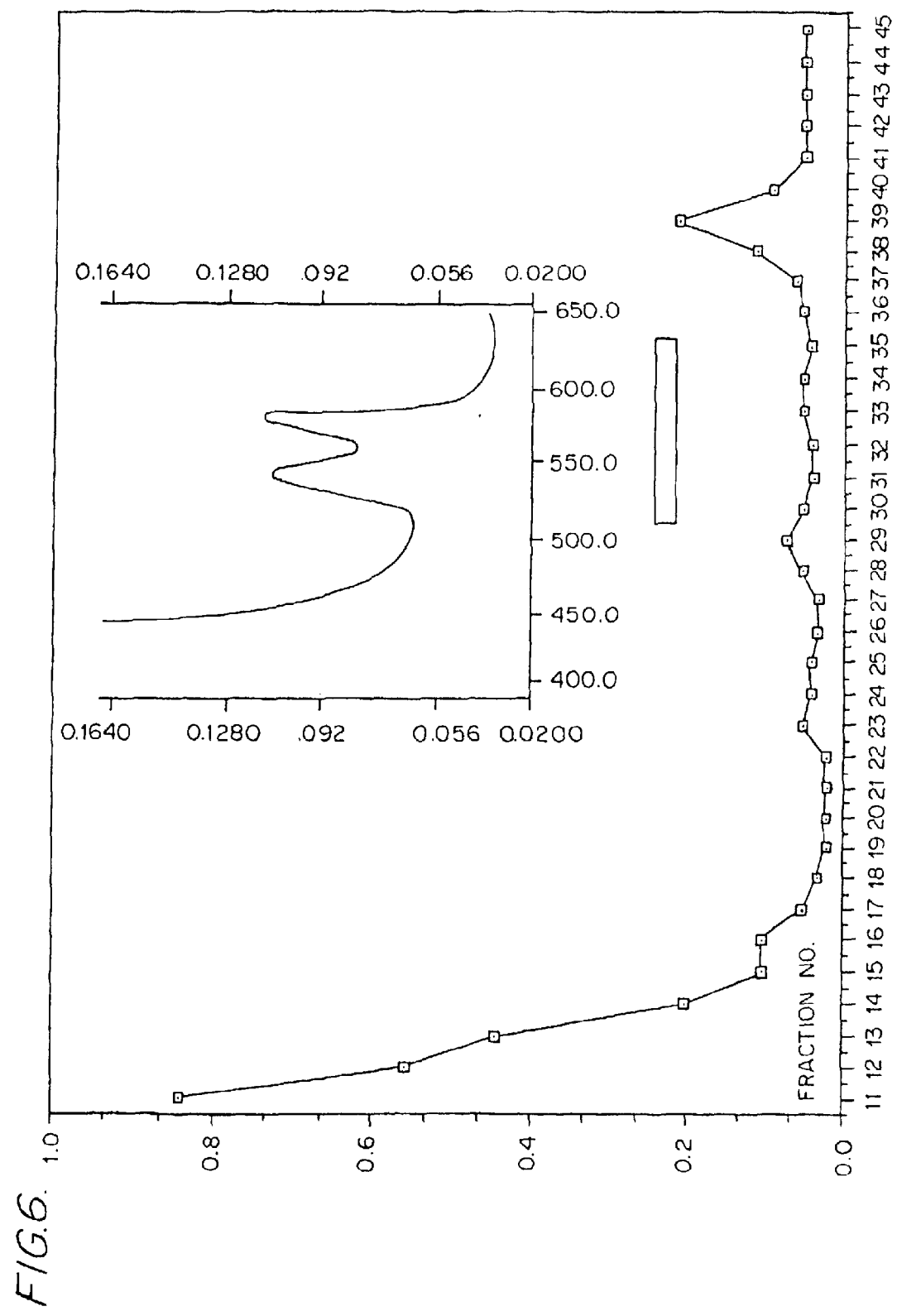
FIG. 6: Elution profile and absorbance spectrum for FX-hemoglobin.
Figure 9:
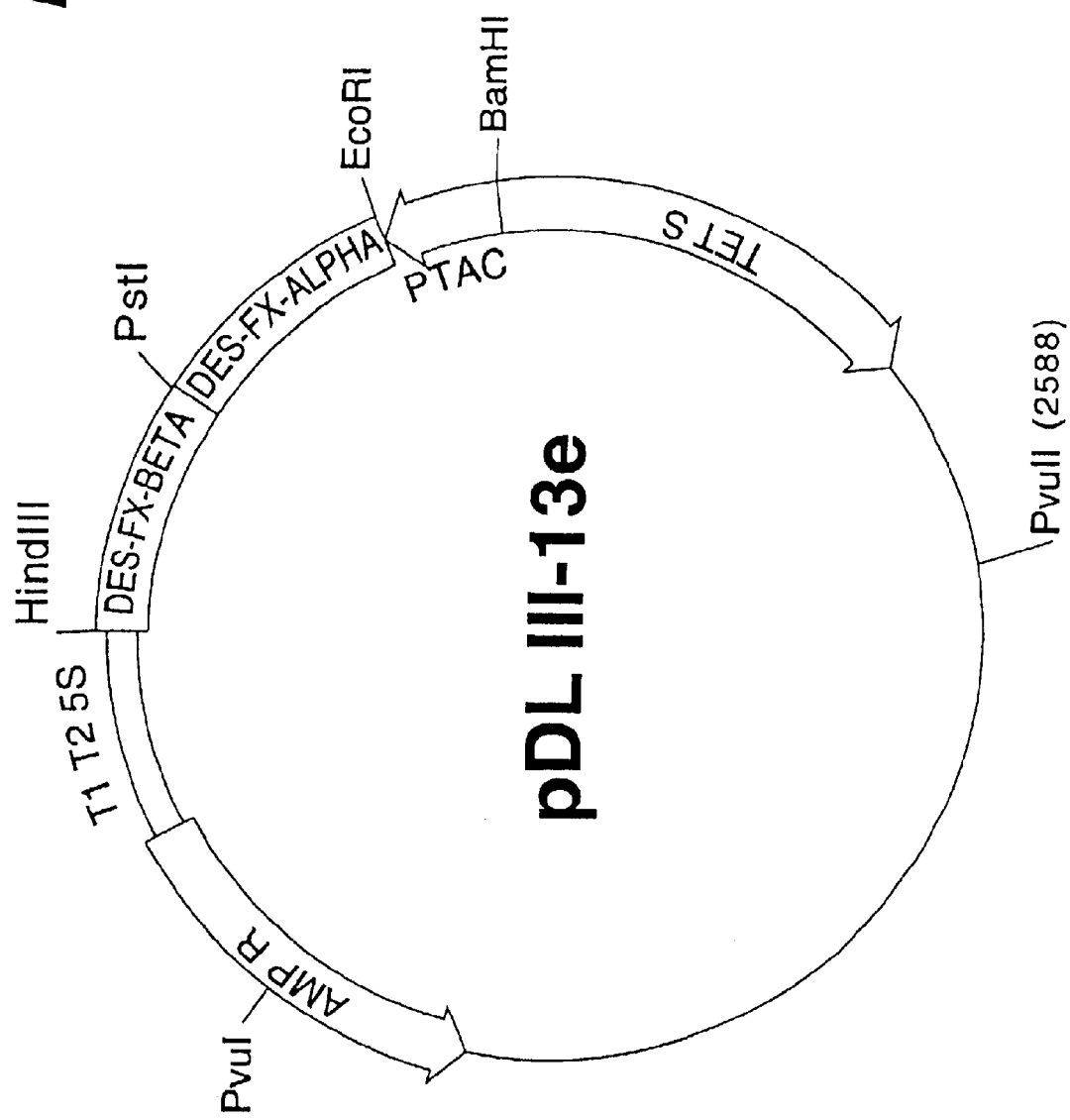
FIG. 9: Map of Plasmid pDL III-13e

Particulate material was removed by centrifugation at 10,000×g for 10 min. The supernatant (~200 mL) was bubbled with carbon monoxide for 5 min and dialyzed overnight against 4 liters of 10 mM NaPO4 buffer, pH 6.0. The cell-free extract was clarified by centrifugation at 10,000×g for 10 min. To the supernatant was added 20 g DE-52 (Whatman. U. K., The pH of the suspension was adjusted to 7.0 and the ion exchange resin was removed by centrifugation. The pH of the supernatant was readjusted to 6.0 and the supernatant was loaded onto a CM-cellulose column (2.5×15 cm) equilibrated in 10 mM NaPO$_4$, pH 6.0 at 4° C. The column was washed with two bed volumes of 10 mM NaPO$_4$, pH 6.0 followed by a linear gradient of 10 mM NaPO$_4$, pH 6.9 to 20 mM NaPO$_4$, pH 9.0 (400 mL total volume) Fractions 36 to 42 contained a red solution and were combined; an aliquot of this solution was scanned from 650 nm to 400 nm revealing a spectrum identical to that for carboxyhemoglobin (FIG. 6). An aliquot of the same peak was analyzed by SDS-PAGE electrophoresis with hemoglobin as molecular weight standard and was found to contain two protein bands of approximate MW 15,500 and 16,200. As expected, these bands migrated at a slightly slower rate than authentic hemoglobin (alpha MW=15,100; beta MW=15,850) presumably due to the five amino acid extension of the Factor X recognition sequence. On this basis the material was designated FX-hemoglobin.

FX-Hemoglobin (2.0 mg) was digested at room temperature for 2 hours in 3 mL of 20 mM HEPES, pH 7.4, 0.1 M NaCl, 10 mM CaCl$_2$ containing 2 mg of trypsin (Sigma, St. Louis, NO., 10,000 units/mg). SDS-/PAGE electrophoresis confirmed the conversion of FX-hemoglobin to material that comigrates with native hemoglobin.

EXAMPLE 3A

Distribution of FX-Globin Products from *E. coli* Expression

One hundred milliliter cultures of *E. coli* clones expressing Fx-alpha globin (plasmid pDL II-62m), Fx-beta globin (plasmid pDL II-10a) and Fx-hemoglobin (plasmid pDL II-66a) were started with 1 ml inocula of overnight cultures. After growth for 4 hours, protein expression was induced by addition of IPTG to 1 mM final concentration. Incubation was continued for an additional 3 hours. The cells were collected by centrifugation, weighed, and lysed as described above except that DNAase treatment was done for 30 minutes on ice. The samples were centrifuged at 5000×g, 10 mm and the supernatants (representing the soluble protein fraction) brought to 2 ml final volume with H$_2$O and frozen at −80° C. The pellets (representing the insoluble protein or inclusion body fraction) were washed twice in 5 mL 0.5% Triton X-100, 1 mM EDTA, resuspended in 2 ml H$_2$O and frozen at −80° C.

Analysis of protein distribution was accomplished by SDS-PAGE and Western blotting. The primary antibody was rabbit anti-human hemoglobin IgG. The western blotting protocol was according to the manufacturer's recommendations (Proto Blot Western Blot AP system, Promega Corp., Madison, Wis.). Samples of soluble and insoluble protein representing 60 µg of wet cell weight were analyzed from the FX-alpha and FX-beta expressing clones. Due to the greater level of expression in the FX-hemoglobin clone, material representing only 15 µg of wet cell weight was analyzed.

As seen in Table 11 the distribution of the proteins varied. Fx-alpha globin was detectable only in the soluble fraction while FX-beta globin partitioned between the insoluble and soluble fractions of the cell. FX-Hgb, which stabilizes each separate subunit, was found only in the soluble fraction, and at a concentration at least 2.6 times that of the individually expressed subunits. These results indicate that FX-beta globin is totally soluble only when allowed to assemble with FX-alpha globin.

EXAMPLE 4

Construction and Expression of Mutant FX-Alpha/ FX-Beta Tetrameric Hemoglobin Expression Vector Hemoglobin Beth Israel: pDL II-10a was digested with restriction enzymes SacI and SpeI, gel purified, and isolated by electro-elution. Oligonucleotides incorporating the appropriate codon change for Hemoglobin Beth Israel (beta$^{102}$ asn→ser) (FIG. 7) were synthesized as previously described above to bridge the SacI to SpeI restriction sites. Purification and quantitation of the individual oligonucleotides was as previously described. The complementary oligonucleotides were annealed by heating to 95° C. for 10 min. followed by slow cooling to room temperature over a 2 hour period. An aliquot of the annealed mixture was then combined with the SacI/SpeI digested, gel purified pDL II-10a plasmid at molar ratios similar to those used for the initial FX-alpha and FX-beta cloning. T$_4$ DNA ligase (2U) was added and the mixture incubated for 1 hour at room temperature. *E. coli* JM109 was transformed with this ligation mixture as previously described. Individual clones were isolated, and plasmids purified and sequenced using primer beta-1 (vida supra). Plasmid sequencing was done with a Sequenase kit (United States Biochemical Corp., Cleveland, Ohio) following the protocol supplied by the manufacturer. The appropriate mutated beta globin sequence was then excised with HindIII and PstI, gel purified, and cloned into pDL II-62m as described above.

Other hemoglobin mutants: The synthetic genes encoding Hemoglobin Cheverly (beta$^{45}$ phe→ser) Hemoglobin Providence/MSR (beta$^{82}$ lys→asp) and Hemoglobin beta$^{67}$ val→ile and Hemoglobin Kansas (beta 102 asn→thr) were prepared similarly except with synthetic oligonucleotides spanning the SacII→BglII, SalI →SpeI, NcoI→KpnI and SacI→SpeI restriction sites respectively (FIG. 7). Synthesis of the mutant oligonucleotides, restriction enzyme digestion, gel purification, and ligation conditions were identical to those used for Hemoglobin Beth Israel. All mutations were first cloned into plasmid pDL II-10a, appropriate clones were sequenced, and the mutated beta globin gene was subcloned into PstI and HindIII digested pDL II-66a. Plasmid sequencing was accomplished as described previously. *E. coli* cells were transformed, cultured, and induced as previously described. FX-hemoglobin mutants were purified by the method of Example 3. oxygen binding of purified hemoglobin mutants is shown in Table 9.

EXAMPLE 5

Production of Synthetic Met-Alpha/Met-Beta Hemoglobin 5.1 Construction of Des-FX Alpha and Des-FX Beta Globin Genes We established that *E. coli* could produce tetrameric fusion-hemoglobin. Elimination of the DNA sequences coding for the Factor X$_a$ substrate recognition site on the N-terminal end of each peptide should result in production of synthetic (FX free; "des-FX") hemoglobin containing the N-terminal methionine as its only extra residue. pDL II-62m was digested with EcoRI and PstI to excise the sequence containing the FX-alpha globin gene. The FX-alpha globin gene was then gel purified. pGEM-1 (Promega Corp.) was linearized with EcoRI and PstI, gel purified, and the FX-alpha globin gene ligated into the plasmid as described previously. Clones (pGEM-FX-A) containing the FX-alpha globin gene in pGEM-1 were identified by digestion of purified plasmids with EcoRI and PstI followed by agarose gel electrophoretic analysis. FX-Alpha PGEM was digested with NdeI and EagI to remove the Factor $X_a$ coding sequence (FIG. 5). Oligonucleotides containing the DNA sequence encoding native alpha globin were synthesized with ends compatible to NdeI and EagI (FIG. 8) restriction sites. After synthesis, the oligoncleotides were purified, annealed, and ligated as described above. The sequence of pGEM-desFX-alpha (pDL II-83a) was confirmed by dideoxy-sequencing of the plasmid using the $T_7$ promoter primer (Promega Corp., Madison, Wis.). A clone containing the correct sequence was then digested with EcoRI and PstI. The des-FX alpha globin gene was gel purified, cloned into EcoRI/PstI digested, gel purified pKK-223-3 to generate pDL II-86c. E. coli strain JM109 was transformed with the ligation mixtures and expression of des-FX alpha globin by individual clones was determined by analysis of total cell protein extracts of induced culture inocula (see above). DesFX alpha globin, in contrast to FX-alpha globin, co-migrates with authentic alpha globin on SDS-PAGE.

The des-FX beta globin sequence was prepared in an analogous fashion using the FX-beta globin gene excised from pDL II-10a with PstI and HindIII. This gel purified beta globin sequence was then ligated into pGEM-1 that had been digested with the same two enzymes. A pGEM-1 plasmid containing the FX-beta globin gene was digested with NdeI and SacII, gel purified, and used for construction of the des-FX beta globin gene. The oligonucleotides conferring the desired sequence (FIG. 20) were synthesized, purified, annealed, and ligated into NdeI, SacII cut pGEM FX-beta to form pGEM-des-FX beta (pDL III-6f) as described above. After confirming that the sequence was correct the des-FX beta gene was removed with PstI and HindIII and gel purified. Des-FX beta was then ligated into the des-FX alpha-containing plasmid pDL II-86c using the PstI/HindIII sites. Clones containing both des-FX alpha and beta globin genes (pDL III-13e) (FIG. 9) were confirmed by EcoRI digestion of purified plasmids (see above), and screened for expression by comparison of IPTG induced and non-induced cultures. Des-FX hemoglobin co-migrates with native hemoglobin on SDS-PAGE.

5.2 Characterization of Met-Hemoglobin (Des-FX Hemoglobin)

Figure 10:
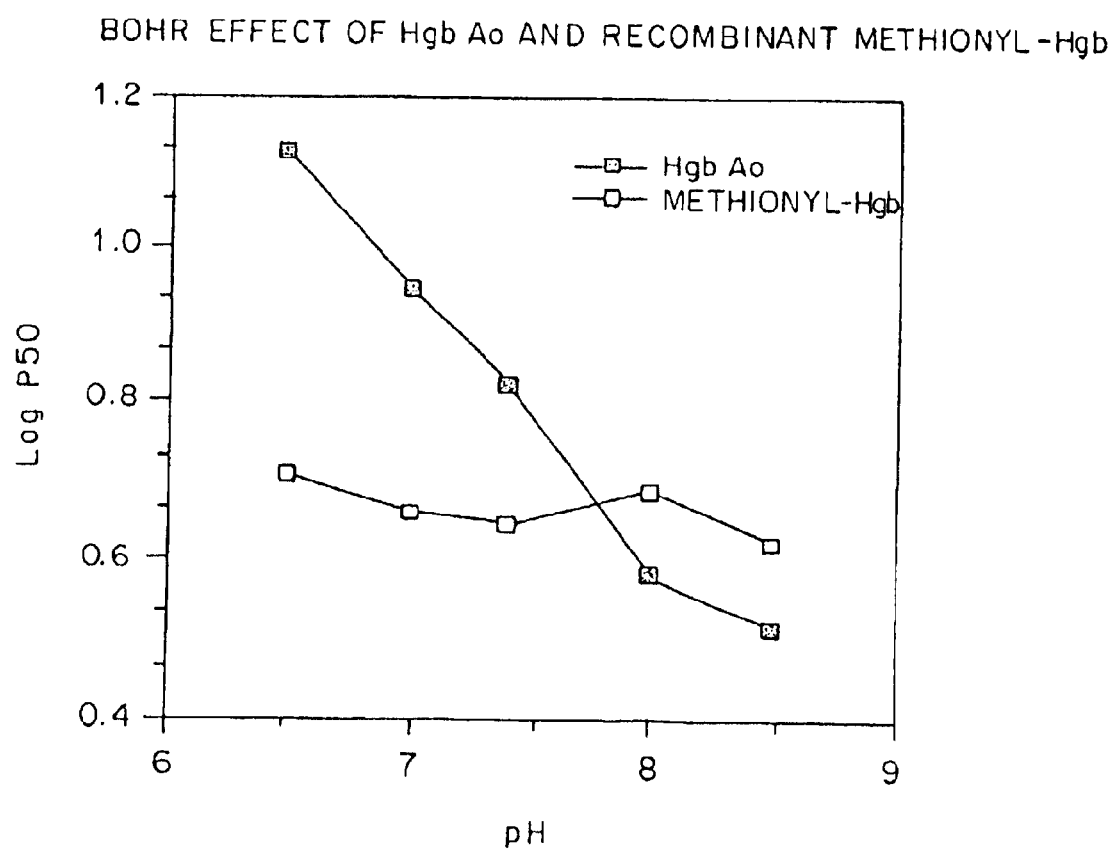
FIG. 10: Oxygen Binding of Des-Fx Hgb
Figure 11A:
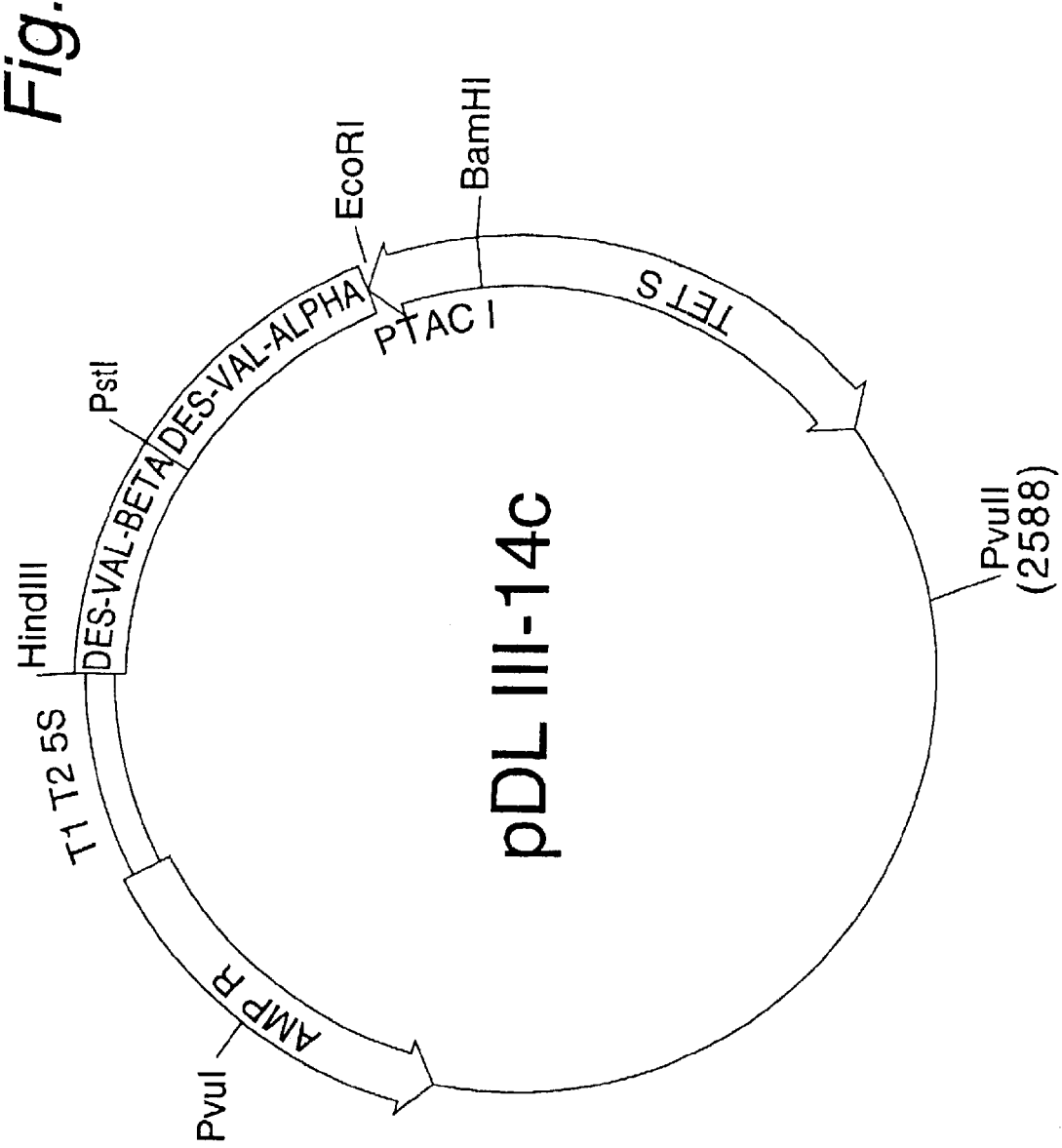
FIGS. 11a and 11b: Plasmids pDL III-14c (11a) and pDL III-38b (11b).
Figure 11B:
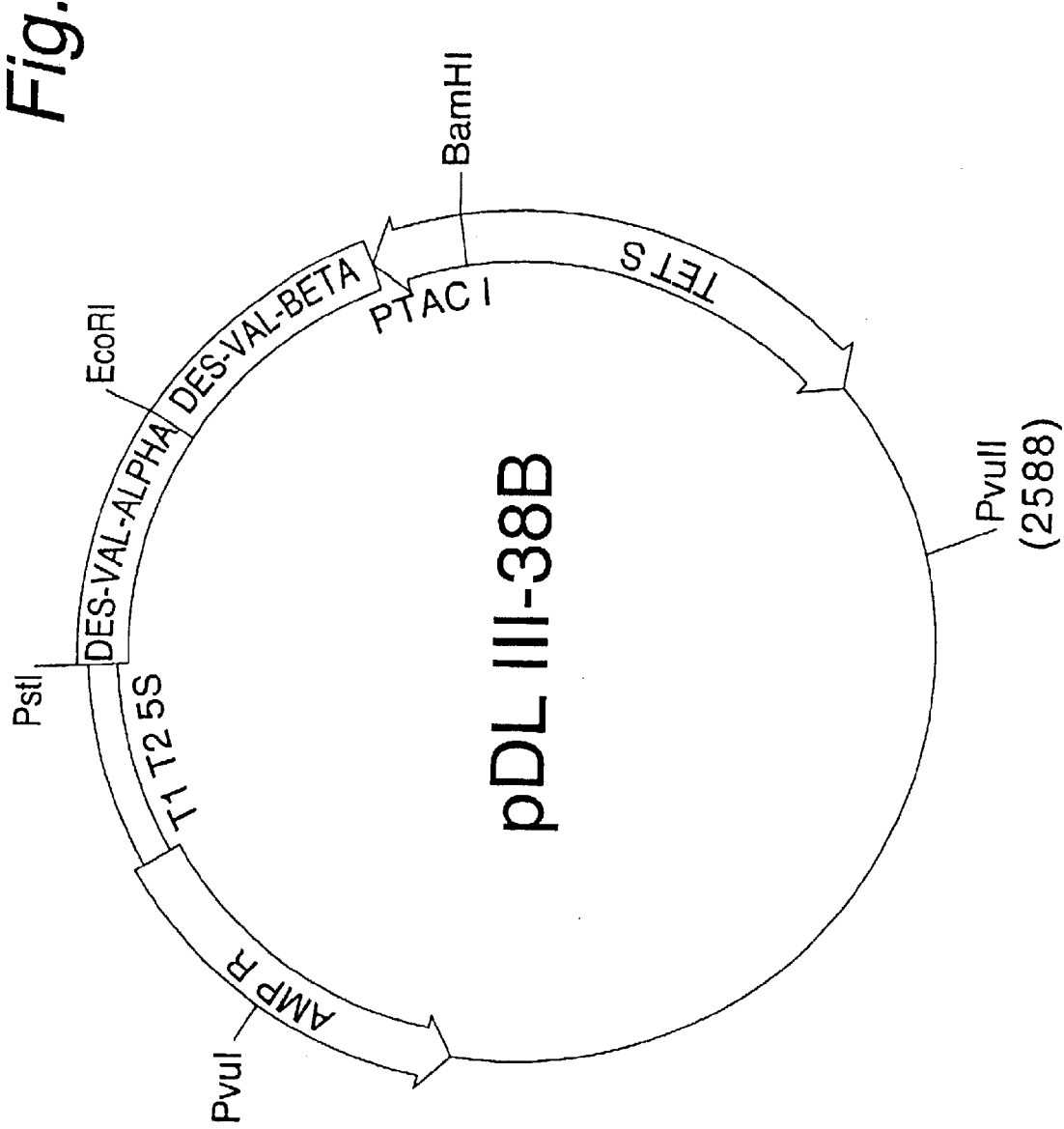

Recombinant methionyl-hemoglobin has different reactivities than hemoglobin $A_0$ in the presence of chloride and phosphate ions (Table 10) and with changes in hydrogen ion concentration (FIG. 10). The reason for this is thought to be the additional amino acid, methionine, on the N-termini of both globins. The N-terminal amino group of the alpha chain is important for the change in $P_{50}$ by phosphate ion. Displacement of the N-terminal amino group in space or changing its electronic state by the addition of the methionine can alter these effects.

The increase in $P_{50}$ seen in the presence of inositol hexaphosphate ion is irrelevant for any hemoglobin found in solution because the concentration of monophosphate ion found in plasma is not enough to significantly increase the $P_{50}$. There is no inositol hexaphosphate ion fount in plasma. The increase in $P_{50}$ needed for hemoglobin in solution to effectively off-load oxygen can be best attained by incorporating mutations to make hemoglobin lower in affinity for oxygen.

The magnitude of change in $P_{50}$ with respect to chloride ion is not important physiologically. The effect, which is interesting in terms of its biochemical mechanism, does not add a significant amount of oxygen off-loading capacity to hemoglobin in solution. Some animal hemoglobin have extremely small chloride effects. Again, the chloride effect is thought to be transmitted by the alpha globin N-terminal amino group; with methionyl-hemoglobin that effect could be changed because of the stearic change or because the pKa of the methionine amino group is different than that of valine.

The $P_{50}$ of hemoglobin is normally most dramatically changed by hydrogen ion concentration. The so-called "Bohr effect" is also thought to, in part, involve the N-terminal amino group of the alpha globin. Numerous mutant human hemoglobin molecules have been shown to have altered Bohr effect changes without any physiological deficiency. There is an advantage in having a limited Bohr effect, as well as phosphate and chloride effects, in a hemoglobin molecule to be used in solution for a number of different medical and biochemical applications. In terms of the Bohr effect, there are several applications for methionyl-Hemoglobin where it could be used in the more alkaline pH range, e.g., tissue culture, organ perfusion. FIG. 10 depicts a preliminary experiment which indicated that the $P_{50}$ is actually greater for methionyl-hemoglobin than for hemoglobin $A_0$ at greater than pH 7.8. It will be noted from FIG. 10 that the slope of the $P_{50}$ to pH plot for Met-hemoglobin is shallower than that for hemoglobin $A_0$, i.e., the Bohr effect is smaller. Subsequent experiments suggest that the difference in Bohr effect between Met-hemoglobin and hemoglobin $A_0$ is smaller than that shown in FIG. 10.

The main advantage for using a hemoglobin molecule with fixed changes in $P_{50}$ relative to pH, chloride and phosphate, is that the practitioner will know the oxygen off-loading capacity of the formulation without regard for the specific conditions of its use.

EXAMPLE 6

Synthesis of Synthetic Hemoglobin (Des-Val Hgb) of Native Size 6.1 Construction of Des-val-Alpha (PDL III-1a) and Des-Val-Beta (pDL III-95a) Globin Genes DNA sequences encoding the globin genes in which the N-terminal valine codon in each gene is replaced by an ATG (methionine) codon were constructed in a manner analogous to the des-FX clones except that the oligonucleotides inserted (FIG. 8) were ones encoding the amino acid sequences "met-leu . . . " and "met-his . . . " for alpha and beta globin genes, respectively. Following confirmation of correct sequence for both des-val alpha (pDL II-91f) and des-val beta (pDL II-95a) genes in pGEM-1, the des-val alpha globin gene was cloned into the EcoRI/PstI cut pKK-223 (see above) to create pDL Ill-1a. The des-val beta globin gene from pDL II-95a was then cloned into pDL III-Ia using the PstI/HindIII restriction sites.

More specifically, the des-val alpha transfer vector was prepared from plasmid pDL II-62m as follows. Plasmid pDL II-62m was digested with EcoRI and PstI to excise the fragment containing the FX alpha globin gene. The FX alpha globin gene was then gel purified. The plasmid pGEM-1 (Promega Corp.) was linearized with EcoRI and PstI, gel purified, and the FX alpha globin gene ligated into the plasmid as described previously. It was necessary to subclone into pGEM-1 because redundant restriction sites in pKK 223-3 prohibited the removal of the FX coding sequence directly from the individual FX-alpha and FX-beta globin genes. Clones containing the FX alpha globin gene in pGEM-1 were identified by digestion of purified plasmids with EcoRI and PstI followed by agarose gel electrophoretic analysis. FX alpha pGEM-1 was digested with NdeI and EagI to remove the FX alpha coding sequence and oligonucleotides containing DNA sequences coding for native alpha globin in which the N-terminal valine is replaced by a methionine were synthesized with ends compatible to NdeI and EagI restriction sites. After synthesis, oligonucleotides were purified, annealed and ligated as described above. The sequence of pGEM des-val alpha (plasmid pDL II-91f) was confirmed by dideodoxy sequencing of the plasmid using the t7 primer (promega corp., Madison, Wis.). A clone containing the correct sequence for des-val alpha (pDL II-91f) was then digested with EcoRI and PstI. The des-val alpha globin gene was gel purified, and ligated into EcoRI/PstI digested, gel purified, pKK-223-3 to generate plasmid pDL III-1a.

The des-val beta globin transfer vector was prepared in an analogous fashion using the FX beta globin gene of plasmid pDL II-10a. FX-beta was excised from pDL II-10a with PstI and HindI. This gel purified beta globin sequence was then ligated into pGEM-1 that had been digested with the same two enzymes. A PGEM clone containing the FX beta globin gene was digested with NdeI and SacII, gel purified, and used for construction of the des-val beta globin gene. The oligonucleotides encoding the desired sequence for des-val beta were synthesized, purified, annealed, and ligated into NdeI, SacII cut, pGEM FX-beta to form pGEM des-val beta (plasmid pDL II-95a). After confirming that the sequence was correct for des-val beta globin, the gene was removed with PstI and HindIII and gel purified.

6.2 Preparation of PDL III-14c and III-38b (des-Val-alpha/des Val beta Polycistronic Gene Clones)

Plasmid PDL III-1a containing the Des-Val alpha globin gene was digested with PstI and HindIII and gel purified. The Des-Val beta globin gene was removed from pDL II-95a using the same method. Following ligation and transformation, individual clones containing the Des-Val alpha/des-val beta globin coexpressing plasmid pDL III-14c were analyzed for Des-Val hemoglobin production by IPTG induction and SDS-PAGE.

Plasmid pDL III-38b which contains the Des-Val beta globin gene 5' to the Des-Val alpha globin gene was then constructed and analyzed.

Plasmid pDL III-1a containing the des-val alpha globin gene was linearized with the restriction enzyme SmaI. The plasmid was then treated with bacterial alkaline phosphatase to remove the 5'-phosphate groups, phenol extracted, ethanol precipitated, and resuspended in TE buffer as above. A pGEM-1 clone (pDL II-95a) containing the des-val beta gene was digested with HindIII, phenol extracted, ethanol precipitated and resuspended in a ligation mixture containing a 50:1 molar ratio of a HindIII-SmaI linker to plasmid. This ligation mixture was then digested with SmaI and the beta globin fragment now containing SmaI restriction sites on both the 5'-and 3'-ends was gel purified and added to a ligation reaction containing the linearized form of plasmid pDL III-1a, above, thus obtaining plasmid pDL III-38b. The orientation of the alpha and beta globin genes in pDL III-14c and pDL III-38b was confirmed by restriction analysis.

Cells of E. coli strain JM109 were transformed with pDL III-14c or pDL III-38b and grown in 2×YT media containing ampicillin. Colonies were induced with IPTG as above. Individual clones were analyzed for their ability to produce des-val alpha and des-val beta globin polypeptides by SDS-PAGE and Western blotting. There was no appreciable difference between expression of immunoreactive des-val alpha or des-val beta globins from the alpha→beta orientation (pDL III-14c) or the beta→alpha orientation (pDL III-38b)

EXAMPLE 7

Analysis and Comparison of the Functional Characteristics of Recombinant Des-FX and Des-Val Hemoglobins JM109 cells expressing either des-FX hemoglobin,(dFX-hgb) or des-Val hemoglobin (dV-hemoglobin) were grown to an $OD_{600}$ of 15 in a 10 liter fermentor and then induced by the addition of 300 $\mu$m IPTG. Induction period was for 6 hrs. Cells were harvested by centrifugation and frozen at −80° C. until processed.

For purification of hemoglobin approximately 200 g of cells were resuspended in 350 mL of 50 mM sodium phosphate (NaPi) buffer, pH 7.0 containing 200 units of aprotinin/mL and 20 $\mu$g/ml DNAase 1. Cells were then lysed by the addition of 1 mg/mL of lysozyme and 4 passages through a Dynomill. Cellular debris was removed by centrifugation at 10,000 rpm in a Beckman JA14 rotor at 4° C. for 40 min. The supernatant was added to 200 mL of a hemoglobin-binding resin equilibrated with 10 mM NaPi, pH 7.0. The pH was adjusted to 7.0 with 10M NaOH or concentrated phosphoric acid. The resin was then loaded into a 5×30 cm chromatography column and allowed to settled. The column was then washed with 2.5 column volumes of 10 mM NaPi. pH 7.0 containing 100 units/mL aprotinin. Hemoglobin was eluted from the column in 20 mM Tris-HCl, pH 7.5 containing 100 units/mL aprotinin. This partially purified hemoglobin was then 0.2 micron filtered and loaded onto a 1.6×10 cm Mono-Q anion exchange column equilibrated with 20 mM Tris-HCl, pH 8.0. Hemoglobin was eluted using a linear gradient of 0 to 0.41M NaCl in 20 mM Tris-Hcl, pH 8.0. The material was then loaded onto a 1.6×10 cm Mono-S cation exchange column. Hemoglobin was eluted with a linear gradient of 10 mM NaPi, pH 7.0 to 10 mM NaPi, pH 8.5, 160 mM NaCl. The major peak of hemoglobin was collected, concentrated to approximately 100 mg/mL. and used for analysis.

Functionality of the recombinant hemoglobin was evaluated using a Hemox analyzer at 25° C. in 50 mM HEPES, pH 7.4 containing 0.11M Cl. The following oxygen binding data were obtained:

| SAMPLE | $P_{50}$ | N |
| --- | --- | --- |
| $A_o$ | 4.3 | 2.9 |
| dFX-hgb | 3.3 | 2.6 |
| dV-hgb | 6.6 | 2.7 |

Of significance in these data are the following:
1) The addition of an extra amino acid, methionine, on the N-termini of alpha and beta globins (dFx-) appears to reduce slightly the $P_{50}$ of the molecule but has little effect upon cooperativity (N).
2) Replacement of the N-terminal valines of alpha and beta globins with methionine (dV-hgb) increases the $P_{50}$ of the molecule but has little effect upon the cooperativity (N).

EXAMPLE 8

Polycistronic Co-expression of Des-Val-Alpha/Alpha (Di-Alpha) and Des-Val Beta Globin The overall synthetic plan for the preparation of a plasmid (pDL III-47a) which co-expresses di-alpha globin and beta globin is given below. The starting materials are the commercially available transfer vectors M13mp19-RF, pKK 223-3 and pGEM-1, and the synthetic oligonucleotides described in the examples.

For convenience, our manipulations began with plasmids, pDL II-62m and pDL h-ba. Plasmid pDL II-62m was obtained by cloning the "FX alpha globin" gene into pKK 223-3 downstream of the Tac promoter. Plasmid pDL II-10a was prepared by an analogous insertion of the "FX beta globin" gene.

As set forth in greater detail in FIG. 12, the "FX alpha globin" operon encodes two cistrons, the first expressing an octapeptide "leader", and the second, alpha globin preceded by Met-Ile-Glu-Gly-Arg (SEQ ID NO:29). The latter four amino acids constitute a recognition site for Factor X cleavage activity. The "FX beta globin" operon is similarly constructed.

Since the Factor X recognition site was not needed here, the genetic material was manipulated to excise the "FX" codons. (This could have been avoided by synthesizing the desired di-alpha globin and des-val-beta globin genes directly rather than using the FX-alpha and FX-beta genes of pDL II-62m and pDLII-10a.) The FX-alpha globin gene cassette was excised and cloned into pGEM-1 to obtain pGEM FX-alpha (pGEM FX-A). Similarly, the FX-beta gene of pDL II-10a was transferred to pGEM-1 to obtain pGEM FX-beta (pGEM FX-B).

The recognition site (FX)-encoding sequence could now be removed from pGEM FX-alpha and PGEM FX-beta to obtain pDL II-91f and pDL II-95a, respectively. The des-val alpha globin gene of pDL II-91f was recloned into pKK 223-3 to generate pDL III-1a, the gene being operably linked to the Tac promoter of pKK-223-3. The des-val beta globin gene of pDL II-95a was purified and inserted downstream of the des-val alpha globin gene of pDL III-1a to form a single transcriptional unit which would encode a polycistronic alpha globin/beta globin mRNA, see pDL III-14c. Finally, a synthetic oligonucleotide comprising the desired di-alpha linker encoding sequence and another copy of the alpha globin gene was inserted into pDL III-14c to create pDL III-47a, wherein a Tac promoter controls transcription of a di-alpha globin gene and a des-val beta globin gene.

8.1 Preparation of pDL III-47a (di alpha/beta globin clone)

The EagI and PstI restriction fragment containing most of the alpha globin gene from the plasmid pDL II-91f was gel purified and ligated to a synthetic DNA linker containing the sequence from the BstBI site of the alpha globin gene to the codon (wild-type Arginine) for its carboxyl terminus, a variable glycine-encoding linker (for example, FIG. 12, RGGv, a di-glycine followed by α Val; other possibilities include RGM, RGV, RGGV, etc., See Table 200), and the codons for the amino terminal region of alpha globin to the EagI site (FIG. 12). After digesting this ligation mixture with Pst I, the resulting fragment was cloned into BstBI/PstI-cut pDL III-14C to create plasmid pDL III-47a (RGM-di-alpha). Plasmids pDL III-82a (RGGV-di-alpha), pDL IV-8a (RGV-di-alpha), pDL IV-976 (RV-di-alpha) and pDL IV-66a (RGGGV-di-alpha) were similarly constructed to incorporate the indicated changes in the di-alpha coding sequences.

8.2 Expression of Di-alpha/Beta Hemoglobin

Individual *E.coli* clones were analyzed by Western blotting for production of dimeric alpha globin protein in combination with monomeric beta globin. Appropriate plasmid construction was confirmed by digestion with EcoRI and 0.8% agarose gel electrophoresis. The EcoRI fragment present in the di-alpha constructs is approximately 1450 bp.

Expression of genetically fused hemoglobin was accomplished using the IPTG induction protocol and S-sepharose purification of recombinant hemoglobin. *E.coli* cells (400 ml) were grown to an $OD_{600}$ of 3.0 and induced with 1 mM IPTG. The cells were allowed to continue to grow for another 4 hours and then harvested by centrifugation. The cell pellet was resuspended in the 10 mM sodium phosphate, pH 6.0 containing 1 mM benzamidine, 1 mM EDTA and 0.1% Triton-X100. The cell suspension was then sonicated, centrifuged at 15,000×g for 15 minutes, and the supernatant loaded on to an S-Sepharose column equilibrated with 10 mM sodium phosphate pH 6.0. After the sample was loaded on the column, the column was washed with 10 bed volumes of 10M sodium phosphate pH 6.8. The dialpha hemoglobin was eluted from the column with 10 mM sodium phosphate, pH 7.4, 30 mM NaCl. Confirmation of hemoglobin production was accomplished by visible light spectroscopy, SDS-PAGE, and Western blot analysis of purified material.

Oxygen binding measurements were made at 37 and 25° C. in a Hemox Analyzer (Southampton, Pa.). The solutions were 50 mM HEPES, pH 7.4, 0.1 M NaCl. The measured P50's and Hill coefficients are given below:

| Protein | P50 (torr) | N | TEMP (° C.) |
|---|---|---|---|
| RV-di-alpha | 2.2 | 1.73 | 25 |
| | 5.0 | 1.49 | 37 |
| RGV-di-alpha | 4.5 | 2.04 | 25 |
| | 9.9 | 2.07 | 37 |
| RGGV-di-alpha | 8.2 | 2.39 | 25 |
| | 15.0 | 2.22 | 37 |
| RGGGV-di-alpha | 7.1 | 2.57 | 25 |

EXAMPLE 9

Preparation of Di-Alpha Hemoglobin Low Affinity Mutants

In order to reduce the oxygen affinity of recombinant di-alpha hemoglobin, several mutations were introduced into the beta globin polypeptides using synthetic oligonucleotides. The restriction sites used to incorporate these mutants are shown in Table 3. For insertion of the Nagai (beta Val 67→Ile) and Arg-Nagai (also beta Lys 82→Arg) mutations, the des-Val-beta plasmid pDL II-95a was digested with the restriction enzymes NcoI and KpnI and gel purified. Oligonucleotides spanning these two restriction sites and containing the appropriate codon changes were synthesized, purified, annealed and ligated into the gel purified plasmid. Following confirmation of correct sequence, the mutant des-Val-beta globin gene was excised with PstI, HindIII, gel purified, and cloned into plasmid pDL III-47a. The beta globin gene containing the Kansas mutation (beta Asn 102→Thr) was similarly constructed using SacI and SpeI restriction sites. Mutated codons for all of these beta globin mutations are shown in lower case letters in Table 3.

EXAMPLE 10

Characterization of Di-Alpha Hemoglobins Oxygen Binding

Oxygen binding measurements were made at 37° C. in a Hemox Analyzer (Southampton, Pa.). The solutions were 50 mM Bis-Tris, pH 7.4, 0.1M NaCl and 60 uM heme equivalents of di-alpha hemoglobin. The solutions were measured between 120 and 1.5 torr oxygen pressure. $P_{50}$ values are given in Table 4.

In Vivo Half Life

Di-Alpha Hgb (wild type) containing a gly-gly linker between $alpha_1$ and $alpha_2$ (RGGV-di-alpha, pDL III-82a) was prepared as described previously. The protein was formulated in 20 mM $NaPO_4$, pH 7.4 at a concentration of 95 mg/ml. Di-alpha hemoglobin was infused into male Sprague-Dawley rats 388–426 gm) at a dose of 875 mg/kg through a central venous catheter over 20–30 sec. Samples of blood were drawn at 2, 30, 80, 90, 120, 150, 180, 210, and 240 min. into heparinized vials. The blood was centrifuged to remove red blood cells and the plasma hemoglobin was assayed by absorbance at 540 nm. The percent hemoglobin remaining versus time was determined by comparison to the 2 min time point which was assumed to be a homogeneously mixed sample. The same experiment was repeated with non—crosslinked des-val hemoglobin at a concentration of 100 mg/ml. The data were averaged for each sample and plotted as percent hemoglobin remaining against time after infusion. The measured half-lives were 205 mm and 104 mm respectively for di-alpha hemoglobin and des-val hemoglobin, respectively.

EXAMPLE 11

Figure 34:
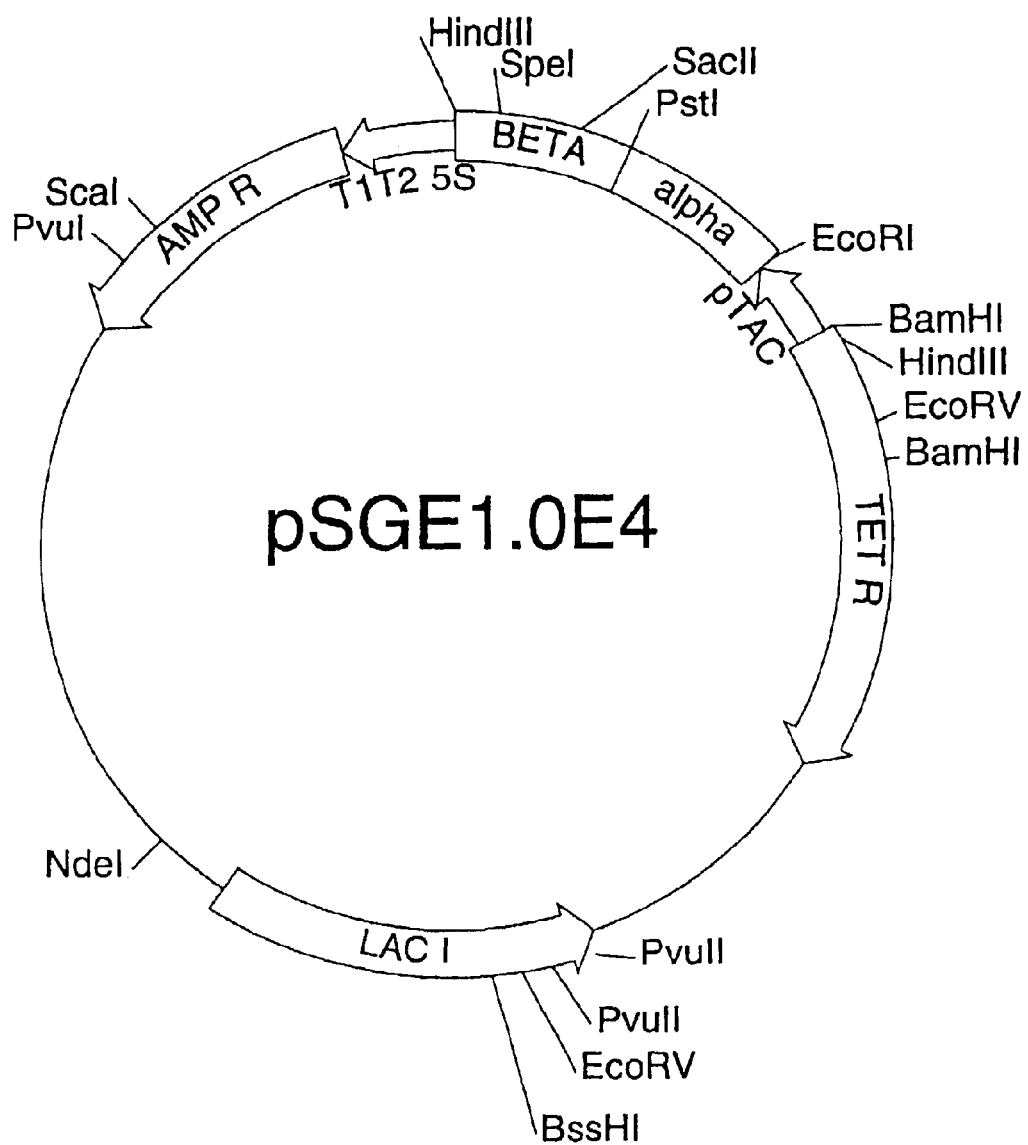
FIG. 34 Map of plasmid pSGE1.0E4.

Co-expression of Wild Type Des-Val Alpha Globin and Di-Alpha Globin with Des-Val Beta Globin Containing the Presbyterian Mutation Plasmid pSGE1.0-E4 is shown in FIG. 34 and contained the following modifications as compared to other expression vectors derived from plasmid pKK223-3:

1) The plasmid now contains a functional tetracycline resistance gene.

2) The lacI gene which encodes for the lac repressor protein has been incorporated into the plasmid. The lac repressor protein represses the TAC promoter until induction with IPTG. The repressor gene was inserted into the plasmid to permit transformation of *E. coli* cell lines which do not have endogenous lac repressor genes.

The desVal beta globin gene in pSGE1.0E4 containing the Presbyterian mutation had been constructed by insertion of a complementary pair of synthetic oligonucleotides between the Sac1 and Spe1 restriction sites of pDL II-95a.

The following oligonucleotides (Pres-A and Pres-B) were used to construct the Presbyterian mutation in dVal-beta globin.

```
Pres-A    5' CCACTGCGACAAACTGCACGTTGACCCGG           (SEQ ID NO:30)
             AAAACTTCCGTCTGCTGGGTaaaGTA 3'

Pres-B    3' TCGAGGTGACGCTGTTTGACGTGCAACTGGGCC       (SEQ ID NO:31)
             SacI
             TTTTGAAGGCAGACGACCCAtttCATGATC 5'
                                       Spe1
```

Following digestion with the two restriction enzymes pDLII-95a was gel purified to remove the wild type encoding DNA fragment. The annealed oligonucleotides were then ligated into the plasmid to create plasmid pJRV-83a. The HindIII to PstI fragment from this plasmid was then ligated into pSGE0.0E5 (Table 200, #45a) to create pSGE1.0E5 (Table 200, #46). The BamHI fragment encoding the tet R 5' end was then ligated into pSGE1.0E5 to create pSGE1.0E4. Following transformation of JM109 cells, individual colonies were selected and analyzed for production of alpha and beta globins by IPTG induction and SDS-PAGE. Dideoxynucleotide sequencing was used to confirm the presence of the Presbyterian mutation.

Figure 14:
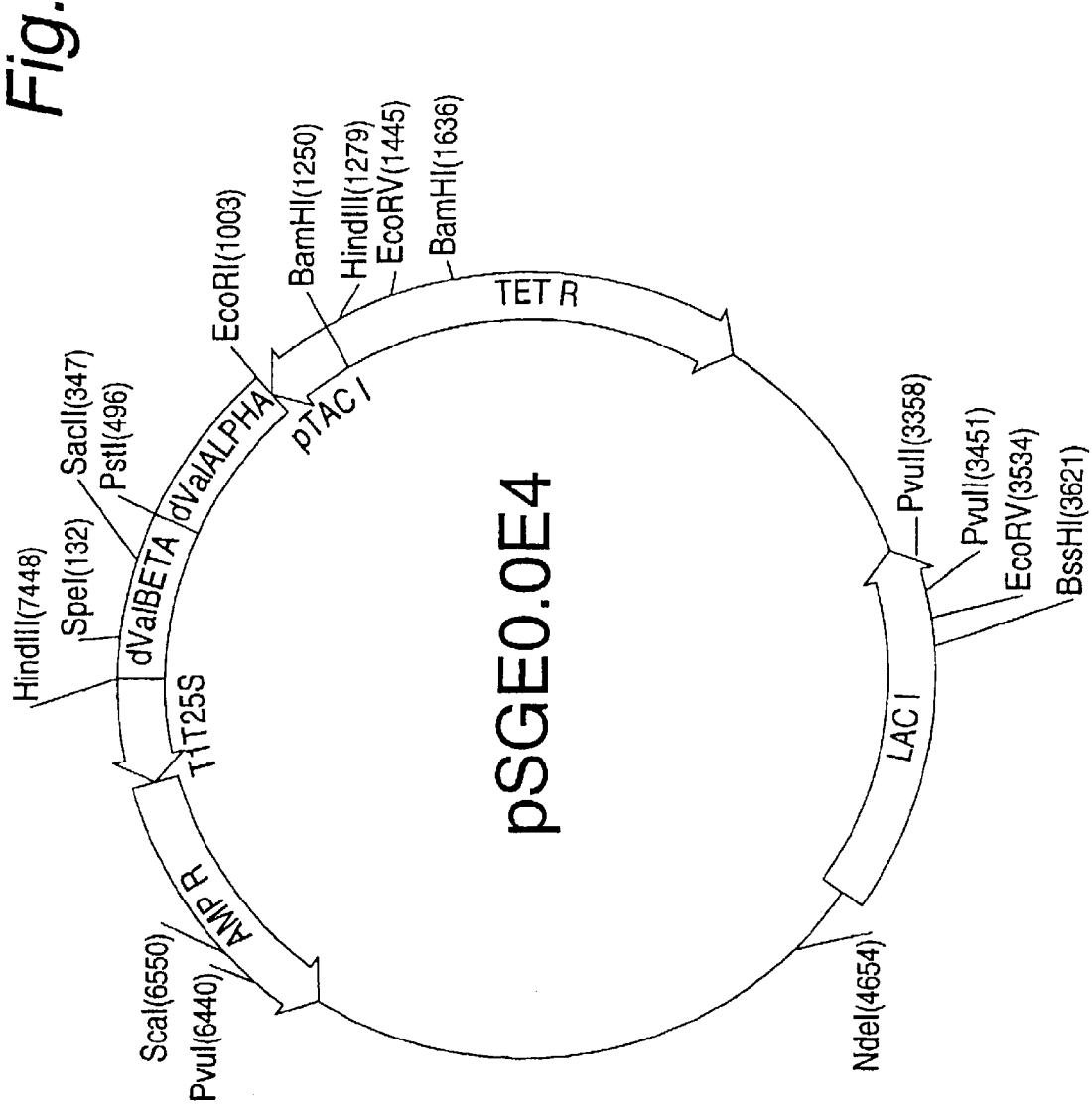
FIG. 14: Plasmid pSGE0.0E4

The mutant hemoglobin was produced, purified, and analyzed as described in Example 7 above. The oxygen affinity ($P_{50}$) and cooperativity (N) of wild-type Hgb $A_0$ (purified from blood), dV-Hgb expressed from pSGE0.0E4 (FIG. 14), and dv-Hgb containing the Presbyterian mutations expressed from pSGE1.0E4 (FIG. 34), were compared:

| SAMPLE | $P_{50}$ | N |
|---|---|---|
| Ao | 4.3 | 2.9 |
| dV-hgb | 6.6 | 2.7 |
| dV-hgbPres | 19.8 | 2.5 |

It should be noted that the Presbyterian mutation, which results in the change of beta asparagine 108 to lysine, cause a large decrease in the affinity of the molecule for oxygen but does not substantially affect the cooperativity of the molecule.

Figure 15:
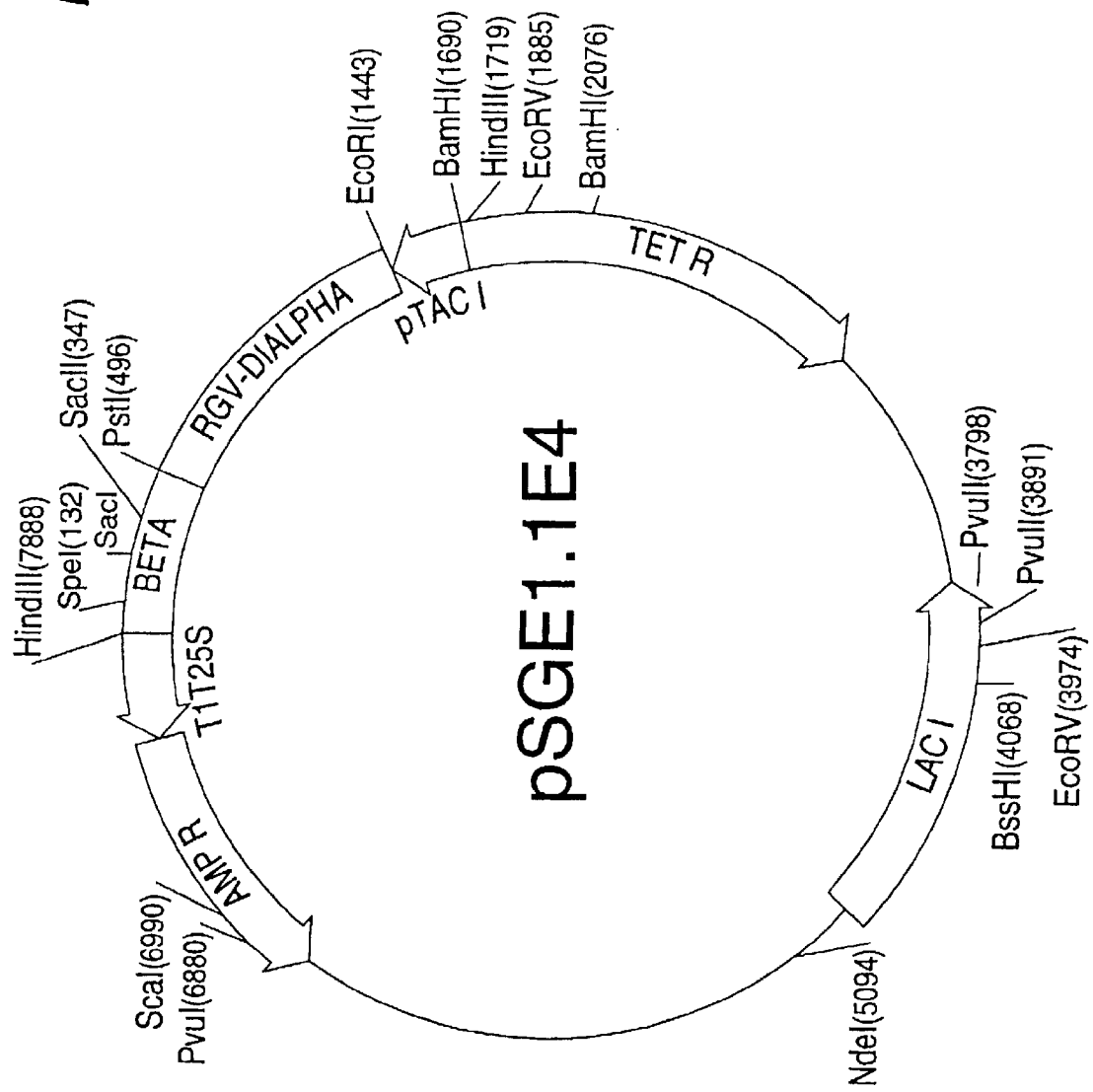
FIG. 15: Plasmid pSGE1.1E4

The beta chain Presbyterian mutation has also been co-expressed with di-alpha globin containing a single glycine linker utilizing plasmid pSGE1.1-E4 (FIG. 15). The result shown below indicates that the joining of the carboxy terminus of alpha 1 to the amino terminus of alpha 2 has relatively little effect on oxygen binding and cooperativity.

| SAMPLE | $P_{50}$ | N |
|---|---|---|
| dV-hgbPres | 19.8 | 2.5 |
| dialpha/Pres | 17.2 | 2.4 |

EXAMPLE 12

Construction of a Two Promoter System for the Co-expression of Di-Alpha Globin and Beta Globin In this example, a di-alpha globin gene is operably linked to one promoter and a beta globin gene to a second promoter, but both genes reside on the same vector. Compare Examples 16 and 17, infra.

Oligonucleotides (see below) encoding the sequence of the complementary strands of the TAC promoter(syn pTAC) and appropriate restriction enzyme sites were synthesized, gel purified, and annealed. Notice that the sequence complementary to the XbaI restriction enzyme site was designed to eliminate this restriction site when ligated into an authentic XbaI site. This was done to facilitate future manipulation of syn pTAC.

Sequence of syn pTAC

BamHI PstI

5' G A T C C T G C A G A G C T G T T G A C A A T T A A T-CATCGGCTCGTATAATGTGTGG (SEQ ID NO:32) (Cont'd)

3' GACGTCTCGACAACTGTTAATTAGTAGC-CGAGCATATTACACACC (Cont'd)(SEQ ID NO:33)

XbaI COMP

AATTGTGAGCGGATAACAATTTCACAC 3'

TTAACACTCGCCTATTGTTAAAGTGTGGATC 5'

Figure 13:
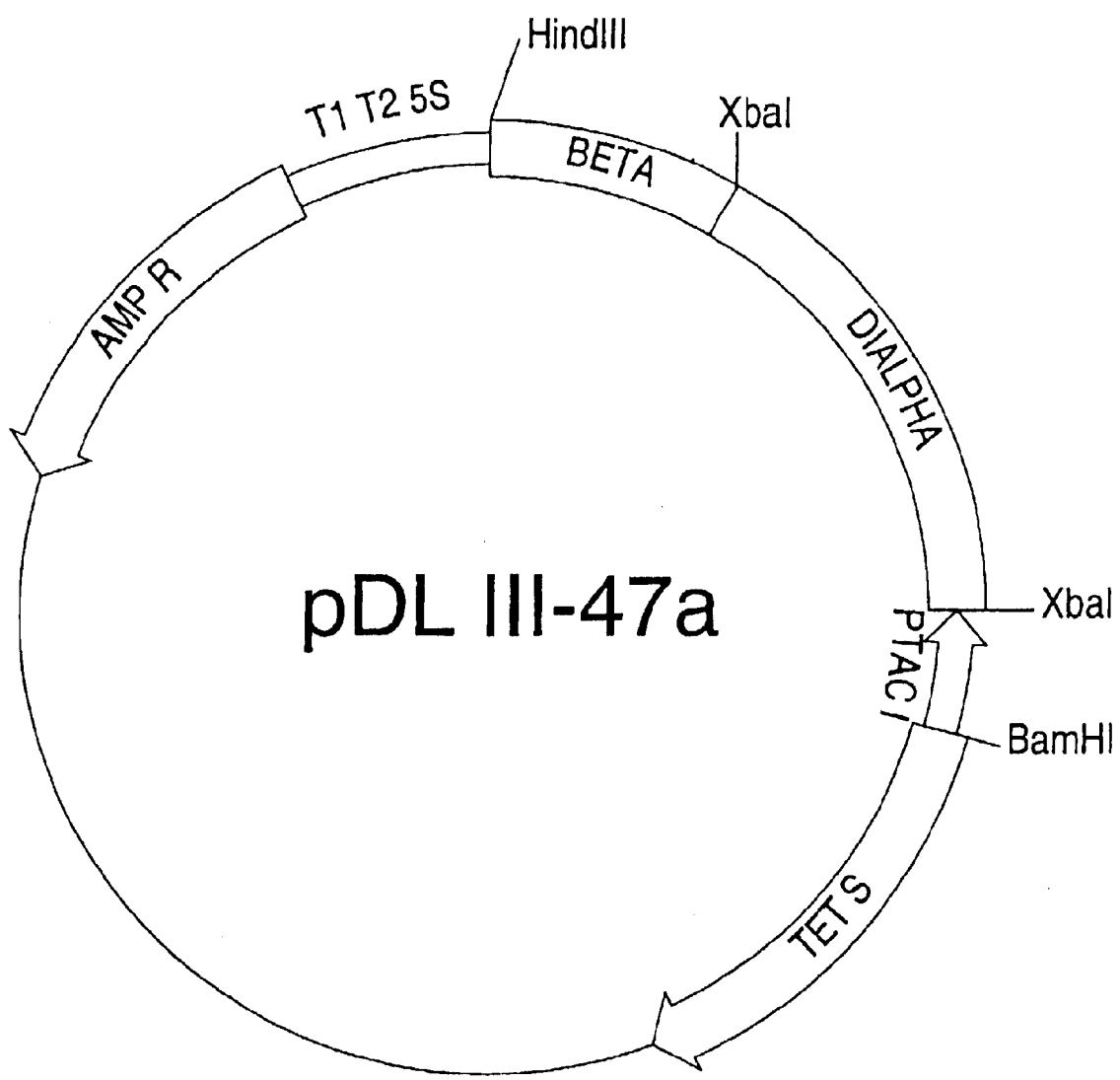
FIG. 13: Shows the structure of the final expression vector pDL III-47a. "PTac" is the Tac promoter, and "ampicillin" is the ampicillin resistance gene.

Plasmid pDL III-47a (FIG. 13) was digested with the restriction enzymes BamH1 and Xbal, and the plasmid, now containing as an insert only part of the beta globin gene from the XbaI site to the HindIII site (FIG. 13a), was gel purified.

Syn pTAC was then ligated into the plasmid to create plasmid pDL IV-64a and JM109 cells were transformed. Individual transformants were isolated and analyzed by IPTG induction and SDS-PAGE to confirm the presence of a functional TAC promoter.

Figure 16:

Plasmid pDL III-47a was digested with the restriction enzymes PstI and HindIII and gel purified to remove the beta globin coding sequences. Plasmid pDL IV-64a was digested with these same enzymes and the fragment encoding syn pTAC/beta gel purified. Ligation of the syn pTAC/beta fragment into the PstI/HindIII digested pDL III-47a created plasmid pDL IV-67a (FIG. 16). Individual transformants were screened for production of di-alpha and beta by IPTG induction and SDSPAGE.

Figure 17:
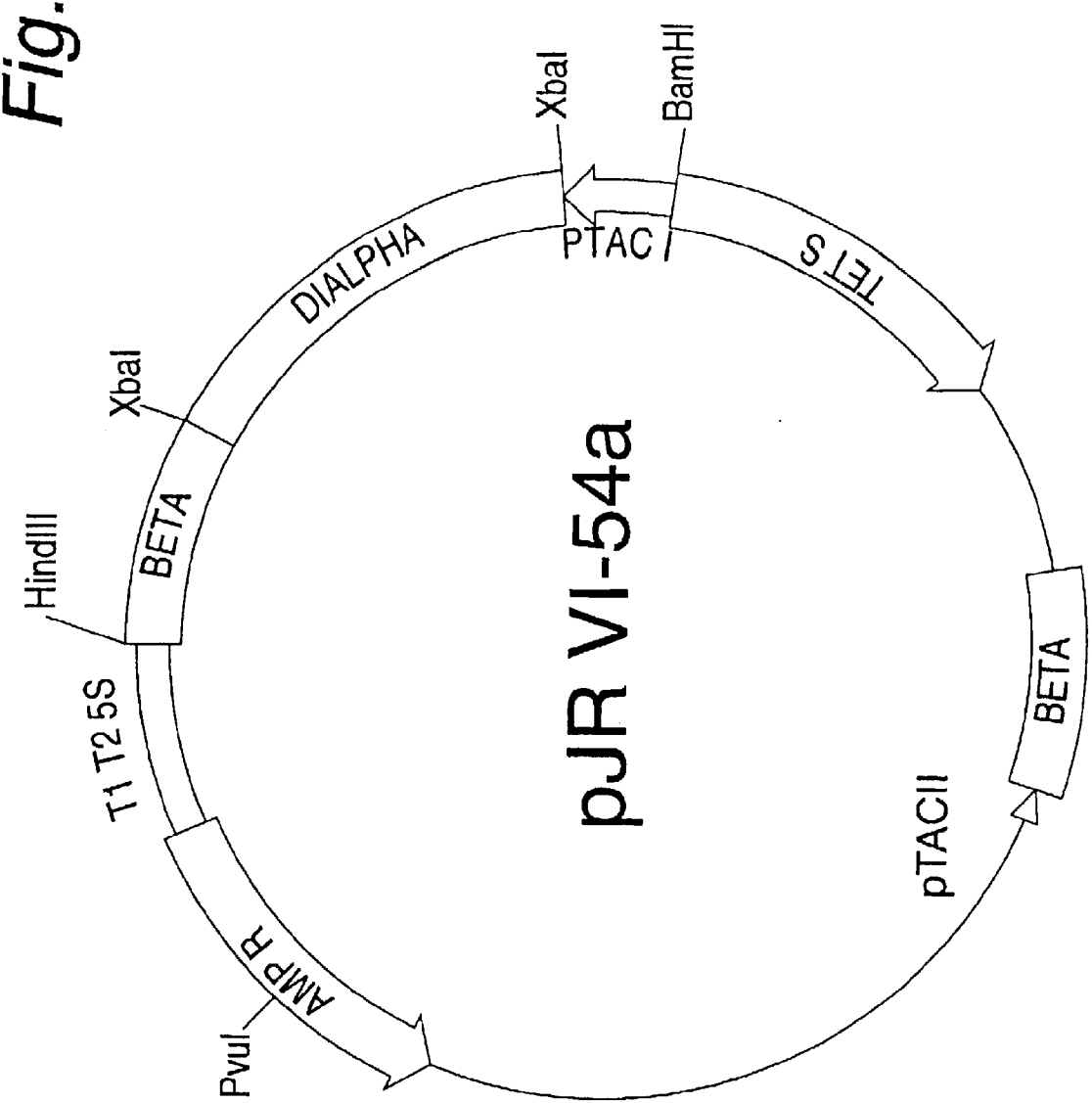
Figure 18:
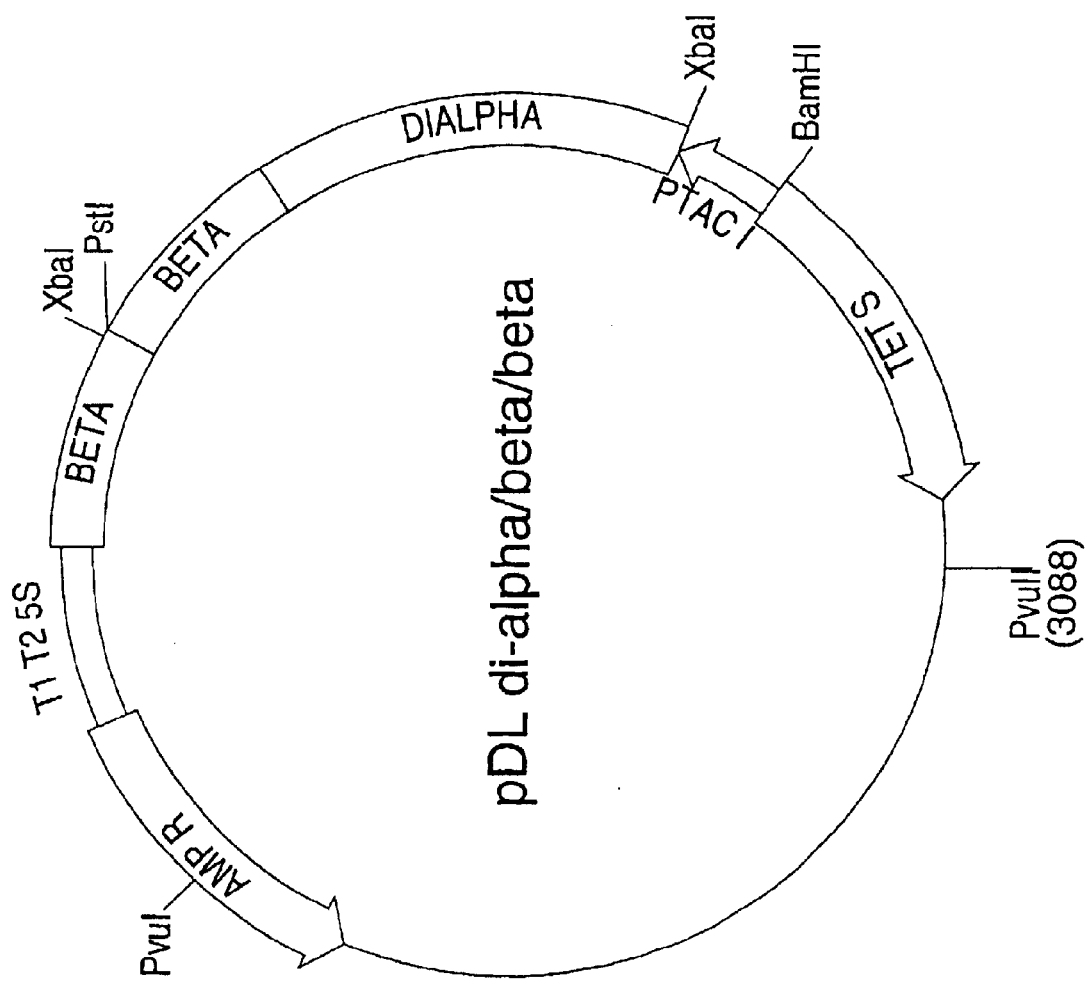
FIG. 18: Plasmid pDL di-alpha/beta/beta

The dVal-beta globin gene under the control of syn PTAC was also ligated into another location in pDL III-47a. Syn pTAC/beta was removed from pDL IV-64a by digestion with Hind III and PstI. The restriction site overhangs were filled with T4 polymerase and blunt end ligated into the Pvu II site of PDL III-47a to create plasmid pJR VI-54a (FIG. 17). IPTG induction and SDS-PAGE analysis were as previously described.

Results of induction experiments as evaluated by SDS-PAGE indicated that control of expression of di-alpha and beta by separate promoters gave little increase in the expression of either protein. Similarly, insertion of a second beta globin gene under regulation of a separate promoter had little effect upon production of the proteins.

EXAMPLE 13

Insertion of a Second Translationally Coupled Beta Globin Gene Into the Di-Alpha/Beta Expression Plasmid The expression plasmid SGE1.1E4 (FIG. 15) contains a di-alpha globin gene followed by a single beta globin gene. Translation of the polycistronic mRNA results in the non-equimolar production of two alpha globin proteins and one beta globin protein. Hemoglobin is composed of equimolar quantities of alpha and beta globin, suggesting that this expression system may underproduce beta globin. In order to test this hypothesis, we inserted a second beta globin gene in front of the di-alpha globin gene and analyzed expression of recombinant hemoglobin from this plasmid. Expression of all genes from a single promoter ought to exert the greatest control over stoichiometry.

Construction of a di-alpha/beta expression plasmid which results in equimolar synthesis of alpha and beta globin proteins and synthesis of genetically stabilized hemoglobin which cannot dissociate into alpha/beta dimers is novel. To our knowledge no such hemoglobin molecule has ever been produced or shown to function as an oxygen carrier.

Figure 29:
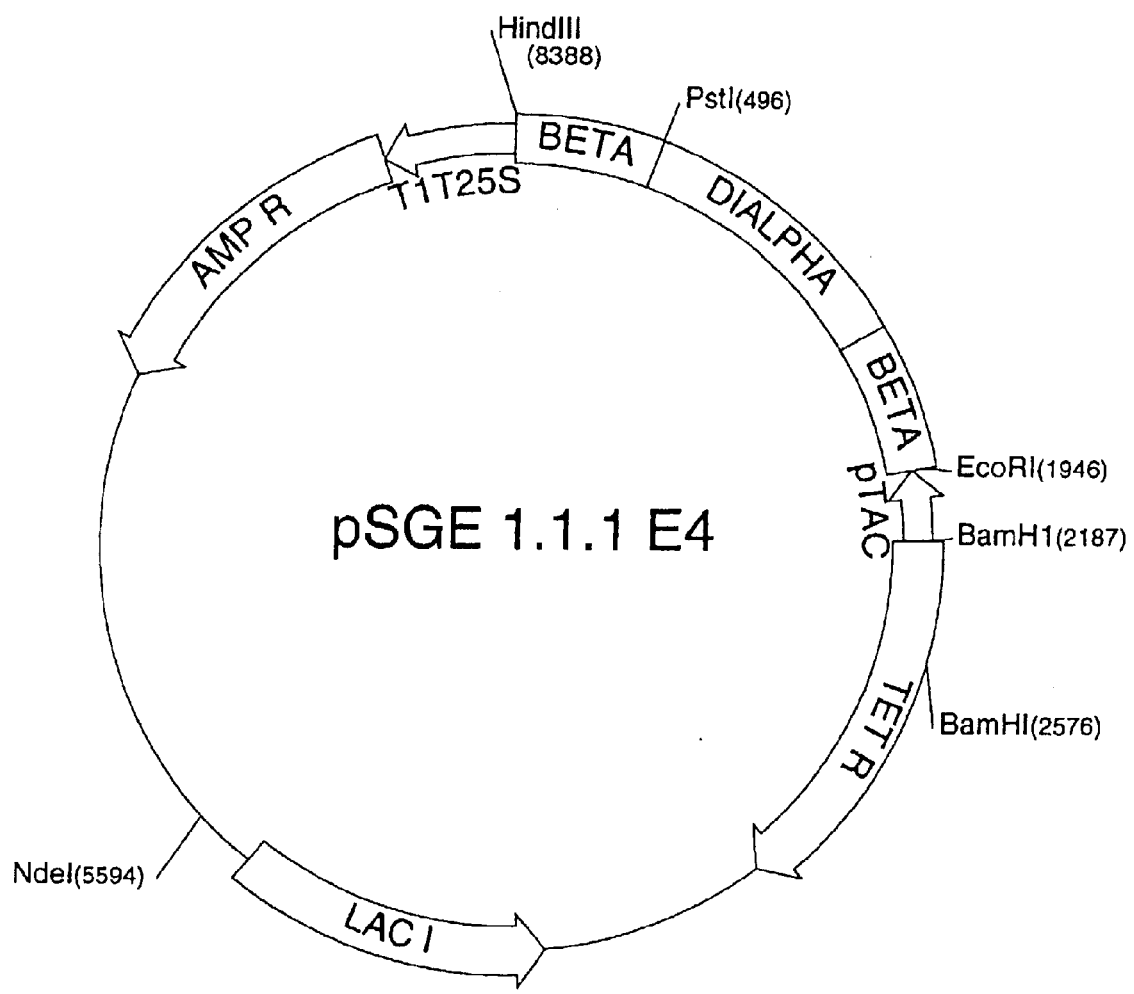
FIG. 29: Plasmid pSGE1.1.1E4.

Plasmid pSGE1.1E4 (FIG. 15) was digested with the restriction enzymes HindIII and PstI. The beta globin gene was gel purified, T4 polymerase filled, and ligated into SmaI linearized pSGE1.1E4. Following ligation, the mixture was again digested with SmaI to linearize plasmids not containing a second beta globin gene. The mixture was then transformed into E. coli strain JM109. Plasmids from individual isolates were screened for the presence of a second beta globin gene by digestion with the restriction enzyme ScaI. An individual isolate was designated SGE157. The plasmid was designated pSGE1.1.1E4 (FIG. 29).

A 2 liter fermentation was performed to obtain material for purification and functionality determinations. Hemoglobin in crude cell extracts, quantitated by the difference assay, was 2.8 mg/gm cell paste. This assay allows us to measure the concentration of functional hemoglobin. The addition of a second beta gene appears to have no significant effect on the production of functional hemoglobin.

EXAMPLE 14

Figure 30A:
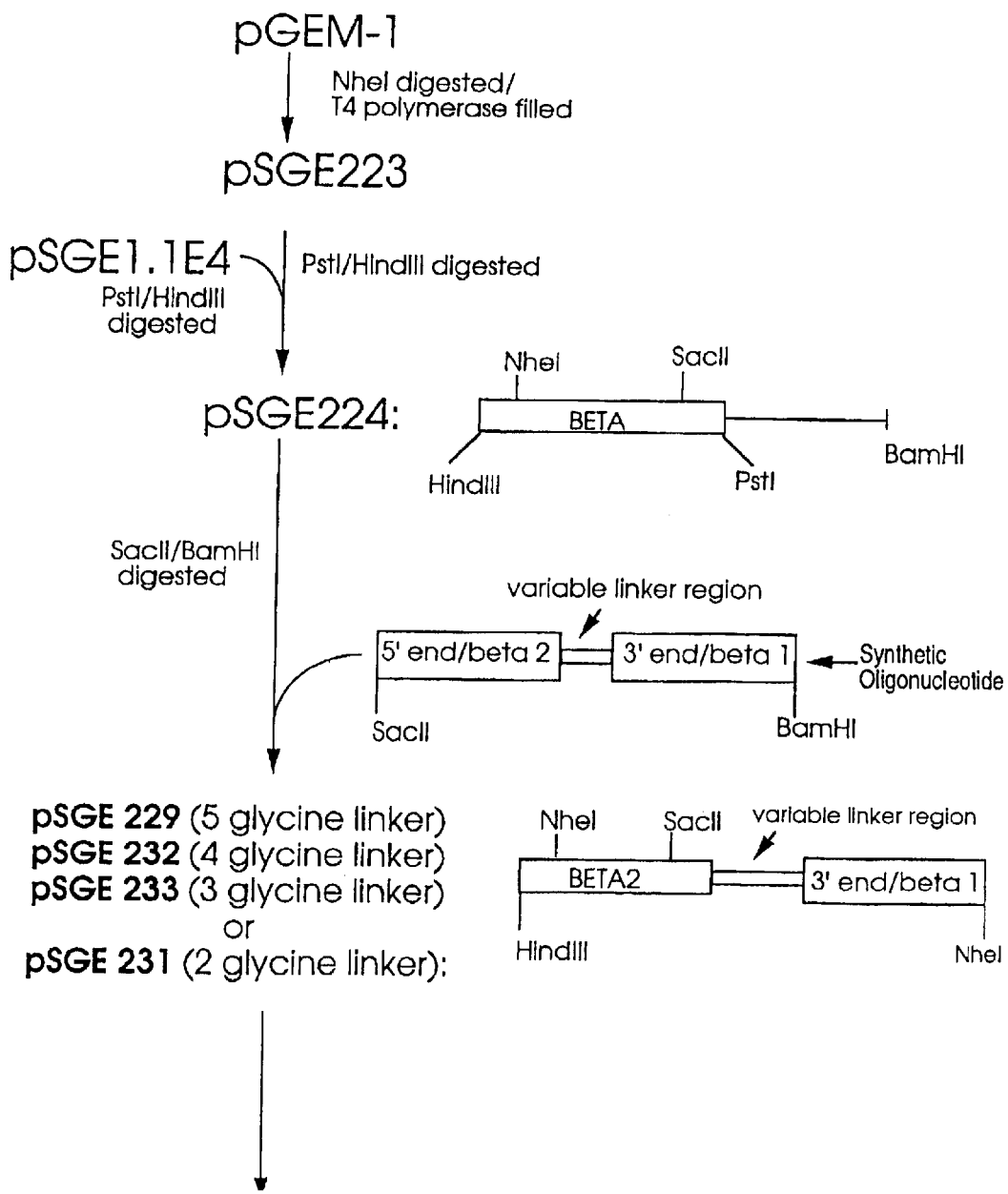
FIGS. 30a to 30c: A flow chart showing the construction of a di-beta hemoglobin expression vector, pSGE1.05E4.
Figure 30B:
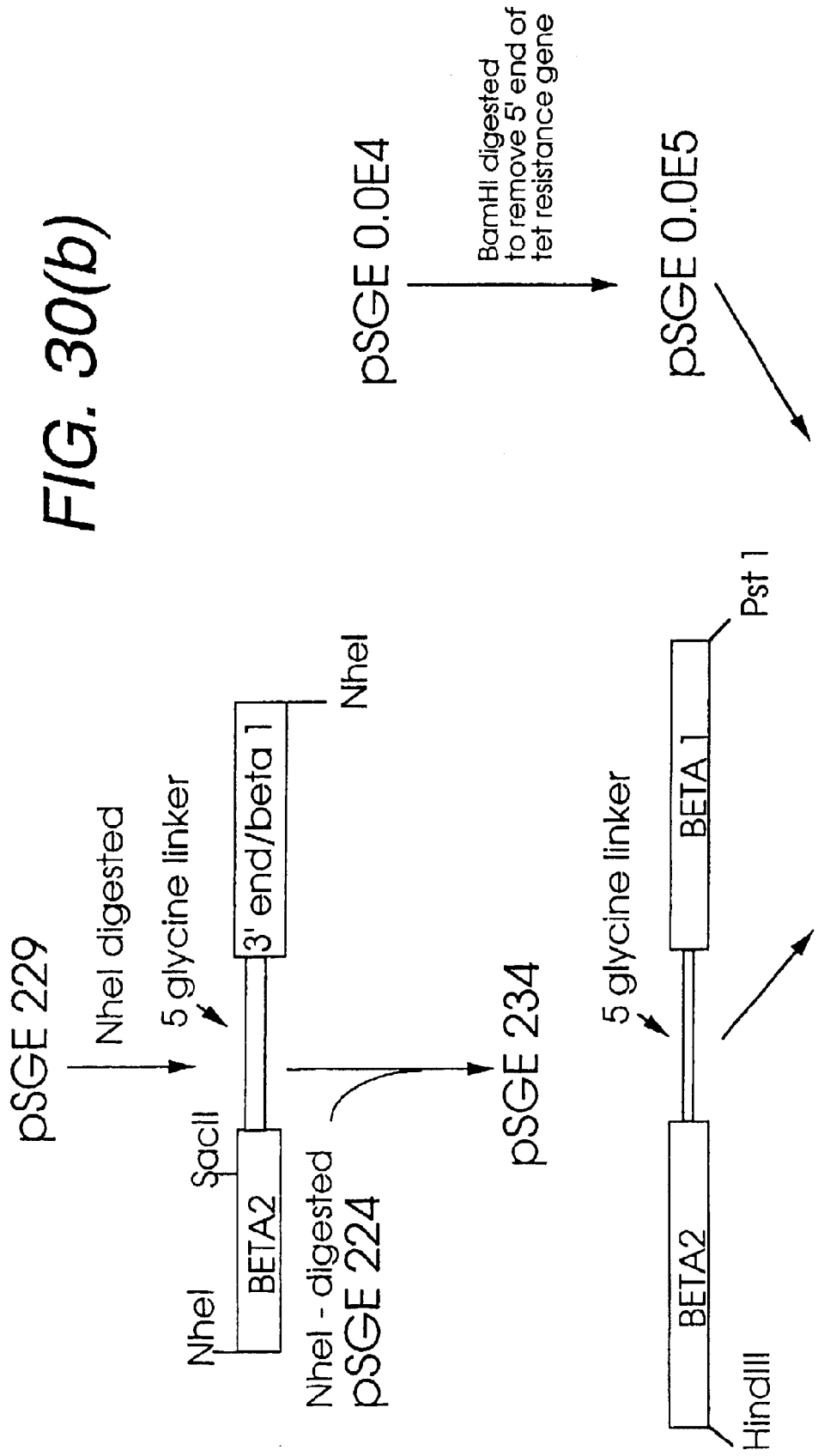
Figure 30C:
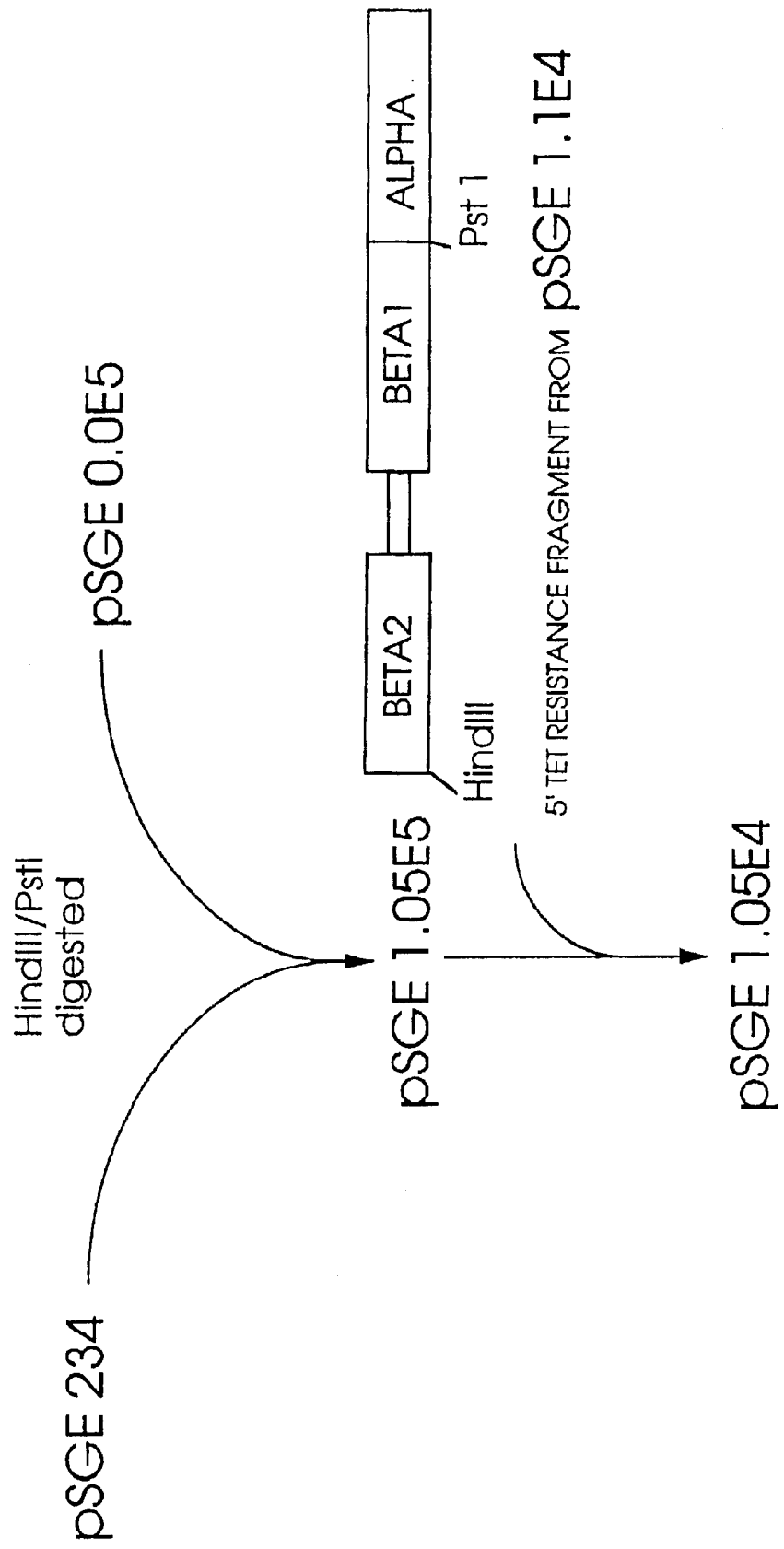

Construction of Di-Beta Globin Expression Vector and Production of Di-Beta Hemoglobin The general flowchart for this protocol is shown in FIG. 30.

a. Elimination of the NheI Site from Plasmid pGEM-1

Plasmid pGEM-1 was digested with restriction enzyme NheI, T4 polymerase filled, ligated, redigested with NheI, and transformed into E. coli strain SGE127.

Strain SGE127 was obtained by screening JM109 for phage resistance.

Plasmids were isolated from individual colonies and screened for loss of the NheI site by digestion with NheI. An E. coli isolate containing the appropriate plasmid was grown up. The plasmid was purified and designated pSGE223.

b. Cloning of Beta $Asn^{108} \rightarrow Lys$ into pSGE223

The gene for beta globin containing the Presbyterian mutation, $ASN^{108} \rightarrow Lys$, was excised from plasmid pSGE1.1E4 (FIG. 15) with the restriction enzymes PstI and HindIII and gel purified. Plasmid pSGE223 was similarly digested and gel purified. The Beta fragment was ligated into pSGE223 and transformed into SGE127. Individual isolates were screened for the presence of the Beta globin fragment by PstI and HindIII digestion. An E. coli isolate containing the appropriate plasmid was grown up. The plasmid was purified and designated pSGE224.

c. Insertion of the di-beta Linker Sequences

Plasmid pSGE224 was digested with the restriction enzymes BamHI and SacII and gel purified. Annealed complementary synthetic oligonucleotides encoding the 2, 3, 4, or 5 glycine (GGT codon) linker sequences were ligated into the plasmid and transformed into SGE127.

Isolates were screened for the presence two NheI sites. E. coli isolates containing the appropriate plasmids were grown up. The plasmids were purified and designated pSGE 229 (5 glycine linker), pSGE232 (4 glycine linker), pSGE233 (3 glycine linker), or pSGE231 (2 glycine linker).

d. Construction of the di-beta Globin Gene Containing the 5 Glycine Linker

Plasmid PSGE 229 was digested with NheI. The fragment containing the 5 glycine linker and the beta globin gene was gel purified and ligated into NheI digested plasmid pSGE224. Individual isolates were screened by digestion w±tn the restriction enzymes HindIII and PstI. An appropriate isolate was grown up. The plasmid was purified and designated pSGE 234.

e. Construction of PSGE 0.0E5

Plasmid pSGE0.0E4 was digested with Bam.HI to remove the 5' coding sequences for the tet resistance gene. After gel purification, the plasmid fragment was re-ligated and transformed into E. coli strain JM109. Isolates were selected for resistance to ampicillin and sensitivity to tetracycline. An individual isolate was grown up, the plasmid purified and digested with BamHI to confirm loss of the BamHI fragment. The isolate was designated SGE0.0E5. The plasmid was designated pSGE0.0E5.

f. Construction of PSGE1.05E5

Plasmids pSGE234 and pSGE0.0E5 were digested with HindIII and PstI. The di-beta-containing fragment was gel purified from pSGE234 and ligated into gel purified pSGE0.0E5 from which the beta fragment had been removed. Following transformation, individual isolates were screened by SDS-PAGE for their ability to produce alpha and di-beta globin proteins subsequent to induction with IPTG. An appropriate isolate was grown up and designated strain SDGE242. The plasmid was designated pSGE1.05E5.

g. Construction of PSGE1.05E4

Figure 31:
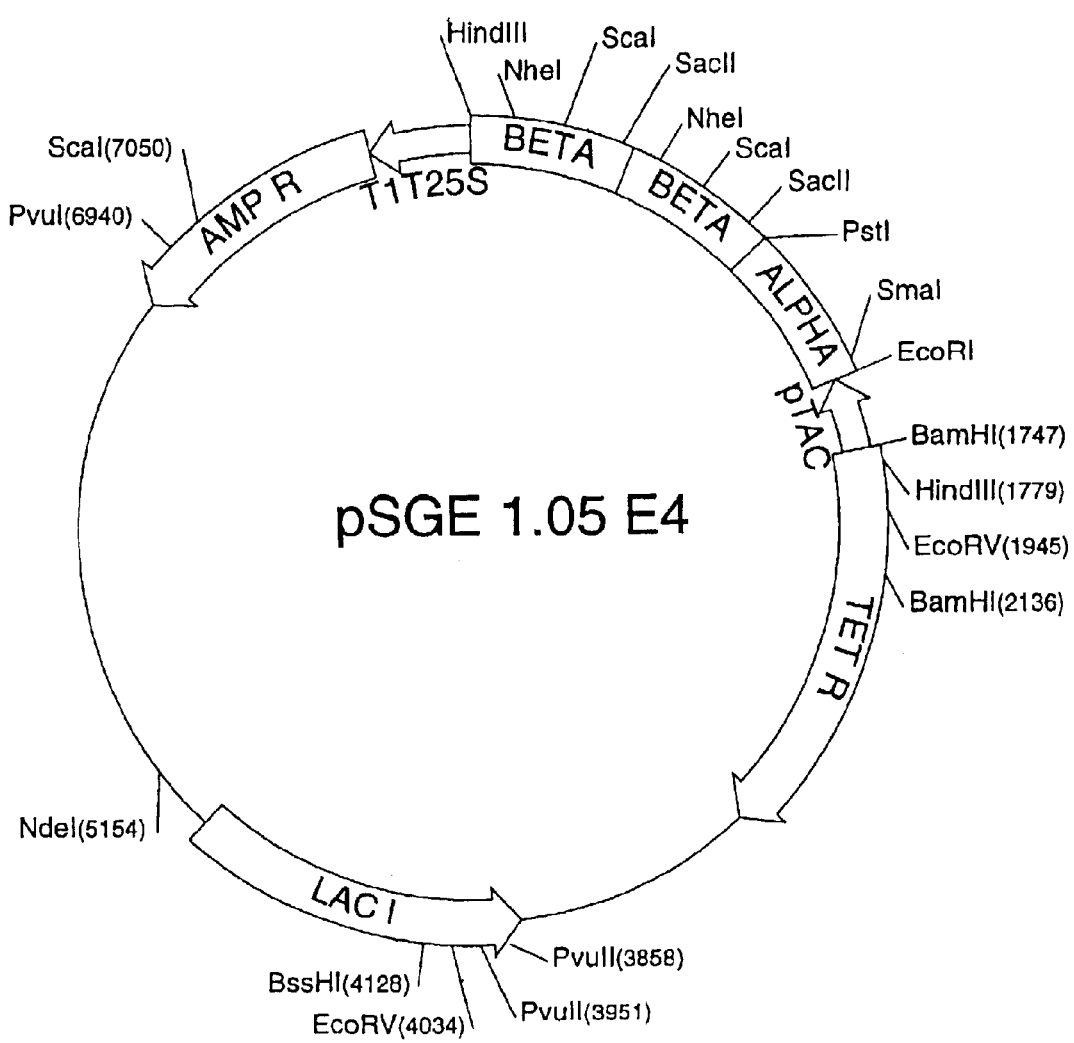
FIG. 31: Plasmid pSGE1.05E4.

The BamHI fragment containing the 5' end of the tetracycline resistance gene was gel purified from plasmid pSGE1.1E4 and ligated into BamHI-linearized plasmid pSGE1.05E5. Isolates were selected by plating the transformation mixtures on tetracycline containing nutrient agar plates. Individual isolates were screened for their ability to produce alpha and di-beta proteins subsequent to IPTG induction. An individual isolate was grown up and designated SGE245. The plasmid was designated pSGE1.05E4 (FIG. 31).

Production of di-beta hemoglobin (5 glycine linker) was achieved with this expression vector in *E. coli* but:
  a. expression levels were low compared to our di-alpha/beta expression system (4 to 5 fold lower yield).
  b. the oxygen affinity of the alpha/di-beta hemoglobin was high $P_{50}$=5.9 torr (±0.6 torr) vs. $^-$32 torr for the di-alpha/beta molecule. (at 37° C.) However, cooperativity, as measured by the Hill constant (n) was similar to the di-alpha construct (n=2.0±0.2 for both di-beta and di-alpha).

Although a molecule with such a low $P_{50}$ may not be useable as blood substitute or an oxygen-carrying plasma expander, it may have other uses. For example, it may be particularly useful for delivering oxygen to regions of tumors where oxygen tension is particularly low. Enhanced oxygen delivery during radiation or chemotherapy is known to enhance the therapeutic effects of anti-neoplastic agents:

References (1) Dowling, S., J. J. fischer and S. Rockwell. (1991) A clinical study of fluosol and hyperbaric oxygen as an adjunct to radiation therapy. Biomat. Art. Cells and Immobil. Biotech 19, 377.
(2) Herman, T. S. and B. A. Teicher (1991) Enhancement of radiation therapy by an experimental concentrated perfluorooctylbromide (Oxygent) emulsion in the Lewis lung carcinoma. Biomat. Art. Cells and Immobil. Biotech. 19, 395.
(3) Holden, S. A., B. A. Teicher and T. S. Herman (1991) Effect of a PFOB Emulsion (Oxygent) and carbogen breathing on the tumor cell survival of the FSaIIC fibrosarcoma after treatment with antitumor alkylating agents. Biomat. Art. Cells and Immobil. Biotech. 19, 399.

EXAMPLE 15

Hypothetical Protocol for Development of Linkers by Mutation and Selection

In this hypothetical example, the linker suitable for genetic fusion of globin subunits is obtained by mutagenesis of a linker-encoding DNA sequence and selection for functional linkers. Oligonucleotides spanning the BstBI site of alpha$_1$ to the EaqI site alpha$_2$ will be synthesized such that the six nucleotides comprising the preferred glycine-glycine linker are randomized. By randomizing these nucleotides, codons for all combinations of amino acids will be present in the oligonucleotide mixture. Following purification and annealing of the oligonucleotides they will be used to construct the di-alpha/beta co-expression genes as described above.

Clones containing the various di-alpha/beta plasmids will then be screened for production of increased levels of recombinant hemoglobin using a protocol developed at the Company. *E. coli* clones will be arrayed on nitrocellulose filters overlayed on 2×YT-ampicillin plates containing 1 mM IPTG. Following overnight incubation of 37° C., the plates will be sealed in a plastic bag in which the air has been displaced by carbon monoxide (CO). CO binding to intracellular recombinant hemoglobin produces a distinctive red color in the *E. coli* colonies. Colonies producing the most intense red color will be further analyzed.

In this experiment the assumption is made that certain combinations of amino acids in the di-alpha linker will permit more stable folding of the individual, linked alpha globin chains and, therefore, result in greater levels of production of intracellular recombinant hemoglobin. This increase level of production will result in a more intense red color in the appropriate *E. coli* clones.

After selection of several clones producing higher levels of recombinant hemoglobin, more detailed analyses will be done on individual clones to determine the optimal di-amino acid linker. The analyses will include determination of quantities of recombinant hemoglobin produced, oxygen affinity, and protein stability. Finally, clones found to be producing the best quality recombinant hemoglobin will be DNA sequenced to determine the amino acids comprising the linker.

This technique is equally applicable to other globin pseudodimers (di-beta and alpha/beta).

EXAMPLE 16

Hypothetical Protocol for the Synthesis of Plasmids Containing Alpha and Beta Globin Genes Under the Regulation of Two Separate Promoters on the Same Plasmid It is anticipated that recombinant hemoglobin can be expressed from constructs where the different globin genes are under the control of separate promoters. This situation would yield two separate mRNA's; one with a dicistronic sequence encoding an alpha globin gene and another with a dicistronic sequence encoding a beta globin gene. For construction of an expression system in which both the alpha and beta globin genes are under the regulation of separate promoters, on the same plasmid, the following protocol would initially be used. Plasmid pDL III-1a containing the des-val alpha globin gene would be digested with the restriction enzyme BamHI, reacted with bacterial alkaline phosphatase, phenol extracted, ethanol precipitated, and resuspended in TE buffer. The plasmid pJR IV 50-a which is the pKK expression plasmid containing the des-val beta construct, would then be digested with the restriction enzymes BamHI and PvuI, to excise a fragment from the plasmid containing the $P_{tac}$ promoter, the des-val beta sequence, the transcriptional terminator sequence and a portion of the ampicillin resistance gene. Following gel purification of this fragment, a PvuI-BamHI linker would be synthesized and ligated onto the insert. The insert would then be back-cut with BamHI to generate BamHI compatible sites on both the 5'-and 3'-ends of the insert. This insert would then be cloned into BamHI linearized plasmid pDL III-1a, resulting in a plasmid in which a translationally coupled des-val beta globin gene under regulation of one $P_{tac}$ promoter is positioned on the 3' side of a translationally coupled des-alpha globin gene under regulation of a separate $P_{tac}$ promoter. Restriction enzyme mapping would be used to confirm the orientation of the beta globin containing insert. E. coli JM-109 would be transformed with the plasmid containing the separate $P_{tac}$-globin constructs and grown in media containing ampicillin to isolate clones containing the plasmid. The clones containing the plasmid would then be induced with IPTG and expression of des-val alpha globin, des-val beta globin and des-val hemoglobin would be assayed by SDS-PAGE analysis, Western blotting with anti-hemoglobin antibodies and isolation of des-val hemoglobin by standard chromatographic methods.

Alternatively, coexpression of both globin genes could be achieved from DNA sequences on separate vectors under the control of separate promoters.

EXAMPLE 17

Hypothetical Protocol for the Construction of Vectors Containing Alpha and Beta Globin Genes Under the Regulation of Separate Promoters and on Different Vectors E. coli clones containing plasmid pDL III-1a which is the pKK223-3 plasmid containing a dicistronic loader gene/des-val alpha construct under the regulation of the $P_{tac}$ promoter would be transformed with a plasmid containing the dicistronic loader gene/des-val beta construct under control of the same promoter, but with a gene conferring additional antibiotic resistance to tetracycline. This could be constructed in the following manner: Plasmid pJR IV-50a contains the des-val beta globin gene under control of the $P_{tac}$ promoter. This plasmid would be cut with PvuII to generate a linear plasmid with blunt ends. This would be ligated with a NotI phosphorylated linker (New England BioLabs). The ligation mixture will be used to transform E. coli. Plasmid DNA would be prepared and plasmids containing a NotI site identified by digestion with NotI agarose gel electrophoresis. This plasmid will contain the $P_{tac}$:des-val beta globin sequence. The gene for resistance to the antibiotic kanamycin is commercially available (pharmacia) and contains EcoRI restriction sites on both ends. The ends will be converted to blunt ends by treatment with T4 DNA polymerase by the method of Maniatis, et al. The resulting fragment will be ligated with a 50 fold excess of phosphorylated NotI linker (25° C., 60 min). The ligation reaction would be made 0.01 M in EDTA, heated to 70° for 20 min and ethanol precipitated. The precipitated DNA will be taken up in 100 ul of NotI buffer and treated with 100 units of NotI (37°) for 2 hr. The fragment would be purified by agarose gel electrophoresis. The NotI adapted kanamycin resistance gene would then be ligated into the NotI linearized pJR IV-50a to yield a plasmid with the gene for des-val beta globin under control of $P_{tac}$ with kanamycin resistance. E. coli JM-109 clones containing plasmid pDL III-1a, the plasmid containing des-val alpha globin under control or $P_{tac}$ with resistance to ampicillin, will then be transformed with kanamycin resistant plasmid containing the gene for des-val beta globin and clones will be selected for resistance to both ampicillin and kanamycin. Other antibiotic resistance genes could be used as well. Expression of alpha and beta globin polypeptides under the regulation of separate promoters will then be analyzed by IPTG induction, SDS page and western blotting.

Should we encounter problems with plasmid exclusion, we could use the same strategy with the pIN plasmids that have been used to express polypeptides from separate plasmids in E. coli (McNally, et al., PNAS 85, 7270, 1980).

One potential problem that we may face with creating plasmids in which the alpha and beta globin genes are separate under but identical promoters is the possibility of homologous recombination within the identical sequences on the plasmids, eg. the promoter region. This could result in deletion of a segment of important DNA sequence. It is therefore preferable to use different, non-homologous promoters for each different globin gene, eg. $P_{tac}$ and $P_{trc}$ or the lambda $P_L$ promoter in appropriate host (containing cI857).

EXAMPLE 18

Synthesis and Assembly of the Di-Aipha Beta Globin Construct in $aP_L$, Regulated Vector System In prior examples, the globin genes were under Tac promoter control, and the alpha (or di-alpha) and beta globin genes were each translationally coupled to the ribosomal loader cistron taught by Schoner, et al. In this example, the lambda $P_L$ promoter and a different translational coupler (see below) are used.

Translational Coupler

```
       SD2                         MET           Sfi
5'AAT AAG GAG GAA TAA CAT ATG CTG TCT CCG GCC GAT (SEQ ID NO:34)
AAG GCC CCA AGC TTG GGG3'

3'TTA TTC CTC CTT ATT GTA TAC GAC AGA GGC CGG CTA (SEQ ID NO:35)
                                              EAGI
TTC CGG GGT TCG AAC CCC5'
         Hind III
```

The pL expression system has a different translation coupler as compared to the pTAC system. Sequences coding an SD and a translational stop were added downstream from the 5' end of the N protein coding sequences to act as a translational coupler. subsequent to that the globin coding sequences are identical to that used in the pTAC system.

Figure 19B:
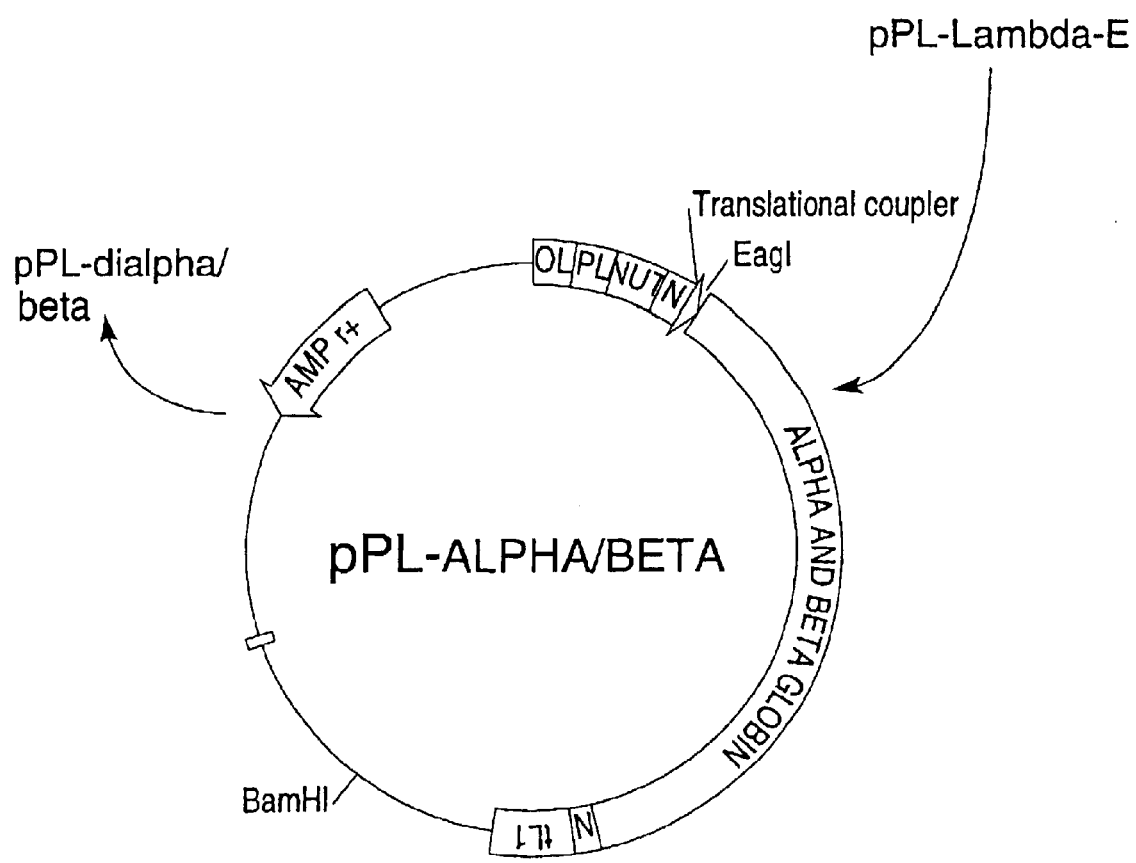

Using the pPL-lambda vector available from Pharmacia, a plasmid construct was assembled to generate a genetically crossed-linked tetrameric human hemoglobin (wild type) in E. coli strains N99Ci+ and N4830-1 (cI857). These bacterial strains were obtained from Pharmacia and are inducable by addition of naladixic acid (40 µg/ml) or mitomycin C (10 µg/ml)in the presence of the wild type Ci+ repressor or heat treatment of the strain containing the cI857 repressor gene (Mott, et al., PNAS 82, 88, 1985 and Gottesmann, M. E., et al., J. Mol. Biol. 140, 57, 1980). A diagramatic representation of the cloning strategy is depicted in FIG. 19.

Removal of the EagI Site from the pPL-Lambda Vector

Removal of the EagI site from pPL-lambda was necessary to enable cloning of the di-alpha gene sequence, because both alpha structural genes contain a EagI site located 6 bp into the coding sequence. The pPL-lambda vector was digested with EagI, and the ends were filled using T4 DNA polymerase. The Bam HI linker (5'-CCCGGATCCGGG-3') (SEQ ID NO:36) (Pharmacia), was blunt-end ligated to the EagI digested pPL-lambda plasmid by standard methods. This eliminated the EagI site in the desired construct. The resulting mixture was digested with EagI to eliminate any plasmids still containing the EagI site. *E. coli* N99Ci+ cells were transformed with resulting plasmid, pPL-lambda-E. Clones containing the desired plasmid were identified by restriction digest analysis.

Incorporation of the Synthetic Co-Translational Coupler into pPL-Lambda-E

Prior to inserting the globin genes into the vector it was necessary to incorporate the synthetic translational coupler sequence into the HpaI site of pPL-lambda-E. This was done by digestion of pPL-lambda-E with HpaI followed by blunt end ligation of the co-translational coupler into the HpaI site of the vector. Ligation of the coupler to the blunt end resulted in destruction of the HpaI site. The ligation mixture was treated with HpaI to digest any plasmid remaining containing the HpaI site. *E. coli* N99Ci+ cells were transformed with the resulting reaction mixture. Clones were screened with EcoRI and Hind III restriction digests to identify clones containing the co-translational coupler in the proper orientation. DNA fragments of 522 bp and 4762 bp were observed for plasmid containing the desired orientation. To confirm the orientation of the coupler, the resulting plasmid was sequenced using a primer (5' CAATGGAAAGCAGCAAATCC-3')(SEQ ID NO:37) complementary to the sequence 30 base pairs upstream from the translational coupler sequence. The desired plasmid was denoted as pPL-lambda-E+TC.

Construction of an Expression Plasmid Containing Des-Val Alpha and Beta Genes Under Control of pPL-Lambda The Des-Val alpha and beta globin genes were obtained from pDL III-14c by digestion with EagI and Hind III, followed by agarose gel purification of the desired 942 bp segment. The purified alpha and beta globin gene fragment was cloned into EagI and HindIII digested pPL-lambda-E+TC. The ligation mixture was used to transform *E. coli* N99Ci+, and clones were screened for the presence of the desired plasmid, pPL-alpha/beta. Digestion with EcoRI (4758 and 1468 bp), and with PstI and HindIII (4005, 1775, 520 bp) confirmed presence of the desired restriction sites. Further confirmation was obtained through sequencing with the 20 bp primer, above, to confirm the sequence between the co-translational coupler and the Des-Val alpha globin gene, and a second primer (5' ACCCGGAAAA-CTTCCGTC-3') (SEQ ID NO:38) to confirm the sequence between Des-Val beta and the pPL vector.

Construction of an Expression Plasmid Containing Di-Alpha and Beta Globin Genes Under Control of pPL-Lambda An RGV crosslinker which encodes for the carboxy terminal portion of alpha globin, linked via a single glycine residue to the native sequence of the amino portion of a second alpha globin chain, was prepared by separately phosphorylating the 5' ends of 5'CGAAATAACGT-GGTGTTCTGTCTGC-3' (SEQ ID NO:39) and 3'TTTATGGCACCACAAGACAGACGCCGG-5' (SEQ ID NO:40) with T4 kinase, followed by annealing. This double stranded oligonucleotide was cloned onto the EagI end of a purified fragment of Des-Val alpha and beta globin prepared form pDL III-14c digested with EagI and HindIII, as described above. The linear DNA sequence generated from this ligation, now containing sticky ends coding for BstBI and HindIII restriction site sequences, was purified by agarose gel electrophoresis and cloned into BstBI and HindIII digested pPL-alpha/beta. The new plasmid designated pPL-dialpha/beta contained a sequence with a co-translational coupler upstream to a sequence containing di-alpha globin linked via a glycine residue, followed by a cotranslational coupler adjacent to a beta globin gene sequence, all under control of a single $P_L$ promoter. These clones were identified through screening minipreps with EagI restriction digestions. Clones without the second alpha globin gene merley linearised upon digestion, whereas clones containing the second gene released 431 bp and 6222 bp DNA fragments.

Construction of the Expression Plasmid pSGE0.1-L0 Containing a ROP-Origin of Replication Mutation pPL-dialpha/beta was digested with PvuII then treated with T4 DNA polymerase to fill in the sticky ends. The linearized plasmid was then blunt end ligated with a NotI linker (Promega Corp., Madison, Wis.) (5'TTGCGGCCGCAA-3')(SEQ ID NO:41). The ligation mixture was then treated with PvuII to remove any remaining plasmid containing the PvuII site. *E. coli* were transformed with pSGE0.1-L0 and positive clones were identified by the presence of the unique NotI restriction site.

Expression of Hemoglobin SGE0.1 in *E. Coli* Under the Control of the Lambda $P_L$ Promoter

*E. coli* N99Ci+ and *E. coli* N4830-1 were transformed with pSGE0.1-L0 and grown on agar plates containing ampicillin, as described previously. These *E. coli* strains contain the cI+ repressor gene and the cI857 heat sensitive repressor gene, respectively.

Inocula of N99Ci+ were grown at 37° C. in TB media to an $OD_{600}$ of ~1.0 and induced with naladixic acid (40 µg/ml). Cultures were incubated for 4–6 hrs. at 37° C. before the cells were harvested. Hemoglobin production was estimated by SDS-PAGE analysis of total cell protein and by western blot analysis. By these techniques, SGE0.1 was estimated to be produced at ~0.02% of the total cell protein in this cell line. Hemoglobin (57 µg) was isolated by Mono Q chromatography and shown to have an optical spectrum representative of that for normal hemoglobin.

Inocula of N4830-1 were incubated at 30° C. in TB media to an $OD_{600}$ of 1.0 and induced by addition of sufficient preheated TB media (65° C.) to raise the temperature of the inocula TO 42° C. The culture was then incubated at 42° for 4–6 hrs. Total cell protein analysis with SDS-PAGE revealed that SGE0.1 was being synthesized at 0.4% the total cell protein, corresponding to 0.18 mg protein per gram of wet cell paste. SGE0.1 prepared from a 2L preparation was purified as described elsewhere, and resulted in isolation of 7.6 mg of purified material. SGE0.1 (7.6 mg) was isolated and had a $P_{50}$ of 4.1 (Hemox Analyzer, pH 7.4, 0.1 M NaCl, 37° C.), and an optical spectrum representative of native hemoglobin.

EXAMPLE 19

Production of Hemoglobin in Yeast

All restriction enzymes and DNA-modifying enzymes were purchased from BRL, New England Biolabs, IBI, Pharmacia or Boehringer-Mannheim. The concentrations of enzymes used were those suggested by the supplier to produce a complete reaction in 30 minutes. The buffers and conditions for the use of these enzymes were those provided with the enzymes, unless otherwise stated. Plasmid DNA was purified from *E. coli* DH5α as described by Birnboim and Doly (Nucleic Acids Research 1979, 7:1513–1520). Electrophoretic analysis of DNA was carried out in agarose gels using tris-acetate electrophoresis buffer (Maniatis et al. *Molecular Cloning*, Cold Spring Harbor, N.Y., 1982). DNA was visualized by staining the gels with 0.5 μg/ml ethidium bromide and exposing the gel to ultraviolet light. DNA fragments were purified from agarose gels using a kit purchased from BIO-101. DNA fragments were purified from acrylamide gels by crushing the excised gel fragment, containing the DNA of interest, in 3.25M ammonium acetate and incubating overnight at 37° C. Gel fragments are removed by centrifugation (12,000×g, 15 mm) and the DNA precipitated with 2 volumes of 95% ethanol, 5% isopropanol. The precipitate is dried in vacuo and dissolved in 0.1×TE (1×TE is 10 mM Tris. HCl pH7.8, 1 mM $Na_3$ EDTA). Acrylamide gel electrophoresis of DNA was done as described by Maniatis, et al. (*Molecular Cloning*, Cold Spring Harbor, N.Y., 1982. ) in tris-acetate electrophoresis buffer. Bacteriological growth media and DNA transformation methods are described by R. W. Davis et al. (Advanced Bacterial Genetics, Cold Spring Harbor Laboratory, New York, 1980, p140–141). Transformation of *S. cerevisiae* with linear or circular DNA was carried out as described by H. Ito et al. (J. Bacteriology 153:163–168 (1983)). Transformants were selected on SD medium lacking uracil or tryptophan (SD-ura, SD-trp) depending on the selectable marker on the plasmid (F. Sherman et al., Methods in Yeast Genetics: A Laboratory Manual, Cold Spring Harbor Laboratory, 1979). All other yeast media used are described by Sherman et al. (ibid.)

Synthesis and Assembly of a Galactose Regulated Promoter

This synthetic promoter consists of two functional parts, a regulatory sequence and sequence that allows efficient initiation of mRNA synthesis. One of the regulatory regions we chose includes the nucleotide sequence that confers positive regulation of transcription in the presence of galactose (M. Johnston and R. Davis, 1984. Molecular and Cellular Biology 4:1440–1448 L. Guarente et al., 1982, Proc Nat Acad Sci (USA)79:7410–7414.). The transcriptional initiation site is derived from the consensus sequence for the *S.cerevisiae* glyceraldehyde-3-phosphate dehydrogenase gene (GAP491) (L. MoAlister and M. J. Holland, J. Biol Chem 260:15019–15027, 1983; J. P. Holland et al., J. Biol Chem 258:5291–5299, 1983).

The synthetic oligonucleotides shown in FIG. 1 were synthesized on a Biosearch 8600 DNA synthesizer. Each oligonucleotide was cleaved from its support column with 28% $NH_4OH$. The blocking groups were removed by incubating the cleaved oligonucleotide in 28% $NH_4OH$ at 65° C. for ≧16 hr. All oligonucleotides were purified by preparative polyacrylamide gel electrophoresis in slabs of 10% acrylamide (19:1 acrylamide:bis-acrylamide) containing 7M urea. oligonucleotides were eluted from acrylamide slices by incubation (16 hr) in 50 mM ammonium acetate (pH7.4), 2.5 mM magnesium acetate, 0.25 mM EDTA and 0.25% SDS at 37° C. Acrylamide fragments were removed by centrifugation (14,000×g, 10 min) and the oligonucleotide precipitated from the aqueous phase by the addition of NaCl to 0.25M and 3 volumes of 100% ethanol. The precipitated oligonucleotides were collected by centrifugation (14,000×g for 30 min), washed twice with 80% ethanol, once with 100% ethanol and the pellets dried. Pellets were dissolved in 0.1×TE. $2 \times 10^{-10}$ moles (each) of oligonucleotides 1–5 (Table 5) were phosphorylated in 0.02 ml of 0.066M Tris HCl (pH 7.6), 0.01M $MgCl_2$, 0.002M dithiothreitol (DTT), 0.001M spermidine and 10 units of T4 polynucleotide kinase. Phosphorylation reactions were carried out at 37° C. for 30 min and terminated by heating to 96° C. for 5 min. $2 \times 10^{-10}$ moles of oligonucleotides 1 and 6 (Table 5) were added to the phosphorylated oligonucleotides in a final volume or 0.04 ml or 0.07M Tris HCl (pH7.6) 0.01M $MgCl_2$. The mixture of oligonucleotides 1–6 (Table 5) was heated to 96° C. for 5 min, 75° C. for 20 min, 55° C. for 30 min, 37° C. for 60 min and 25° C. for 15 min. T4 DNA ligase (10 units), DTT (0.002M final concentration), and ATP (0.001M) were added and the mixture incubated at 4° C. for 16 hr. The resulting 210 bp oligonucleotide contains a 5' end compatible with a SalI restriction endonuclease site and a 3' end compatible with an XbaI site. Because the oligonucleotides comprising the two ends of the intact oligonucleotide were not phosphorylated, they cannot ligate to each other. This oligonucleotide was cloned into the vector pSK+ (Stratagene, Inc.) (FIG. 21(a)) that had been digested with XbaI and SalI. The ligation mixture contained 50 ng of XbaI, SalI digested pSK(+), and 5 pMoles of the ligated oligonucleotide in a volume of 0.01 ml. *E. coli* DH5α was transformed with a portion of the ligation reaction and clones that contain inserts were identified by screening for white colonies on LB-ampicillin (0.15 mg/ml) agar plates supplemented with XGAL (4 μg/ml). Positive identification was made by preparing plasmid DNA from these isolates and digesting with XbaI and SalI. The restriction digests were analyzed by agarose gel electrophoresis and three clones containing a fragment of the expected size (~250 bp) were identified. The DNA sequence of all three clones was determined and one was chosen for further use and designated pGS2488 (FIG. 21(a)).

Assembly of the Synthetic Galactose Upstream Activator ($GAL_{UAS}$) Sequence

The oligonucleotides shown in Table 6 were synthesized and purified as described above. Oligonucleotides 2–5 were phosphorylated, annealed with oligonucleotides 1 and 6 and ligated as described for the assembly of GAP. The full length oligonucleotide generated by this protocol has non-phosphorylated ends compatible with the restriction endonuclease sites generated by SphI and SalI. However, when the oligonucleotide is ligated to a SalI site the resulting junction formed between the two fragments will no longer contain a cleavable SalI site.

Figure 21B:
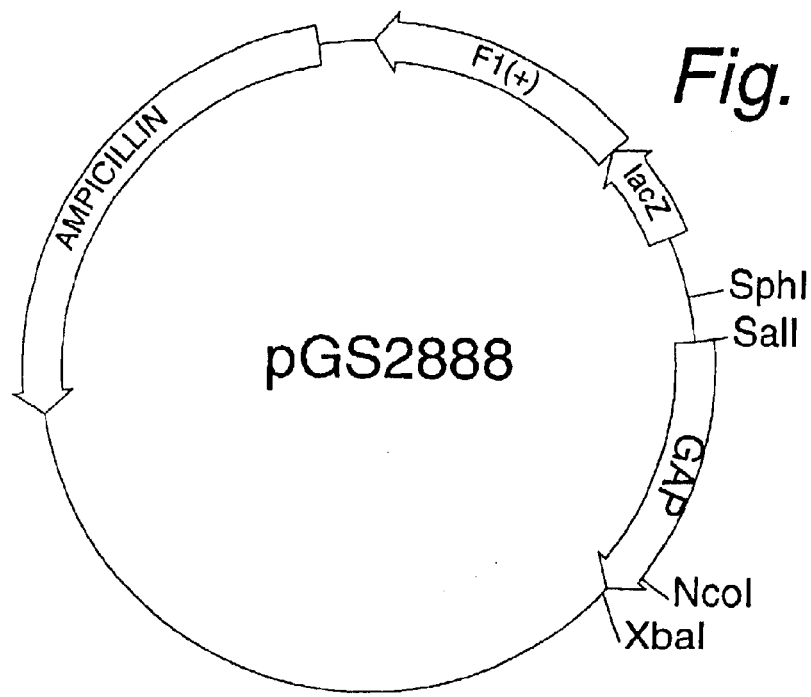
Figure 1:
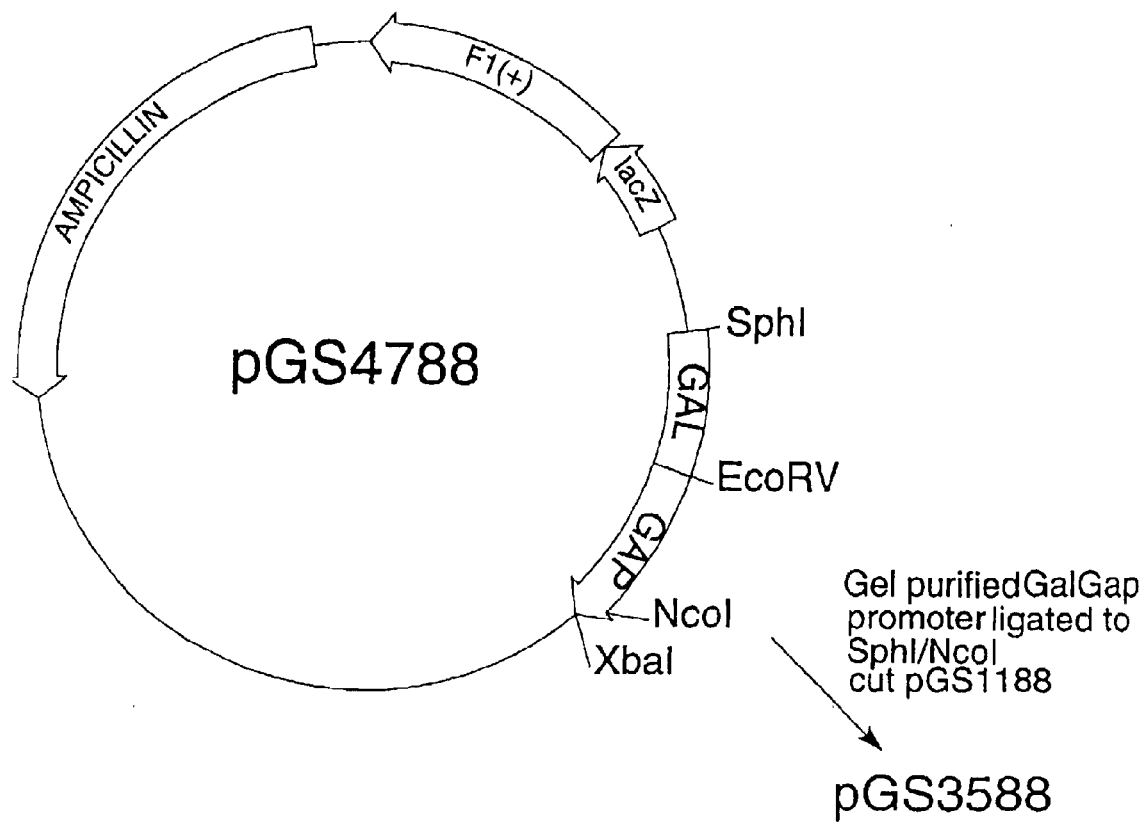
Figures 2, 21B:
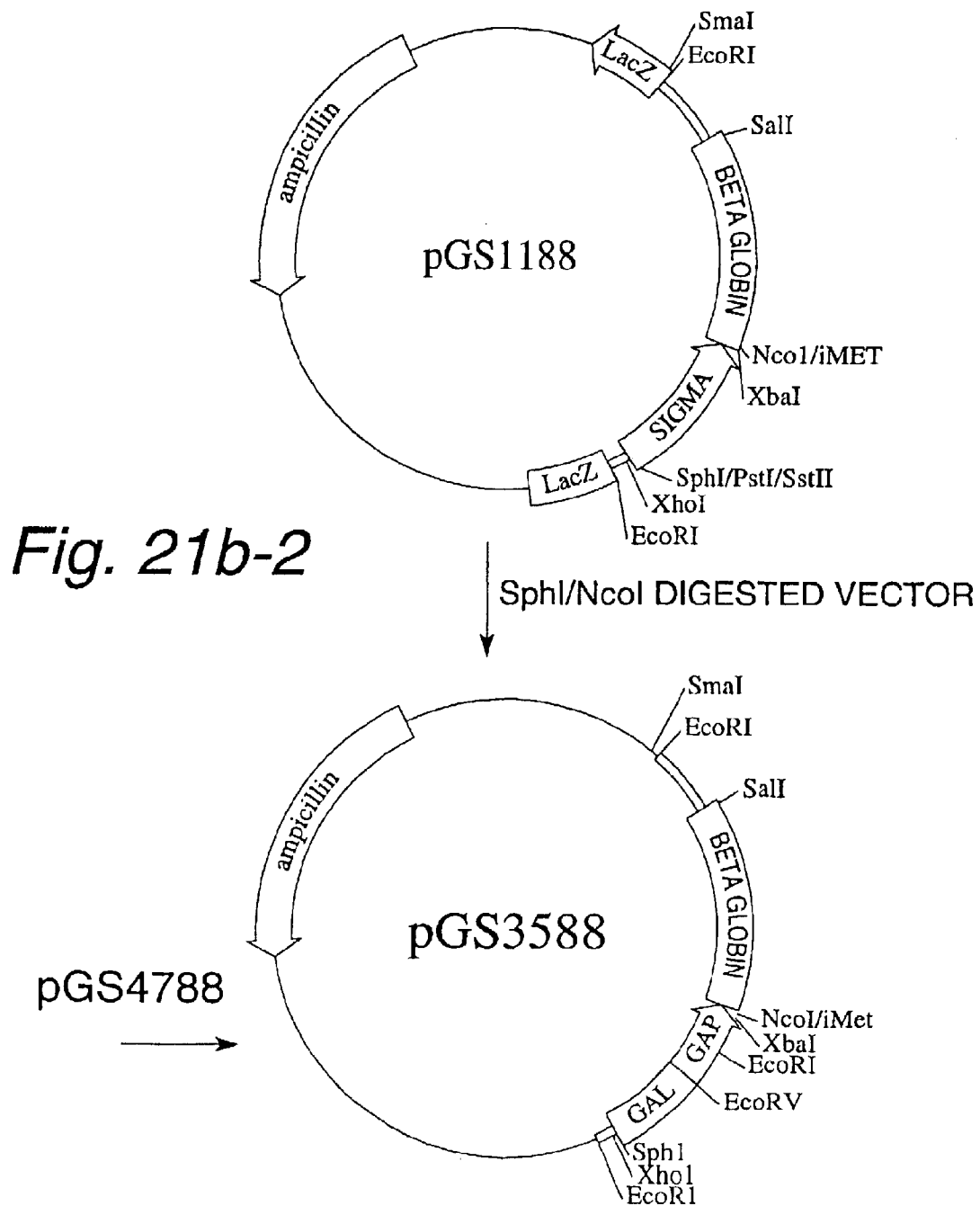
Figures 3, 21B:
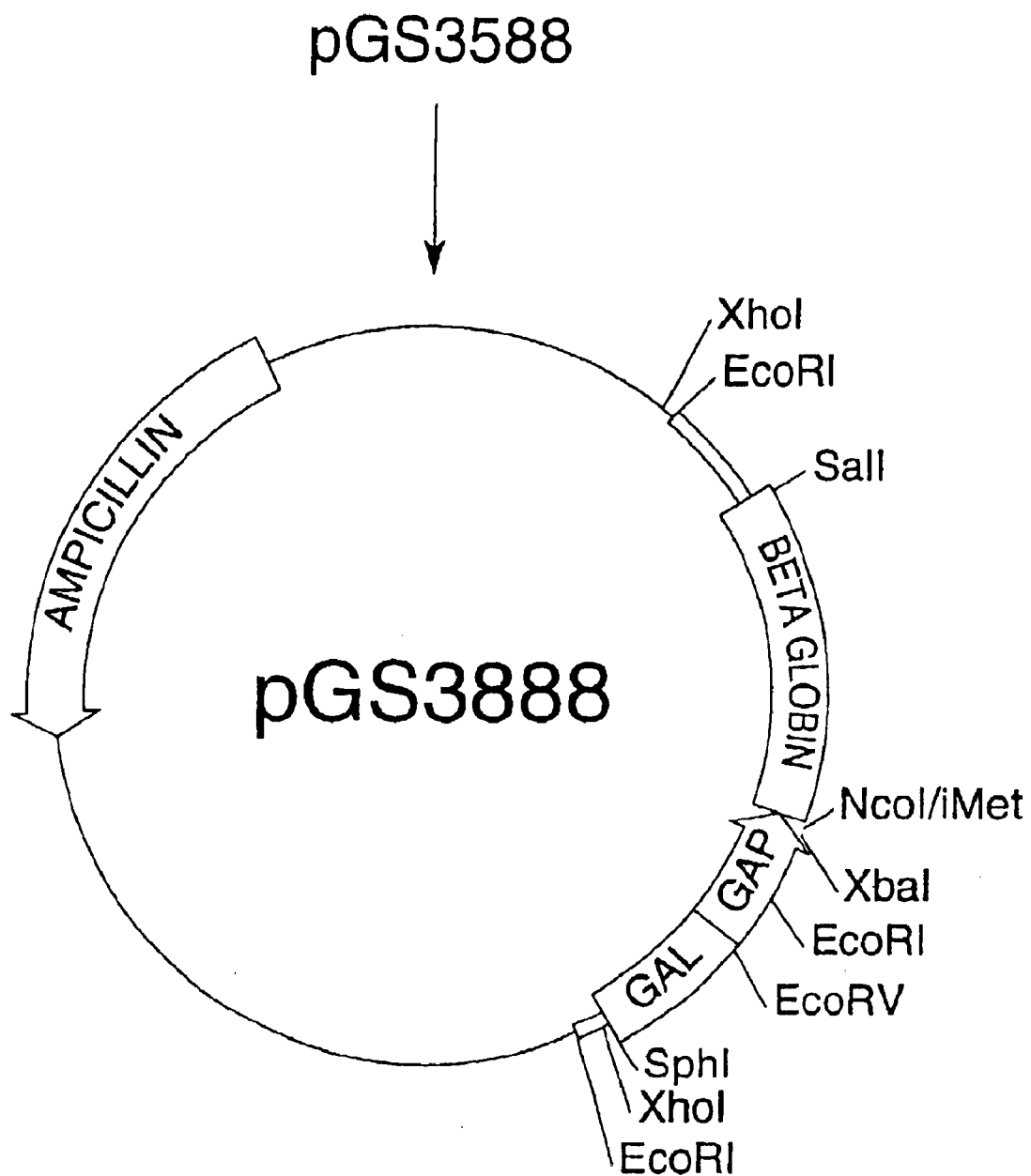

The $GAL_{UAS}$ is contained on an SPHI-SalI fragment. To clone this fragment into pGS2488 required that we change the KpnI site of this plasmid to an SphI site. The plasmid pGS2488 was modified by cleaving with KpnI. The KpnI digested plasmid was incubated with 2 units of T4 polymerase in 0.05 ml buffer containing 50 μM of each deoxyribonucleotide triphosphate (A,G,C,T), 0.033M Tris-acetate (pH 7.9), 0.066M potassium acetate, 0.01M magnesium acetate, 0.5 mM DTT and 100 μg/ml bovine serum albumin (BSA). $Na_3EDTA$ was added to 0.015M and the mixture extracted 1× with phenol-chloroform. DNA was precipitated with ethanol. The dry pellet was dissolved in 0.008 ml of T4 DNA ligase buffer, 50 ng phosphorylated SphI linkers (New England Biolabs) and 10 units of T4 DNA ligase. The mixture was incubated for 1 hour at 25° C. and used to transform *E. coli* DH5α. Plasmid DNA was prepared from 12 transformants and tested by restriction enzyme digestion and agarose gel electrophoresis, for the presence of an SphI site and the absence of a KpnI site. A clone containing a plasmid with these characteristics was identified and the plasmid was designated pGS2888 (FIG. 21(b)).

Figure 20B:
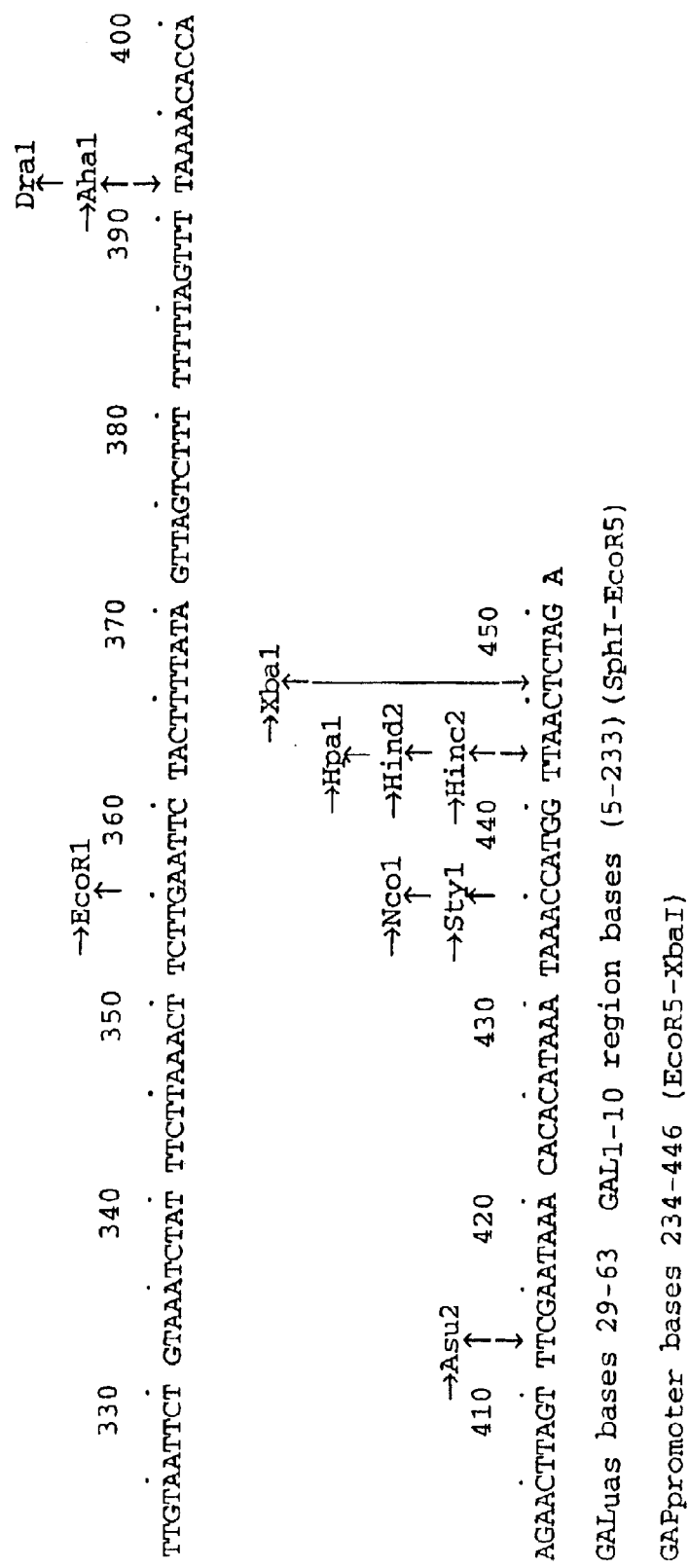

The next step in the assembly of this hybrid promoter was to clone the SphI-SalI fragment containing the $GAL_{UAS}$ into pGS2888. pGS2888 was digested with SphI and SalI, phenol-chloroform extracted and ethanol precipitated. Fifty nanograms of SphI, SalI digested pGS2888 was incubated with 25 ng of the annealed, ligated $GAL_{UAS}$ mixture in 0.005 ml 1× ligase buffer containing 10 units of T4 DNA ligase. The ligation mixture was incubated overnight at 4° C. and a portion used to transform *E. coli* DH5α. Ampicillin resistant clones were isolated and plasmid DNA prepared. The plasmid DNA (digested with XbaI and SpI) was analyzed by agarose gel electrophoresis. A plasmid containing a fragment of the expected size (~500 bp) was identified. The sequence of the putative GALUAS portion of this plasmid was determined and the plasmid was designated pGS4788 (FIG. 21(b)). The complete sequence of the synthetic GAL-GAP promoter (pGGAP) is shown in FIG. 20.

Construction of a pGGAP-β-globin Expression Cassette

The plasmid pLCIIFX-β-globin (K. Nagai, M. Perutz and C. Payart, Proc Nat Acad Sci (USA) 82:7252–7255) was used as the source of human β-globin cDNA. The coding region of the β-globin cDNA can be excised as an ApaL1 to Hind3 fragment that is missing only the first four nucleotides of the β-globin coding (translated) sequence. pLCIIFX β-globin (5 μg) was digested with ApaL1 and Hind3 and a 550 bp fragment containing the cDNA was purified by acrylamide gel electrophoresis. The ApaL1-Hind3 fragment containing the β-globin cDNA was cloned into Xba1, Hind3 digested pUC19 using the following adaptor (synthesized and purified as described above):

XbaI NcoI ApaL1 YH1a/b5'-CTAGAACCATGG
    TTGGTACCACGT-5'

The two oligonucleotides were mixed (12.6 μg of each), NaCl was added to 0.25M and three volumes of ethanol (anhydrous) was added. The precipitated oligonucleotides were collected by centrifugation (14,000×g, 15 min) and the pellet washed twice with 80% ethanol, once with anhydrous ethanol and dried in vacuo. The adaptors were dissolved in 1 ml of 0.1×TE. Ligation rections were conducted using fifty nanograms of Xba1-Hind3 fragments containing the β-globin cDNA and 12.5ng of the ethanol precipitated (non-phosphorylated) YH1a,b oligonucleotide in a total of 10 μl of T4 DNA ligase buffer containing 10 units of T4 DNA ligase. The ligation mixture was incubated at 4° C. for 16 hr. and a portion used to transform *E. coli* DH5α. Transformants were selected on LB-ampicillin plates containing 4 μg/ml XGAL. Plasmid DNA was prepared from 12 white colonies. The DNA was digested with Nco1 or ApaL1 and analyzed by agarose gel electrophoresis. Four of these colonies contained plasmids with the expected restriction fragments and one was designated pUC19β-globin (FIG. 21(a)). The plasmid pSUC2-6Σ (G. Stetler et al. Biotechnology 7:55–60 (1989)) (FIG. 21(a)) was digested with Hind3 and Xba1 and the large fragment was purified by agarose gel electrophoresis. The Xba1 to Hind3 fragment containing β-globin cDNA was also purified (agarose gel electrophoresis) from pUC19β-globin. Ten nanograms of gel-purified Xba1, Hind3 digested pSUC2-6Σ was mixed with 16 nanograms of the Xba1, Hind3 fragment from pUC19β-globin in 0.01 ml of ligase buffer containing 10 units of T4 DNA ligase. The ligation mixture was incubated at 25° C. for 1 hr. and a portion used to transform *E. coli* DH5α. Transformants were selected on LB-ampicillin medium and three were used to prepare plasmid DNA. These were analyzed by digestion with EcoR1 and analyzed by agarose gel electrophoresis. Two of these contained plasmids with the expected restriction fragments and one was designated pGS1188 (FIG. 21(b)). This plasmid contains β-globin under the transcriptional control of the sigma promoter and contains the 3' transcriptional termination signals and polyadenylation signals of the MFα1 gene.

Replacement of the Promoter with pGGAP

The plasmid pGS1188 was digested with SphI and NcoI and the vector plus β-globin cDNA was separated from the sigma promoter by agarose gel electrophoresis and purified as described previously. Plasmid pGS4788 (10 ug) was also digested with SphI and NcoI and the ~500 bp fragment (containing pGGAP) produced by this digest was purified by agarose gel electrophoresis. Fifty nanograms of the gel-purified β-globin containing vector was incubated with 50 ng of NcoI-SphI fragment containing the pGGAP promotor in 0.01 ml of 1× ligase buffer with 10 units of T4 DNA ligase. The mixture was incubated for 1 hour at 25° C. and a portion of the ligation mixture used to transform *E. coli* DH5α. Ampicillin resistant clones were selected. Plasmid DNA isolated from 12 of these clones was analyzed by digestion with SphI and NcoI to identify plasmids containing the ~500 bp GGAP promoter. The presence of the β-globin cDNA was confirmed by digestion with XbaI and SalI, followed by agarose gel electrophoresis analysis. A plasmid containing the expected fragments was identified and designated pGS3588 (FIG. 21(b)). To aid the subcloning of this fragment into a yeast vector, the SmaI site of pGS3588 was converted to a XhoI site as follows: 1 μg of pGS3588 was digested with SmaI, the digest was extracted once with phenol-chloroform and ethanol precipitated. The precipitated DNA was dissolved in T4 DNA ligase buffer, with 100 ng of phosphorylated XhoI linker and 10 units of T4 DNA ligase (final volume of 0.01 ml). The ligation was incubated at room temperature for 2 hr and a portion of the ligation mixture was used to transform *E. coli* DH5α (excess linkers were not removed prior to transformation). Ampicillin resistant clones were isolated and plasmid DNA prepared. Plasmids containing the additional XhoI site were identified by digestion with XhoI and agarose gel electrophoresis analysis. A plasmid containing the pGGAP-β-globin expression cassette was identified and has been designated pGS3888 (FIG. 21(b)).

Construction of an α-globin Expression Cassette

We obtained a partial length cDNA (pα-MRC) clone from K. Nagai (MRC, Cambridge). To adapt the cDNA encoding α-globin for expression from the pGGAP promotor, two oligonucleotide primers were synthesized (synthesis and purification of oligonucleotides was as described above).

α-1: 5'-GAATTCCATGGTGCTGTCTCCTGCCGA-
    CAAGACC-3'.

α-2: 5'-CTGCAGTCGACTTAACGGTATTTGG-
    AGGTCAGCACGGTGCT-3'.

Figure 22A:
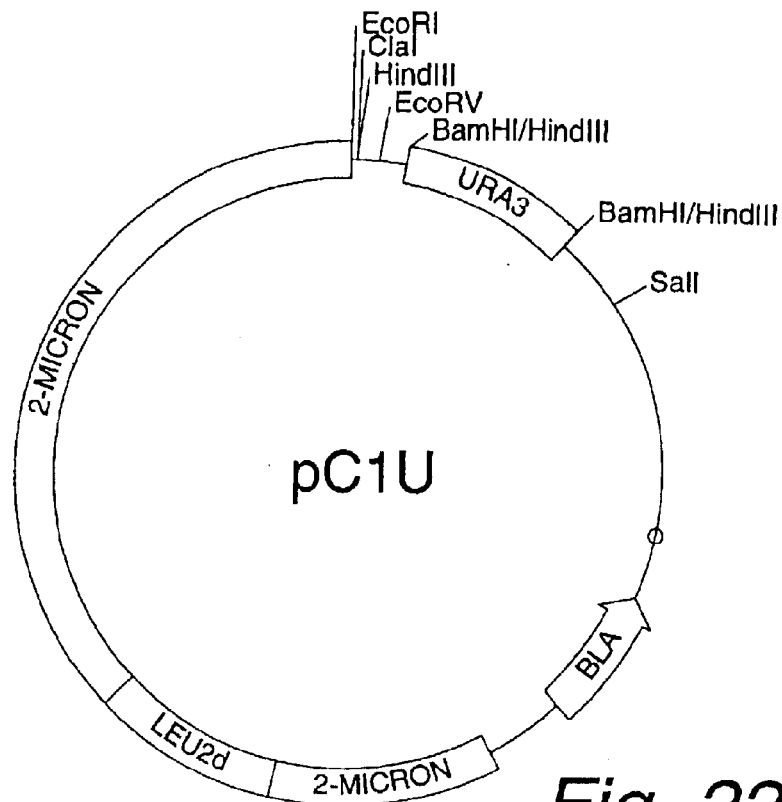
Figure 1:
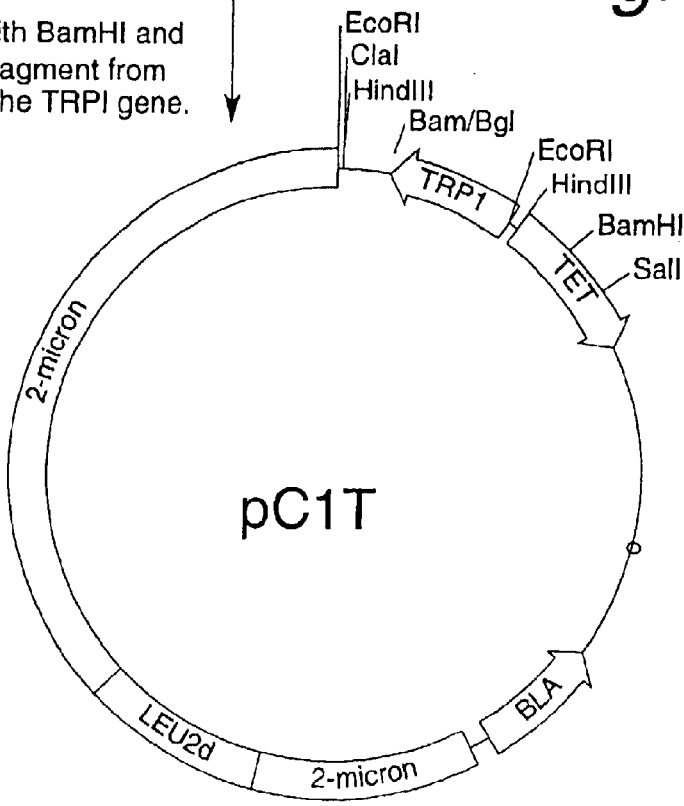
Figures 2, 22A:
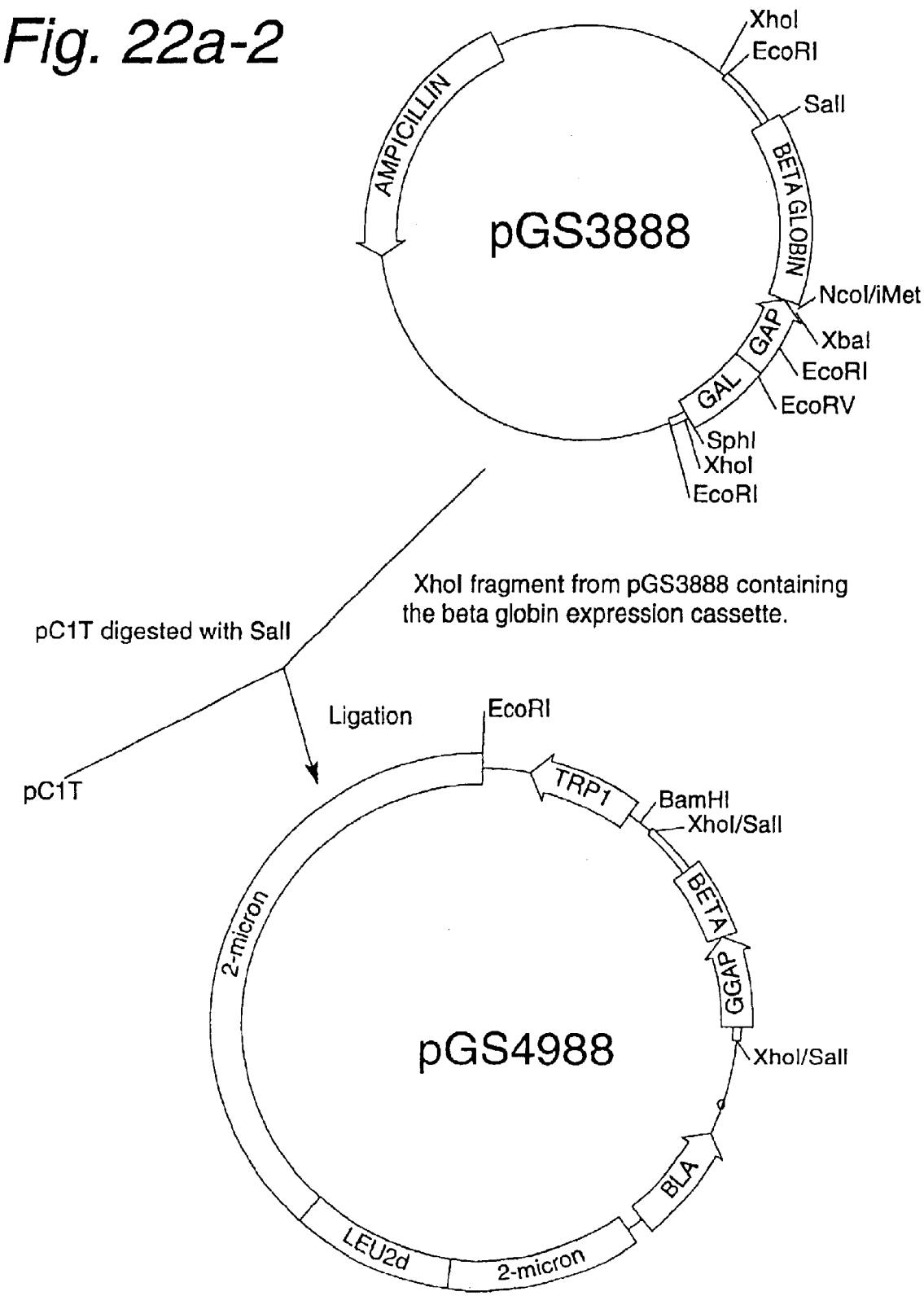
Figure 22B:
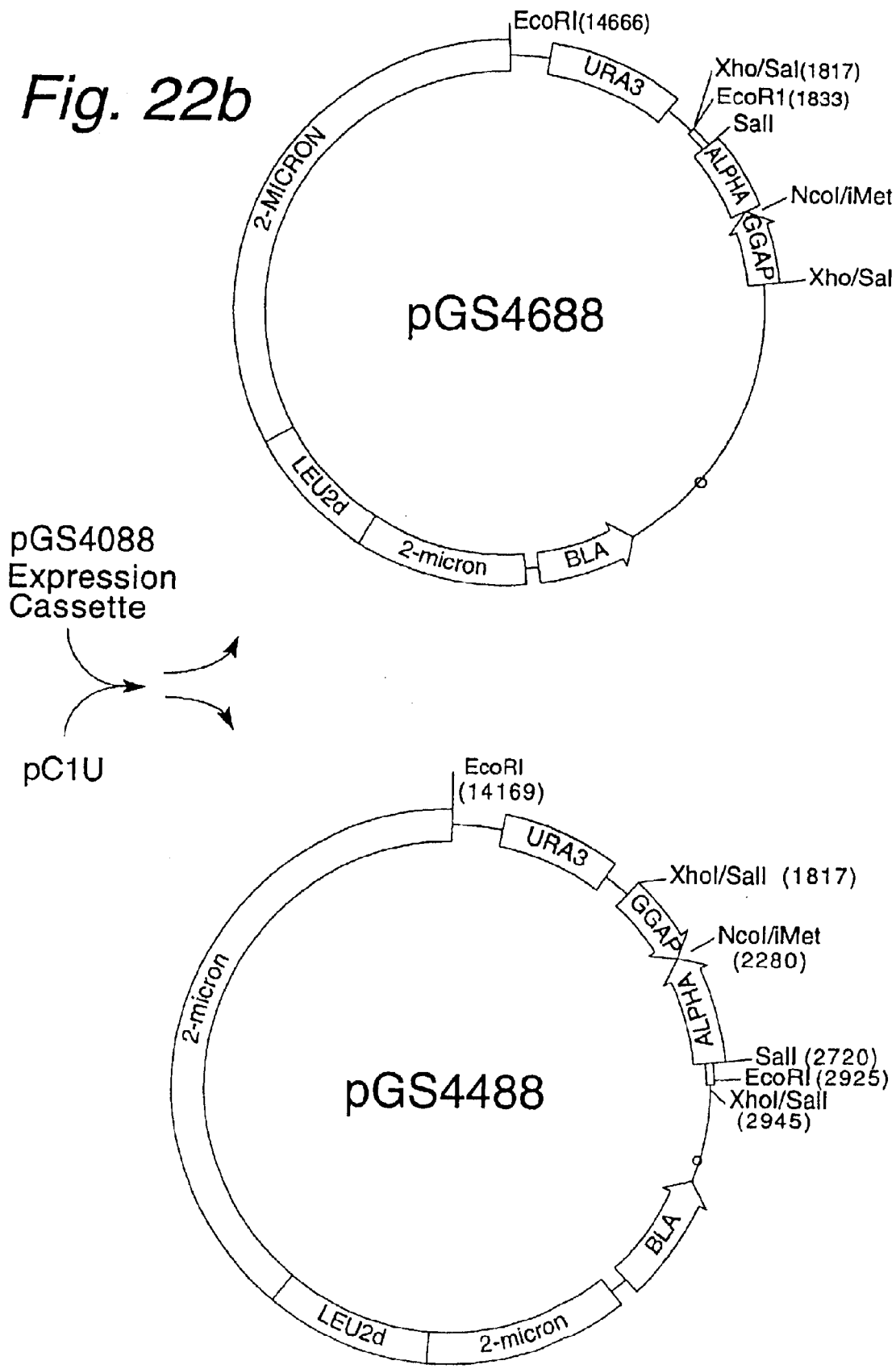

These two oligonucleotides were used as primers for a polymerase chain reaction (PCR) (R. K. Sakai et al., 1985. Science 230:1350–1354) using a Perkin Elmer-Cetus PCR kit and pα-MRC as template α-globin cDNA (8.3 ug/ml) in 0.018 ml $H_2O$ was denatured by the addition of 0.005 ml 10M NaOH. The mixture was incubated at 25° C. for 5 min. Denatured DNA was precipitated by the addition of 0.003 ml 3M sodium acetate (pH 5.2) and 0.075 ml anhydrous ethanol. The precipitated DNA was washed twice with 80% ethanol, once with 100% ethanol and dried. The dried pellet was dissolved in: 0.005 ml 20 μM α-1, 0.005 ml 20 μM α-2, 0.010 ml 10×Taq polymerase buffer (Perkin Elmer-Cetus), 0.0005 ml TaqI polymerase (Perkin Elmer-Cetus), 0.663 ml $H_2O$, 0.016 ml of all four deoxyribonucleotide-triphosphates (1.25 mM each). TaqI polymerase was added after heating the solution to 94° C. for 1 min. After addition of the enzyme the aqueous solution was overlayed with 0.100 ml paraffin oil. The reaction-mixture was cycled, by hand, 25 times at the following temperatures: 37° C. for 2 min, 68.5° C. for 3 min and 94° C. for 1 min. After the twenty-fifth cycle, the reaction mix was incubated at 37° C. for 2 min and 68.5° C. for 10 min. A portion (0.005 ml) of the reaction mixture was analyzed by agarose gel electrophoresis and revealed a band of the expected size (~430 bp). The PCR-amplified DNA fragment should contain a 5' extension, that includes an ATG codon embedded in an optimal sequence context for initiation of translation (M. Kozack 1986, Cell 44:283–292). The 3' end should contain an extension that includes a translational terminator and a SalI restriction endonuclease site. The PCR-amplification reaction was phenol-chloroform extracted and ethanol precipitated. The dry pellet was dissolved in 0.05 ml 1 mM Tris-HCl (pH 7.8). A portion of this material (0.025 ml, 1.25 ug) was digested with NcoI and SalI and purified by acrylamide gel (5%) electrophoresis. A gel slice containing the fragment was eluted by crushing the gel slice in 0.3 ml 2.5 ammonium acetate (pH 7.4) and incubating at 37° C. for 16 hr. Acrylamide fragments were removed by centrifugation and the DNA precipitated by the addition of 0.75 ml of ethanol. The pellet was collected and dissolved in 0.020 ml 1 mM Tris HCl (pH 7.8) 0.1 mM EDTA. This fragment was cloned into NcoI, SI digested and agarose gel purified pGS3888. Fifty nanograms of NcoI, SalI digested pGS3888 was incubated (2 hr, 25° C.) with 50 ng of gel purified, PCR-amplified NcoI-SalI fragment containing the α-globin cDNA in 0.01 ml ligase buffer with 10 units of T4 DNA ligase. A portion of this reaction mixture was used to transform $E.\ coli$ DH5α- and ampicillin resistant clones were selected on LB-ampicillin medium. Plasmid DNA was prepared from 12 independent isolates and digested with Nco1 and SalI. The restriction digests were analyzed by acrylamide gel electrophoresis (5%), all twelve contained a fragment of the expected size. One of these was designated pGS4088 (FIG. 22). The α-globin insert in pGS4088 was completely sequenced to assure that no mutations had been introduced by PCR-amplification.

Construction of a Yeast Expression Plasmid that Co-expresses α-and β-globin Genes rom a Single Plasmid The α-globin and β-globin expression cassettes from the plasmids pGS3888 and pGS4088 were cloned into a single plasmid in a way that allows them to be excised on a single NotI fragment. This NotI fragment was then cloned into the high copy yeast plasmid pC1N to generate a plasmid carrying and expressing both α-and β-globin chains under the control of separate (though identical) promoters. The details are presented below.

Introduction of NOTI Site into pSK(+)

Figures 1, 23A:
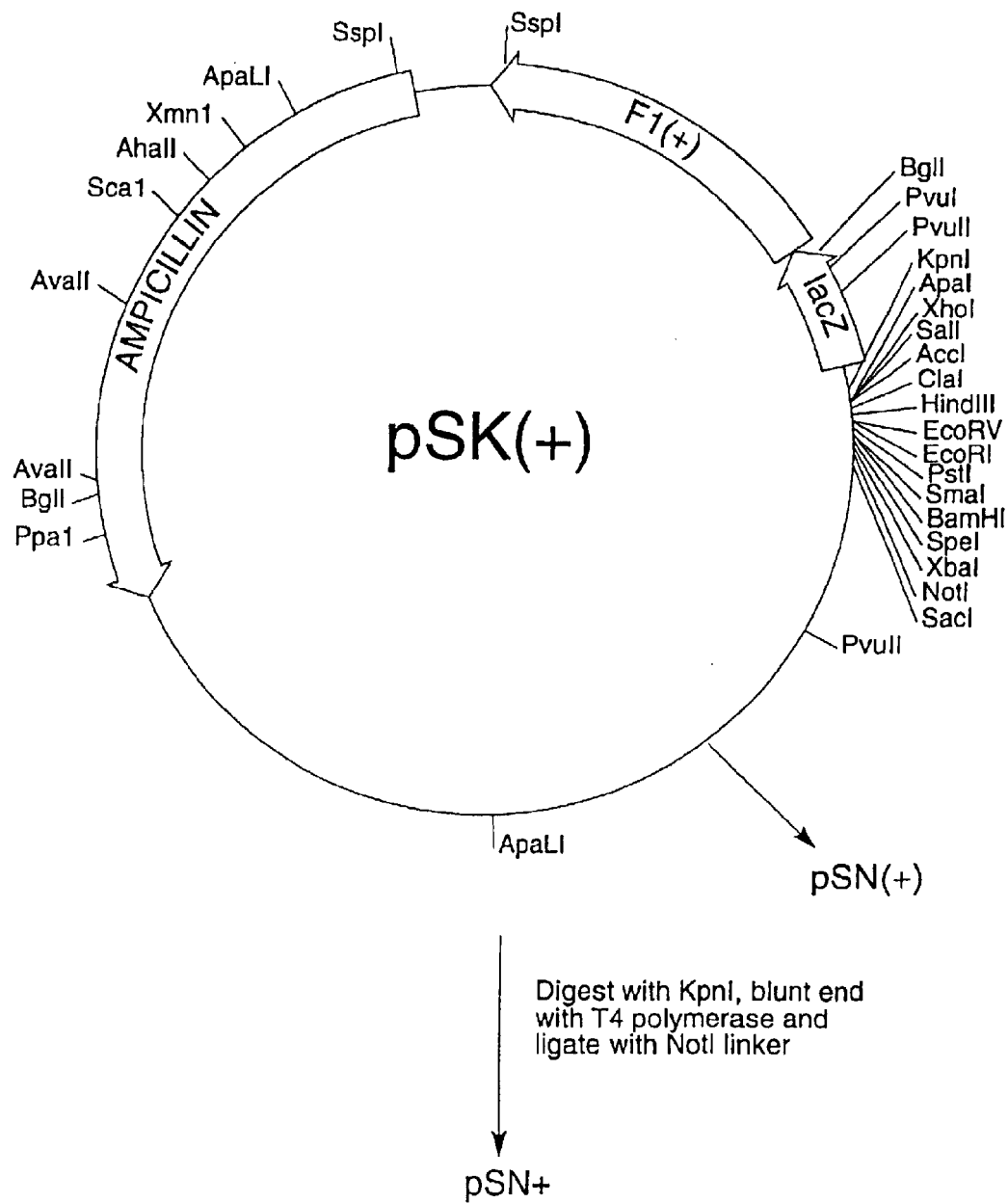
Figures 2, 23A:
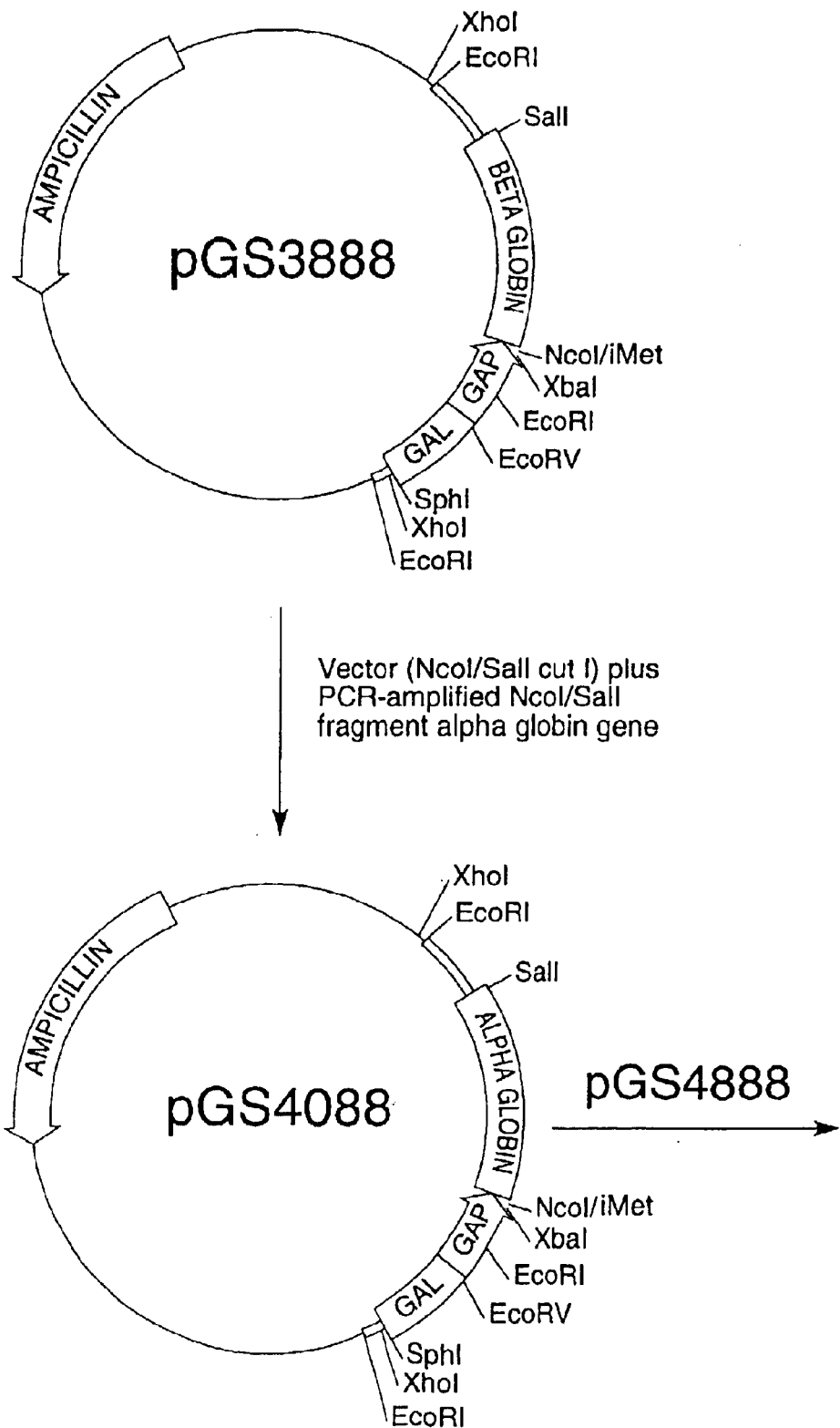
Figure 23A:
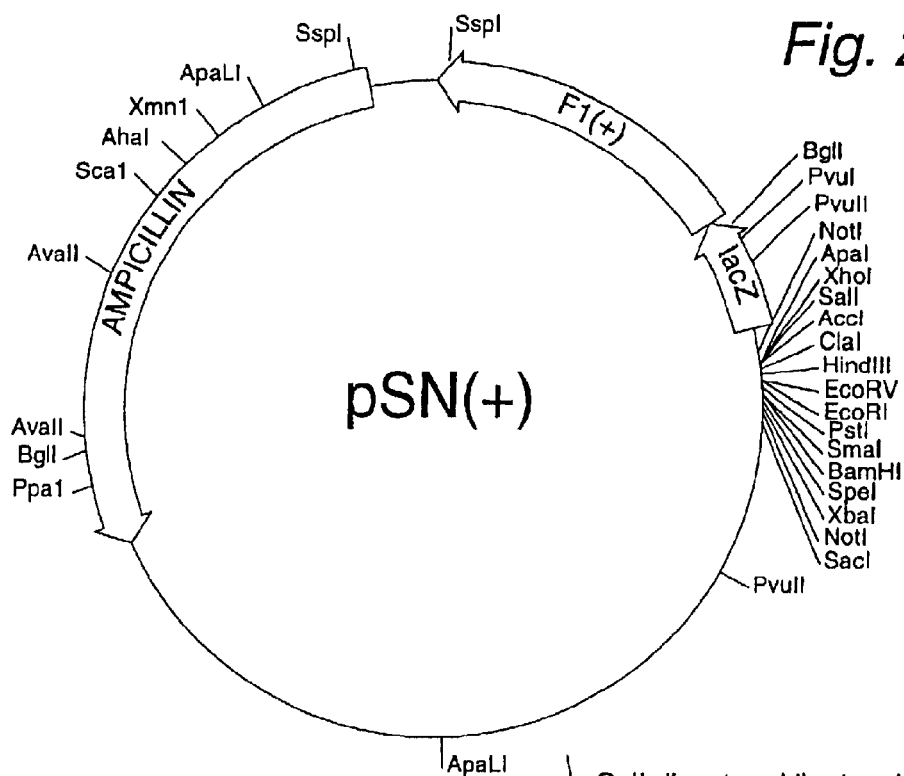
Figure 3:
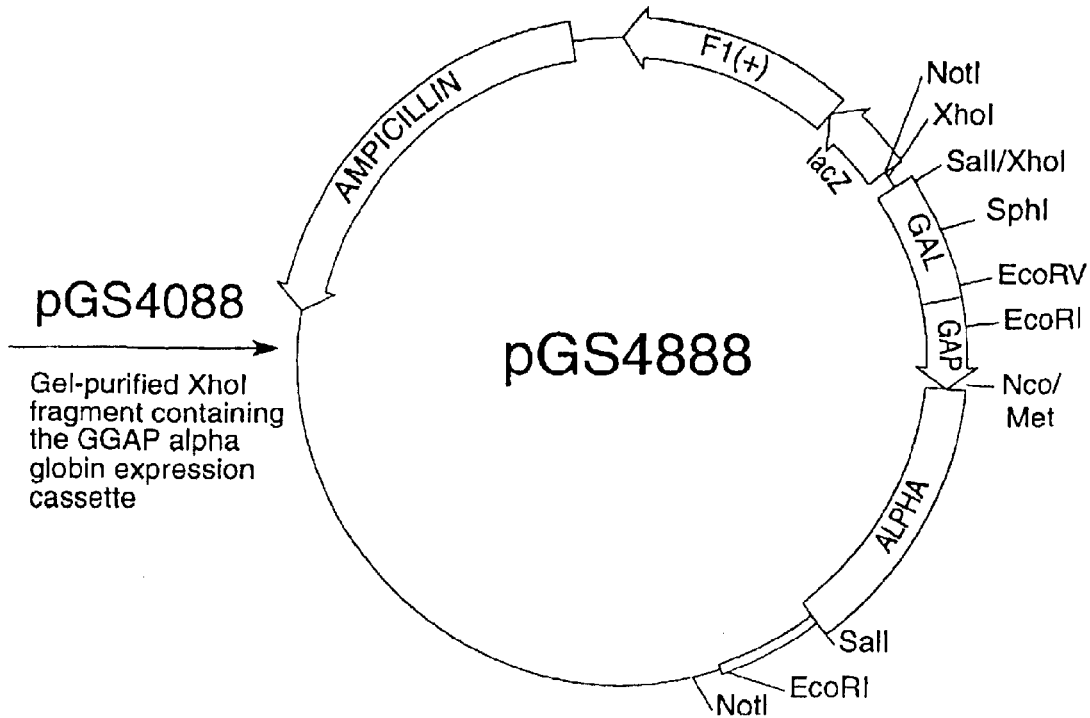

The plasmid pSK(+) (Stratagene, Inc.) (FIG. 23(a)) was modified by digesting 100 ng of purified plasmid DNA with KpnI. After digestion was complete, the DNA was ethanol precipitated and the dry pellet dissolved in 0.05 ml T4 DNA polymerase buffer containing 10 units of T4 DNA polymerase. The reaction mixture was incubated at 37° C. for 20 min, $Na_3EDTA$ (10 mM) was added and the sample heated to 70° C. for 10 min. The digested DNA was precipitated with ethanol and the dry pellet dissolved in 0.01 ml of 10 mM Tris-HCl (pH 7.8) 1 mM EDTA. A portion of this material (20 ug) was dissolved in 0.005 ml of ligase buffer containing 10 units of T4 DNA ligase and 50 ng of phosphorylated NotI linkers. The ligation mixture was incubated at 25° C. for 2 hr and a portion used to transform $E.\ coli$ DH5α. Ampicillin resistant colonies were selected on LB-ampicillin medium. Plasmid DNA was isolated, digested with Not1 and analyzed by acrylamide gel (5%) electrophoresis. A plasmid containing the additional NotI site is expected to generate a new, ~90 bp fragment. Such a plasmid was identified and designated pSN(+) (FIG. 23(a)).

Cloning the pGGAP-α-globin Expression Cassette into pSN (+)

pSN(+) was digested with SalI, phenol-chloroform extracted and ethanol precipitated. The precipitated DNA was dissolved (50 ug/ml) in 1 mM Tris-HCl (pH 7.8), 0.1 mM EDTA. pGS4088 was digested with XhoI and the ~1100 bp fragment containing the α-globin expression cassette was isolated from an agarose gel. The purified fragment was dissolved (20 ug/ml) in 0.1×TE. Twenty-five nanograms of SalI digested pSN(+) was mixed with 50 ng of the gel-purified α-globin fragment in 0.01 ml ligase buffer containing 10 units of T4 DNA ligase. The ligation mixture was incubated for 1.5 hr at 25° C. and a portion used to transform $E.\ coli$ DH5α. Ampicillin resistant clones were isolated. One hundred transformants were transferred, in a grid pattern, to fresh plates. Replicas of the grid were made on a nitrocellulose filter and prepared for colony hybridization (R. W. Davis et al. Adv Bacterial Genetics, Cold Springs Harbor, N.Y., 1980.). The hybridization probe was oligonucleotide 4 (Table 6). This oligonucleotide (20 pM) was labelled with $^{32}$P-ATP in a 0.02 ml reaction mixture containing 0.050M Tris-HCl (pH 7.6), 0.01M $MgCl_2$, 0.005M DTT, 0.0001M spermidine, 0.0001M EDTA, 50 pM of $^{32}$P-ATP and 10 units of T4 polynucleotide kinase. The reaction mixture was incubated for 2 hr at 37° C., unincorporated ATP was removed by spin-column chromatography (BIORAD) used according to the manufactures instructions. The filters were incubated (37° C.) in hybridization solution (6×SSC, 50% formamide, 2% SDS, 20 pMoles of $^{32}$P labelled probe) for 16 hr. The filters were washed 4 times (15 min each) with 1×SSC, 0.1% SDS at 55° C.; twice (5 min each) with 0.2×SSC, 0.1% SDS at 50° C. and twice (5 min each) with 0.2×SSC. Autoradiographs were made of the filters. Colonies that produced a hybridization signal were used to prepare plasmid DNA. This DNA was digested with EcoR1 and the fragments produced by this digest were analyzed by agarose gel electrophoresis. A plasmid containing a fragment of the correct size was identified and designated pGS4888 (FIG. 23(a)).

Cloning the pGGAP-β-globin Expression Cassette into pGS4888

Figure 23B:
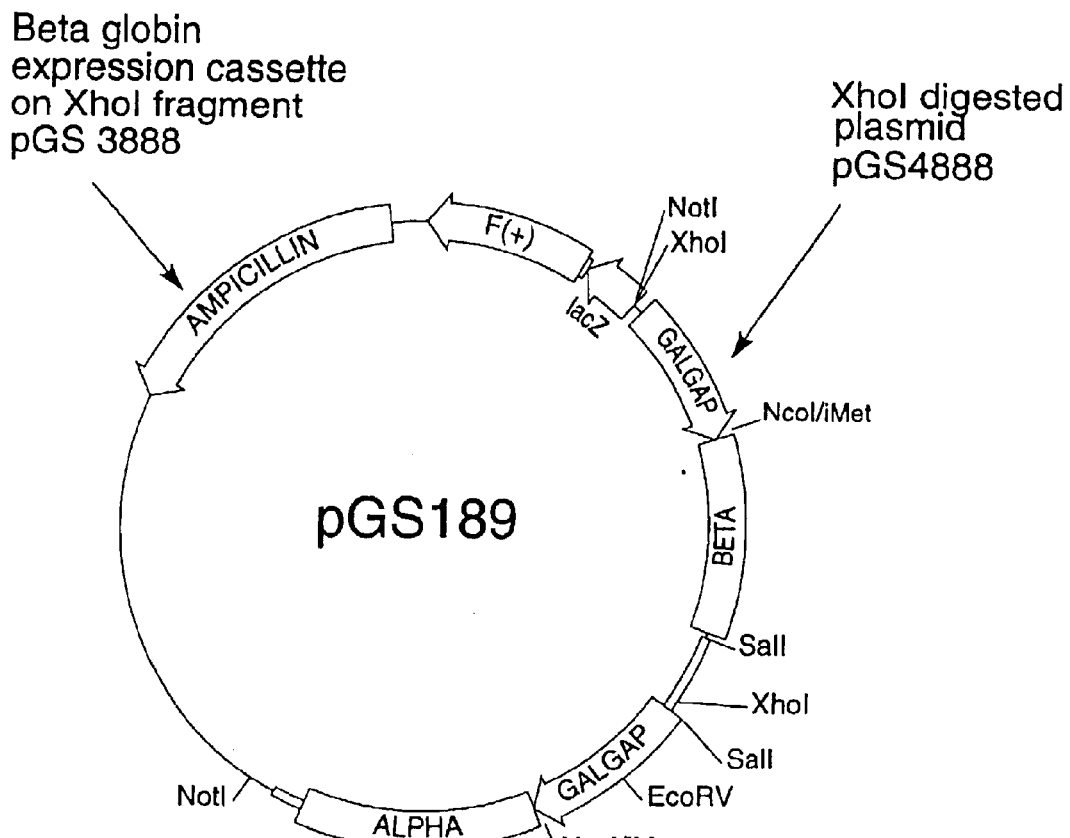
Figure 1:
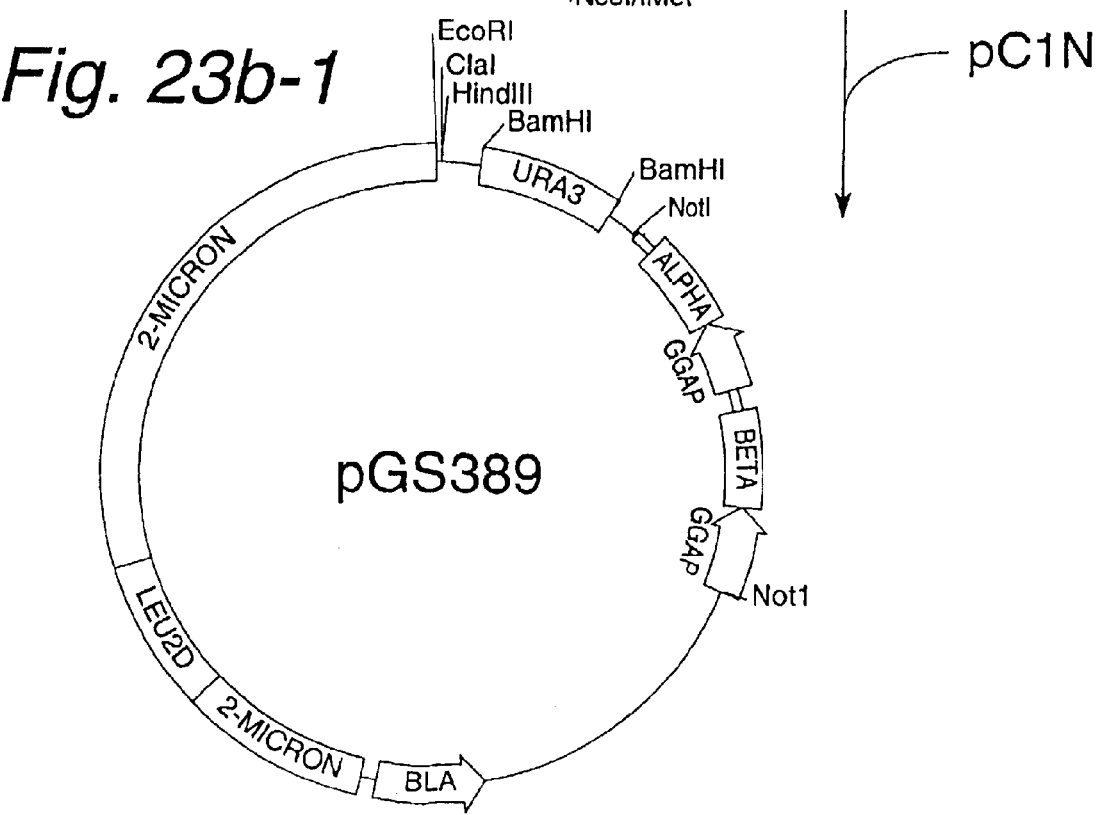
Figure 23B:
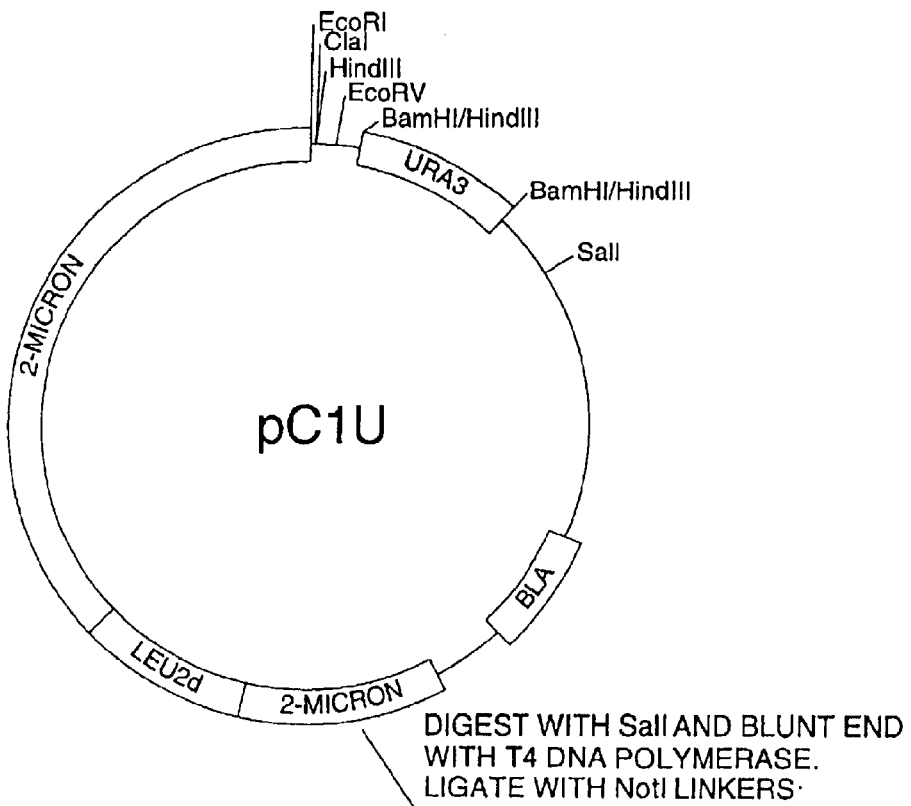
Figure 2:
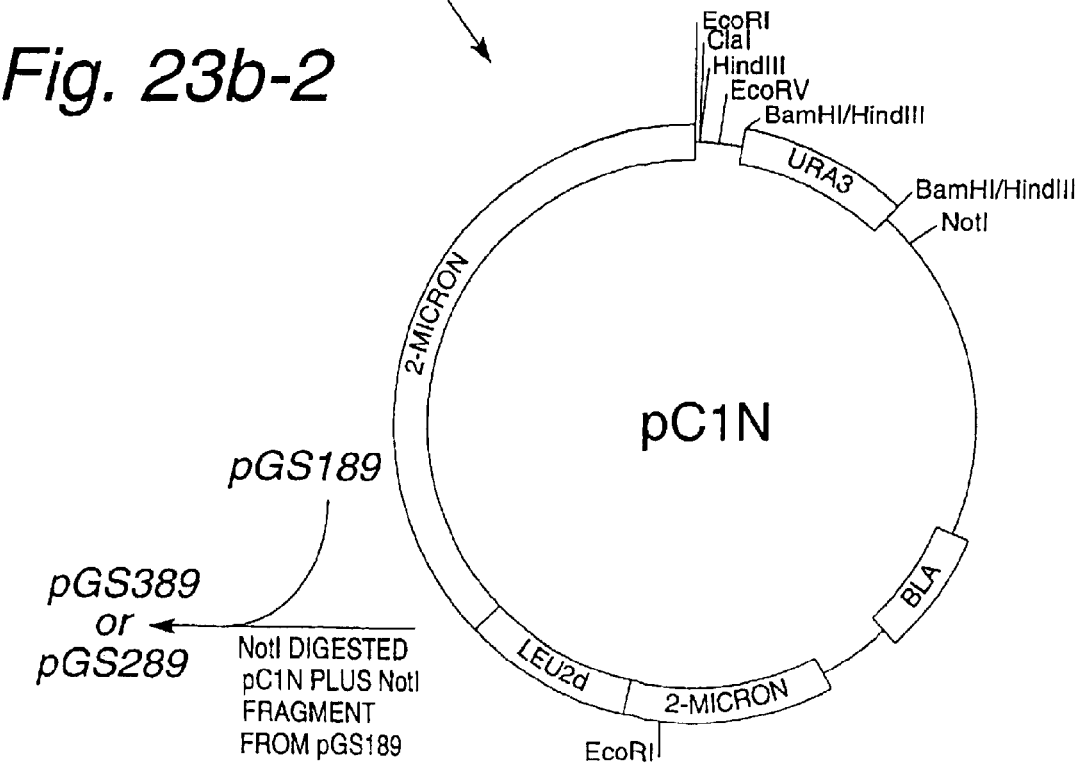
Figures 3, 23B:
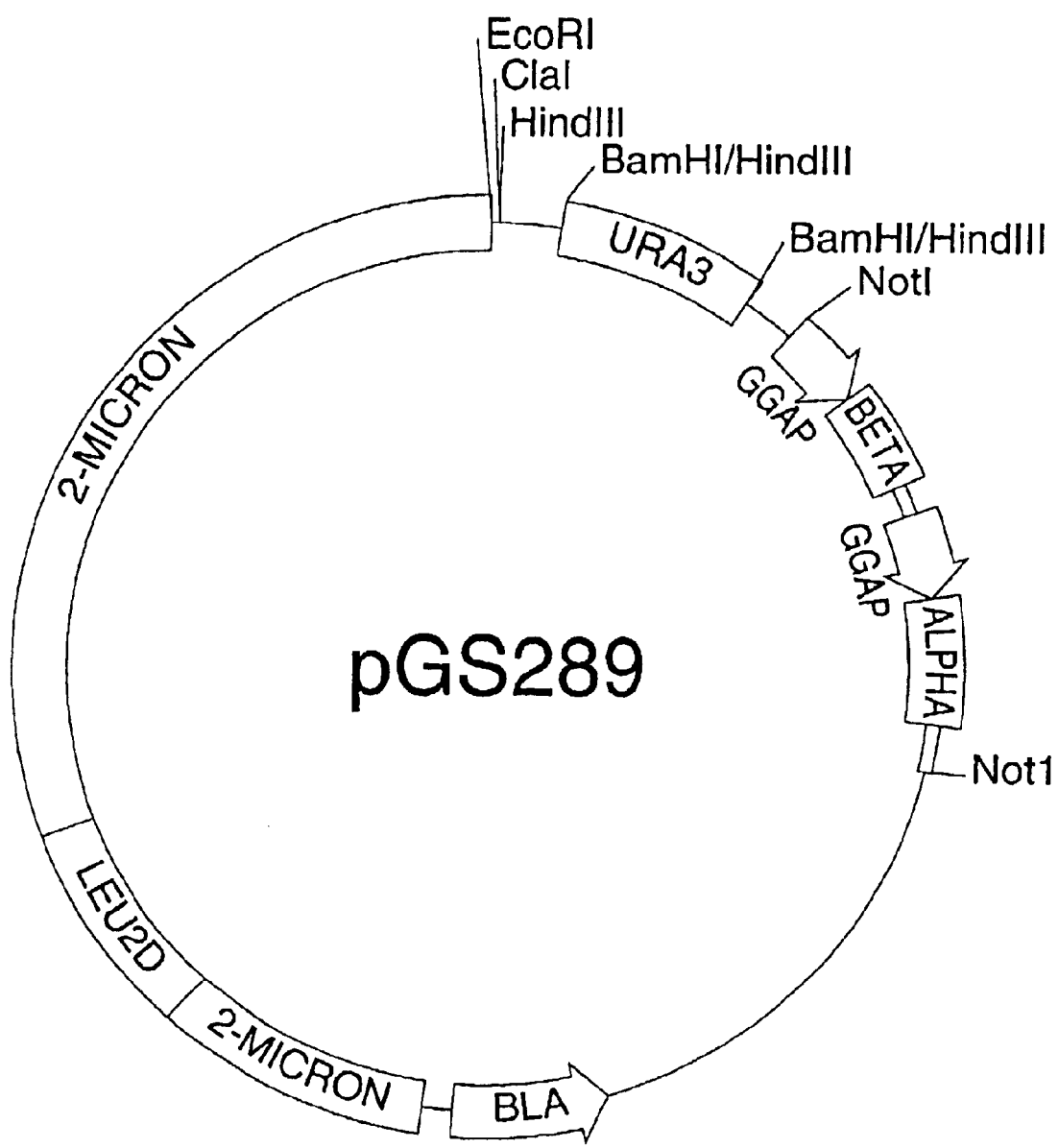

The construction of pGS4888 required cloning an XhoI fragment (pGGAP-α-globin) into a SalI site. The combination of a XhoI site with a SalI site destroys the recognition sites for both XhoI and SalI restriction endonucleases, leaving pGS4888 with a single unique XhoI site. An XhoI fragment from pGS3888 was purified by agarose gel electrophoresis and cloned into XhoI digested pGS4888 essentially as described for the construction of pGS4888. Colony filter hybridizations were performed using the NcoI-SalI fragment (containing β-globin cDNA) from pGS3888 as a hybridization probe. This fragment was purified by agarose gel electrophoresis and radioactively labelled with $α^{32}$P-dCTP using an Amerham random oligonucleotide labelling kit. Filters were hybridized, washed and autoradiographs made as described for the construction of pGS4888. Plasmid DNA was prepared from colonies producing a hybridization signal and digested with either NcoI or NcoI and SphI. These digests allow identification of plasmids that contain both the α- and β-globin expression cassettes and reveals the relative orientation of the α- and β-globin transcriptional units. A plasmid containing both transcriptional units was identified and given the designation pGS189 (FIG. 23(b)).

Construction of Plasmid pC1N

The plasmid pC1U was modified to introduce a NotI site. pC1U DNA (100 ug) was digested with SalI, phenol-chloroform extracted and ethanol precipitated. The SalI ends were modified with T4 DNA polymerase to produce "blunt" ends and phosphorylated NotI linkers were added. The procedures used for these modifications are essentially the same as those used to produce pSN(+) (described above). The plasmid resulting from these manipulations is called pCIN (FIG. 23(b)). This pC1N was digested with Not1, phenol-chloroform extracted and ethanol precipitated. A ~2.4 kb NotI fragment (carrying α- and β-globin expression cassettes) was purified from NotI digested pGS189 DNA by agarose gel electrophoresis. Fifty nanograms of NotI digested pC1N was mixed with 50 ng of the gel purified, 2.4 kb fragment isolated from pGS189 in 0.01 ml of ligase buffer containing 10 units of T4 DNA ligase. The reaction mixture was incubated at 25° C. for 2 hr and a portion used to transform $E.$ $coli$ DH5α. Ampicillin resistant clones were selected on LB-ampicillin plates and plasmid DNA prepared. The purified DNA was digested with EcoR1 and analyzed by agarose gel electrophoresis to identify plasmids carrying the α- and β-globin genes and to determine the orientation of the insert with respect to the vector. Two plasmids were identified, representing the two possible orientations and have been designated pGS289 (FIG. 23(b)) and pGS389 (FIG. 23(b)).

Expression of Recombinant Human Hemoglobin in $Saccharomyces$ $Cerevisiae$ $S.$ $cerevisiae$ strains GSY112 (MATαpep4:: H1S3prb1 1.6R his3 200 ura3-52 leu2:: hisG can1 cir°) and RSY334 (MATα- reg1-501 pep4-3 prb1-1122 ura3-52 leu2-3, leu2-112) were transformed with plasmids pGS289 or pGS389 by the method of Ito et al. (J. Bacteriology 153:163–168 (1983)). Transformants were selected on yeast SD-ura. Single colony isolates were picked and streaked to SD medium lacking uracil and leucine. Colonies from this selective medium (SD-ura,-leu) were used to inoculate 2 ml of SD-ura,-leu. The cultures were incubated at 30° C. for 24 hr and used to inoculate 20 ml cultures of YP+3% ethanol. These were incubated for an additional 24 hr and galactose was added to a concentration of 2%. Samples were removed at 4, 8, 24, 28, 32 and 48 hours post induction. Cells were collected by centrifugation and washed with 1 ml 10 mM Tris HCl (pH 7.8), 1 mM EDTA and resuspended in SDS-PAGE sample buffer (2×108 cells/ml). Samples were boiled for 10 min and the insoluble material removed by centrifugation. Samples 0.005 ml were analyzed by SDS-PAGE (12.5% gel) followed by transfer to nitrocellulose. α- and β-globin chains were stained using commercially available rabbit anti-human hemoglobin and an immunoblotting kit purchased from Promega. The protocols used were supplied by Promega. The immunoblot indicated that both chains are synthesized and that pGS289 produces slightly less material than pGS389. An apparent lack of stoichiometry between the α-chain (lower band) and β-chain is due to a difference in immunoreactivity of the antibody to the two chains. This was demonstrated by comparing Commassie brilliant blue stained gels of purified human and recombinant hemoglobin with immunoblotted samples.

EXAMPLE 20

Characterization of Human Recombinant Hemoglobin Synthesized in Yeast

Figure 24:
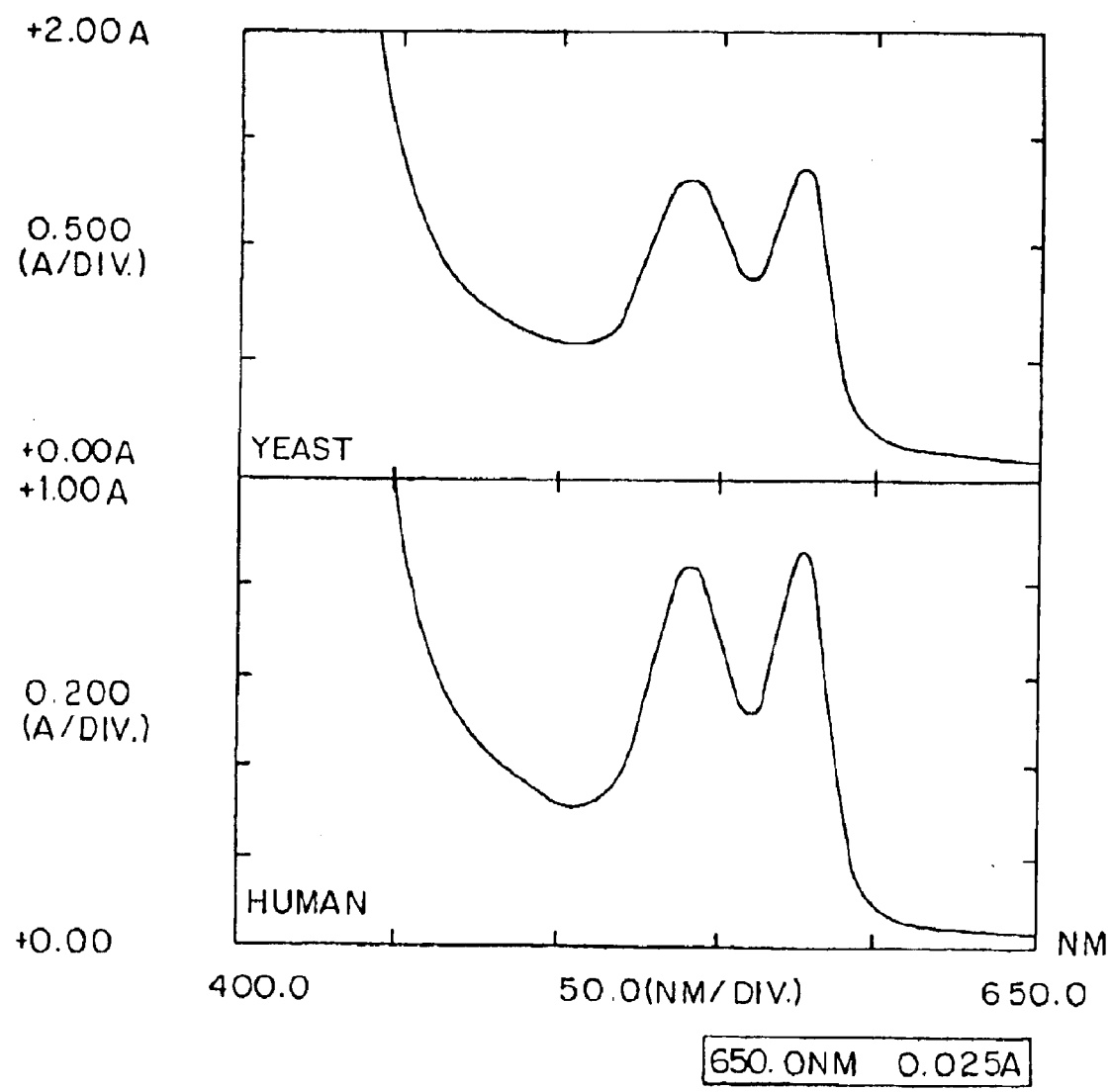
FIG. 24: Absorption spectra for yeast-produced recombinant and native human hemoglobin.
Figures 1, 25A:
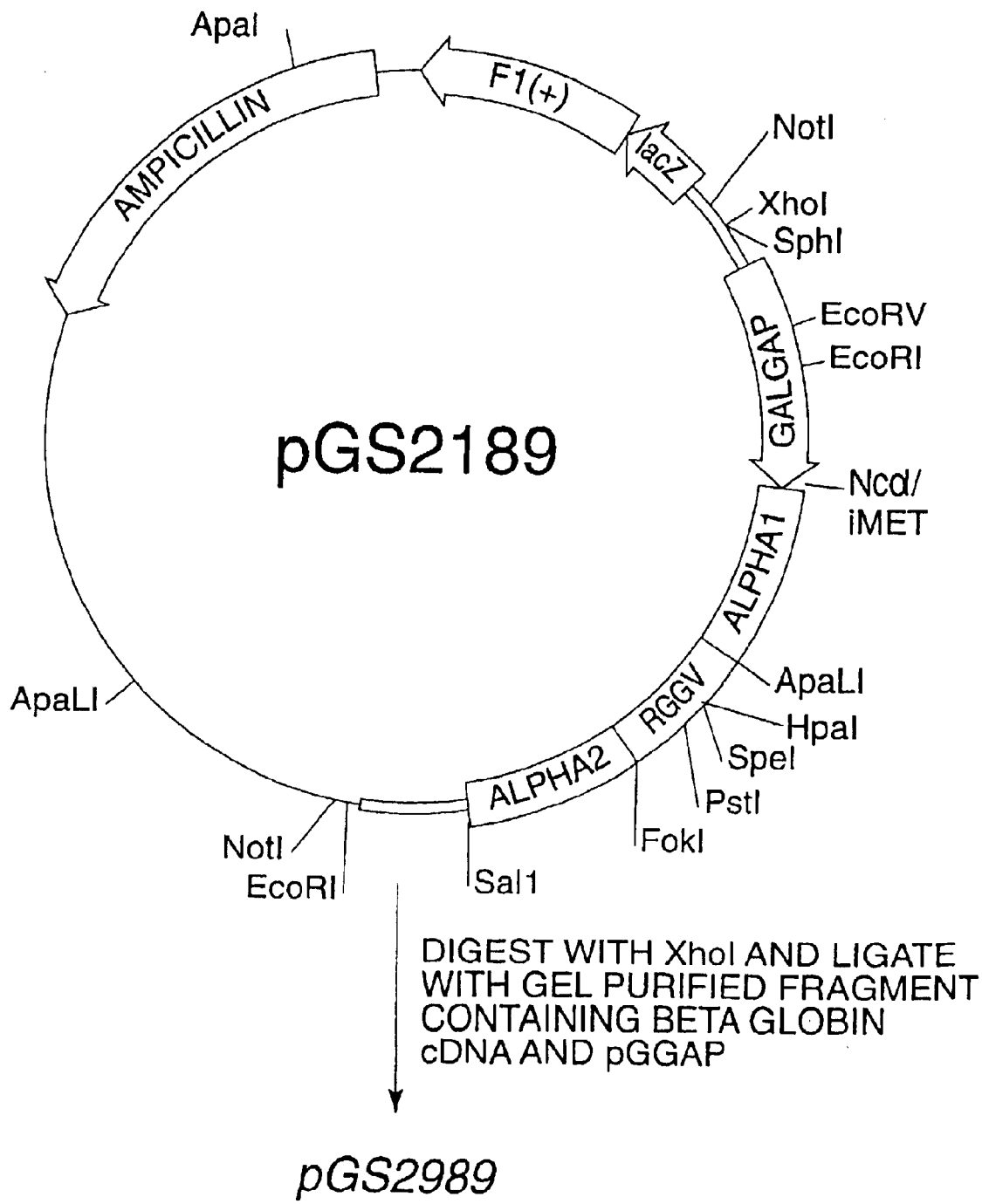
Figures 2, 25A:
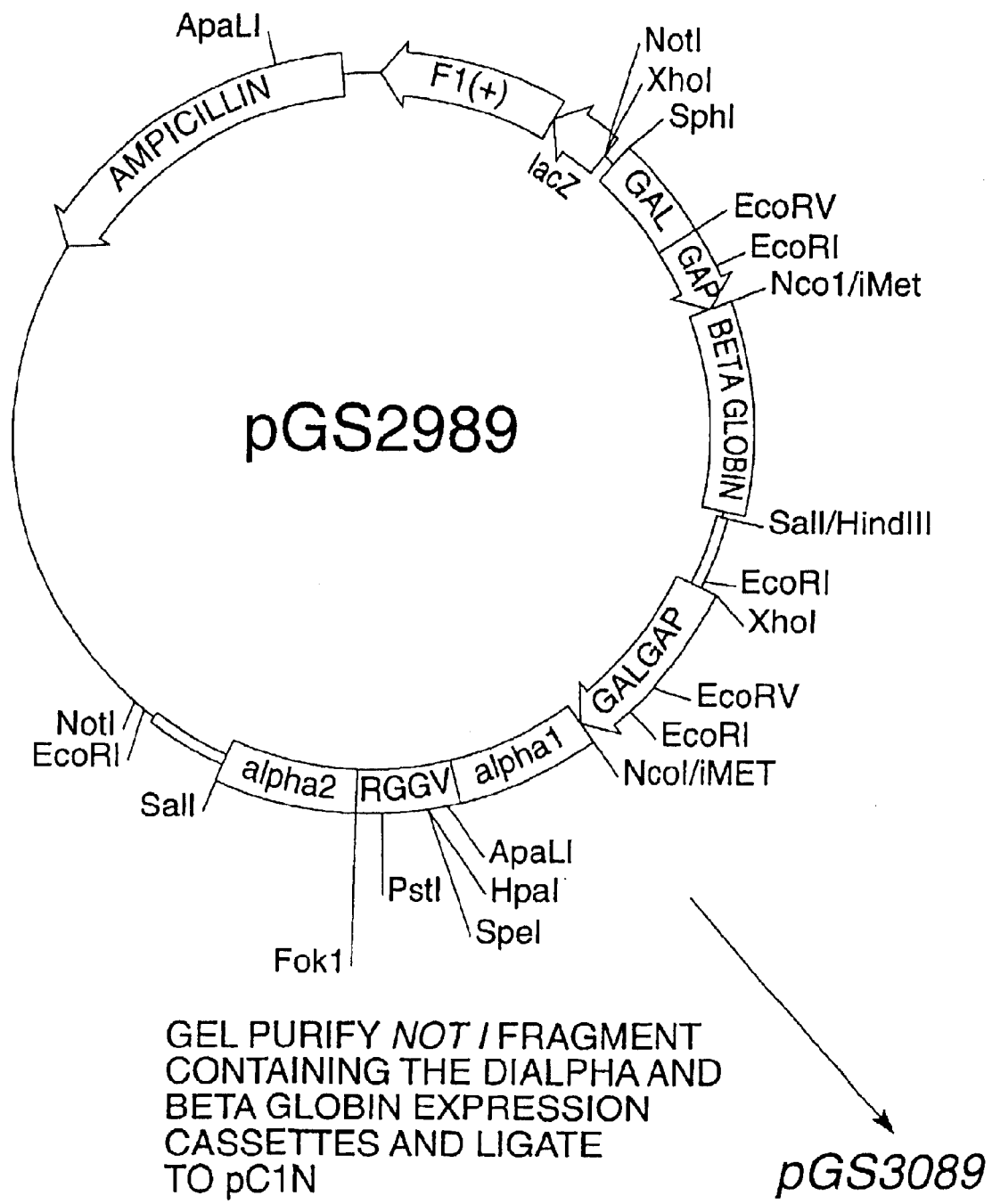
Figures 3, 25A:
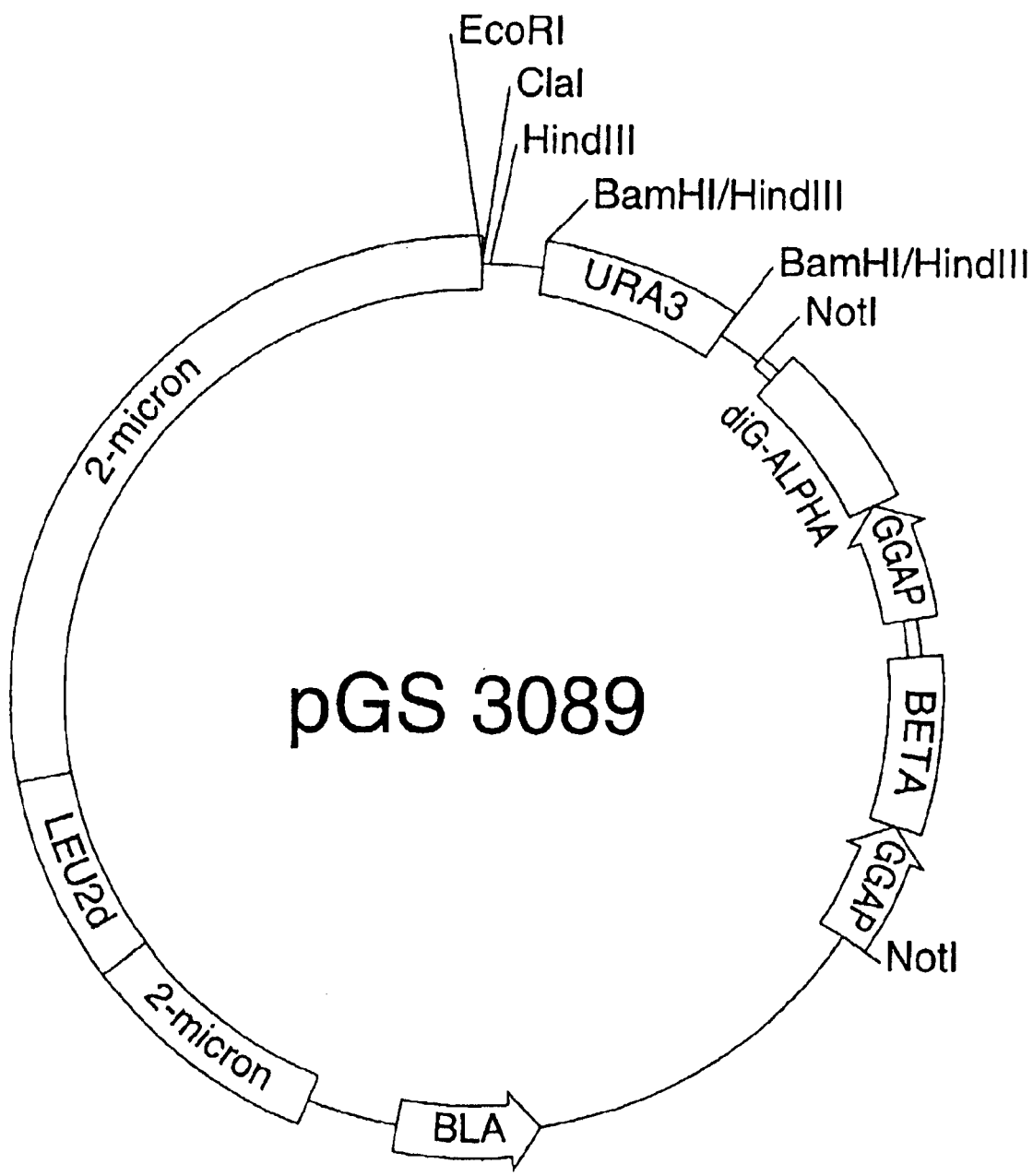
Figure 25B:
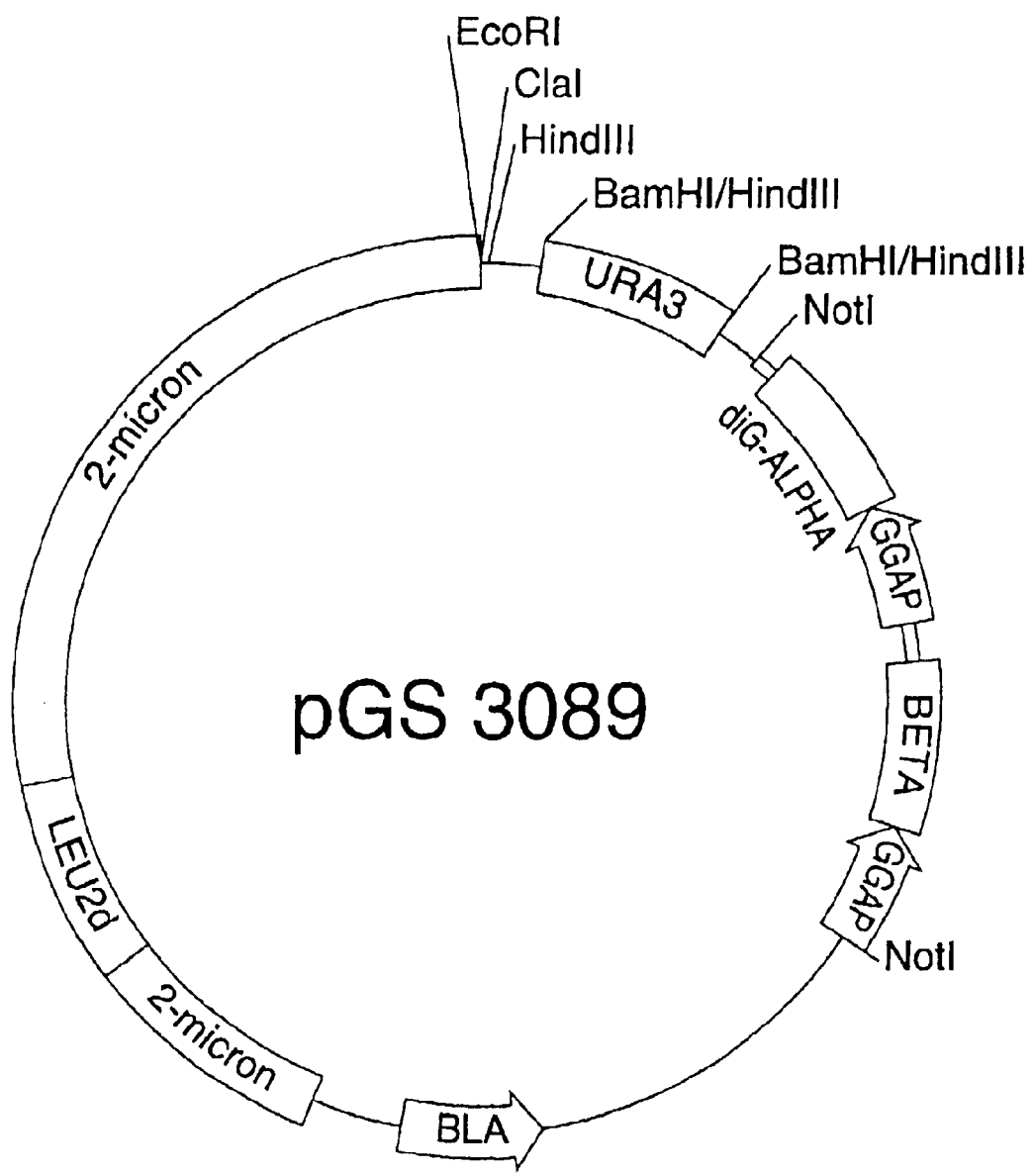

RSY334[pGS389] was grown in 100 ml SD-leucine to an $OD_{600}$ of 2.4. This was used to inoculate 1L of YPE. This culture was shaken at 30° C., for 24 hr at which time 50 ml of 40% galactose was added. The incubation was continued and the cells harvested 24 hr later ($OD_{600}$ of 9). The cell pellet was resuspended in 100 ml of 0.01M Tris-HCl (pH 7.18), 0.001M EDTA and carbon monoxide bubbled through the cell suspension for 3 min. The cells were collected by centrifugation and after the CO treatment were distinctly red. The cell pellet (19 gm) was resuspended in 19 ml of lysis buffer (0.01M $NaPO_4$ pH 6.0, 0.020M DTT, 1% Triton X 100, 0.001M PMSF, 0.005M benzamidine and 0.06 mM leupeptin) and bubbled with carbon monoxide for 2 min. The cell suspension was sonicated with Branson 250 sonicator equipped with a 0.5 inch disrupter horn. The sonication time was 2 min (0.5 sec pulses) at full power. This was repeated 4 times with 2 min cool-down periods between sonication intervals. The cell debris was removed by centrifugation (27,000×g for 15 min) and the supernatant saved (0° C.). The pellet was resuspended in 5 ml of lysis buffer. The resuspended pellet was sonicated with the microtip as described above (70% of maximum output). The cell debris was removed by centrifugation as described above and this supernatant combined with the first. The combined solutions were clarified by centrifugation (38,000×g, 20 min), producing a clear, red solution. This was loaded (after adjusting the pH to 6.0, with 10 mM phosphoric acid) onto a 5 ml S-Sepharose fast flow column equilibrated with 0.01M sodium phosphate (pH 6.0). All of the red material bound to the column and the column was washed with 20 ml of 0.01M sodium phosphate (pH 6.0). The column was eluted with 0.05M sodium phosphate (pH 7.5), 0.1M NaCl and 1 ml fractions were collected. The red color eluted in two fractions. The purity of this material was analyzed by SDS-PAGE and appears to be ≧50% pure after the first chromatography step. This material was dialyzed against 10 mM sodium phosphate (pH 6.0), 0.001M EDTA for 16 hr at 0° C. and re-chromatographed on a mono-S FPLC column (ph 6.8-pH 9.0, 0.02M sodium phosphate gradient). The peak fraction from this is ≧85% pure. An absorbtion spectrum was obtained by scanning the mono-S purified material from 400 mM to 650 mM with a Shimadzu spectrophotometer (FIG. 24, top). The spectrum obtained was identical to that of human hemoglobin (FIG. 24, bottom), indicating that the protein had folded and incorporated heme. The amount of hemoglobin recovered in the two peak fractions was determined from the extinction coefficient ($1.23 \times 10^4$ A450/ M) to be ~20 mg.

EXAMPLE 21

Construction of Vectors for the Expression of α- and β-Globin from Separate Yeast Plasmids In addition to the development of a single yeast vector that carries both α- and β-globin expression cassettes we also developed a system that uses separate plasmids for each of the two globin cDNA's. The two plasmids each carry two yeast genes that are used to maintain the plasmid in yeast. Both have the LEU2 gene in common and one (pGS4688) has the URA3 gene, the other (pGS4988) has the TRP1 gene. By using a host that carries mutations in URA3, LEU2 and TRP1 both plasmids (one with α-globin and the other with the β-globin expression cassette) can be maintained. The constructions of these vectors is described below.

Construction of pC1T

The plasmid pC1U (5 ug) was digested with BamHI and SalI and the largest fragment was purified by agarose gel electrophoresis. The plasmid YRp7 (10 ug) (J. Strathern, E. Jones, and J. Broach, $The$ $Molecular$ $Biology$ $of$ $the$ $Yeast$ $Saccharomyces$, Cold Spring Harbor, N.Y., 1981) was digested with BglII and SalI and the fragment containing the TRPI gene was purified by agarose gel electrophoresis. Twenty-five ng of gel-purified, BamHI and SalI digested pC1U was mixed with 50 ng of the BglII-SalI fragment in ligase buffer containing 10 units of T4 DNA ligase. The reaction mixture was incubated at 25° C. for 1.5 hr and a portion of the ligation reaction mixture used to transform *E. coli* DH5α. Tetracycline resistant colonies were selected on LB-tetracycline medium. Plasmid DNA was prepared from 15 transformants, digested with EcoRI and analyzed by agarose gel electrophoresis. One isolate with the expected EcoRI restriction fragments was chosen and was designated pC1T (FIG. 22(*a*)).

Cloning the β-globin Expression Cassette in pC1T

One hundred nanograms of pC1T was digested with SalI, phenol extracted, ethanol precipitated and dissolved in 0.01 ml of 10 mM Tris-HCl (pH 7.8), 1 mM EDTA. The plasmid pGS3888 was digested with XhoI and the ~1.2 kb XhoI fragment containing the β-globin expression cassette was purified by agarose gel electrophoresis. Ten nanograms of SalI digested pC1T was mixed with 60 ng of the XhoI fragment containing the β-globin expression cassette in 0.01 ml of ligase buffer containing 10 units of T4 DNA ligase. The reaction mixture was incubated at 25° C. for 30 min. A portion of this material was used to transform *E. coli* DH5α. One hundred ampicillin resistant transformants were picked and patched to LB-ampicillin agar. They were incubated for 5 hr at 37° C. and overlayed with a nitrocellulose filter. Plasmids containing the XhoI fragment were identified by colony hybridization, using the XhoI fragment as a hybridization probe, as described above. Colonies producing an autoradiographic signal were used to prepare plasmid DNA. The purified DNA was digested with EcoR1 and analyzed by agarose gel electrophoresis for the presence of the expected restriction fragments. Two clones containing the desired XhoI insert were identified and the orientation of the insert was determined by agarose gel analysis of EcoRI digests or SphI digest of the plasmid DNA. Both isolates contained the desired insert in the same orientation and one was designated pGS4988 (FIG. 22(*a*)).

Cloning α-globin Expression Cassette in pC1U

The Xho1 fragment from pGS4088 containing the α-globin expression cassette was purified by agarose gel electrophoresis and the recovered fragment dissolved (100 ng/0.01 ml) in 1 mM Tris-HCl pH 7.8, 0.1 mM EDTA. Twenty-five nanograms of the gel purified fragment was mixed with long of SalI digested (phenol-chloroform extracted, ethanol precipitated) pC1U in 0.01 ml lipase buffer containing 10 units of T4 DNA ligase. The reaction mixture was incubated at 25° C for 1. 5 hr and a portion used to transform *E. coli* DH5α. Ampicillin resistant colonies were selected on LB-ampicillin plates. Plasmid DNA was prepared from 12 transformants, digested with HindIII and analyzed by agarose gel electrophoresis. The two possible orientations were isolated and given the designation pGS4488 (FIG. 22(*b*)) and pGS4688 (FIG. 22(*b*)).

Construction of Diploid Strains Expressing α- and β-globin Chains from Separate Plasmids

*S. cerevisiae* RSY330 (MATα pep4-3 prb1-112 hist7 ura3-52 trp1-289 can1 gal1) was transformed (Ito et al.) with pGS4488 or pGS4688. Trp$^+$ transformants were selected on SD-trp medium and streaked for single colonies. *S.cerevisiae* BJY1991 (MATα prb1-112 pep4-3 leu2-3,112 trp1-101 ura3-52 gal2 can1) was transformed with pGS4988. URA transformants were selected on SD-ura medium and streaked for single colonies. These strains were each tested for the production of α- and β-globin as follows: (1) Single colonies were picked from SD-selective medium and used to inoculate 2 ml of SD-selective (liquid) medium. The cultures were incubated for 24 hr at 30° C. and diluted into 25 ml of fresh SD-selective medium and incubated for an additional 24 hr. The cells were collected by centrifugation and resuspended in 25 ml of YP-galactose (2%) and the incubation continued for an additional 24 hr. The cells were harvested (8,000×g, 10 min) and the pellet washed with 50 ml 0.010M TrisHCl (pH 7.8), 0.001M EDTA. The pellets were dissolved by heating to 96° C. for 10 min in SDS-PAGE sample buffer and the debris removed by centrifugation (15,000×g, 10 min). The cleared supernatants from 1×10$^6$ cells each were analyzed by SDS-polyacrylamide gel electrophoresis and Western immunoblotting as described above. β-globin was readily detectable in extracts from BJY3505[pGS4988]. We were also able to detect α-globin cross-reacting material, although the signal strength was considerably weaker. The production of tetrameric hemoglobin requires the presence of both α and β chains, ideally these would be expressed in the same cell. Because strains BJY3505, BJY1991 and RSY330 are haploids they each can be mated with a yeast strain of the opposite mating type. Strains RSY330 and BJY1991 are both mating type α, whereas BJY3505 is mating type a. BJY3505 [pGS4988], RSY330 [4688] or BJY1991 [4688] or RSY330 [pGS4988] matings were done and diploids selected by streaking onto SD minimal medium with no additional amino acids or other nutrients. Neither of the plasmid-bearing parental strains are capable of growth on this medium, diploids, however, can grow. Because the diploids are homozygous for the mutations in TRP1 and URA3 both plasmids must be present for the cells to grow in the absence of these nutrients. These diploid strains were analyzed for the synthesis of α and β-globin as described above. A most surprising result was obtained. Although α-globin and β-globin are synthesized at low levels in the haploid strains, co-expression in a diploid strain results in a substantial increase in the levels of both chains. Furthermore, after induction (24 hr) with galactose the cell pellets develop a distinct, pink-red color. These results suggest that: (a) co-expression of α-and β-globin stabilizes the two proteins, perhaps as a consequence of their interaction and (b) the protein is apparently folding and incorporating heme.

EXAMPLE 22

Oxygen Binding Properties of Yeast-Derived Hemoglobin

The $P_{50}$ of the yeast derived hemoglobin is nearly identical to that of Hgb Ao. Depending on how we measure it, the $P_{50}$ ranges from about 5 to 10 torr in a phosphate free solution. At 25° C. it is about 4–6 torr in 50 mM BisTris, pH 7.4, NaCl 0.1M. In the same solution, at 37° C., the $P_{50}$ is from 8.5 to 11.

EXAMPLE 23

Expression of Di-Alpha Hemoglobin in *S. cerevisiae*

Methods

Unless stated otherwise, all enzymes (restriction endonucleases, T4 DNA ligase, T4 DNA polymerase, T4 polynucleotide kinase) were purchased from New England Biolabs, Pharmacia, BRL, Stratagene or Boerhinger Mannheim. Restriction enzymes and T4 DNA ligase were used with the buffers supplied by the manufacturers.

Ethanol precipitation of nucleic acids was carried out by the addition of 0.5 volumes or 7.5M ammonium acetate and 2 volumes of 20:1 ethanol-isopropanol. The pellet was collected by centrifugation at 14,000×g for 15 minutes, washed twice with 80% ethanol, once with 95% ethanol and dried in vacuo. Phenol extractions were done by the addition of 50:49:1 mixture of phenol:chloroform:isoamyl alcohol. Phases were separated by centrifugation at 14,000×g and the aqueous phase collected. Plasmid DNA was purified from *E. coli* DH5α as described by Birnborn and Doly (Nucleic Acids Research 1979, 7:1513–1520). Electrophoretic analysis of DNA was carried out in agarose gels using tris-acetate electrophoresis buffer (Maniatis, et al. *Molecular Cloning*, Cold Springs Harbor, N.Y., 1982). DNA was visualized by staining the gels with 0.5 µg/ml ethidium bromide and exposing the gels to ultraviolet light. DNA fragments were purified from agarose gels using a kit purchased from BIO-101. DNA fragments were purified from acrylamide gels by crushing the excised gel fragment in 3.25M ammonium acetate and incubating overnight at 37° C. Gel fragments are removed by centrifugation (14,000×g, 15 min) and the DNA precipitated with ethanol. The precipitate is dissolved in TE (10 mM Tris HCl, pH7.8, 1 mM Na$_3$ EDTA). Acrylamide gel electrophoresis of DNA was done as described by Maniatis, et al. (*Molecular Cloning*, Cold Spring Harbor Laboratory, NY, 1982). Bacteriological growth media and DNA transformation methods are as described by R. W. Davis, et al. (*Advanced Bacterial Genetics*, Cold Spring Harbor Laboratory, NY, 1980). Media for the growth of *S.cerevisiae* has been described by F. Sherman et al. (*Methods in Yeast Genetics: A Laboratory Manual*, Cold Spring Harbor Laboratory, NY, 1979). Transformation of *S.cerevisiae* with linear or circular DNA was carried out as described by H. Ito, et al. (J. Bacteriology, 153:163–168(1983)).

Removal of the PstI and SpeI sites from pGS4888. The design of the synthetic linker for joining two α-globin chains allows the inclusion of PstI and SpeI sites flanking a 30 bp sequence that includes the junction of the two α-globin coding sequences. Because we anticipate testing several different linker sequences, these sites will allow directional cloning of relatively short synthetic oligonucleotides encoding different linker sequences. Removal of the PstI and SpeI sites from the vector sequence is, therefore, necessary so that the sites in the coding region are usable. One µg of the plasmid pGS4888 was digested with PstI and ethanol precipitated. The dry pellet was resuspended in 50 µl of 33 mM Tris-acetate, pH7.9, 66 mM potassium acetate, 10 mM magnesium acetate, 0.5 mM DTT and 50 µM of each dNTP (T4 polymerase buffer). Two units of T4 DNA polymerase were added and the reaction mixture incubated for 15 min at 37° C. Na$_3$ EDTA was added to 12.5 mM and the reaction mixture heated to 65° C. for 15 min, phenol extracted and ethanol precipitated. The dry pellet was dissolved in 14 µl of T4 DNA ligase buffer (BRL) and 1 µl (10 units) of DNA ligase added. The ligation mixture was incubated a 4° C. for 16 hr. A portion of the ligation reaction was used to transform *E. coli* DH5α and transformants were selected on LB-ampicillin plates. Plasmid DNA was prepared from 12 transformants. The DNA was analyzed by agarose gel electrophoresis of PstI digests. Five transformants had lost the PstI site and one of these was designated pGS1889. The SpeI site of this plasmid was removed as described above after digestion of pGS1889 with SpeI. A plasmid was identified that had lost both the PstI and the SpeI site and was designated pGS1989.

Strategy for Joining Two Copies of the α-globin cDNA. A fragment containing the 5'-363 bp of the α-globin coding region can be excised from pGS4888 as an NcoI to ApaL1 fragment. A second fragment containing nucleotides 109 through the 3' untranslated region can be removed as a FokI to SalI fragment. These two fragments can then be joined together to create a single translation unit encoding two tandem copies the of α-chain cDNA by using a synthetic oligonucleotide adaptor (Table 8). The purification and assembly of these fragments is described below.

The plasmid pGS4888 was sequentially digested with ApaL1 and NcoI and a ~365 bp fragment (α-chain 1) purified by acrylamide gel electrophoresis. A second fragment of ~351 bp (α-chain 2) was prepared by sequential digest with FokI and SalI followed by acrylamide gel electrophoresis. Four oligonucleotides were synthesized (Table 8) and assembled into a ~173 bp linker (RGGV) containing ApaL1 and FokI ends. Synthesis, purification and assembly of oligonucleotides was as described previously. This adaptor encodes an amino acid bridge linking the carboxy-terminus of α-chain1 with the amino-terminus of α-chain2 as well as portions of the 3' end of α-chain1 and the 5' end of α-chain2. The carboxy terminal arginine residue of α-chain1 is separated from the amino terminal valine of α-chain2 in this construct by 2 glycine residues. The "diglycine bridge" portion is flanked by HpaI, SpeI and PstI sites. These sites allow the substitution of a variety of bridges by the use of ~30 bp adaptors to connect the two α-chains. The assembly of the two α-chain genes into an expression cassette was carried out in a four part ligation as described below.

Plasmid pGS1989 was sequentially digested with NcoI and SalI and the large fragment containing the plasmid vector and pGALGAP was purified by agarose gel electrophoresis (gp1989). Fifty nanograms of gp1989 were mixed with 200 ng each of the gel purified ApaL1-NcoI α-chain1 fragment and the FokI-SalI α-chain2 fragment. A twentyfold molar excess of the synthetic ApaL1-FokI adaptor was added (the 5'-ends of the adaptor segment are not phosphorylated). The ligation reaction was carried out in a volume of 20 µl for 4 hr at 23° C. A portion of this reaction mixture was used to transform *E. coli* DH5α and ampicillin resistant colonies were selected. Transformants were patched to nitrocellulose filters and screened by hybridization with the $^{32}$P-labelled oligonucleotide AL2as (Table 8). Five pMoles of oligo AL2-as were incubated in 20 µl of a solution containing 2 units of T4 polynucleotide kinase, 50 mM Tris-HCl (pH7.6), 10 mM MgCl$_2$, 6 mM DTT. 0.1 mM spermidine. 0.1 mM EDTA, and 10 pMoles of c$^{32}$P-ATP (7000 Ci/mMole) for 2 hr at 37° C. Filters were processed as described by Maniatis, et al. and the hybridization was done at 37° C. in 5×SSC, 50% formamide, 100 µg/ml yeast tRNA and 2% SDS for 16 hr. The filters were washed, sequentially, in 2×SSC and 1×SSC at 55° C. for 15 min (twice in each, all wash solutions contained 1% SDS). Dried filters were exposed to X-ray film and colonies giving a hybridization signal were used to prepare plasmid DNA. Plasmid DNA was analyzed by restriction enzyme digestion to identify plasmids that contained inserts of a size consistent with two α-chains (NcoI-SalI digest) and that contained unique PstI, SpeI and HpaI sites. A plasmid identified in this manner was designated pGS2189 (FIG. 25).

An XhoI fragment from pCS3888 containing the β-globin expression cassette was purified by agarose gel electrophoresis. XhoI digested pGS2189 (50 ng) was combined with 150 ng of the gel purified insert from pGS3888 in 10 µl of ligation buffer containing 10 units of T4 DNA ligase. A portion of this mixture was used to transform *E. coli* DH5α and ampicillin resistant colonies were selected. Plasmid DNA was isolated and analyzed by digestion with XhoI, BamHI or NcoI. Several plasmids were identified that produced restriction fragments of the expected sizes, all contained inserts in the orientation shown in FIG. 25. One of these was designated pGS2989. Although this plasmid contains the linked α-globin genes and a β-globin gene under the control of separate promoters, it is not capable of replication in S.cerevisiae. The entire expression cassette, containing the two genes (diα and β-globin), can be purified as a NotI fragment. Ten μg of pGS2989 was digested with PvuI and NotI and the NotI fragment gel purified. The digestion with PvuI was done to reduce the size of the vector sequences which otherwise would comigrate with the desired NotI fragment. Two hundred ng of the gel purified NotI fragment was combined with 50 ng of NotI digested pC1N in 10 μL of ligation buffer containing 10 units of T4 DNA ligase. The reaction mixture was incubated at 4° C. overnight and a portion was used to transform E. coli DH5α. Ampicillin resistant transformants were selected and plasmid DNA prepared. DNA was digested with NcoI-SalI, PstI or NotI to identify plasmids with the diα, β-globin expression cassette and to determine the orientation of the inserted fragment. Several plasmids were identified that contained the correct insert, all of which have the inserted fragment in the same orientation. One of these was designated pGS3089 (FIG. 25). This plasmid was used to transform strains GSY112 and RSY334.

Expression and Purification

S.cerevisiae strains GSY112[pGS3089] and RSY334 [pGS3089] were grown to saturation in SD-uracil medium and diluted into 2L of YPD medium (all cultures were incubated at 30° C.). Twenty-four hours after inoculation (of the YPD culture), galactose was added to 1% and the cultures incubated for another 24 hr. Carbon monoxide was bubbled through the culture and the cells collected by centrifugation. A 1:1 mixture (weight:vol) of cells and breakage buffer (10 mM sodium phosphate (pH7.2), 1 mM EDTA, 1 mM EGTA and 5 mM DTT) were disrupted in a "Bead-Beater" (Biospec Products, Bartlesville, OK). Debris was removed by centrifugation (10,000×g, 30 min). The soluble fraction was adjusted to pH6.0 with phosphoric acid and chromatographed on a column of S-sepharose (fast flow) equilibrated in 10 mM sodium phosphate pH6.0. The loaded column was washed with 10 mM Tris-HCl, pH6.7 and hemoglobin eluted by washing with 20 mM Tris-HCl, pH7.5. A bright red band was collected and the pH adjusted to 8.0, by the addition of NaOH. This material was then chromatographed on Q-sepharose (fast flow) equilibrated in 20 mM Tris-HCl, pH8.0. Hemoglobin was eluted with a NaCl gradient (0–0.4M). A final chromatography step was carried out on Sephacryl S-200 equilibrated in 5 mM NaPO$_4$, pH7.4, 0.1M NaCl. Each step of the purification protocol was analyzed by SDS-polyacrylamide gel electrophoresis (Laemmli, U.K., 1970, Nature 227:680–685) and staining with Commassie brilliant blue. The purified protein contains a band that comigrates with monomer β-globin and a band in the expected position for α-globin dimer. This material comigrates with human tetrameric hemoglobin when analyzed by size exclusion chromatography (Progel TSK G3000 SWXL HPLC column). This protein is red and binds $O_2$ with a 50% binding affinity ($P_{50}$) of 8–10 Torr, indicating that it has incorporated heme and is capable of reversible $O_2$ binding.

The purified protein was separated into α- and β-chains by reverse phase HPLC and the sequence of the 10 amino-terminal residues of each chain were determined. The sequence matched that of bona fide human hemoglobin, indicating that the initiating methionine had been efficiently removed from both the α-globin dimer and the β-globin dimer.

EXAMPLE 24

Construction of Low Affinity, Genetically Cross-linked, Hemoglobin Mutants and Expression in Yeast 24.1 Construction of vector for site directed mutagenesis. The XhoI fragment containing the β-globin gene and its GALGAP promoter was isolated from pGS2989 by preparative agarose gel electrophoresis and ligated with XhoI digested Phagescript (RF-form, obtained from Stratagene, Inc.). E. coli XL1-Blue was transformed with the DNA ligation mixture and phage containing inserts were identified (white plaques on medium containing XGAL). Single plaques were isolated and DNA was prepared and analyzed by digestion with XhoI and agarose gel electrophoresis. This construct was designated M13β-globin.

24.2 Preparation of single stranded template. A saturated culture of E. coli XL1-Blue (available commercially from Stratagene, 11099 North Torrey Pines Road, LaJolla, Calif. 92037) (200 μl) was used to inoculate 4 ml of 2×YT broth. This culture was incubated for 2 hr. at 37° C. and then infected with a single M13β-globin phage plaque and the incubation continued for 6–8 hrs. Cells were removed by centrifugation and discarded. Phage were precipitated from 1.6 ml of clarified medium by the addition of 320 μl of cold 30% PEG 8000 in 3.5M ammonium acetate followed by incubation on ice for 30 min. Phage were collected by centrifugation and resuspended in 0.1 ml of 10 mM Tris-HCl pH 8.0, 1 mM EDTA (TE). DNA was isolated by extracting twice with phenol/cholorform. DNA (contained in the aqueous phase) was precipitated by the addition of NaCl to 0.5M and two volumes of 95% ethanol. The DNA pellet is dissolved in 20 μl of water.

24.3 In vitro mutagenesis reactions. Two hundred ng of template DNA are mixed with a twenty-fold molar excess of the appropriate, phosphorylated mutagenic oligonucleotide in 10 μl of 20 mM Tris-HCl, pH 7.4, 2 mM $MgCl_2$, 50 mM NaCl and heated to 70° C. for 5 minutes. The annealing reaction is allowed to slowly cool (40 min) to 40° C. and then to 30° C. (15 min). After the last annealing step the mixture is transferred to ice for 5 min. To this mixture 1 μl of synthesis buffer (4 mM each dNTP, 7.5 mM ATP, 175 mM Tris-HCl pH 7.4. 37.5 mM $MaCl_2$ 215 mM DTT). 0.5 μl of T4 gene32 protein (2 μg/μl), 1 μl of T4 DNA ligase (3 units), and 1 ml of T4 DNA polymerase (1 unit) are added. The mixture is incubated at 37° C. for 90 min (following 5 min at room temperature). The reaction is stopped by the addition of 90 ml of 0.1M Tris-HCl (pH 8.0) and 0.1M EDTA. Approximately 0.1 μl of the reaction mix was used to transfect E. coli XL1-Blue cells (Cells were prepared for transformation by the method of D. Hanahan, 1983. J. Mol. Biol. 166:557).

24.4 Screening for phage containing the mutant gene. Approximately 50–100 plaques were picked to fresh plates seeded with the appropriate host strain (XL1-Blue) in ordered arrays. After incubation for 6–8 hrs. at 27° C. the plates were overlaid with nitrocellulose filters and prepared for hybridization essentially as described in Davis, R. W. et al. (Advanced Bacterial Genetics: A Manual of Genetic Engineering. Cold Spring Harbor Laboratory, New York 1980). The choice of hybridization temperature with the mutagenic oligonucleotide was determined on the basis of the nucleotide composition of the oligonucleotide. The oligonucleotide was labelled with $c^{32}P$-ATP and polynucleotide kinase (T. Maniatis et al. Molecular Cloning: A Laboratory Manual. Cold Spring Harbor Laboratory, 1982).

Hybridizations were done at 2–5° C. below the calculated Tm for the correct match in 6×SSC, 2%SDS, 100 μg/ml yeast tRNA using $10^5$ cpm/ml of the labelled oligonucleotide for >6 hr. The Tm was calculated using the formula: 4° C. for every GC pair +2° C. for each AT pair assuming an Na+ concentration of 1M. Filters were washed at the same temperature as the hybridization in 5×SSC, 2% SDS and exposed to XRay film. Plaques giving positive hybridization signals were used to prepare single stranded DNA, as described above. The single-stranded DNA was used as template for sequencing reactions (Sanger, F. and Coulson, A. R. 1975, J. Mol. Biol. 94:441) to confirm that the mutant sequence was indeed present.

Oligonucleotides used for mutagenesis.

βN108K-"Presbyterian"
  5'-AGGCTCCTGGGCAAGGTGCTGGTCTGT-3'
βE90K-"Agenogi"
  5'-GCCACACTGAGTAAGCTGCACTGTGAC-3'
βV67I-(No Alias)
  5'-CATGGCAAGAAAATCCTCGGTGCCTTT-3'
βN102T-"Kansas"
  5'-GTGGATCCTGAGACTTTCAGGCTCCTG-3'

Figure 26:
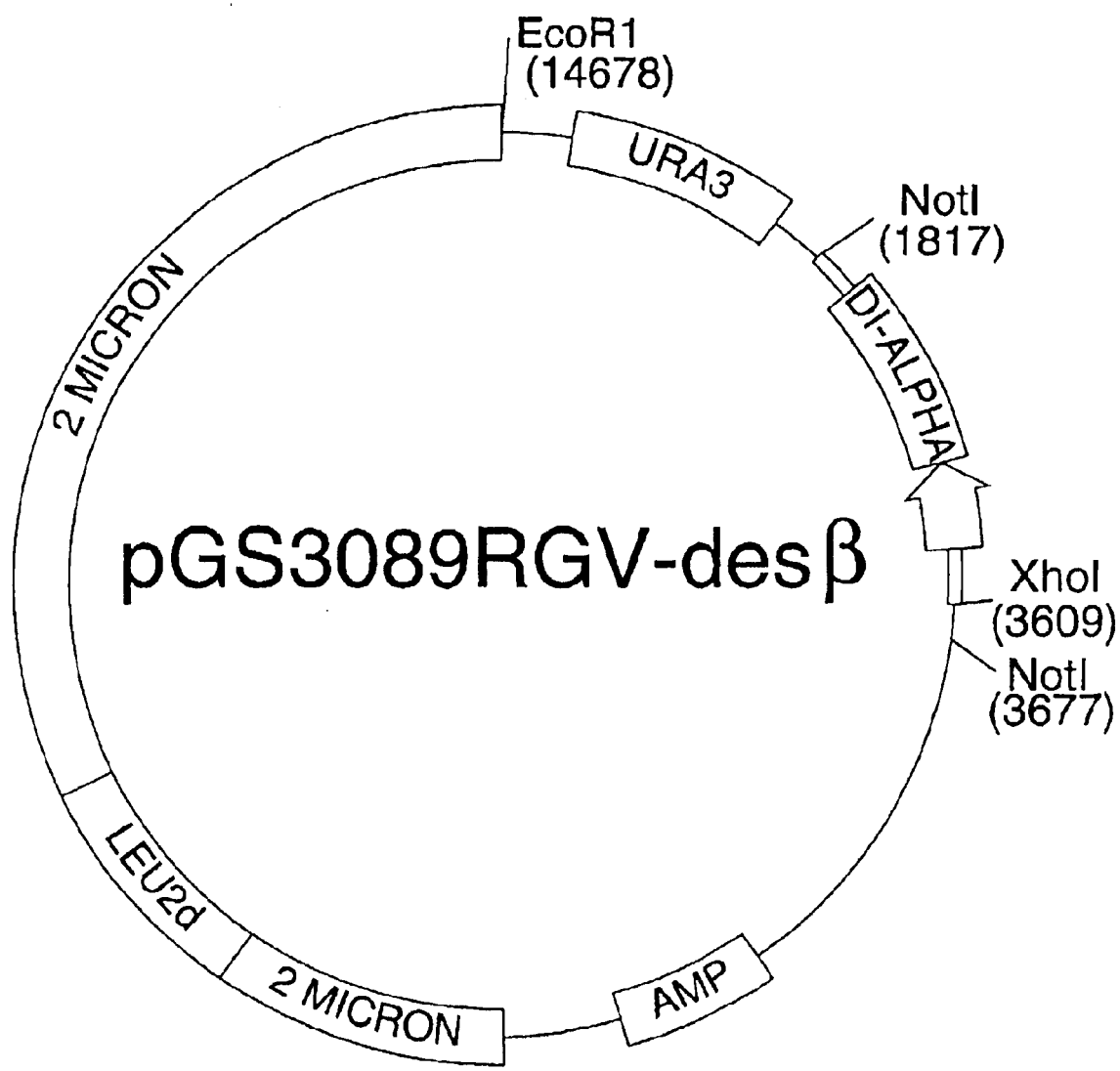
FIG. 26: Map of plasmid pGS3089RGV desβ.

24.5 Cloning into yeast expression vectors. Phage RF DNA was prepared from phage-infected cells that had been confirmed to have the mutant sequence and the XhoI fragment containing the altered β-globin gone was purified by agarese gel electrophoresis. This fragment was cloned into a derivative of pGS3089 that had been altered to change the di-α-crosslink from the diGly configuration to a single glycine bridge, and from which the β-globin gene had been deleted, and designated pGS3889RGVdesβ (FIG. 26). This created a unique XhoI site into which altered β-globin expression cassettes could be inserted, allowing coexpression with the α-globin dimer. The expression plasmids generated in this way (pGS3889 for "Presbyterian", pGS5189 for "Agenogi", pGS5689 for "Kansas" and pGS4989 for "βV67I", all identical to pGS3089 except for mutation in specified codon) were used to transform S. cerevisiae strains GSY112 and RSY334.

24.6 Characteristics of a genetically crosslinked low affinity mutant Protein expressed in yeast. Cells bearing the plasmid pGS3889 (single gly bridge, BN108K alias "Presbyterian") were grown and hemoglobin purified as previously described. This material when analyzed for functionality was substantially "right-shifted" compared to the crosslinked protein with a wild type β-chain ($P_{50}$=23–25 for the mutant, with N=2.5).

EXAMPLE 25

Effect of Choice of Strain and Induction Temperature on Expression of Di-Alpha Hemoglobin in E. coli Table 100 contains comparisons of di-alpha/beta fermentations. It also provides comparison of temperatures of induction. The column labeled "mg di-A+B" is total mg di-alpha and beta polypeptides per fermentation. The adjacent column "mg/OD-L" simply expresses the first column number on a cell density basis. The two columns labeled RHGB present total and cell density-corrected output of functional recombinant hemoglobin. The last column shows that in terms of final functional hemoglobin recovery, strain JM109 is preferable. Without binding ourselves to any theory, we believe that this difference has to do with the proteases expressed in different strains. It is interesting to note that of the two best JM109 runs, one induction was at 30° and one at 37° with roughly equivalent amounts of final functional Hb produced.

EXAMPLE 26

Construction of Genetically Cross-linked α-Globin Dimers Connected by a Single Glycine or Proline Residue The following synthetic adaptors for altering the diα-globin bridge were synthesized and purified as described in previous sections.

```
         T   S   K   Y   R   P   V   L   S   P   A
5'-A ACT AGT AAG TAC AGA CCT GTT TTG TCT CCT GCA-3'      RPV
3'-T TGA TCA TTC ATG TCT GGA CAA AAC AGA GG-5'
    HpaI                                        PstI

T   S   K   Y   R   G   V   L   S   P   A
5'-A ACT AGT AAG TAC AGA GGT GTT TTG TCT CCT GCA-3'      RGV
3'-T TGA TCA TTC ATG TCT CCA CAA AAC AGA GG-5'
    HpaI                                        PstI
```

Complementary pairs of RPV and RGV oligonucleotides were combined (2.4 μg of each oligonucleotide) in 0.05 ml of water. The two pairs of adaptors were precipitated (separately) by the addition of 2. μl of 4M NaCl and 0.58 mL of 100% ethanol followed by centrifugation. The pellets were washed with 80% and 100% ethanol and dried. The adaptors were dissolved in 24 μl of TE.

26.1 Cloning of the RGV and RPV adaptors. The plasmid of pGS2989 was sequentially digested with the enzymes HpaI and PstI and the vector was purified after agarose gel electrophoresis. The digested plasmid was then ligated with a 10-fold molar excess of either the RGV or RPV adaptor (these adaptors were not phosphorylated) as previously described. A portion of the ligation mixture was used to transform E. coli DH5. Transformants were selected on LB plates containing ampicillin. Clones containing the new adaptor were identified by colony filter hybridization. The hybridization probes were either the RPV or RGV upper strands (as shown above). These proves were labelled with c32P-ATP and T4 polynucleotide kinase. Filters were hybridized with the appropriate probes ($10^5$ cpm/ml) at 37° C. in a solution containing 6×SSC. 50% formamide, 2% SDS and 150 μg/ml yeast tRNA. Filters were incubated for >12 hrs. and washed 4 times with 2×SSC, 2%SDS (250 ml, 20 min each) and exposed to X-ray film. Colonies that produced autoradiographic signals were used to prepare plasmid DNA which was sequenced using the following primer: 5'-AAGCTTCAGCACCGTATTCA-3' ($α^2$seql). This primer was specifically designed to minimize homology with the corresponding sequence in the α1 subunit of the dimer and to maximize homology with sequences near the 5' end of the α2 subunit of the diα dimer. This allows sequence to be determined reading from the α region through the sequence that bridges the two α-domains without a background sequence reading from a similar sequence near the 5'-end of the α1-domain. The plasmids constructed in this way were designated pGS2989RPV(single proline crosslink) or pGS2989RGV (single glycine crosslink).

26.2 Cloning into yeast expression plasmids. The NotI fragments from either pGS2989RPV or pGS2989RGV that contain the hemoglobin expression cassette were purified by agarose gel electrophoresis and subcloned into pC1N that had been digested with NotI. Plasmid DNA from ampicillin resistant transformants was isolated and analyzed by digestion with NotI and agarose gel electrophoresis. These plasmids were designated pGS3089RPV or pGS3089RGV. A second set of plasmids was generated from these to facilitate the substitution of different β-chain mutants. These plasmids were generated by digestion with XhoI and religation under dilute conditions <1 µg/ml). This favors deletion of the β-chain expression cassette. Plasmid DNA was isolated from ampicillin resistant transformants and the structures confirmed by digestion with NotI and XhoI (these plasmids have been designated pGS3089RGV-desβ, see FIG. 26, and pGS3089RPV-desβ).

EXAMPLE 27

Comparison of Renal Toxicity of Di-Alpha Hemoglobin and Des-Val Hemoglobin

Safety studies were conducted in both rats and dogs. Two rats received non-stabilized rHb and two rats received stabilized rHb (a di-alpha Hb with a di-glycine linker between the alpha globin domains) The following serum chemistry parameters were evaluated:

CK creatinine kinase
ALT alanine aminotransferase
AST aspartate aminotransferase
BUN blood urea nitrogen.

A substantial increase in these parameters, relative to baseline, 24 hours after administration, is indicative of renal toxicity: The following values were obtained:

| TEST | Non-Stabilized rHb | Stabilized rHb |
| --- | --- | --- |
| BUN baseline | 19.5 | 17.5 |
| BUN 24 hours | 109.5 | 26.5 |
| CK baseline | 0.45 | 0.5 |
| CK 24 hours | 1.35 | 0.5 |
| AST(SGOT) baseline | 155.5 | 212.5 |
| AST(SGOT) 24 hours | 3444.0 | 942.0 |
| ALT(SGPT) baseline | 62.0 | 80.5 |
| ALT(SGPT) 24 hours | 958.5 | 192.5 |

It is noted that the increase for the stabilized rHb is much lass pronounced.

Dogs were first stressed by withdrawing approximately 30% of their blood volume, allowing them to stabilize for 30 mins, and then resuscitating with either rHb1.1, saline, human serum albumin or autologous blood.

Histopathology:

No macroscopic or microscopic lesions were observed in organs (i.e., kidneys) at the end of the study that could be directly attributed to the administration of recombinant, stabilized hemoglobin.

Serum Chemistry

Serum chemistry data for dogs treated with rHb1.1 were evaluated for study day 2 (22–24 hours after hypovolemic stress) for CK (creatine Kinase), ALT (Alarine Aminotransferase), AST (Aspartate Aminotransferase) and Urea (Blood Urea Nitrogen, BUN). The AST and CK were notably increased in the rHb1.1 treated animals at day 2, however, these values returned to pretreatment levels by study day 4.

Urine Biochemistry:

Urinalysis was not affected by the administration of rHb1.1. Other than a very slight decrease in NAG activity in all females (in all treatments) on study day 2, no notable findings were observed.

In summary, the magnitude and time course of cardiovascular and hemodynamic effects observed in severely hemorrhagic dogs resuscitated with recombinant di-alpha hemoglobin were nearly identical to those observed in dogs resuscitated with autologous blood. This study demonstrates that recombinant hemoglobin does not cause adverse cardiovascular, or hemodynamic effects when compared to HSA or autologous blood resuscitation in severely stressed dogs. Moreover, 30% blood volume resuscitation with recombinant di-alpha hemoglobin (1.1 g/kg) in hypovolemic dogs produced only limited, reversible effects, including transient neutropenia and elevation of blood plasma enzymes of skeletal muscle origin. No major organ systems were affected, no hemoglobin was found in the urine of recombinant hemoglobin treated dogs, and no histopathological changes were observed.

EXAMPLE 28

Construction of di-α globin Mono-cysteine (A71C, D75C, or S81C) Mutant Expression Vector 28.1 Subcloning of the α Gene into Phagescript The desfxα pGem (pDLII-83a) vector was cut with EcoR1 and Pst1 endonucleases and ligated into EcoR1/Pst1 digested phagescript (obtained from Stratagene). *E. coli* strain DH5α was transformed with the ligation mixture and cells were plated on 2×YT plates overlaid with 3 ml top agar containing 10 µl 100 mM IPTG, 25 µl 2% X-Gal in DMSO and 150 µl XL-1 cells (stratagene). Clear plaques were picked and grown at 37° C. in 2×YT containing XL-1 cells. Double stranded DNA was isolated from the cultures and checked for the presence of the 500 bp α gene by restriction analysis and agarose gel electrophoresis. Single stranded DNA was isolated from one of the desfxα phagescript transformants (named f 191). The single stranded DNA was sequenced to confirm the presence of the desfxα gene in the phagescript.

28.2 Mutagenic Oligonucleotides

Three mutagenic oligonucleotides were used in three separate mutagenic reactions. The sequences of the oligonucleotides were as follows (mutant codon is underlined):

Nigeria mutation: αS81C

5' CCG AAC GCG TTG TGC GCT CTG TCT GAT 3' (SEQ ID:5)

αD75C

5' GGT GCT CAC GTT GAT TGC ATG CCG AAC GCG 3' (SEQ ID:6)

αA71C

5' CTG ACC AAC GCT GTT TGC CAC GTT GAT GAT 3' (SEQ ID:7)

28.3 Kinase reaction Conditions for mutagenic Oligonucleotides A71C D75C and S81C.

1 µl oligonucleotide (approx. 300 pmol)
2 µl 10× kinase buffer containing 10 mM ATP
0.5 µl T4 polynucleotide kinase (10 U/µl, New England Biolabs)

15.5 µl H$_2$O

1 µl 1 mM spermidine

Reactions were incubated for 1 hr. at 37° C., then 80 µl H$_2$O was added and the reaction was terminated by heat inactivation at 65° C. for 10 min.

28.4 Mutagenesis Reaction

1 µl f 191 ss DNA (0.5 pmol)

3 µl kinased oligonucleotide (either A71C, D75C or S81C approx. 45 pmol)

2 µl 10× annealing buffer (Promega)

14 µl H$_2$O

The no primer control contained:

1 µl f 191 ss DNA

2 µl 10× annealing buffer

17 µl H$_2$O

Reactions were heated to 65° C., cooled slowly to 35° C. (approx. 70 min), and put on ice for 5 min. The following reagents were added and the reactions were incubated at 37° C. for 90 min.

3 µl 10× synthesis buffer (Promega)

1 µl T4 gene 32 protein (0.5 µg/µl, Biorad)

1 µl T4 DNA polymerase (3 U/µl, NEB)

0.5 µl T4 DNA ligase (10U/µl, NEB)

5 µl H$_2$O

200 µl 71-18 mut S competent cells (made according to Promega Altered Sites procedure) were transformed with 10 µl of each mutagenesis reaction, put on ice for 30 min and heat shocked for 2 min at 42° C. The transformation mixture was added to 3 ml 2×YT media and grown at 37° C. (with shaking) for 5.5 hr. After incubation, 1 ml of each of the three cultures was removed, centrifuged and 800 µl was stored in a fresh tube at 4° C. as the stock solution of mutant phage.

28.5 Screening for Mutants of D75C

100 µl of a 10$^{-5}$ dilution of the D75C mutant phage stock was plated on 153 mm 2×YT plates overlain with top agar containing 0.5 ml XL-1 cells. Plates were incubated at 37° C. for approx. 5 hrs. Duplicate nitrocellulose filters were lifted off each plate and the plaques were lysed in 6 ml 0.5 M NaOH/1.5 M NaCl, neutralized in 10 ml 1 M Tris-HCl pH 8.0/1.5 M NaCl and washed in 500 ml 6×SSC. The filters were air dried and baked at 75° C. for 45 min. The filters were then boiled briefly in 1% SDS prior to prehybridization. Filters were prehybridized in 20 ml solution for 4 hr at 68° C. The prehybridization solution was as follows:

5×SSC (20×SSC prepared according to recipe in Maniatis).

0.1% (w/v) N-lauroylsarcosine 0.02% (w/v) SDS 0.5% blocking reagent (Genius Kit, Boehringer Mannheim)

The D75C oligonucleotide was labelled with γ[32]P ATP follows:

1 µl oligonucleotide (80 pmol)

10 µl 10×kinase buffer

1 µl γ[$^{32}$]P ATP (10 µC/µl. Specific activity>3000 Ci/mmol).

87 µl H$_2$O

1 µl kinase (10U/µl, NEB)

The reaction was incubated for 5 hrs. at 37° C. Unincorporated ATP was removed by centrifugation through a Biospin 30 column (Biorad). The entire probe (17,000 cpm/µl) was added to the prehybridization mixture and the filters were hybridized overnight at 46° C. along with a no primer control filter. The following day, filters were washed for 10 min. at room temperature (RT) in 6×SSC and exposed overnight at −70° C. on Kodak X-Omat film. Filters were washed in 6×SSC at 57° C. for 10 min, dried and exposed overnight, then washed in 6×SSC/0.1% SDS at 67° C. for 10 min, and dried and re-exposed overnight. The final was was in 6×SSC/0.1% SDS at 70° C. for 10 min and the filters were again dried and exposed overnight.

Ten plaques were picked which hybridized differentially to the mutant oligonucleotide (compared to the no primer control plaques). The plaques were placed in 5 ml 2×YT media containing 0.25 ml XL-1 cells. The cultures were incubated with shaking at 37° C. for 7.5 hr. 1 ml of each culture was removed, centrifuged 5 min, placed in a fresh tube and stored at 4° C. for subsequent sequencing and plaque purification.

28.6 Screening for Mutants of A71C and S81C

1 µl of a 10$^{-3}$ dilution of the A71C stock phage mutagenesis reaction and 20 µl of a 10$^{-5}$ dilution of the S81C mutagenesis reaction were plated on four separate 82 mm 2×YT/tet(10 mg/ml) plates overlaid with 3 ml top agar and 100 µl XL-1 cells. A no primer control was also plated as above. The plates were incubated at 37° C. for 5 hr; plaques were lifted from each plate onto nitrocellulose filters and the filters dried overnight at room temperature. The following day, the plaques were lysed with 0.5 M NaOH/1.5 M NaCl for 3 min, neutralized in 1 M Tris-HCl pH 7.0/1.5 M NaCl for 3 min and washed in 6×SSC for 5 min. Filters were air dried then baked at 75° C. for 1 hr. The filters were boiled briefly in 1.5% SDS prior to prehybridization at 60° C. for 6 hr. in 10 ml prehybridization solution as described above.

28.7 Labelling of A71C and S81C Oligonucleotides Using Digoxigenin (All reagents supplied by Boehringer Mannheim)

2 µl A71C (100 pmol) or 1 µl S81C (110 pmol)

10 µl terminal transferase buffer

5 µl 25 mM CoCl$_2$

1 µl 1 mM dUTP-digoxigenin

30 µl −31 µl H$_2$O (A71C and S81C reactions respectively)

1 µl terminal transferase (25U/µl)

Reactions were incubated at 37° C. for 3 hr. followed by 6 hr. at RT. Digoxigenin-labelled A71C and S81C probes (20 µl) were added to the appropriate filters in 10 ml prehybridization solution along with a no primer control filter. The filters were hybridized overnight at 47° C.

28.8 Filter Washes and Development

All filters were initially washed in 6×SSC/0.1% SDS for 15 min at 30° C., then for 15 min at 42° C.

Each of the four filters which had been probed with either the labelled A71C or S81C oligonucleotides were then separated and washed at increasingly higher temperatures along with a no primer control filter. One each of the A71C and S81C filters were placed in plastic bags containing 10 ml of 6×SSC/0.1% SDS and washed for 10 min at one of three temperatures, i.e., 50° C., 60° C. or 65° C. After the high temperature washes, each set of filters were developed according to the Genius Kit protocol.

Initially, bags containing the filters were filled with 10 ml of 100 mM Tris-HCl, pH 7.5/150 mM NaCl (buffer A) and incubated for 15 min. The buffer was removed and replaced with 10 ml buffer A containing 0.5% blocking reagent and incubated a further 15 min at RT without shaking. Anti-digoxigenin antibody (2 µl) was added directly to each bag and incubated with for 30 min at RT. The filters were then removed from their respective bags and washed altogether in 100 ml buffer A/0.05% blocking reagent for 15 min at RT, followed by a 15 min wash in buffer A alone at RT. The final wash was 100 ml 100 mM Tris-HCl, pH 9.5/100 mM NaCl/50 mM $MgCl_2$ (buffer B) for 5 min at RT. Each set of filters from a given temperature was placed in a separate bag along with 5 ml of color development solution (5 ml buffer B containing 22.5 µl 75 mg/ml NBT/15 µl 50 mg/ml X-phosphate). The filters were incubated for 30 min in the dark at RT. After 30 min, the filters were removed from the development solution, washed for 5 min in 100 ml 10×TE and 5 min in 100 ml 1×TE, both at RT. Filters were dried at RT.

Using the results from the Genius Kit screening procedure, 10 plaques which differentially hybridized to the labelled oligonucleotides A71C or S81C were picked and placed in 3 ml 2×YT media containing 0.25 ml XL-1 cells and incubated for 7.5 hr. at 37° C. with shaking. 1 ml of each culture was removed, centrifuged 5 min, placed in a fresh tube and stored at 4° C. for subsequent sequencing and plaque purification.

28.9 Confirmation of Mutations by Sequencing

Single stranded DNA was isolated from 800 µl mutant phage stock supernatant and sequenced using the Sequenase kit (USB) with the α 179 oligonucleotide as the primer. The α 179 aligonucleotide is an 18-mer homolog cys to a region about 100 bps upstream of the mutation site.) Sequencing confirmed the presence of the αA71C, αD75C and α S81C mutations.

Phage stock was plaque purified by plating 10 µl of $10^{-8}$ and $10^{-10}$ dilutions on 2×YT/tet (10 mg/ml) plates overlaid with 3 ml top agar containing 200 µl XL-1 cells. After 7 hrs incubation at 37° C., a single isolated plaque from each mutant plate was picked and used to inoculate 90 ml 2×YT/tet (10 mg/ml) media containing 10 ml XL-1 cells. Cultures were grown overnight at 37° C. with shaking. 1 ml of each mutant phage culture was removed, centrifuged and the supernatant was frozen at −80° C. as the respective purified mutant phage stock. Double stranded DNA was prepared from the remaining culture for use in the subsequent subcloning steps into the final expression vector 1.1E4.

28.10 Subcloning of the α Cys Mutants into 1.1E4

Construction of the di-α gene with each of the three cysteine mutations in either the N-terminal or C-terminal domain of the di-α protein required three subcloning steps:

1) Transfer of the cys mutant α gene from phagescript as an Eag1-Pst1 fragment into the Eag1-Pst1 digested desval α pGem vector (pDL II-91f, see #10, table 200). This step provided the mutant α gene with the correct 5' terminus.

2) A mutant di-α gene with each of the cys mutations in the 3' α gene was constructed by inserting the Eag1 DNA fragment from di-α pGem (see pGem di-alpha, #5a, table 200) into the Eag1 site of the relevant cys mutant desval α pGem plasmid. The mutant diα gene with the cys mutation in the 5' α gene was constructed by inserting the BstB1 DNA fragment from diα pGem into the BstB1 site of the cys mutant desval α pGem plasmid.

3) Finally each of the mutant diα genes were cloned into the 1.1E4 expression vector as a Sma1-Pst1 fragment.

Transformations into DH5α at each step in the subcloning procedure were carried out as described in the methods of subcloning of the β G83C mutation into 1.1E4 (see below). The presence of the relevant cys mutation in the correct α gene was confirmed by sequencing at each stage in the subcloning procedure. Each of the diα cys mutants in 1.1E4 were transformed into E. coli strain 127, grown in TB complete media and induced with IPTG. Expression of the diα and β proteins was confirmed by SDS-PAGE and Western blot analysis.

EXAMPLE 29

Hypothetical Protocol for the Oxidation of Two SGE1.1 Mono-cys's to Form a Pseudo-octamer The surface cysteine mutants (MW=64 kDa) can be oxidized to the disulfide-linked dimer under oxidative conditions. This can be accomplished by stirring a concentrated solution of the expressed protein at pH 8 under pure oxygen at 4° C. or room temperature in the dark. Trace levels of transition metal ions such as $CU^{+2}$ may be added to level below 1 uM to catalyze the oxidation (1). Formation of the 128 kDa octamer can be monitored by gel filtration. Saturation of the solution with oxygen at elevated pH should minimize autooxidation of recombinant hemoglobin.

An alternative procedure, which may be the preferred method of catalyzing this reaction, involves the use of redox buffers such as reduced and oxidized glutathione, or reduced and oxidized dithiothreitol (2). This catalysis of the reaction through disulfide interchange may be necessary to control trace transition metal catalysis (3). An second, similar approach involves conversion of the surface cysteines in the 65 kDa species to sulfonates before purification (to avoid 128 kDa species formation during purification), followed by conversion to the disulfide-linked 128 kDa species with reduced glutathione (2).

(1) Freedman, R. B. and Hillson, D. A. (1980) "Formation of Disulfide Bonds"IN: The Enzymology of Post Translational Modification of Proteins, Vol. 1, p. 157 ff. (Academic Press).

(2) DiMarchi, R., et al. (1988) Chemical synthesis of human epidermal growth factor (EGF) and human type a transforming growth factor (TGFa) IN: Peptides: Chemistry and Biology (G. R. Marshall, ed.) pp. 202–203 (Leiden:ESCOM).

(3) Creighton, T E (1978) Experimental studies of protein folding and unfolding. Prog. Biophys. Molec. Biol. 33:231–297

Example 30

Characterization of Di-Alpha Hemoglobin

We constructed an E. coli expression vector that contains two copies of the α globin gene fused in tandem by a single codon encoding a glycine residue; this created a fusion junction with the sequence Arg(141α1)-Gly-Val(1α2). In this construct a single operon encoding a diα-globin and a β-globin chain is transcribed from a single TAC promoter. Hoffman, S. J., Looker, D. L., Roehrich, J. M., Cozart, P., Durfee, S., Stetler, G., Proc. Nat. Acad. Sci. (USA) 87, 8521–25 (1990). To decrease the oxygen affinity of this engineered Hb we have introduced an additional Asn-108β→Lys mutation. In its naturally occurring form (Hb Presbyterian) this substitution reduced the oxygen affinity and slightly increased the Bohr effect. Moo-Penn, W., Wolff, J., Simon, G., Vacek, J., Jue, H., Johnson, M., FEBS Lett. 92, 33–37 (1978). Upon induction of the Hb operon with IPTG, E. coli cells carrying a plasmid containing the fused α globin gene produce two polypeptides corresponding to α globin and fused diα globin.

To fully assess the separate effects of the α-globin fusion and the Asn-190β→Lys mutation, we also constructed vectors to express four related proteins: (1) A mutant form of the tetramer that contains Val to Met changes at the amino termini of both α and β chains and the Asn-108β→Lys mutation (rHb1.0); (2) pseudotetrameric diα-haemoglobin with Asn-108β→Lys and amino-termini modified as described above (rHb1.1); (3) a pseudotetramer without the Asn-108μ→Lys (rHb0.1); and (4) tetramer with neither the α fusion nor the β globin mutation (rHb0.0). The four forms of recombinant hemoglobin described above were purified from E. coli and analyzed for functionality. The table below summarizes these results and compares them to adult human native haemoglobin (Hb A) purified blood. For analytical methods, see Hoffman, S. J., Looker, D. L., Roehrich, J. M., Cozart, P., Durfee, S., Stetler, G., Proc. Nat. Acad. Sci. (USA) 87, 8521–25 (1990). Wagenbach, M., O'Rourke, K., Vitez, L., Wieczorek, A., Hoffman, S., Durfee, S., Tedesco., J. Stetler, G. Biotechnology, 9, 57–61 (1991). The Bohr coefficient is the slope of the line generated by plotting log $P_{50}$ as a function of increasing pH (pH6.8–7.8). oxygen equilibrium binding data were collected at 20° C. in 50 mM HEPES beffer containing 100 mM NaCl. Also shown are the amino acids present at the amino termini of the α and β-chains, at position 108 of the β-chain and the structure of the α-chain.

The Asn-108μ→Lys mutation causes a substantial decrease in oxygen affinity of both the pseudotetramer and the tetramer when compared to wild type human haemoglobin or rHb0.0. The Asn-108μ→Lys mutation apparently also causes an increase in the Bohr effect which is consistent with the initial characterization of human Hb Presbyterian. Fusion of the two α globin subunits causes a substantial increase in oxygen affinity and a slight decrease in cooperativity. Finally, the valine to methionine alteration at the amino termini of the α and β subunits results in a decrease in the oxygen affinity that is apparently completely compensated for by the fusion of the two α-globin subunits.

|  | WT | 1.1 | 1.0 | 0.1 | 0.0 |
| --- | --- | --- | --- | --- | --- |
| Bohr Coefficient | −0.47 | −0.32 | −0.35 | −0.25 | −0.27 |
| p50 (torr) (20° C.) | 4.5 | 17.2 | 19.8 | 4.5 | 7.3 |
| Hill Coeff (n max) | 2.90 | 2.35 | 2.53 | 2.04 | 2.59 |
| α-chain | WT | diα | WT | diα | WT |
| α-chain (NH3) | VL | ML | ML | ML | ML |
| β-chain (β108) | N | K | K | N | N |
| β-chain (NH3) | VH | MH | MH | MH | MH |

Figure 32:
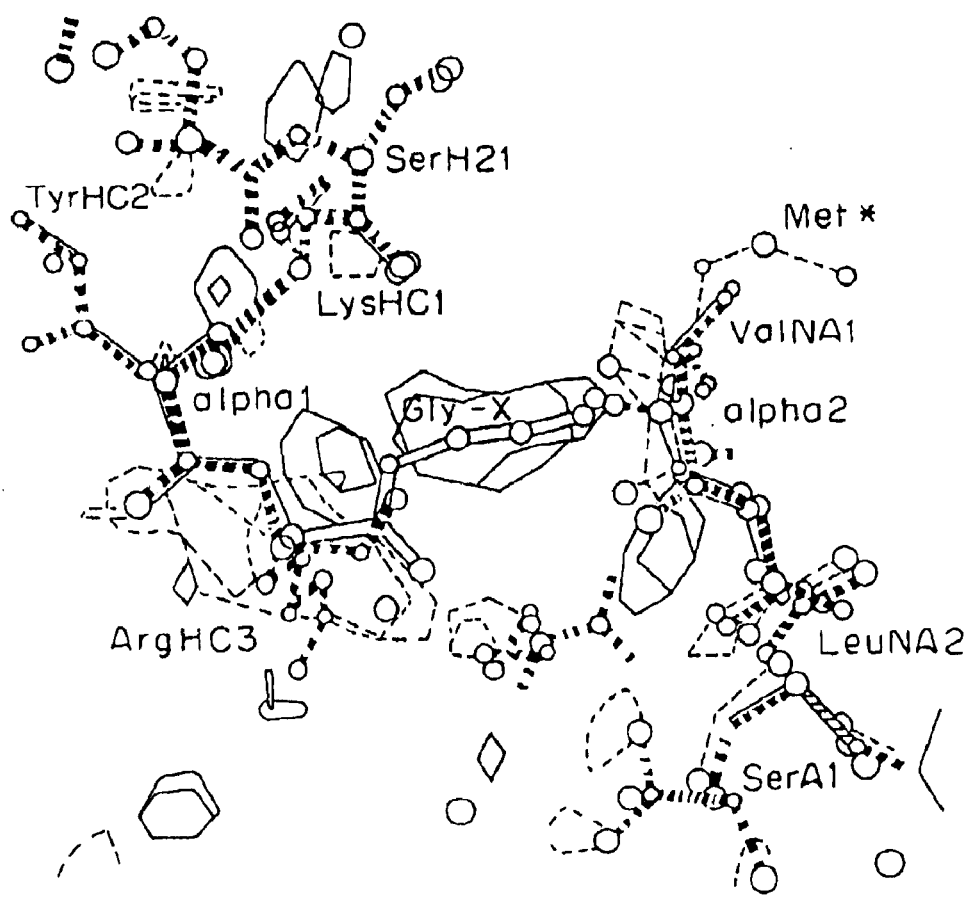
FIG. 32: The symmetry-averaged difference map rHb1.1-HbA superimposed on the atomic model. The map is contoured at plus (solid contours) and minus (broken contours) about 2 times the root-mean-square value of the electron density prior to symmetry averaging about the molecular dyad. Filled bonds represent the refined coordinates of the deoxy HbA, Fermi, G., Perutz, M., Shaanan, B., Fourme, R., J. Mol. Biol. 175, 159–174 (1984). Open bonds and single broken bonds represent approximate coordinates of the two symmetry-related configurations of the Hb1.1 di$\alpha$-chain termini: $\alpha$1-Gly-$\alpha$2 (open bonds) and $\alpha$2-Gly-$\alpha$1 (broken bonds). X-ray data to 2.5 Å resolutions were collected from a single crystal on a FAST/MADNES area detector with a rotating anode source. Absorption, Lorentz and polarization corrections, and batch scale and temperature factors (batches of 5 degrees rotation in angle $\Phi$), were applied to the raw X-ray data, which were then merged to yield 18231 unique reflections, or 96% of the total between 10 and 2.5 Å resolution. Friedel pairs were measured for 76% of unique reflections; the R-factor of intensity between Friedel pairs in the reduced data set was 6.6% on intensity. The reduced data were converted to amplitudes and scaled to native deoxy HbA data with an R-Factor of 16%. The difference map was calculated with phases obtained from the atomic model of deoxy Hb.

In order to study the effect of these modifications on the structure of Hb we crystallized rHb1.1 in the deoxy form and solved the structure by X-ray crystallography. FIG. 32. shows a symmetry averaged difference Fourier map of rHb1.1 minus deoxy Hb A in the C-terminal region of one α subunit. The peptide linkage between the two α subunits breaks the molecular, dyad symmetry of the Hb tetramer. In deoxyhemoglobin crystals with space group P21, the molecular two-fold axis is not a crystallographic two-fold axis, so that the electron density maps outline the structure of the symmetry-related αβ-dimers separately. In FIG. 32 these are superimposed. The filled bonds and single broken bonds represent approximate coordinates of the two symmetry-related configurations of the rHb1.1 α-chain termini: α 1-Gly-α2 (open bonds) and α2-Gly-α1 (broken bonds). α1 and α2 refer to two α subunits related by a non-crystallographic dyad axis in each asymmetric unit of the p21 deoxyhemoglobin crystals, but not the order in the tandemly duplicated polypeptide. The similarity of the unaveraged difference map in the two regions near Na1α1/HC3α2 and NA1α2/HC3α1 indicates that the two configurations are present at nearly equal occupancies. Positive densities bridging the N- and C-termini indicate that the glycine residue link the C-terminus of one α chain to the N-terminus of the symmetry related α subunits. The negative and positive densities around a few residues near both N- and C-termini indicate that fusion of the two α subunit slightly constrains the conformation of both termini. The Asn-108μ→Lys 5 mg/ml mutation causes substantial structural changes including a shift of the B and G helices shown by paired positive and negative densities along these two helices (not illustrated) but the structural basis of the reduced affinity is not clear.

Figure 33:
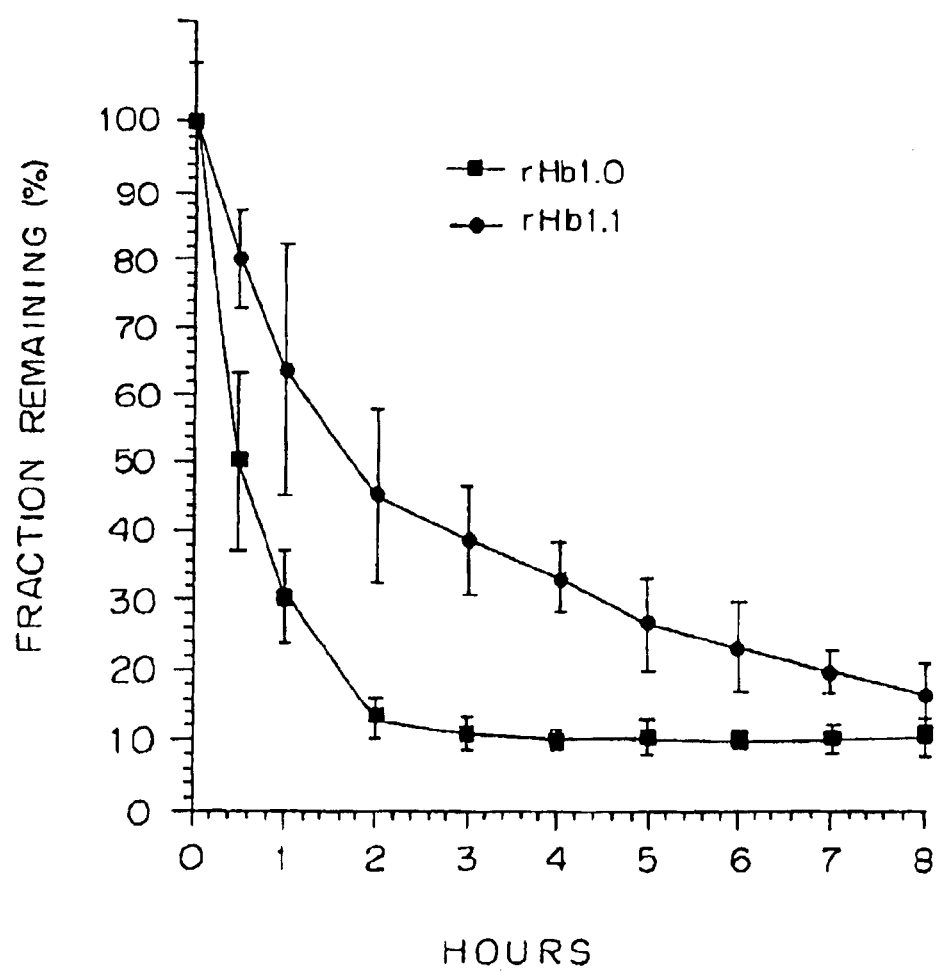
FIG. 33 In vivo half-life of rHb1.1 and rHb1.0. The fraction of $^3$H-rHb1.0 or rHb1.1 remaining in the intravascular compartment is shown in the y axis. The value for 100% was determined from samples taken 5 min. after administration of the hemoglobin samples. Radioactive hemoglobin was prepared by adding 5 C mCi or $^3$H-leucine (Anersham, 1100–1500 Ci/mMole) to 2L fermentors of E. coli JM109[pSGE1.1-E4] or JM109[pSGE1.0-E4] 15 min. prior to induction with IPTG. Hemoglobin was purified essentially as described, Hoffman, S. J., Looker, D. L., Roehrich, J. M., Cozart P., Durfee, S., Stetler G., Proc. Nat. Acad. Sci. (USA) 87, 8521–25 (1990), and combined with unlabeled rHb1.1 or rHb1.0 to adjust the specific activity to $8.3\times10^3$ dpm/mg (rHb1.1.) and $9.5\times10^3$ dpm/mg (rHb1.0). Eight Sprague-Dawley rats (200–300 gm) in two groups of four were administered either 1 ml of $^3$H-rHb1.1 (156 mg/ml) or 1 ml of $^3$H-rHb1.0 through a venous catheter. Blood samples (0.2 ml) were removed at 5 min. 30 min. 1,2,3,4,5,6,7, and 8 hours from an arterial catheter. The animals were anesthetized with a mixture of ketamine hydrochloride and xylazine by intramuscular injection prior to insertion of catheters and allowed to recover for three days prior to administration of hemoglobin solutions.

To test whether or not the fusion of the a subunits extends the intravascular half-life of hemoglobin, we prepared radioactively labelled rHb1.1 and rHb1.0 for in vivo studies in rats. As shown in FIG. 33, rHb1.1 containing fused a subunits shows a significant increase in intravascular half-life compared to its non-fused homologue. More comprehensive toxicology and pharmacokinetic studies in rats and dogs indicate that renal toxicity associated with tetrameric hemoglobin has been eliminated by the fusion of the two α-chains of rHb1.1. These results are consistent with those reported for chemically crosslinked hemoglobins. Bucci, E., Razynska, A., Urbaitis, B., Fronticelli, C., J. Biol. Chem. 264, 6191–95 (1989); Manning, L. R., et al., Proc. Natl. Acad. Sci (USA) 88, 3329–33 (1991). However, in contrast to chemically cross-linked hemoglobins, large amounts of genetically fused diα-haemoglobin can be produced by simple microbial fermentations and purified without the additional steps or chemicals required to produce chemically cross-linked hemoglobins. Our novel engineered Hb therefore provides a most promising way of producing a safe blood substitute.

EXAMPLE 31

Hypothetical Protocol for the Construction of Hemoglobin Molecules Stabilized Against Dimer Formation by Fusion Across the Alpha 1- Beta 2 or Alpha 2- Beta 1 Dimer Interface Region The currently employed inter-dimer di-alpha fusion between the C terminus of one alpha subunit and the N terminus of the adjacent alpha subunit, represents a successful protein engineering approach to stabilizing hemoglobin against dimer formation. In this case, use was made of the fortunate juxtaposition of the two termini which originate from different dimers. One might also make a di-beta polypeptide, as has been described, or a hemoglobin with both di-alpha and di-beta polypeptide, as has been described, or a hemoglobin with both di-alpha and di-beta linked subunits. Alternatively, one can envision other types of fusion in which the alpha subunit of one alpha/beta dimer is fused to the beta subunit of the other dimer (FIG. 1). In this, two individual, linked polypeptides woudl dimerize to form the psuedo-tetrameric hemoglobin. This approach is based on the fact that dimerization involves specific, identical pairs of subunits, generally referred to as α 1μ1 and α2β2.

As an example of this alternative fusion approach, the alpha subunit C terminal residue (Arg 141) of dimer 1 could be fused, either directly or with an intervening fusion sequence, to the N-terminal amino acid of the beta subunit C helix (Tyr 35) of dimer 2. This would create a new C terminal residue at the end of the beta B helix (Val 34) and would leave a "free" piece of polypeptide comprised of the beta A and B helices (residues 1 to 34 inclusive). These alterations would give rise to a protein comprised of alpha subunit helices A through H fused to beta subunit helices C through H. The polypeptide composed of the beta subunit A and B helices would be covalently attached to the protein by introducing a new helix into the molecule. The helix would be designed to span the distance between the beta C terminus (His 146) and the original beta N terminus of helix A (Val 1). Following these changes, the sequence of helices from the N to C terminus of the new protein would be (alpha) A-B-C-E-F'-F-G-H-(beta)-C-D-E-F'-F-G-H-NEW-A-B. The actual arrangement or the fusion regions would require careful design so that new regions of structure did not extend into the dimer-dimer interface region which is critical to cooperativity. Introduction of amino acids containing basic or acidic residues into the molecule at certain positions could allow some restoration of functionally important salt bridges and hydrogen bonds which could be lost as a result of manipulating the normal N and C termini. The above approach could also extend to the production of the entire hemoglobin molecule or individual dimers as single polypeptide chains, although in the latter case this would not be expected to offer stabilization against dimer formation.

For the purpose of providing the potential for disulfide bond formation, a cysteine may be introduced into either the α or β globin domain of the $\alpha_1\beta_2$ pseudodimer.

EXAMPLE 32

Production of Recombinant Hemoglobin in *E. Coli*

32.1 Fermentation

The two liter fermentation procedures described below can be used to obtain material for purification and functionality determinations.

To prepare the fermenter inoculum, 400 μl of seed stock are inoculated into 200 mL of 4.1 g/L $KH_2PO_4$, 7.0 g/L $KHPO_4$, 2.0 g/L $(NH_4)_2SO_4$, 1.0 g/L $Na_3Citrate.2H_2O$, 154 mg/L $MgSO_4.7H_2O$, up to 230 mg of proline, 0.2% yeast extract, 1% glucose, 300 μl of 20 mg/ml thiamine in sterile-filtered solution, 133 μl of 15 mg/ml tetracycline, and 0.6 ml of a trace metla solution. The trace metal solution contains 25 μg/ml $FeCl_3+6H_2O$, 1.3 μg/ml $ZnCl_2$, 2.0 μg/ml $CoCl_2+6H_2O$, 2 μg/ml $Na_2MoO_4+2H_2O$, 1.0 μg/ml $CaCl_2+2H_2O$, 2.54 μg/ml $Cu(II)SO_4+5H_2O$, 0.5 μg/ml $H_3BO_3$, 1.2 μg/ml $MnCl_2+4H_2O$, and 100 μl/ml HCl dissolved in a 0.5 M Na-citrate solution. This culture is allowed to grow at 37° C. on a shaker until an O.D. 600 nm of 0.4–0.6 is achieved. The entire inoculum is then aseptically transferred to a 2-liter fermentor containing 2 g/L $KH_2PO_4$, 3.6 g/L $KHPO_4$, 2.0 g/L $(NH_4)_2SO_4$, 1 mL/L polypropylene glycol-2000, 50 mL/L of 50% glucose, 100 mg/L of thiamine, 9.75 mg/L of tetracycline, 4 mL/L of trace metals, 1.54 g/L $MgSO_4.7H_2O$ and 3.68 g/L $Na_3Citrate.2H_2O$. The pH is maintained at 6.8 by addition of 15% to 30% $NH_4OH$, dissolved oxygen is maintained at or above 30%, and 60% glucose is added throughout the growth period, sufficient to maintain low but adequate levels of glucose in the culture (0.5 g/L–10 g/L). The culture is grown between 25 and 30° C. to an OD600 10–40 prior to induction with 10–1000 μM IPTG. Upon induction of hemoglobin synthesis, the *E. coli* heme biosynthesis is supplemented by addition of hemin, either by addition of the total mass of hemin required at induction, or by periodic addition of hemin dissolved in 50 mM to 1 M NaOH (e.g. one third of the total mass of hemin to be added to the fermentor is added at induction, another third is added after ¼ of the total time after fermentation has elapsed, and the last third is added half-way through the induction period). Total hemin added can range from 50 to 300 mg/L. The fermentor is allowed to continue for 8–12 hours post-induction. At the end of this period, several 1 ml aliquots are removed from the broth for determination of hemoglobin production.

32.2 Culture Harvest Breakage and Lysate Preparation

Cells can be harvested by centrifugation at 10,000×g for 10 minutes or they can be collected by filtration by cross-flow filtration with 0.2 μm membranes (e.g., Millipore Prostak). The cells are washed or resuspended to 309% (w/v) in a 25 mM Na-borate/2 mM EDTA buffer (pH 9.3). Lysozyme (final conc. 0.02 g/L) and protease inhibitor(e.g., 1 mM benzamidine or 50,000 I.U./L aprotonin) are added to the preparation. The suspended cells are allowed to incubate for 30 minutes at 30–31° C., and then are broken by one or more passes through a homogenizer such as a Gaulin Model 30-CD™ Homogenizer operated between 10 and 14 Kpsi or a Microfluidics Corp. Cell Disruptor Microfluidizer™ set at 13 Kpsi. The remainder of the process may be performed either under oxygen or nitrogen. The temperature of the lysate may be adjusted to 40° C. or the solution may be utilized directly.

The lysed cells are then titrated to above pH 6.8, preferably about 8.3, with 5 N NaOH. Conductivity is adjusted to 30 Kmhos by addition of NaCl. The broken cell extract is clarified and the cell debris washed with borate buffer containing protease inhibitor (as above) by ultrafiltration. Since the hemoglobin product is soluble, it passes through the filtration membranes.

After clarification all subsequent steps are performed in the cold (<10° C.). The solution may be purified by passage through either a strong cation exchange column (C), followed by a second strong cation exchange column (C) followed by a strong anion exchange column (A), or by passage through C, then A then C, or alternatively. A, C, then A, or finally simply by passage through only one strong cation exchange column followed by A. Below we describe one possible purification scheme. The CCA column purification order is described here.

The solution is oxygenated, then enough 10mM sodium phosphate buffer is added to the preparation to bring the conductivity down to ≧1800 mmhos. The resulting solution is then titrated to pH 6.7–7.0 with 0.5–5N $H_3PO_4$, loaded onto a strong cation exchange column (such as BioRad Macro-Prep 50 S column, IPF Biotechnics S-CPI or S-Spherodex columns, PerSeptive Biosystems Poros™ S or HS/MII columns, a Pharmacia S-Sepharose Fast Flow column, a TosoHaas Toyopearl™ SP-550C colum, or Whatman SE52 or SE53 columns) pre-equilibrated with 10 mM sodium phosphate, washed, and then eluted with 14–20 mM sodium phosphate buffer at pH 7.4–7.7. A fraction collector can be used to collect fractions of interest. Alternatively, the solution may be further processed as described below.

A second cation exchange step can De performed. The solution from the first cation exchange step is diluted with an equal volume of deionized water, and the pH is adjusted to 6.8 with 5N phosphoric acid to provide adequate binding conditions for the second cation exchange column. A strong cation exchanger such as those listed above is used. The column is pre-equilibrated with 10 mM sodium phosphate, pH6.8. After loading, the bound protein on the column is washed with approximately 2 column volumes of the equilibration buffer. A 14 mM sodium phosphate, pH7.4 wash, is then used to selectively elute the protein. During elution, the column effluent is monitored for total protein by UV absorbance at 280 nm.

Additional purification of recombinant hemoglobin can be achieved by means of an anion exchange column such as BioRad Macro-Prep 50 Q column, PerSeptive BioSystems Poros™ Q column, Pharmacia Q-Sepharose Fast Flow column, TosoHaas Toyopearl™ QAE-550C column, or Whatman BioSystems QA52 or DE53 column. Prior to use, the column is equilibrated with 20 mM tris-HCl buffer, pH 8.3. Material from the second cation exchange elution is diluted or diafiltered with 20 mM tris-HCl buffer, pH 8.3 to allow binding to the chromatography resin. After loading, the column is washed with 2 column volumes of equilibration buffer, and the protein eluted with 30 mM tris-HCl buffer, pH 7.2.

Concentration/Buffer Exchange

Protein from the final chromatography step can be concentrated and exchanged into 5 mM sodium phosphate/150 mM sodium chloride, pH 7.3 with a 30,000 molecular weight cutoff ultrafiltration membrane.

REFERENCE EXAMPLE A

Reconstitution of Recombinant Alpha-Globin and Recombinant Beta-Globin with Heme and Chemical Reduction to Yield Artificial Hemoglobin Conventional methods of preparing artificial hemoglobin are exemplified by the following procedure.

The lyophilized recombinant alpha and beta-globins (100 mg each) were individually dissolved in 8M urea/50 mM TrisCl, pH 8.01/1 mM EDTA/1 mM DTT, diluted to a concentration of 5 mg/ml and incubated at room temperature for 3–4 hours. The alpha-globin was then diluted to 0.3 mg/ml with chilled 20 mM $K_2HPO_4$, pH 5.7/1 mM EDTA/1 mM DTT. Hemin (25 mg) was dissolved in 2.4 mg 0.1M KOH, diluted with an equal volume of 1M KCN; this solution was then made 0.1 mg/ml in hemin and 20 mM $K_2HPO_4$, pH 6.7 with stock phosphate buffer. Hemin from this solution was added at a 2.8 molar excess to the chilled alpha globin; and equal molar amount of beta globin was added and the solution was dialyzed at 4° C. overnight against 0.114 $K_2HPO_4$, pH 7.6/1 mM EDTA/1 mM KCN. The artificial hemoglobin solution was concentrated by ultra-filtration using a PM-10 membrane (Amicon) and transferred into a 200 ml screw-top test tube with a rubber septum. The hemoglobin solution was deoxygenated by evacuation and flushing with $N_2$, and then the solution was saturated with CO. 100 mM sodium dithionite solution was prepared anaerobically in a 20 ml screw-top test tube with rubber septum. 4.5 equivalents of dithionite were added to the hemoglobin solution with a syringe, and the mixture incubated on ice for 15 min. The hemoglobin solution was gel-filtered against 10 mM Na phosphate buffer pH 6.0 on a 4×40 cm Sephadex G-25 (fine) column. The colored solution was then applied to a 2×10 cm-52 (Whatman) column equilibrated with the same buffer and the chromatography was developed with a linear gradient of 500 ml 10 mM Na phosphate buffer pH 6.0 and 500 ml of 70 mM sodium phosphate buffer pH 6.9. CO was removed from hemoglobin by photolysis under a stream of oxygen. Artificial hemoglobin prepared this way is isolated in only about 25% yield from the fusion peptides but shows native oxygen binding properties.

REFERENCE EXAMPLE B

$P_{50}$ Determination

Our preferred method of measuring P50 of purified hemoglobin solutions for the purpose of the appended claims is as follows:

Hemoglobin-Oxygen equilibrium curves are measured using a Hemox Analyzer™ (TCS Medical Products, Southampton, Pa.) at either 25° C. or 37° C.+0.1° C. in 50 mM HEPES buffer/0.1 M NaCl, pH 7.4. Oxygen equilibrium curves are measured by $N_2$ deoxygenation of an oxyhemoglobin solution that has been previously equilibrated with water-saturated $O_2$ (for samples with a P50>10 torr) or with water-saturated compressed air. Absorbance readings at 568 and 558 nm are measured throughout the run for determination of percent oxyhemoglobin in the sample. Percent oxyhemoglobin is directly proportional to log $A\lambda558/10$ g $A\lambda568$ and is independent of path length. Both the absorbances and the oxygen pressure are sampled by a programmable-gain 12-bit analog-to-digital converter (Labmaster PGH, Scientific Solutions, Solon, Ohio) under computer control. The oxygen equilibrium curve is subjected to a low-pass digital filter. $P_{50}$ values (partial pressure of $O_2$ required for 50% saturation of oxygen binding sites) and Hill coefficients ("max) are calculated from the digitally filtered data by using software developed in our laboratory. The Hill coefficients are determined as the maximum slope of the functions $dlog[y/(1-y)]/dlog\ p$, where y is % $O_2$ saturation and p is partial pressure of $O_2$.

$P_{50}$ may also be measured under other conditions, but it should be noted that many environmental factors affect hemoglobin's oxygen affinity. The effect of pH, $CO_2$ inorganic anions, organic phosphates and temperature on $P_{50}$ are discussed in Bunn and Forget, HEMOGLOBIN: MOLECULAR, GENETIC AND CLINICAL ASPECTS 37–47, 95–98 (W. B. Saunders Co., 1986).

Since many determinations of whole blood oxygen binding curves are made under standard physiologic conditions (37° C., pH, 7.4, $PCO_2$40 mm Hg), it may be necessary to adjust literature figures. In this context, it should be noted that a 10° C. increase results in nearly a two-fold increase in $P_{50}$, while the dependence of $P_{50}$ on pH is approximately given as delta log $P_{50}$/delta pH=–0.5.

Comparing $P_{50}$ values of purified hemoglobin preparations to $P_{50}$ values of whole blood can be problematic. Whole blood, or isolated red blood cell's contain many components that naturally modulate the shape of the hemoglobin-oxygen binding curve. The red blood cell encapsulates Hemoglobin in the presence of a high concentration of the effector molecule 2,3-DPG; a molecule that causes hemoglobin to have a markedly lower affinity for $O_2$. Other intra-erythrocyte components also affect the shape of the binding curve: ATP, $ClCO_2$, H+, orthophosphate, methemoglobin and carboxyhemoglobin. The levels of these substances may vary with age, sex and condition. These substances are not normally present in purified hemoglobin solutions and thus, the $P_{50}$ value of purified hemoglobin is lower than that found in whole blood. One very important modulator of hemoglobin-oxygen affinity is Cl- ion. Cl ion is found outside the erythrocyte in the blood serum at a physiologic concentration of approximately 0.15M. Since Cl- causes a lower $O_2$ affinity, a hemoglobin solution with a $P_{50}$ measured in vitro may well have much lower $O_2$ affinity if infused into the blood stream. Another problem with measuring $O_2$ binding of whole blood is that red blood cells are quite fragile and in the process of manipulating the erythrocyte into the instrument used to measure the $O_2$ binding it is inevitable that at least a small percentage of the red blood cells will lyse. Lysed red blood cells leak hemoglobin into the surrounding media away from 2,3-DPG; hence, since free hemoglobin has a higher affinity than intraerythrocyte hemoglobin, lysed red blood cells will have a higher $O_2$ affinity and can cause a falsely low $P_{50}$ value for whole blood $P_{50}$ determinations. It is widely accepted that under physiologic conditions while blood has a $P_{50}$ value of 26–28 mm Hg. When hemoglobin is isolated from whole blood, however, the measured $P_{50}$ is on the order of 1–10 mm hg depending on the investigator's experimental conditions. For these reasons it is most accurate to measure hemoglobin-oxygen equilibria with purified Hemoglobin molecules under strict conditions of buffer, pH and salt concentrations. Unfortunately, there are no accepted "standards" for all investigators to measure hemoglobin oxygen binding for in vitro systems.

Still, as many mutant hemoglobins are first to compare the relative affinities of native and mutant hemoglobin for $O_2$, between whole blood and purified hemoglobin preparations. An example of this is hemoglobin Chico (beta $lys^{66}$-thr). If one examined only the $P_{50}$ value of the purified mutant hemoglobin (10.1 mmHg) one would note that hemoglobin has a $P_{50}$ value less than that for normal whole blood (27.2 mmHg). Still, when that hemoglobin is measured in red blood cells under physiologic conditions it is apparent that it does have a higher $P_{50}$ than normal whole blood (38 mmHg). One cannot predict the degree that the $P_{50}$ value will change going from whole blood Chico to a purified hemoglobin Chico if it were infused into the blood stream as a blood substitute. One can conclude however, that the $P_{50}$ will be higher than it is in pure form and that by reacting the mutant hemoglobin with organic phosphates that $P_{50}$ will be even higher.

TABLE 1

PRIMARY STRUCTURE OF HUMAN GLOBIN SUBUNITS

| Helix | α | Zeta | Helix* | β | δ | Gamma | ε |
|---|---|---|---|---|---|---|---|
| NA1 | 1 Val | Ser | NA1 | 1 Val | Val | GLY | Val |
|  |  |  | NA2 | 2 His | His | His | His |
| NA2 | 2 Leu | Leu | NA3 | 3 Leu | Leu | Phe | Phe |
| A1 | 3 Ser | Thr | A1 | 4 Thr | Thr | Thr | Thr |
| A2 | 4 Pro | Lys | A2 | 5 Pro | Pro | Glu | Ala |
| A3 | 5 Ala | Thr | A3 | 6 Glu | Glu | Glu | Glu |
| A4 | 6 Asp | Glu | A4 | 7 Glu | Glu | Asp | Glu |
| A5 | 7 Lys | Arg | A5 | 8 Lys | Lys | Lys | Lys |
| A6 | 8 Thr | Thr | A6 | 9 Ser | Thr | Ala | Ala |
| A7 | 9 Asn | Ile | A7 | 10 Ala | Ala | Thr | Ala |
| A8 | 10 Val | Ile | A8 | 11 Val | Val | Ile | Val |
| A9 | 11 Lys | Val | A9 | 12 Thr | Asn | Thr | Thr |
| A10 | 12 Ala | Ser | A10 | 13 Ala | Ala | Ser | Ser |
| A11 | 13 Ala | Met | A11 | 14 Leu | Leu | Leu | Leu |
| A12 | 14 Trp | Trp | A12 | 15 Trp | Trp | Trp | Trp |
| A13 | 15 Gly | Ala | A13 | 16 Gly | Gly | Gly | Ser |
| A14 | 16 Lys | Lys | A14 | 17 Lys | Lys | Lys | Lys |
| A15 | 17 Val | Ile | A15 | 18 Val | Val | Val | Met |
| A16 | 18 Gly | Ser |  |  |  |  |  |
| AB1 | 19 Ala | Thr |  |  |  |  |  |
| B1 | 20 His | Gln | B1 | 19 Asn | Asn | Asn | Asn |
| B2 | 21 Ala | Ala | B2 | 20 Val | Val | Val | Val |
| B3 | 22 Gly | Asp | B3 | 21 Asp | Asp | Glu | Glu |
| B4 | 23 Glu | Thr | B4 | 22 Glu | Ala | Asp | Glu |
| B5 | 24 Tyr | Ile | B5 | 23 Val | Val | Ala | Ala |
| B6 | 25 Gly | Gly | B6 | 24 Gly | Gly | Gly | Gly |
| B7 | 26 Ala | Thr | B7 | 25 Gly | Gly | Gly | Gly |
| B8 | 27 Glu | Glu | B8 | 26 Glu | Glu | Glu | Glu |
| B9 | 28 Ala | Thr | B9 | 27 Ala | Ala | Thr | Ala |
| B10 | 29 Leu | Leu | B10 | 28 Leu | Leu | Leu | Leu |
| B11 | 30 Glu | Glu | B11 | 29 Gly | Gly | Gly | Gly |
| B12 | 31 Arg | Arg | B12 | 30 Arg | Arg | Arg | Arg |
| B13 | 32 Met | Leu | B13 | 31 Leu | Leu | Leu | Leu |
| B14 | 33 Phe | Phe | B14 | 32 Leu | Leu | Leu | Leu |
| B15 | 34 Leu | Leu | B15 | 33 Val | Val | Val | Val |
| B16 | 35 Ser | Ser | B16 | 34 Val | Val | Val | Val |
| C1 | 36 Phe | His | C1 | 35 Tyr | Tyr | Tyr | Tyr |
| C2 | 37 Pro | Pro | C2 | 36 Pro | Pro | Pro | Pro |
| C3 | 38 Thr | Gln | C3 | 37 Trp | Trp | Trp | Trp |
| C4 | 39 Thr | Thr | C4 | 38 Thr | Thr | Thr | Thr |
| C5 | 40 Lys | Lys | C5 | 39 Gln | Gln | Gln | Gln |
| C6 | 41 Thr | Thr | C6 | 40 Arg | Arg | Arg | Arg |
| C7 | 42 Tyr | Tyr | C7 | 41 Phe | Phe | Phe | Phe |
| CE1 | 43 Phe | Phe | CD1 | 42 Phe | Phe | Phe | Phe |
| CE2 | 44 Pro | Pro | CD2 | 43 Glu | Glu | Asp | Asp |
| CE3 | 45 His | His | CD3 | 44 Ser | Ser | Ser | Ser |
| CE4 | 46 Phe | Phe | CD4 | 45 Phe | Phe | Phe | Phe |
|  |  |  | CD5 | 46 Gly | Gly | Gly | Gly |
| CE5 | 47 Asp | Asp | CD6 | 47 Asp | Asp | Asn | Asn |
| CE6 | 48 Leu | Leu | CD7 | 48 Leu | Leu | Leu | Leu |
| CE7 | 49 Ser | His | CD8 | 49 Ser | Ser | Ser | Ser |
| CE8 | 50 His | Pro | D1 | 50 Thr | Ser | Ser | Ser |
|  |  |  | D2 | 51 Pro | Pro | Ala | Pro |
|  |  |  | D3 | 52 Asp | Asp | Ser | Ser |
|  |  |  | D4 | 53 Ala | Ala | Ala | Ala |
|  |  |  | D5 | 54 Val | Val | Ile | Ile |
|  |  |  | D6 | 55 Met | Met | Met | Leu |
| CE9 | 51 Gly | Gly | D7 | 56 Gly | Gly | Gly | Gly |
| E1 | 52 Ser | Ser | E1 | 57 Asn | Asn | Asn | Asn |
| E2 | 53 Ala | Ala | E2 | 58 Pro | Pro | Pro | Pro |
| E3 | 54 Gln | Gln | E3 | 59 Lys | Lys | Lys | Lys |
| E4 | 55 Val | Leu | E4 | 60 Val | Val | Val | Val |
| E5 | 56 Lys | Arg | E5 | 61 Lys | Lys | Lys | Lys |
| E6 | 57 Gly | Ala | E6 | 62 Ala | Ala | Ala | Ala |
| E7 | 58 His | His | E7 | 63 His | His | His | His |
| E8 | 59 Gly | Gly | E8 | 64 Gly | Gly | Gly | Gly |
| E9 | 60 Lys | Ser | E9 | 65 Lys | Lys | Lys | Lys |
| E10 | 61 Lys | Lys | E10 | 66 Lys | Lys | Lys | Lys |
| E11 | 62 Val | Val | E11 | 67 Val | Val | Val | Val |
| E12 | 63 Ala | Val | E12 | 68 Leu | Leu | Leu | Leu |
| E13 | 64 Asp | Ala | E13 | 69 Gly | Gly | Thr | Thr |
| E14 | 65 Ala | Ala | E14 | 70 Ala | Ala | Ser | Ser |
| E15 | 66 Leu | Val | E15 | 71 Phe | Phe | Leu | Phe |
| E16 | 66 Thr | Gly | E16 | 72 Ser | Ser | Gly | Gly |
| E17 | 68 Asn | Asp | E17 | 73 Asp | Asp | Asp | Asp |
| E18 | 69 Ala | Ala | E18 | 74 Gly | Gly | Ala | Ala |
| E19 | 70 Val | Val | E19 | 75 Leu | Leu | Ile, Thr | Ile |
| E20 | 71 Ala | Lys | E20 | 76 Ala | Ala | Lys | Lys |
| EF1 | 72 His | Ser | EF1 | 77 His | His | His | Asn |
| EF2 | 73 Val | Ile | EF2 | 78 Leu | Leu | Leu | Met |
| EF3 | 74 Asp | Asp | EF3 | 79 Asp | Asp | Asp | Asp |
| EF4 | 75 Asp | Asp | EF4 | 80 Asn | Asn | Asp | Asn |
| EF5 | 76 Met | Ile | EF5 | 81 Leu | Leu | Leu | Leu |
| EF6 | 77 Pro | Gly | EF6 | 82 Lys | Lys | Lys | Lys |
| EF7 | 78 Asn | Gly | EF7 | 83 Gly | Gly | Gly | Pro |
| EF8 | 79 Ala | Ala | EF8 | 84 Thr | Thr | Thr | Ala |
| F1 | 80 Leu | Leu | F1 | 85 Phe | Phe | Phe | Phe |
| F2 | 81 Ser | Ser | F2 | 86 Ala | Ser | Ala | Ala |
| F3 | 82 Ala | Lys | F3 | 87 Thr | Gln | Gln | Lys |
| F4 | 83 Leu | Leu | F4 | 88 Leu | Leu | Leu | Leu |
| F5 | 84 Ser | Ser | F5 | 89 Ser | Ser | Ser | Ser |
| F6 | 85 Asp | Glu | F6 | 90 Glu | Glu | Glu | Glu |
| F7 | 86 Leu | Leu | F7 | 91 Leu | Leu | Leu | Leu |
| F8 | 87 His | His | F8 | 92 His | His | His | His |
| F9 | 88 Ala | Ala | F9 | 93 Cys | Cys | Cys | Cys |
| FG1 | 89 His | Tyr | FG1 | 94 Asp | Asp | Asp | Asp |
| FG2 | 90 Lys | Ile | FG2 | 95 Lys | Lys | Lys | Lys |
| FG3 | 91 Leu | Leu | FG3 | 96 Leu | Leu | Leu | Leu |
| FG4 | 92 Arg | Arg | FG4 | 97 His | His | His | His |
| FG5 | 93 Val | Val | FG5 | 98 Val | Val | Val | Val |
| G1 | 94 Asp | Asp | G1 | 99 Asp | Asp | Asp | Asp |
| G2 | 95 Pro | Pro | G2 | 100 Pro | Pro | Pro | Pro |
| G3 | 96 Val | Val | G3 | 101 Glu | Glu | Glu | Glu |
| G4 | 97 Asn | Asn | G4 | 102 Asn | Asn | Asn | Asn |
| G5 | 98 Phe | Phe | G5 | 103 Phe | Phe | Phe | Phe |
| G6 | 99 Lys | Lys | G6 | 104 Arg | Arg | Lys | Lys |
| G7 | 100 Leu | Leu | G7 | 105 Leu | Leu | Leu | Leu |
| G8 | 101 Leu | Leu | G8 | 106 Leu | Leu | Leu | Leu |
| G9 | 102 Ser | Ser | G9 | 107 Gly | Gly | Gly | Gly |
| G10 | 103 His | His | G10 | 108 Asn | Asn | Asn | Asn |
| G11 | 104 Cys | Cys | G11 | 109 Val | Val | Val | Val |
| G12 | 105 Leu | Leu | G12 | 110 Leu | Leu | Leu | Met |
| G13 | 106 Leu | Leu | G13 | 111 Val | Val | Val | Val |
| G14 | 107 Val | Val | G14 | 112 Cys | Cys | Thr | Ile |
| G15 | 198 Thr | Thr | G15 | 113 Val | Val | Val | Ile |
| G16 | 109 Leu | Leu | G16 | 114 Leu | Leu | Leu | Leu |
| G17 | 110 Ala | Ala | G17 | 115 Ala | Ala | Ala | Ala |

TABLE 1-continued

PRIMARY STRUCTURE OF HUMAN GLOBIN SUBUNITS

| Helix | α | Zeta | Helix* | β | δ | Gamma | ε |
|---|---|---|---|---|---|---|---|
| G18 | 111 Ala | Ala | G18 | 116 His | Arg | Ile | Thr |
| G19 | 112 His | Arg | G19 | 117 His | Asn | His | His |
| GH1 | 113 Leu | Phe | GH1 | 118 Phe | Phe | Phe | Phe |
| GH2 | 114 Pro | Pro | GH2 | 119 Gly | Gly | Gly | Gly |
| GH3 | 115 Ala | Ala | GH3 | 120 Lys | Lys | Lys | Lys |
| GH4 | 116 Glu | Asp | GH4 | 121 Glu | Glu | Glu | Glu |
| GH5 | 117 Phe | Phe | GH5 | 122 Phe | Phe | Phe | Phe |
| H1 | 118 Thr | Thr | H1 | 123 Thr | Thr | Thr | Thr |
| H2 | 119 Pro | Ala | H2 | 124 Pro | Pro | Pro | Pro |
| H3 | 120 Ala | Glu | H3 | 125 Pro | Gln | Glu | Glu |
| H4 | 121 Val | Ala | H4 | 126 Val | Met | Val | Val |
| H5 | 122 His | His | H5 | 127 Gln | Gln | Gln | Gln |
| H6 | 123 Ala | Ala | H6 | 128 Ala | Ala | Ala | Ala |
| H7 | 124 Ser | Ala | H7 | 129 Ala | Ala | Ser | Ala |
| H8 | 125 Leu | Trp | H8 | 130 Tyr | Tyr | Trp | Trp |
| H9 | 126 Asp | Asp | H10 | 131 Gln | Gln | Gln | Gln |
| 10 | 127 Lys | Lys | H10 | 132 Lys | Lys | Lys | Lys |
| H11 | 128 Phe | Phe | H11 | 133 Val | Val | Met | Leu |
| H12 | 129 Leu | Leu | H12 | 134 Val | Val | Val | Val |
| H13 | 130 Ala | Ser | H13 | 135 Ala | Ala | Thr | Ser |
| H14 | 131 Ser | Val | H14 | 136 Gly | Gly | Gly, Ala | Ala |
| H15 | 132 Val | Val | H15 | 137 Val | Val | Val | Val |
| H16 | 133 Ser | Ser | H16 | 138 Ala | Ala | Ala | Ala |
| H17 | 134 Thr | Ser | H17 | 139 Asn | Asn | Ser | Ile |
| H18 | 135 Val | Val | H18 | 140 Ala | Ala | Ala | Ala |
| H19 | 136 Leu | Leu | H19 | 141 Leu | Leu | Leu | Leu |
| H20 | 137 Thr | Thr | H20 | 142 Ala | Ala | Ser | Ala |
| H21 | 138 Ser | Glu | H21 | 143 His | His | Ser | His |
| HC1 | 139 Lys | Lys | HC1 | 144 Lys | Lys | Arg | Lys |
| HC2 | 140 Tyr | Tyr | HC2 | 145 Tyr | Tyr | Tyr | Tyr |
| HC3 | 141 Arg | Arg | HC3 | 146 His | His | His | His |

TABLE 2

Oligonucleotide Sequences Used to Create Di-Alpha Globin Genes $\alpha^1$(Arg)-Gly-Met(Leu)$\alpha_2$ Linker
BstBI                                           EagI
         CGAAATACCGTGGTATGCTGTCTCC (SEQ ID NO:55)
         TTTATGGCACCATACGACAGAGGCCGG (SEQ ID NO:56)

$\alpha^1$(Arg)-Gly-Gly(Val)$\alpha_2$ Linker
BstBI                                           EagI
         CGAAATACCGTGGTGGTGTTCTGTCTCC (SEQ ID NO:57)
         TTTATGGCACCACCACAAGACAGAGGCCGG (SEQ ID NO:58)

$\alpha^1$(Arg)-Gly(Val)$\alpha_2$ Linker
BstBI                                           EagI
         CGAAATACCGTGGTGTTCTGTCTCC (SEQ ID NO:59)
         TTTATGGCACCACAAGACAGAGGCCGG (SEQ ID NO:60)

$\alpha^1$(Arg)-Gly-Gly(Leu)$\alpha_2$
BstBI                                           EagI
         CGAAATACCGTGGTGGTCTGTCTCC (SEQ ID NO:61)
         TTTATGGCACCACCAGACAGAGGCCGG (SEQ ID NO:62)

$\alpha^1$(Arg)-(Val)$\alpha_2$
BstBI                                           EagI
         CGAAATACCGTGTTCTGTCTCC (SEQ ID NO:63)
         TTTATGGCACAAGACAGAGGCCGG (SEQ ID NO:64)

TABLE 3

Oligonucleotide Sequences to Create Beta Globin Mutations $\beta^{67}$val-->ile
    NcoI                                                              Kpn1
    CATGGTAAAAAAatcCTGGGTGCTTTCTCTGACGGTCTGGCTCACCTGGACAACCTGAAAGGTAC (SEQ ID NO:65)
         CATTTTTTtagGACCCACGAAAGAGACTGCCAGACCGAGTGGACCTGTTGGACTTTC (SEQ ID NO:66)
$\beta^{67}$val-->ile;$\beta^{82}$ lys-->arg
    NcoI                                                              Kpn1
    CATGGTAAAAAAatcCTGGGTGCTTTCTCTGACGGTCTGGCTCACCTGGACAACCTGcgtGGTAC (SEQ ID NO:67)
         CATTTTTTtagGACCCACGAAAGAGACTGCCAGACCGAGTGGACCTGTTGGACgcaC (SEQ ID NO:68)
$\beta^{102}$asn-->thr
    SacI                                                              SpeI
    CCACTGCGACAAACTGCACGTTGACCCGGAAaccTTCCGTCTGCTGGGTAACGTA (SEQ ID NO:69)
    TCGAGGTGACGCTGTTTGACGTGCAACTGGGCCTTtggAAGGCAGACGACCCATTGCATGATC (SEQ ID NO:70)

TABLE 4

P$_{50}$ Values for Hemoglobin-Like Proteins (37° C.)
Hemoglobin

| des-val | Hgb | 13.3 |
|---|---|---|
| dialpha | (arg-gly-met) Hgb | 9.0 |
| dialpha | beta$^{67}$val->ile Hgb | 24.7 |
| dialpha | (arg-gly-gly-val) Hgb | 9.0 |

TABLE 5

Synthetic Oligonucleotides Used For The Synthesis of pGAP

TCGACTGAAA AAAAAGGTTT AAACCAGTTC CCTGAAATTA TTCCCCTACT TGACTAATAA GTATATAAAG (SEQ ID NO:71)

CAATACCTAC CGTTTATATA CTTATTAGTC AAGTAGGGGA ATAATTTCAG GGAACTGGTT TAAACCTTTT TTTTCAG (SEQ ID NO:72)

ACGGTAGGTA TTGATTGTAA TTCTGTAAAT CTATTTCTTA AACTTCTTGA ATTCTACTTT TATAGTTAGT CTTTTTTTA GTTTT (SEQ ID NO:73)

AAGTTCTTGG TGTTTTAAAA CTAAAAAAAA GACTAACTAT AAAAGTAGAA AGAAGTTTAA GAAATAGATT TACAGAATTA CAAT (SEQ ID NO:74)

AAAACACCAA GAACTTAGTT TCGAATAAAC ACACATAAAT AAACCATGGT TAACT (SEQ ID NO:75)

CTAGAGTTAA CCATGGTTTA TTTATGTGTG TTTATTCGAA ACT (SEQ ID NO:76)

TABLE 6

Synthetic Oiigonucleotides Used For The Synthesis Of The Galctose Upstream Activator CGTACGGATTAGAAGCCGCCGAGCGGGTGACAGCCCTCCGAAGGAAGACTCTCCTCCGTGCG TCCTCGTC TTCACCGGTCGC (SEQ ID NO:77)

AGGACGCACGGAGGAGAGTCTTCCTTCGGAGGGCTGTCACCCGCTCGGGGCTTCTAATCCGT ACGCATG (SEQ ID NO:78)

GTTCCTGAAACGCAGATGTGCCTCGCGCCGCACTGCTCCGAACAAT AAAGATTCTACAATACTAGCTTTT ATGGTTATGAAGAGGAAAAT (SEQ ID NO:79)

ATAACCATAAAAGCTAGTATTGTAGAATCTTTATTGTTCGGAGCAGTGCG GCGCGAGGCACATCTGCGTT TCAGGACGCGAACCGGTGAAGAC (SEQ ID NO:80)

TGGCAGTAACCTGGCCCCACAAACCTCAAATGAACGAAATCAAATTA ACAACCAGATATC TCGAGATATCTGGTTG (SEQ ID NO:81)

TTAATTTGATTCGTTCATTTGAGGTTTGTGG GGCCAGGTTACTGCCAATTTTCCTCTTC (SEQ ID NO:82)

TABLE 7

Codon Preferences in Yeast

| Ala | GCU, GCC |
| Ser | UCU, UCC |
| Thr | ACU, ACC |
| Val | GUU, GUC |
| Ile | AUU, AUC |
| ASP | GAC |
| Phe | UUC |
| Tyr | UAC |
| Cys | UGU |
| Asn | AAC |
| His | CAC |
| Arg | AGA |
| Glu | GAA |
| Leu | UUG |
| Lys | AAG |
| Gly | GGU |
| Gln | CAA |
| Pro | CCA |
| Met | AUG (No alternative codons) |
| Trp | UGG (No alternative codons) |

Source: Bennetzen and Hall, J. Biol. Chem., 257: 3026–31 (1982).

TABLE 8

OLIGONUCLEOTIDES USED FOR THE CONSTRUCTION OF A GENE ENCODING A TANDEM ALPHA GLOBIN DIMER

AL-1SS
    5'-tgcacgcttctttggacaagttcttggcttctgtttctactgtgttaactagtaagt
    acagaggtggtgttttgtctcctgcagacaagactaac-3' (SEQ ID NO:83)
AL-2SS
    5'gttaaggctgcttggggtaaggttggtgctcacgctggtgaatacggtgctgaagcttt
    ggaaaggatgttcttgtct-3' (SEQ ID NO:84)
AL-1AS
    5'-tgcaggagacaaaacaccacctctgtacttactagttaacacagtagaaacagaagcca
    agaacttgtccaaagaagcg-3' (SEQ ID NO:85)
AL-2AS
    5'-ggaaagacaagaacatcctttccaaagcttcagcaccgtattcacccagcgtgagcacc
    aaccttaccccaagcagccttaacgttagtcttgtc-3' (SEQ ID NO:86)

Note:
NcoI-ALPHA-1-ApaLI; FOKI-ALPHA-2-SalI; ApaLI-RGGV-FokI

TABLE 9

Oxygen Affinity Recombinant Mutant Hemoglobin Generated From FX-Hgb and Tryptic Digestion

Oxygen affinity measured at 37° C. in 50 mM Bis-Tris (as opposed to 50 mM HEPES buffer) pH 7.4, 0.1 M NaCl on a Hemox-Analyzer. Solutions were 60 uM in heme and measured between 130 and 1.2 torr oxygen tension.

|  | $P_{50}$ |
| --- | --- |
| AgB $A_0$ | 9.5 |
| rHgB $A_0$ | 9.2 |
| HgB Providence | 10.2 |
| Hgb Kansas | 11.3 |
| HgB (beta$^{67}$val -->ile) | 22.4 |

The value of Hgb $A_0$ is of course for free hemoglobin in solution. The $P_{50}$ of whole blood is much higher.

TABLE 10

Effects of NaCl and Inositol Hexaphosphate on Oxygen Binding to Hemoglobin $A_0$ and Recombinant des-Fx Hgb

|  | $P_{50}$ | | $P_{50}$ | |
| --- | --- | --- | --- | --- |
|  | 0.1 M NaCl | 0 M NaCl | 2.2 mM IHP | 0 M 1HP |
| Hgb $A_0$ | 6.6 | 2.8 | 51.1 | 6.6 |
| des-Fx Hgb | 4.9 | 3.9 | 5.5 | 4.9 |

TABLE 11

**Distribution of FX-Alpha, FX-Beta and FX-Hab in *E. coli*.**

|  | milligrams of protein per OD-liter of *E. coli* | |
| --- | --- | --- |
|  | Soluble | Insoluble |
| FX-Alpha | 36 | 0 |
| FX-Beta | 21 | 21 |
| FX-Hgb | 188 | 0 |

TABLE 100

FERM DATA

| RFE | STRAIN | INDUCT TEMP | FINAL OD | MG DI-A + B | MG/OD-L | MG RHGB | RHGB MG/OD-L |
| --- | --- | --- | --- | --- | --- | --- | --- |
| 1 | BL21 | 30.0 | 6.6 |  |  | 0.0 | 0.0 |
| 5 | BL21HA | 37.0 | 9.3 |  |  | 0.0 | 0.0 |
| 6 | JM109 | 37.0 | 7.1 | 234.0 | 16.5 | 5.5 | 0.6 |
| 7 | JM109 | 37.0 | 11.3 | 372.0 | 16.5 | 25.0 | 1.1 |
| 8 | JM109 | 37.0 | 6.6 | 442.0 | 33.5 | 49.0 | 3.7 |
| 10 | SCS1 | 37.0 | 15.2 | 754.0 | 24.8 | 38.0 | 1.2 |
| 11 | JM109 | 25.0 | 11.5 |  |  | 26.0 | 1.1 |
| 12 | JM109 | 25.0 | 9.5 |  |  | 31.0 | 1.6 |
| 13 | JM109 | 30.0 | 9.0 |  |  | 64.0 | 3.5 |
| 17 | JM109 | 37.0 | 14.4 |  |  | 51.2 | 1.8 |
| 25 | JM110 | 30.0 | 20.5 |  |  | 25.0 | 0.6 |
| 26 | LE392 | 37.0 | 23.0 | 1040.0 | 22.6 | 4.1 | 0.1 |
| 27 | JM110 | 30.0 | 27.0 | 334.0 | 6.2 | 47.0 | 0.9 |
| 30 | JM110 | 37.0 | 23.6 |  |  | 16.0 | 0.3 |
| 31 | 23722 | 30.0 | 25.4 |  |  | 59.0 | 1.2 |
| 35 | W3110 | 30.0 | 18.6 |  |  | 13.0 | 0.3 |
| 38 | AG-1 | 30.0 | 13.0 |  |  | 57.0 | 2.1 |
| 49 | DH-1 | 30.0 | 4.0 |  |  | 7.7 | 0.9 |

TABLE 100-continued

FERM DATA

| RFE | STRAIN | INDUCT TEMP | FINAL OD | MG DI-A + B | MG/OD-L | MG RHGB | RHGB MG/OD-L |
|---|---|---|---|---|---|---|---|
| 50 | NM554 | 30.0 | 14.0 | | | 56.0 | 2.0 |
| 51 | NM554 | 37.0 | 14.5 | | | 18.0 | 0.6 |

TABLE 200

Bacterial and Yeast Vectors

DEFINITIONS:

| | |
|---|---|
| ROP: | Gene which regulates plasmid copy number |
| ROP+: | Low copy number |
| ROP−: | High copy number |
| AR: | ampicillin resistance used for plasmid selection |
| TR: | tetracycline resistance used for plasmid selection |
| TS: | tetracycline sensitive, TR gene not functional |
| E4 | tetracycline resistance used for plasmid selection |
| E5 | tetracycline sensitive, TR gene not functional |
| FX-A: | FX-alpha globin gene |
| FX-B: | FX-beta globin gene |
| DFX-A: | Des-FX alpha globin gene |
| DFX-B: | Des-FX beta globin gene |
| DV-A: | Des-Val alpha globin gene |
| DV-B: | Des-Val beta globin gene |
| RV-Di-alpha: | Di-alpha gene containing no amino acid spacer (R = Arginine; V-Valine) |
| RGV-Di-alpha: | Di-alpha globin gene containing a single glycine (G) linker followed by a valine |
| RGM-Di-alpha: | Di-alpha globin gene containing a single glycine (G) linker followed by a methionine (M) |
| RGGV-Di-alpha: | Di-alpha globin gene containing a two glycine (G) linker followed by a valine |
| RGGGV-Di-alpha: | Di-alpha globin gene containing a three glycine (G) linker followed by a valine |
| RPV-di-alpha: | Di-alpha gene fused by a single proline (P) (yeast only) |
| LACI: | gene encoding a represser which regulates the TAC promoter |
| LAC+: | Lac repressor gene on plasmid |
| LAC−: | no Lac repressor gene on plasmid |

All bacterial plasmids listed below which contain alpha, di-alpha and/or beta genes also have translational couplers. The pPL expression system translationally couples the lambda N protein gene to a globin gene. The designations "E4" and "E5" appear in the names of certain plasmids, and have the meanings above.

pKK223-3

Parental plasmid obtained commercially from Pharmacia LKB, 800 Centennial Ave., P.O. Box 1327 Piscataway, N.J. 08855-1327; all other plasmids derived from this parental plasmid. pKK223-3 has a TAC promoter followed by a poly-restriction site region to facilitate gene insertion.

AR, TS, ROP+, LAC−

1. pDL II-62 m pKK223-3 containing FX-A

AR, TS, ROP+, LAC−

2. pDL II-10a pKK223-2 containing FX-B

AR, TS, ROP+, LAC−

3. PDL II-66A

Parental plasmids are (1) and (2); contains both FX-A and FX-B in single operon

AR, TS, ROP+, LAC−

4. PGEM FX-A

Parental plasmids are (1) and pGem1 which is commerically available from Promega Corporation, 2800 Woods Hollow Rd., Madison, Wis. 53711.

5. PGEM FX-B pGEM containing FX-B, AR

Parental plasmids are (2) and pGEM1

5a. pGEM di-alpha

Parentals are pGEM1 (see discussion of #4) and (2). The SmaI/PstI fragment of (29), containing the di-alpha gene, is excised and ligated into SmaI/PstI-cut pGEM1.

6. pDL II-83a

Parental is 4; contains DFX-A 7. pDL III-6f

Parental is 5; contains DFX-B, AR 8. pDL II-86c

Parentals are pKK223-3 and (6), contains DFX-A, AR, TS, ROP+, LAC−

9. pDL III-13e

Parentals are (7) and (8), pKK223-3 containing both DFX-A and DFX-B, AR, TS, ROP+, LAC−

10. pDL II-91f

Parental is (4) contains DV-A, AR 11. pDL II-95a

Parental is (7) contains DV-B, AR 12. pDL III-1a

Parentals are pKK223-3 and (10), contains DV-A AR, TS, ROP+, LAC−

13. pDL III-14c

Parentals are (11) and (12), contains DV-A and DV-B, AR, TS, ROP+, LAC−

13a. pDL III-38b

Parentals are (11) and (23) p1 AR, TS, ROP+, LAC−

14. pDL III-47a

Parental is (13), contains RGM-di-alpha and DV-B, AR, TS, ROP+, LAC−

15. pDL III-82A Parental is (13), contains RGGV-di-alpha and DV-B, AR, TS, ROP+, LAC−

16. pDL IV-8a

Parental is (13), contains RGV-di-alpha and DV-B, AR, TS, ROP+, LAC−

17. pDL IV-47b

Parental is (13), contains RV-di-alpha and DV-B AR, TS, ROP+, LAC−

18. pDL IV-66a

Parental is (13), contains RGGGV-di-alpha and DV-B, AR, TS, ROP+, LAC−

19. pDL IV-3a

Parental is (15), ROP gene is inactivated by insertion of a Not I linker into the PvuII site within the ROP gene AR, TS, ROP−, LAC−
20. pDL IV-38a
   Parental is (15), contains the Nagai mutation in
   AR, TS, ROP+, LAC−
21. pDL IV-58f
   Parental is (20), ROP gene inactivated as in (19),
   AR, TS, ROP−, LAC−
22. pDL IV-59a
   Parental is (21) and pBR322, which is commercially available from a number of different suppliers. Contains a functional TR gene constructed in the following manner:
      The EcoR1 site of pBR322 was changed to a BamH1 linker. This permitted the removal of the 5' end 5' end of the TR gene from pBR322 as a BamH1 fragment. This fragment was then inserted into the BamH1 site located at the junction of the TAC promoter and the inactive TR gene of pKK223-3. Insertion of this fragment reactivates the TR gene if the fragment inserts in the proper orientation. Selection of colonies on tetracycline plates assures presence of the fragment in the proper orientation.
   AR, TR, ROP−, LAC−
23. pJR V-83a
   Parental is (11), contains DV-B with the Presbyterian mutation (asn108→lys),
   AR, TS, ROP+, LAC−
24. pJR VI-29a
   Parentals are (15) and (23), contains RGGV-di-alpha and DV-B with Presbyterian mutation,
   AR, TS, ROP+, LAC−
25. pJR VI-53b
   Parental is (24), made TR by insertion of BAMH1 fragment,
   AR, TR, ROP+, LAC−
26. pJR VI-61a
   Parental is (25), made ROP− by insertion of Not I linker into PvuII site
   AR, TR, ROP−, LAC−
27. pDL V-4a
   Parentals are (16) and (26), contains RGV-di-alpha and DV-B with Presbyterian mutation
   AR, TS, ROP−, LAC−
28. pDL V-10a
   Parental is (27), insertion of BamH1 fragment to convert to TR
   AR, TR, ROP−, LAC−
29. pDL V-16d (also named pSGE1.1E4 or simply pSGE1.1)
   Parental is (28), contains LACI gene inserted into Not I site. LACI gene obtained using following protocol:
   Polymerase chain reaction (PCR) primers containing NOTI sites at their 5' ends were used to amplify the LACI gen. Following gel purification, the gene was inserted into the NOT I site of pDL V-1a
   AR, TR, ROP−, LAC+
   Several other plasmid constructs have been designed to facilitate the incorporation of a second beta globin gene under regulation of its own TAC promoter.
30. pDL IV-64a
   Parental is (14), contains beta globin under regulation of a synthetic TAC promoter
   AR, TS, ROP+, LAC−
31. pDL IV-67a
   Parental plasmids are (14) and (30), contains di-alpha under regulation of one pTAC, and DV-B under regulation of a second PTAC, DV-B is adjacent to di-alpha
   AR, TS, ROP−, LAC−
32. pJR VI-54a
   Parental plasmids are (14) and (30), contains di-alpha and DV-B under regulation of one pTAC and a second DV-B under regulation of another pTAC. The second DV-B is inserted into the Pvu II site of the plasmid
   AR, TS, ROP−, LAC−
33. pPL Lambda,
   Commercially available plasmid from Pharmacia LKB (see above); contains pL promoter and coding region for N protein of lambda which can be used for expression of fusion or translationally coupled recombinant proteins.
34. pPL-alpha/beta
   Parental plasmids are (13) and (33), contains DV-A and DV-B
   AR, ROP+
35. pPL-dialpha/beta
   Parental is (34), contains RGV-di-alpha and DV-B
   AR, TS, ROP+, LAC−
36. pSGE0.1-L0
   Parental plasmid is (35), ROP gene inactivated by insertion of NotI linker into PvuII site in ROP gene
   AR, ROP−
37. pSGE0.1E4
   Parentals are pSGE1.1E4 (29) and pDL II-95a (11), contains di-alpha globin gene followed by wild type beta globin gene. The wild type beta globin gene from pDL II-95a was excised with PstI and HindIII, gel purified, and ligated into pSGE1.1E4 from which the beta Presbyterian gene had been removed with the same restriction enzymes.
38. pSGE0.0E4
   Parentals are pSGE0.1E4 (37) and pDL II-91f (10), contains di-alpha globin gene followed by wild type beta globin gene. The alpha globin gene from pDL II-91f was excised with SmaI and PstI, gel purified, and ligated into pSGE0.1E4 from which the di-alpha globin gene removed using the same restriction enzymes.
39. pPL lambda+TC
   Parental is pPL lambda (33). pPL lambda was linearized with the restriction enzyme HpaI and synthetic oligonucleotides encoding the translational coupler region, and a portion of the 5' coding region of alpha globin ligated into the HpaI site.
40. pSGE1.0E4
   Parentals are pSGE1.1E4 (29) and pSGE0.0E4 (38), contains a single alpha globin followed by beta globin gene containing the Presbyterian mutation. pSGE0.0E4 was digested with SmaI and PstI, the alpha globin gene gel purified, and ligated into pSGE1.1E4 from which the di-alpha gene had been removed with the same restriction enzymes.
41. pSGE223
   Parental is commercially available pGEM-1. NheI restriction site has been elimiated by digestion with NheI, T4 polymerase filing, and ligation.
42. pSGE224
   pSGE223 containing the beta Presbyterian gene. Parentals are pSGE223 (41) and pSGE1.1E4 (29)

43. pSGE229 pSGE224 containing the 5 glycine di-beta linker sequences

Parental plasmid is pSGE224 (42) The linker sequences are synthetic DNA.

44. pSGE234 contains the di-beta globin gene. Parentals are pSGE224 (42) and pSGE229 (43). The NheI fragment from pSGE229 contains the beta Presbyterian gene and the 5 glycine di-beta linker was ligated into NheI digested pSGE224.

45. pSge1.1E5

Parental is pSGE1.1E4 (29). 5' end of the tet R gene was removed by digestion with BamHI.

45a. pSGE0.0E5

Parental is pSGE0.0E4 (38). BamHI fragment encoding 5' end of tet R gene has been removed.

46. pSGE1.0E5 single alpha globin gene followed by beta Presbyterian gene. Parentals are pSGE0.0E5 (45a) and pJRV-83a (23). The beta globin gene containing the Presbyterian mutation was excised from (23) and ligated into (45a), from which the wild type beta globin gene had been removed with the same two restriction enzymes.

47. pSGE1.05E5 single alpha globin gene followed by 5 glycine linked di-beta gene. Parentals are pSGE234 (44) and pSGE1.0E5 (46). The PstI into HindIII fragment from pSGE234 containing the di-beta gene was ligated into pSGE1.0E5 from which the single beta globin gene had been removed using the same restriction enzymes.

48. pSGE1.05E4

Parentals are pSGE1.05E5 (47) and pSGE1.1E4 (29). The BamHI fragment encoding the 5' end of the tet R gene from pSGE1.1E4 was ligated into the BamHI site of pSGE1.05E5.

Yeast Vectors 49. pSK+

Commercially available from stratagene, LaJolla, Calif.

50. pGS2488

Derived from (49) by insertion of synthetic GAP 491 transcriptional initiation site.

51. pGS2888

Derived from (50) by conversion of KpnI site to SphI site.

52. pGS4788

Derived from (51) by insertion of synthetic $GAL_{UAS}$ into (51) to form GALGAP hybrid promoter.

53. pLC IIFX-β-globin

Plasmid available from Kiyoshi Nagai, Medical Research Council, London, England; bears α globin gene 54. pUC19

Plasmid commercially available from Bethesda Research Laboratories, Gaithersburg, Md.

55. pSUC2-6Σ

Plasmid described by Stetler, et al., Biotechnology, 7:55–60 (1989)

56. pUC19β-globin

Derived from (53) and (54)

57. pGS1188

β-globin gene (from 56) is under control of the sigma promoter and the MFalpha terminator both from (55).

58. pGS3588

Derived from (57) and (52); sigma promoter replaced by GALGAP promoter of (52).

59. pGS3888

Derived from (58) by conversion of SmaI site to XhoI site.

60. pα-MRC

Plasmid available from K. Nagai, MRC; bears alpha-globin gene.

61. pGS4088

Derived from (59) by insertion of α-qlobin gene, replacing the β-globin gene.

62. pSN(+)

Derived from (49) by changing KpnI site to NotI site.

63. pGS4888

Derived from (62) by insertion of pGGAP-α-globin expression cassette from (48).

64. pGS189

Derived from (63) by insertion of pGGAP-β-globin expression cassette from (47). Plasmid thus bears both GALGAP α globin and GALGAP β globin genes.

65. pC1U

Plasmid described by Stetler, et al.; Biotechnology, 7:55–60 (1989)

66. pC1N

Derived from (65) by addition of NotI site.

67. pGS289

Derived from (66) and (64) by insertion of α-globin and β-globin expression cassettes.

68. pGS389

Same as (67), but with insert orientation reversed.

69. pYRp7

Plasmid described in Strathern, et al., *The Molecular Biology of the Yeast Saccharomyces* (Cold Spring Harbor, 1981); source of TRP1 gene.

70. pC1T

Derived from (65) and (69) by replacing Ura3 gene (65) with Trp1 gene (69).

71. pGS4988

Derived from (70) by insertion of β-globin expression cassette from (59).

72. pGS4488

Derived from (65) by insertion of α-globin expression cassette from (61).

73. pGS4688

Same as (72), but with insert orientation reversed.

74. pGS4888

Derived from (62) by insertion of GGAP-alpha globin expression cassette from (61).

75. pGS1889

Derived from (74) by removal of PstI site.

76. pGS1989

Derived from (75) by removal of SpeI site.

77. pGS2189

Derived from (74) and (76); encodes di-alpha globin with RGGV linker.

78. pGS2989

Derived from (77) and (60), contains di-alpha globin gene and beta globin gene.

79. pGS3089

Derived from (66) by insertion of expression cassette from (78).

80. Phagescript

Phage commercially available from Stratagene.

81. Phage Mpβ-globin

Derived from (80) by insertion of GALGAP promoter and β-globin gene from (78).

82. pGS3089 RGV desβ

Derived from (79) by deletion of XhoI fragment containing β-globin expression cassette.

83. pGS3889

(79) with Presbyterian (βN108K) mutation.

84. pGS5189

(79) with Agenogi (βE90K) mutation.

85. pGS5689

(79) with Kansas (βN102T) mutation.

86. pGS4989

(79) with βV67I mutation.

87. pGS2989 RPV

(77) with RPV di-alpha linker 88. pGS2989 RGV

(77) with RGV di-alpha linker 89. pGS3089

(66) with Hgb expression cassette from (88)

90. pGS3089 RPV

(66) with Hgb expression cassette from (87)

TABLE 300

TABLE OF BACTERIAL STRAINS

|   | Strain | Availability | Expression |
|---|--------|--------------|------------|
| 1 | BL21 | Brookhaven | TAC |
| 2 | JM109 | Commercial | TAC |
| 3 | SCS1 | Commercial | TAC |
| 4 | JM110 | ATCC | TAC |
| 5 | LE392 | ATCC | TAC |
| 6 | 23722 | ATCC | TAC |
| 7 | TW3110 | ATCC | TAC |
| 8 | AG-1 | Commercial | TAC |
| 9 | DH1 | ATCC | TAC |
| 10 | NM554 | Commercial | TAC |
| 11 | N99c1+ | Commercial | PL |
| 12 | N4830-1 | Commercial | PL |

TABLE 400

HIGH OXYGEN AFFINITY, NATURALLY OCCURRING HEMOGLOBIN MUTANTS

| Structure | | Name |
|-----------|---|------|
| A. Alpha Chain Mutants | | |
| 6 (A4) | Asp->Ala | Sawara |
|  | Asp->Asn | Dunn |
|  | Asp->Val | Ferndown |
|  | Asp->Tyr | Woodville |
| 11 (A9) | Lys->Asn | Albany-Suma |
| 40 (C5) | Lys->Glu | Kariya |
| 44 (CE2) | Pro->Leu | Milledgeville |
|  | Pro->Arg | Kawachi |
| 45 (CE3) | His->Arg | Fort de France |
| 85 (F6) | Asp->Asn | G-Norfolk |
| 92 (FG4) | Arg->Gln | J-Cape Town |
|  | Arg->Leu | Chesapeake |
| 95 (G2) | Pro->Leu | G-Georgia |
|  | Pro->Ser | Rampa |
|  | Pro->Ala | Denmark Hill |
|  | Pro->Arg | St. Luke's |
| 97 (G4) | Asn->Lys | Dallas |
| 126 (H9) | Asp->Asn | Tarrant |
| 141 (HC3) | Arg->His | Suresnes |
|  | Arg->Ser | J-Cubujuqui |
|  | Arg->Leu | Legnano |

TABLE 400-continued

HIGH OXYGEN AFFINITY, NATURALLY OCCURRING HEMOGLOBIN MUTANTS

| Structure | | Name |
|-----------|---|------|
| B. Beta Chain Mutants | | |
| 2 (NA2) | His->Arg | Deer Lodge |
|  | His->Gln | Okayama |
| 20 (B2) | Val->Met | Olympia |
| 23 (B5) | Val->Asp | Strasbourg |
|  | Val->Phe | Palmerston North |
| 34 (B16) | Val->Phe | Pitie-Salpetriere |
| 36 (C2) | Pro->Thr | Linkoping |
| 37 (C3) | Trp->Ser | Hirose |
| 40 (C6) | Arg->Lys | Athens-Ga |
|  | Arg->Ser | Austin |
| 51 (D2) | Pro->Arg | Willamette |
| 68 (E12) | Leu->His | Brisbane |
| 79 (EF3) | Asp->Gly | G-Hsi-Tsou |
| 82 (EF6) | Lys->Thr | Rahere |
| 82 (EF6) | Lys->Met | Helsinki |
| 89 (F5) | Ser->Asn | Creteil |
|  | Ser->Arg | Vanderbilt |
| 94 (FG1) | Asp->His | Barcelona |
|  | Asp->Asn | Bunbury |
| 96 (FG3) | Leu->Val | Regina |
| 97 (FG4) | His->Gln | Malmo |
|  | His->Leu | Wood |
| 99 (G1) | Asp->Asn | Kempsey |
|  | Asp->His | Yakima |
|  | Asp->Ala | Radcliffe |
|  | Asp->Tyr | Ypsilanti |
|  | Asp->Gly | Hotel-Dieu |
|  | Asp->Val | Chemilly |
| 100 (G2) | Pro->Leu | Brigham |
| 101 (G3) | Glu->Lys | British Columbia |
|  | Glu->Gly | Alberta |
|  | Glu->Asp | Potomac |
| 103 (G5) | Phe->Leu | Heathrow |
| 109 (G11) | Val->Met | San Diego |
| 121 (GH4) | Glu->Gln | D-Los Angeles |
| 124 (H2) | Pro->Gln | Tu Gard |
| 129 (H7) | Ala->Pro | Crete |
| 140 (H18) | Ala->Thr | St. -Jacques |
| 142 (H20) | Ala->Asp | Ohio |
| 143 (H21) | His->Arg | Abruzzo |
|  | His->Gln | Little Rock |
|  | His->Pro | Syracuse |
| 144 (HC1) | Lys->Asn | Andrew-Minneapolis |
| 145 (HC2) | Tyr->His | Bethesda |
|  | Tyr->Cys | Rainier |
|  | Tyr->Asp | Fort Gordon |
|  | Tyr->Term | McKees Rocks |
| 146 (HC3) | His->Asp | Hiroshima |
|  | His->Pro | York |
|  | His->Leu | Cowtown |

What is claimed is:

1. A DNA molecule comprising a first DNA sequence encoding a non-naturally occurring genetically fused pseudooligomeric polypeptide comprising two or more alpha globin-like domains connected by one or more peptide bonds into a single unbranched polypeptide chain, said chain being capable of associating with beta globin and incorporating heme to form a hemoglobin-like protein.

2. The DNA molecule of claim 1 which comprises only two globin-like domains.

3. The DNA molecule of claim 1 wherein a first and a second globin-like polypeptide domain are connected by a peptide linker of one or more amino acids.

4. The DNA molecule of claim 3 wherein the peptide linker is not more than nine amino acids.

5. The DNA molecule of claim 3 wherein the amino acids of the linker are selected from the group consisting of lysine, aspartic acid, arginine, serine, asparagine, proline and glycine.

6. The DNA molecule of claim 5 wherein the linker consists of one or more glycines.

7. The DNA molecule of claim 5 wherein the amino acids of the linker are selected from the group consisting of glycine and proline.

8. The DNA molecule of claim 1 wherein each globin-like domain has at least 75% sequence identity with human alpha globin.

9. The DNA molecule of claim 1 wherein each globin-like domain is essentially identical in sequence with human alpha globin.

10. The DNA molecule of claim 1 wherein said polypeptide comprises only two globin-like domains.

11. The DNA molecule of claim 1 wherein said globin-like domains are essentially identical, but wherein at a predetermined position, a first globin-like domain has a cysteine residue and a second globin-like domain has a residue other than cysteine.

12. The DNA molecule of claim 1 wherein said protein is a low affinity hemoglobin mutant.

13. The DNA molecule of claim 1 wherein said protein is a high affinity hemoglobin mutant.

14. The recombinant DNA molecule of claim 1 further comprising a second DNA sequence encoding a beta globin-like polypeptide.

15. The DNA molecule of claim 14 wherein the beta globin-like polypeptide comprises a Presbyterian mutation.

16. The molecule of claim 14, wherein the DNA sequence encoding the pseudooligomeric polypeptide defines a single cistron of a polycistronic operon, and the second DNA sequence which defines another cistron of the polycistronic operon, wherein the cistrons are transcribed from a common promoter.

17. The molecule of claim 16 wherein the common promoter is the Tac promoter.

18. The DNA molecule of claim 1 wherein the linker comprises one more glycines.

19. The DNA molecule of claim 1 wherein each globin-like domain is essentially identical in sequence with a vertebrate alpha globin.

20. The DNA molecule of claim 1 wherein each globin-like domain is essentially identical in sequence with a mammalian alpha globin.

21. The DNA molecule of claim 1 wherein each globin-like domain comprises, at corresponding positions, the amino acids residues which are invariant among vertebrate alpha globins.

22. The DNA molecule claim 1 wherein each globin-like domain comprises, at corresponding positions, the amino acid residues which are invariant among mammalian alpha globins.

23. The DNA molecule of claim 1 wherein each alpha globin-like domain differs from at least one vertebrate alpha globin solely by mutations corresponding to an allelic variation in human alpha globin and/or substitutions wherein each substituted amino acid is replaced by another in the same exchange group, the exchange groups being:

I Ala, Ser, Thr, Pro, Gly
II Asn, Asp, Glu, Gln
III His, Arg, Lys
IV Met, Leu, Ile, Val, Cys
V Phe, Tyr, Trp.

24. The DNA molecule of claim 1 wherein each alpha globin-like domain differs from at least one mammalian alpha globin solely by mutations corresponding to an allelic variation in human alpha globin and/or substitutions wherein each substituted amino acid is replaced by another in the same exchange group, the exchange groups being:

I Ala, Ser, Thr, Pro, Gly
II Asn, Asp, Glu, Gln
III His, Arg, Lys
IV Met, Leu, Ile, Val, Cys
V Phe, Thy, Trp.

25. The DNA molecule of claim 1 wherein each alpha globin-like domain differs from at least one human alpha globin solely by mutations corresponding to an allelic variation in human alpha globin and/or substitutions wherein each substituted amino acid is replaced by another in the same exchange group, the exchange groups being:

I Ala, Ser, Thr, Pro, Gly
II Asn, Asp, Glu, Gln
III His, Arg, Lys
IV Met, Leu, Ile, Val, Cys
V Phe, Tyr, Trp.

26. The DNA molecule of claim 1 wherein each alpha globin-like domain has at least 75% sequence identity with a mammalian alpha globin.

27. The DNA molecule of claim 1 wherein each alpha globin-like domain has at least the same degree of sequence identity with human alpha globin as does the corresponding chicken globin.

28. The DNA molecule of claim 1 wherein each alpha globin-like domain has at least the same degree of sequence identity with human alpha globin as does the corresponding carp globin.

29. The DNA molecule of claim 1 wherein each alpha globin-like domain has at least the same degree of sequence identity with human alpha globin as does the corresponding platypus globin.

30. The DNA molecule of claim 1 wherein the linker comprises two or more glycines, and at least the first and last amino acids of the liner are glycines.

31. The DNA molecule of claim 30 wherein the amino acids of the linker are selected from the group consisting of alanine, threonine, lysine, aspartic acid, arginine, serine, asparagine, proline and glycine.

32. The DNA molecule of claim 1 wherein said pseudooligomeric polypeptide comprises two or more pairs of alpha globin-like domains, and is capable of associating with one or more beta globin-like polypeptides to form a polytetrameric hemoglobin-like protein with reversible oxygen binding activity.

33. The DNA molecule of claim 32 wherein the polypeptide further comprises a peptide linker between at least one pair of successive alpha globin-like domains is at least 17 Å in length.

34. The DNA molecule of claim 32 wherein the polypeptide further comprises a peptide linker between at least one pair of successive alpha globin-like domains is at least 22 Å in length.

35. The DNA molecule of claim 32 wherein said polypeptide genetically fuses two or more di-alpha globin-like polypeptides.

36. The DNA molecule of claim 1 wherein said hemoglobin-like protein is a low oxygen affinity mutant hemoglobin.

37. The DNA molecule of claim 36 wherein at least one of said low affinity mutations is a mutation of an alpha-globin mutation selected from the group consisting of 43 phe→leu, 43 phe→val, 86 leu→arg, 94 asp→asn, 46 phe→thr, 46 phe→ser, 46 phe→ala, 58 his→phe, 58 his→trp, 61 lys→thr, 61 lys→ser, 61 lys→met, 61 lys→asn, 62 val→leu, 62 val→ile, 62 val→phe, 62 val→trp, 65 ala→asp, 94 asp→gln, 94 asp→thr, 94 asp→ser, 94 asp→lys, 94 asp→gly, and 94 asp→arg.

38. The DNA molecule of claim 1 wherein said hemoglobin-like protein is a high oxygen affinity mutant hemoglobin.

39. The DNA molecule of claim 38 wherein at least one of said high affinity mutations is a mutation of an alpha globin-like domain which corresponds to a human alpha globin mutation selected from the group consisting of 6 Asp→Ala, 6 Asp→Asn, 6 Asp→Val, 6 Asp→Tyr, 6 Lys→Asn, 40 Lys→Glu, 44 Pro→Leu, 44 Pro→Arg, 45 His→Arg, 85 Asp→Asn, 92 Arg→Gln, 92 Arg→Leu, 95 Pro→Leu, 95 Pro→Ser, 95 Pro→Ala, 95 Pro→Arg, 97 Asn→Lys, 126 Asp→Asn, 141 Arg→His, 141 Arg→Ser, and 141 Arg→Leu.

40. The DNA molecule of claim 1 wherein at least one alpha globin-like domain has a cysteine at a position which is not a cysteine in human alpha globin.

41. The DNA molecule of claim 1 wherein cysteine is at a position in said domain corresponding to a position in the alpha globin-like domain corresponding to a human alpha globin position selected from the group consisting of his72, asn78, asn68, ala71, thr67, lys7, lys11, thr8, ala12, thr118, lys16, ala45, glu116, gly15, his112, thr24, glu23, lys60, lys56, his50, gly51, glu53, ser49, asp47, gln54, his45, lys90, ala82, lys61, ala19, his20, asp85, ser81, asp75, asp74, lys139, asp64, and gly18.

42. The DNA molecule of claim 1 wherein each alpha globin-like domain of said genetically fused polypeptide is identical to human alpha globin save for (a) one or more an oxygen affinity-modifying modifications characterized as (i) one or more low affinity mutations, selected from the group consisting of 43 phe→leu, 43 phe→val, 86 leu→arg, 94 asp→asn, 46 phe→thr, 46 phe→ser, 46 phe→ala, 58 his→phe, 58 his→trp, 61 lys→thr, 61 lys→ser, 61 lys→met, 61 lys→asn, 62 val→leu, 62 val→ile, 62 val→phe, 62 val→trp, 65 ala→asp, 94 asp→gln, 94 asp→thr, 94 asp→ser, 94 asp→lys, 94 asp→gly, and 94 asp→arg, or (ii) one or more high affinity mutations selected from the group consisting of 6 Asp→Ala, 6 Asp→Asn, 6 Asp→Val, 6 Asp→Tyr, 6 Lys→Asn, 40 Lys→Glu, 44 Pro→Leu, 44 Pro→Arg, 45 His→Arg, 85 Asp→Asn, 92 Arg→Gln, 92 Arg→Leu, 95 Pro→Leu, 95 Pro→Ser, 95 Pro→Ala, 95 Pro→Arg, 97 Asn→Lys, 126 Asp→Asn, 141 Arg→His, 141 Arg→Ser, and 141 Arg→Leu;

and/or (b) a Cys substitution at one or more sites selected from the group consisting of: his72, asn78, asn68, ala71, thr67, lys7, lys11, thr8, ala12, thr118, lys16, ala45, glu16, gly15, his112, thr24, glu23, lys60, lys56, his50, gly51, glu53, ser49, asp47, gln54, his45, lys90, ala82, lys61, ala19, his20, asp85, ser81, asp75, asp74, lys139, asp64, and gly18.

43. A method of producing a human hemoglobin-like protein with reversible oxygen binding activity which comprises providing a host transformed with a recombinant DNA molecule according to claim 1, cultivating said host under conditions whereunder it expresses said pseudooligomeric polypeptide, and combining said polypeptide with beta globin and heme to obtain a human hemoglobin like protein.

44. The method of claim 43 wherein the host is a yeast cell.

45. The method of claim 43 wherein the host is a bacterial cell.

46. A method of producing a human hemoglobin-like protein with reversible oxygen binding activity which comprises providing a host transformed with a recombinant DNA molecule according to claim 16, cultivating the host under conditions where under it expresses the pseudooligomeric polypeptide and the beta globin-like polypeptide, wherein the di-alpha globin pseudooligomeric polypeptide and the beta-globin-like polypeptide, are co-expressed from the recombinant DNA molecule and heme is provided by said host and incorporated to form said hemoglobin-like protein.

* * * * *

UNITED STATES PATENT AND TRADEMARK OFFICE
CERTIFICATE OF CORRECTION

PATENT NO. : 6,828,125 B1
DATED : December 7, 2004
INVENTOR(S) : Hoffman et al.

It is certified that error appears in the above-identified patent and that said Letters Patent is hereby corrected as shown below:

Title page,
Item [75], Inventors, reads "Stephen J. Hoffman, Denver, CO (US); Douglas L. Looker, Lafayette, CO (US); Kiyoshi Nagai, Cambridge (GB)" and should read
-- Stephen J. Hoffman, Denver, CO (US); Douglas L. Looker, Lafayette, CO (US); Gary L. Stetler, Denver, CO (US); Michael Wagenbach, Osaka, Japan (US); Kiyoshi Nagai, Cambridge, (GB) --

Signed and Sealed this

Twenty-second Day of March, 2005

JON W. DUDAS
*Director of the United States Patent and Trademark Office*